US012746270B2

(12) United States Patent
Barasch et al.

(10) Patent No.: US 12,746,270 B2
(45) Date of Patent: Sep. 29, 2026

(54) MUTANT NGAL PROTEINS AND USES THEREOF

(71) Applicant: The Trustees of Columbia University in the City of New York, New York, NY (US)

(72) Inventors: Jonathan Barasch, New York, NY (US); Andong Qiu, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 96 days.

(21) Appl. No.: 18/343,508

(22) Filed: Jun. 28, 2023

(65) Prior Publication Data

US 2023/0414709 A1 Dec. 28, 2023

Related U.S. Application Data

(60) Continuation of application No. 16/819,891, filed on Mar. 16, 2020, now Pat. No. 11,730,790, which is a continuation of application No. 15/376,327, filed on Dec. 12, 2016, now Pat. No. 10,588,937, which is a division of application No. 13/684,060, filed on Nov. 21, 2012, now Pat. No. 9,534,027, which is a continuation-in-part of application No. PCT/US2011/037774, filed on May 24, 2011.

(60) Provisional application No. 61/354,973, filed on Jun. 15, 2010, provisional application No. 61/347,587, filed on May 24, 2010.

(51) Int. Cl.
*A61K 38/17* (2006.01)
*C07K 14/47* (2006.01)
*A61K 31/357* (2006.01)

(52) U.S. Cl.
CPC .......... *A61K 38/1709* (2013.01); *C07K 14/47* (2013.01); *A61K 31/357* (2013.01)

(58) Field of Classification Search
None
See application file for complete search history.

(56) References Cited

U.S. PATENT DOCUMENTS

| | | | | |
|---|---|---|---|---|
| 3,710,795 | A | 1/1973 | Higuchi et al. | |
| 4,640,909 | A | 2/1987 | Ramsden et al. | |
| 5,627,034 | A | 5/1997 | Gould et al. | |
| 6,071,880 | A | 6/2000 | Acott et al. | |
| 6,114,123 | A | 9/2000 | Murry et al. | |
| 6,136,526 | A | 10/2000 | Venge | |
| 6,447,989 | B1 | 9/2002 | Comper | |
| 6,492,325 | B1 | 12/2002 | Cosgrove | |
| 6,664,385 | B1 | 12/2003 | Sanicola-Nadel et al. | |
| 6,710,028 | B2 | 3/2004 | Lehmann et al. | |
| 6,825,037 | B1 | 11/2004 | Funk et al. | |
| 6,861,404 | B1 | 3/2005 | Cohen et al. | |
| 7,141,382 | B1 | 11/2006 | Parikh et al. | |
| 7,153,660 | B2 | 12/2006 | Moses et al. | |
| 7,776,824 | B2 | 8/2010 | Barasch et al. | |
| 8,247,376 | B2 | 8/2012 | Barasch et al. | |
| 9,534,027 | B2 | 1/2017 | Barasch et al. | |
| 9,578,541 | B2 | 2/2017 | Seenappa et al. | |
| 9,624,281 | B2 * | 4/2017 | Barasch | C07K 14/47 |
| 10,588,937 | B2 | 3/2020 | Barasch et al. | |
| 10,829,525 | B2 | 11/2020 | Barasch et al. | |
| 11,730,790 | B2 | 8/2023 | Barasch et al. | |
| 12,173,037 | B1 * | 12/2024 | Barasch | C07K 14/47 |
| 2002/0128194 | A1 | 9/2002 | Green et al. | |
| 2003/0109420 | A1 | 6/2003 | Valkirs et al. | |
| 2004/0102383 | A1 | 5/2004 | Cincotta et al. | |
| 2004/0132984 | A1 | 7/2004 | Dieckmann et al. | |
| 2004/0219603 | A1 | 11/2004 | Devarajan et al. | |
| 2005/0201981 | A1 | 9/2005 | Liu et al. | |
| 2005/0214219 | A1 | 9/2005 | Green et al. | |
| 2005/0261191 | A1 | 11/2005 | Barasch et al. | |
| 2005/0272101 | A1 | 12/2005 | Devarajan et al. | |
| 2007/0037232 | A1 | 2/2007 | Barasch et al. | |
| 2007/0092911 | A1 | 4/2007 | Buechler et al. | |
| 2007/0105166 | A1 | 5/2007 | Moses et al. | |
| 2007/0154897 | A1 | 7/2007 | Yen et al. | |
| 2007/0161125 | A1 | 7/2007 | Rosenfeld et al. | |

(Continued)

FOREIGN PATENT DOCUMENTS

| | | | |
|---|---|---|---|
| WO | WO-02/24866 | A2 | 3/2002 |
| WO | WO-03/029462 | A1 | 4/2003 |

(Continued)

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Abergel et al., "Anthrax pathogen evades the mammalian immune system through stealth siderophore production," PNAS, vol. 103, No. 49, pp. 18499-18503 (2006).

(Continued)

*Primary Examiner* — Brian Gangle
*Assistant Examiner* — Andrea K Mccollum
(74) *Attorney, Agent, or Firm* — Wilmer Cutler Pickering Hale and Dorr LLP

(57) ABSTRACT

In one aspect the present invention is directed to mutant Neutrophil gelatinase-associated lipocalin (NGAL) proteins that have the ability to bind to siderophores, such as enterochelin, and to chelate and transport iron, and that are excreted in the urine. Such NGAL mutants, and complexes thereof with siderophores, can be used to clear excess iron from the body, for example in the treatment of iron overload. The NGAL mutants of the invention also have antibacterial activity and can be used in the treatment of bacterial infections, such as those of the urinary tract.

20 Claims, 38 Drawing Sheets

Specification includes a Sequence Listing.

(56) References Cited

U.S. PATENT DOCUMENTS

| | | | |
|---|---|---|---|
| 2007/0172906 | A1 | 7/2007 | Valkirs et al. |
| 2007/0196876 | A1 | 8/2007 | Moses et al. |
| 2007/0254370 | A1 | 11/2007 | Devarajan et al. |
| 2008/0014604 | A1 | 1/2008 | Devarajan et al. |
| 2008/0014644 | A1 | 1/2008 | Barasch et al. |
| 2008/0050832 | A1 | 2/2008 | Buechler et al. |
| 2008/0057590 | A1 | 3/2008 | Urdea et al. |
| 2008/0090304 | A1 | 4/2008 | Barasch et al. |
| 2008/0095782 | A1 | 4/2008 | Xu et al. |
| 2008/0254485 | A1 | 10/2008 | Valkirs et al. |
| 2009/0019551 | A1 | 1/2009 | Haga et al. |
| 2009/0055099 | A1 | 2/2009 | Rosenfeld et al. |
| 2009/0082443 | A1 | 3/2009 | Otto et al. |
| 2009/0123941 | A1 | 5/2009 | Devarajan et al. |
| 2009/0123970 | A1 | 5/2009 | Tu et al. |
| 2009/0124572 | A1 | 5/2009 | Nelson |
| 2009/0142774 | A1 | 6/2009 | Devarajan et al. |
| 2009/0170143 | A1 | 7/2009 | Uttenthal et al. |
| 2009/0181407 | A1 | 7/2009 | Devarajan et al. |
| 2009/0191551 | A1 | 7/2009 | Morrow et al. |
| 2009/0215094 | A1 | 8/2009 | Barasch et al. |
| 2009/0269777 | A1 | 10/2009 | Birkenmeyer et al. |
| 2009/0298073 | A1 | 12/2009 | Gerhold et al. |
| 2009/0305963 | A1 | 12/2009 | Sukhatme et al. |
| 2009/0311213 | A1 | 12/2009 | Thiboutot et al. |
| 2010/0015648 | A1 | 1/2010 | Barasch et al. |
| 2010/0028919 | A1 | 2/2010 | Devarajan et al. |
| 2010/0047837 | A1 | 2/2010 | Devarajan et al. |
| 2010/0093812 | A1 | 4/2010 | Bergeron, Jr. |
| 2010/0105150 | A1 | 4/2010 | Adamczyk et al. |
| 2010/0122355 | A1 | 5/2010 | Paragas et al. |
| 2010/0184089 | A1 | 7/2010 | Barasch et al. |
| 2010/0189643 | A1 | 7/2010 | Chilkoti et al. |
| 2010/0227418 | A1 | 9/2010 | Devarajan et al. |
| 2010/0233728 | A1 | 9/2010 | Devarajan et al. |
| 2010/0233739 | A1 | 9/2010 | Barasch et al. |
| 2010/0233740 | A1 | 9/2010 | Barasch et al. |
| 2010/0234765 | A1 | 9/2010 | Barasch et al. |
| 2010/0254970 | A1 | 10/2010 | Barasch et al. |
| 2011/0091912 | A1 | 4/2011 | Barasch et al. |
| 2011/0262353 | A1 | 10/2011 | Skerra et al. |
| 2011/0268818 | A1 | 11/2011 | Barasch et al. |
| 2012/0083421 | A1 | 4/2012 | Barasch et al. |
| 2012/0214177 | A1 | 8/2012 | Barasch et al. |
| 2013/0072580 | A1 | 3/2013 | Barasch et al. |
| 2013/0149725 | A1 | 6/2013 | Barasch et al. |
| 2013/0157932 | A1 | 6/2013 | Barasch et al. |
| 2017/0016923 | A1 | 1/2017 | Nielsen |
| 2018/0153889 | A1 | 6/2018 | Henry et al. |
| 2019/0211341 | A1 | 7/2019 | Butler et al. |
| 2021/0038686 | A1 | 2/2021 | Barasch et al. |
| 2023/0414709 | A1 | 12/2023 | Barasch |

FOREIGN PATENT DOCUMENTS

| | | | |
|---|---|---|---|
| WO | WO-2004/005544 | A2 | 1/2004 |
| WO | WO-04/088276 | A2 | 10/2004 |
| WO | WO-2005/107793 | | 11/2005 |
| WO | WO-2005/107993 | | 11/2005 |
| WO | WO-05/121788 | A2 | 12/2005 |
| WO | WO-2006/066587 | | 6/2006 |
| WO | WO-2006078717 | A2 | 7/2006 |
| WO | WO-06/091035 | A1 | 8/2006 |
| WO | WO-2007013919 | A2 | 2/2007 |
| WO | WO-07/047458 | A2 | 4/2007 |
| WO | WO-2007/044994 | | 4/2007 |
| WO | WO-2008116867 | A1 | 10/2008 |
| WO | WO-09/114699 | A2 | 9/2009 |
| WO | WO-2009/114699 | | 9/2009 |
| WO | WO-2010/033847 | | 3/2010 |
| WO | WO-2010/045585 | | 4/2010 |
| WO | WO-2010057184 | A2 | 5/2010 |
| WO | WO-2010/148216 | | 12/2010 |
| WO | WO-2011/053832 | | 5/2011 |
| WO | WO-2011062469 | A2 | 5/2011 |
| WO | WO-2011069992 | A2 | 6/2011 |
| WO | WO-2011/140554 | | 11/2011 |
| WO | WO-2011/149962 | | 12/2011 |
| WO | WO-2012/022742 | A1 | 2/2012 |
| WO | WO-2012/042061 | A1 | 4/2012 |
| WO | WO-2012068545 | A1 | 5/2012 |
| WO | WO-2014/081980 | A2 | 5/2014 |

OTHER PUBLICATIONS

Abergel et al., "Microbial Evasion of the Immune System: Structural Modifications of Enterobactin Impair Siderocalin Recognition," Author Manuscript, 9 pages, Published in final edited form as: J. Am. Chem. Soc., vol. 128, pp. 10998-10999 (2006).

Abergel et al., "The Siderocalin/Enterobactin Interaction: A Link between Mammalian Immunity and Bacterial Iron Transport," Author Manuscript, 28 pages, Published in final edited form as: J. Am. Chem. Soc., vol. 130, pp. 11524-11534 (2008).

Allen, K.J., et al., "Iron-Overload-Related Disease in HFE Hereditary Hemochromatosis," N. Engl. J. Med., vol. 358, pp. 221-230 (2008).

Alteri et al., "Mucosal Immunization with Iron Receptor Antigens Protects against Urinary Tract Infection," PLoS Pathogens, vol. 5, Issue 9, e1000586, pp. 1-12 (Sep. 2009).

American Hemochromatosis Society, "FAQ's About Hemochromatosis/Iron Overload", pp. 1-14 (2019).

Andrews, "Disorders of Iron Metabolism," N. Engl. J. Med., vol. 341, pp. 1986-1995 (1999).

Andrews, "Iron homeostasis: insights from genetics and animal models," Nature Reviews, vol. 1, pp. 208-217 (Dec. 2000).

Andrews, "Iron Metabolism: Iron Deficiency and Iron Overload," Annual Review of Genomics and Human Genetics, vol. 1, pp. 75-98 (2000).

Argyropoulou et al., "Liver, bone marrow, pancreas and pituitary gland iron overload in young and adult thalassemic patients: A T2 relaxometry study," Eur. Radiol., vol. 17, 3025-3030 (2007).

Argyropoulou et al., "MRI evaluation of tissue iron burden in patients with β-thalassaemia major," Pediatr. Radiol., vol. 37, pp. 1191-1200 (2007).

Avdeef et al. "Coordination Chemistry of Microbial Iron Transport Compounds. 9. Stability Constants for Catechol Models of Enterobactin," J. Am. Chem. Soc., vol. 100, No. 17, pp. 5362-5370 (Aug. 16, 1978).

Axelsson et al., "Studies of the release and turnover of a human neutrophil lipocalin," Scand. J. Clin. Lab Invest., vol. 55, No. 7, pp. 577-588 (Nov. 1995).

Bachman et al., "Interaction of Lipocalin 2, Transferrin, and Siderophores Determines the Replicative Niche of Klebsiella pneumoniae during Pneumonia," mBio, vol. 3, No. 6, pp. 1-8 (2012).

Bahram et al., "Experimental hemochromatosis due to MHC class I HFE deficiency: Immune status and iron metabolism," Proc. Natl. Acad. Sci. USA., 96, No. 23, pp. 13312-13317 (1999).

Baliga et al., "Evidence for cytochrome P-450 as a source of catalytic iron in myoglobinuric acute renal failure," Kidney Int., vol. 49, pp. 362-369 (1996).

Baliga et al., "In vitro and in vivo evidence suggesting a role for iron in cisplatin-induced nephrotoxicity," Kidney Int., vol. 53, pp. 394-401 (1998).

Baliga et al., "Increase in bleomycin-detectable iron in ischaemia/reperfusion injury to rat kidneys," Biochem. J., vol. 291, pp. 901-905 (1993).

Bander et al., "Long-term effects of 24-hour unilateral ureteral obstruction on renal function in the rat," Kidney Int., vol. 28, pp. 614-620 (1985).

Bao et al. "Iron Traffics in Circulation Bound to a Siderocalin (Ngal)-Catechol Complex," Author Manuscript, 20 pages, Published in final edited form as: Nat. Chem. Biol., vol. 6, No. 8, pp. 602-609 (2010).

Barasch and Mori, "Cell Biology: Iron Thievery," Nature, vol. 432, pp. 811-813 (2004).

(56) References Cited

OTHER PUBLICATIONS

Barasch et al., "A ureteric bud cell line induces nephrogenesis in two steps by two distinct signals," American Journal of Physiology, Renal Physiology, vol. 271, No. 1, pp. F50-F61 (Jul. 1, 1996).
Baron et al., "Renal Preservation after Warm Ischemia Using Oxygen Free Radical Scavengers to Prevent Reperfusion Injury," Journal of Surgical Research, vol. 51, pp. 60-65 (1991).
Barr et al., "Urinary Creatinine Concentrations in the U.S. Population: Implications for Urinary Biologic Monitoring Measurements," Environmental Health Perspectives, vol. 113, pp. 192-200 (2005).
Bennett et al., "Urine NGAL predicts severity of acute injury after cardiac surgery: A prospective Study," Clin. J. Am. Soc. Nephrol., 3(3), pp. 665-673 (May 2008).
Berdoukas et al., "Liver iron concentration and fibrosis in a cohort of transfusion-dependent patients on long-term desferrioxamine therapy," The Hematology Journal, vol. 5, pp. 572-578 (2005).
Berger et al., "Lipocailn 2-deficient mice exhibit increased sensitivity to *Escherichia coli* infection but not to ischemia-reperfusion injury," Proc. Nat. Acad. Sci. USA, vol. 103, No. 6, pp. 1834-1839 (2006).
Bernhardt, "Coordination chemistry and biology of chelators for the treatment of iron overload disorders," Dalton Trans., pp. 3214-3220 (2007).
BioPorto Diagnostice A/S, "NGal Rapid ELISA Kit (Kit 037)," Revision: NR2007-12-EN, Dec. 2007 (84 pages), Retrieved from internet <www.piercenet.com/files/kit037.PDF>.
BioPorto Diagnostics A/S, "Human NGAL Rapid ELISA Kit (Kit 037)," Revision: 2010-09, Sep. 2010 (4 pages), Retrieved from internet <www.bioporto.com/products/bioporto_diagnostics/ngal_elisa_kits/ngal_rapid_elisa_kit_ce_ivd>.
Bläser et al., "A sandwich enzyme immunoassay for the determination of neutrophil lipocalin in body fluids," Clin. Chim. Acta vol. 235, pp. 137-145 (1995).
Boelaert and Locht, "Side-effects of desferrioxamine in dialysis patients," Nephrol. Dial. Transplant., Suppl. 1, pp. 43-46 (1993).
Bohle et al., "Significance of Tubulointerstitial Changes in the Renal Cortex for the Excretory Function and Concentration Ability of the Kidney: A Morphometric Contribution," Am. J. Nephrol., vol. 7, pp. 421-433 (1987).
Bolignano et al., "Neutrophil Gelatinase Associated Lipocalin Reflects the Severity of Renal Impairment in Subjects Affected by Chronic Kidney Disease," Kidney Blood Press. Res., vol. 31, pp. 255-258 (2008).
Bolignano et al., "Neutrophil Gelatinase-Associated Lipocalin in Patients with Autosomal-Dominant Polycystic Kidney Disease," Am. J. Nephrol., vol. 27, pp. 373-378 (2007).
Bolignano et al., "Urinary Neutrophil Gelatinase Associated Lipocalin (Ngal) is Associated with Severity of Renal Disease in Proteinuric Patients," Nephrol. Dial. Transplant., vol. 23, pp. 414-416 (2008).
Bork, "Powers and Pitfalls in Sequence Analysis: The 70% Hurdle," Genome Res., vol. 10, pp. 398-400 (2000).
Borregaard et al., "Neutrophil gelatinase-associated lipocalin, a siderophore-binding eukaryotic protein," BioMetals, vol. 19, pp. 211-215 (2006).
Borwein et al., "Diagnostic efficacy of screening tests for hereditary hemochromatosis," Can. Med. Assoc. J., vol. 131, pp. 895-901 (1984).
Bosque et al., "Assessment of the developmental toxicity of deferoxamine in mice," Arch. Toxicol., 69, pp. 467-471 (1995).
Bowie et al., "Deciphering the Message in Protein Sequences: Tolerance to Amino Acid Substitutions," Science, vol. 247, pp. 1306-1310 (1990).
Brenner et al., "Effects of losartan on renal and cardiovascular outcomes in patients with type 2 diabetes and nephropathy," N. Engl. J. Med., vol. 345, No. 12, pp. 861-869 (Sep. 20, 2001).
Breuer et al., "The assessment of serum nontransferrin-bound iron in chelation therapy and iron supplementation," Blood, vol. 95. No. 9, pp. 2975-2982 (2000).
Bundgaard et al., "Molecular Cloning and Expression of a cDNA Encoding NGAL: A Lipocalin Expressed in Human Neutrophils," Biochem. Biophys. Res. Commun., vol. 202, pp. 1468-1475 (1994).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., vol. 111, pp. 2129-2138 (1990).
Burrus, et al., "Identification of a Cysteine-Rich Receptor for Fibroblast Growth Factors", Mol. Cell Biol. 12(12): 5600-5609, Dec. 1992 (10 pages).
Carmella et al., "Quantitative analysis of catechol and 4-methylcatechol in human urine," Food Chem. Toxic., vol. 20, pp. 587-590 (1982).
Christensen and Birn, "Megalin and cubilin: multifunction endocytic receptors," Nature Reviews Molecular Cell Biology, vol. 3, pp. 258-268 (Apr. 2002).
Chu et al., "Siderophore uptake in bacteria and the battle for iron with the host; a bird's eye view," Biometals, vol. 23, pp. 601-611 (2010).
Chua et al., "Nontransferrin-bound iron uptake by hepatocytes is increased in the Hfe knockout mouse model of hereditary hemochromatosis," Blood, vol. 104, pp. 1519-1525 (2004).
Cohen, "New Advances in Iron Chelation Therapy," Hematology-American Hematology Society Hematology Education Program, pp. 42-47 (2006).
Cooper et al., "Urinary Iron Speciation in Nephrotic Syndrome," Am. J. Kidney Dis., vol. 25, pp. 314-319 (1995).
Cowland et al., "Neutrophil Gelatinase-Associated Lipocalin Is Up-Regulated in Human Epithelial Cells by IL-1$\beta$, but not by TNF-$\alpha$," J. Immunol., vol. 171, pp. 6630-6639 (2003).
Crisponi and Remelli "Iron chelating agents for the treatment of iron overload" Coordination Chemistry Reviews, vol. 252, pp. 1225-1240 (2008).
Cunningham et al., "Complications of $\beta$-thalassemia major in North America," Blood, vol. 104, No. 1, 34-39 (2004).
D'Amico et al., "Tubulointerstitial Damage in Glomerular Diseases: Its Role in the Progression of Renal Damage," Am. J. Kidney Dis., vol. 26, pp. 124-132 (1995).
Damman et al., "Urinary neutrophil gelatinase associated lipocalin (NGAL), a marker of tubular damage, is increased in patients with chronic heart failure," European Journal of Heart Failure, vol. 10, pp. 997-1000 (2008).
Darbari, D.S., et al., "Circumstances of Death in Adult Sickle Cell Disease Patients," Am. J. Hematol., 81, pp. 858-863 (2006).
De Vries et al., "Exogenous alpha-1-acid glycoprotein protects against renal ischemia-reper-fusion injury by inhibition of inflammation and apoptosis," Transplantation 78(8), pp. 1116-1124 (Oct. 27, 2004).
De Vries et al., "Reduction of circulating redox-active iron by apotransferrin protects against renal ischemia-reperfusion injury," Transplantation, vol. 77, No. 5, pp. 669-675 (Mar. 15, 2004).
De Zeeuw, D. et al., "Renal risk and renoprotection among ethnic groups with type 2 diabetic nephropathy: a post hoc analysis of RENAAL," Kidney International, vol. 69, pp. 1675-1682 (2006).
Dent et al., "Plasma neutrophil gelatinase-associated lipocalin predicts acute kidney injury, morbidity and mortality after pediatric cardiac surgery: a prospective uncontrolled cohort study." Critical Care, vol. 11, No. 6, 8 pages (2007).
Devarajan et al., "Gene expression in early ischemic renal injury: clues toward pathogenesis, biomarker discovery, and novel therapeutics," Molecular Genetics and Metabolism, vol. 80, pp. 365-376 (2003).
Devarajan, "Neutrophil gelatinase-associated lipocalin: new paths for an old shuttle," Author Manuscript, 12 pages, Published in final edited form as: Cancer Therapy, vol. 5(B), pp. 463-470 (2007).
Devarajan, "Novel biomarkers for the early prediction of acute kidney injury," Cancer Therapy, vol. 3, pp. 477-488 (2005).
Devireddy et al., "A Cell-Surface Receptor for Lipocalin 24p3 Selectively Mediates Apoptosis and Iron Uptake," Cell, vol. 123, pp. 1293-1305 (2005).
Ding et al., "Urinary neutrophil gelatinase-associated lipocalin (NGAL) is an early biomarker for renal tubulointerstitial injury in IgA nephropathy," Clin. Immunol., vol. 123, pp. 227-234 (2007).

(56) References Cited

OTHER PUBLICATIONS

Doneanu et al., "Characterization of a Noncovalent Lipocalin Complex by Liquid Chromatography/Electrospray Ionization Mass Spectrometry," J. Biomol. Tech., vol. 15, pp. 208-212 (2004).
Eddy et al., "A Relationship Between Proteinuria and Acute Tubulointerstitial Disease in Rats with Experimental Nephrotic Syndrome," Am. J. Pathol., vol. 138, No. 5, pp. 1111-1123, 1991.
Eddy, "Progression in Chronic Kidney Disease," Adv. Chronic Kidney Dis., vol. 12, No. 4, 353-365 (2005.
Eddy, "Proteinuria and interstitial injury," Nephrol. Dial. Transplant., vol. 19, 277-281 (2004).
Eichler et al., "Human neutrophil lipocalin, a highly specific marker for acute exacerbation in cystic fibrosis," Eur. Respir. J., vol. 14, pp. 1145-1149 (1999).
Emery, Thomas, "Exchange of Iron by Gallium in Siderophores," Biochemistry, vol. 25, pp. 4629-4633 (1986).
Esbach and Adamson, "Iron overload in renal failure patients: Changes since the introduction of erythropoietin therapy," Kidney International, vol. 55, pp. S35-S43 (1999).
Esson et al., "Diagnosis and Treatment of Acute Tubular Necrosis," Ann. Intern. Med. vol. 137, pp. 744-753 (2002).
Evans et al., "Nature of non-transferrin-bound iron: studies on iron citrate complexes and thalassemic sera," Journal of Biological Inorganic Chemistry, vol. 13, pp. 57-74 (2008).
Extended European Search Report issued by the European Patent Office for Application No. 11787264.8 on Oct. 7, 2014 (5 pages).
Extended European Search Report mailed Oct. 30, 2013, for European Patent Application No. 09815299.4 (7 pages).
Fernández et al., "The Matrix Metalloproteinase-9/Neutrophil Gelatinase-Associated Lipocalin Complex Plays a Role in Breast Tumor Growth and Is Present in the Urine of Breast Cancer Patients," Clin. Cancer Res., vol. 11, No. 15, pp. 5390-5395 (Aug. 1, 2005).
Fischbach et al., "The pathogen-associated iroA gene cluster mediates bacterial evasion of lipocalin 2," Proc. Natl. Acad. Sci. USA, vol. 103, pp. 16502-16507 (2006).
Fjaertoft et al., "Human Neutrophil Lipocalin (HNL) as a Diagnostic Tool in Children with Acute Infections: A Study of the Kinetics," Acta Paediatrica, vol. 94, pp. 661-666 (2005).
Flo et al., "Lipocalin 2 mediates an innate immune response to bacterial infection by sequestrating iron," Nature, vol. 432, pp. 917-921 (2004).
Fluckinger et al., "Human Tear Lipocalin Exhibits Antimicrobial Activity by Scavenging Microbial Siderophores," Antimicrob. Agents Chemother., vol. 48, No. 9, pp. 3367-3372 (2004).
Fung et al., "Increased prevalence of iron-overload associated endocrinopathy in thalassaemia versus sickle-cell disease," Br. J. Haematol., vol. 135, pp. 574-582 (2006).
Garcia et al., "Redundancy and Specificity of *Escherichia coli* Iron Acquisition Systems during Urinary Tract Infection," Infection and Immunity, vol. 79, No. 3, pp. 1225-1235 (Mar. 2011).
Garcia-Tsao et al., "Acute Kidney Injury in Cirrhosis," Hepatology, vol. 48, No. 6, pp. 2064-2077 (2008).
Gaspari et al., "Plasma Clearance of Nonradioactive lohexol as a Measure of Glomerular Filtration Rate," J. Am. Soc. Nephrol., vol. 6, pp. 257-263 (1995).
Goetz et al., "Ligand Preference Inferred from The Structure of Neutrophil Gelatinase Associated Lipocalin," Biochemistry, vol. 39, pp. 1935-1941 (2000).
Goetz et al., "The Neutrophil Lipocalin NGAL Is a Bacteriostatic Agent that Interferes with Siderophore-Mediated Iron Acquisition," Mol. Cell, vol. 10, pp. 1033-1043 (2002).
Gonzalez-Michaca et al., "Heme: a determinant of life and death in renal tubular epithelial cells," Am. J. Physiol. Renal. Physiol., vol. 286, pp. F370-F377 (2004).
Guterman et al., "Feasability of enterochelin as an iron-chelating drug: studies with human serum and a mouse model system," Gen. Pharmacol., vol. 9, pp. 123-127 (1978).
Gwira et al., "Expression of Neutrophil Gelatinase-Associated Lipocalin Regulates Epithelial Morphogenesis in Vitro," J. Biol. Chem., vol. 280, pp. 7875-7882 (2005).
Hall et al., "IL-18 and Urinary NGAL Predict Dialysis and Graft Recovery After Kidney Transplantation," J. Am. Soc. Nephrol., vol. 21, pp. 189-197 (2010).
Han et al., "Kidney Injury Molecule-1 (KIM-1): A novel biomarker for human renal proximal tubule injury," Kidney Int. vol. 62, pp. 237-244 (2002).
Han et al., "Urinary Biomarkers in the Early Diagnosis of Acute Kidney Injury," Author Manuscript, 17 pages, Published in final edited form as: Kidney Int., vol. 73, No. 7, pp. 863-869 (2008).
Harris et al., "Lysosomal iron accumulation and tubular damage in rat puromycin nephrosis and ageing," Clin. Exp. Pharmacol. Physiol., vol. 21, pp. 73-81 (1994).
Herget-Rosenthal et al., "Early detection of acute renal failure by serum cystatin C," Kidney Int. vol. 66, pp. 1115-1122 (2004).
Herget-Rosenthal et al., "Prognostic Value of Tubular Proteinuria and Enzymuria in Nonoliguric Acute Tubular Necrosis," Clin. Chem., vol. 50, No. 3, pp. 552-558 (2004).
Hershko and Peto, "Non-transferrin Plasma Iron," British Journal of Haematology, vol. 66, pp. 149-151 (Jun. 1987).
Hill et al., "A new morphologic index for the evaluation of renal biopsies in lupus nephritis," Kidney Int., vol. 58, pp. 1160-1173 (2000).
Hod et al., "Transfusion of red blood cells after prolonged storage produces harmful effects that are mediated by iron and inflammation," Blood, vol. 115, pp. 4284-4292 (2010).
Hoette et al., "The Role of Electrostatics in Siderophore Recognition by the Immunoprotein Siderocalin," Author Manuscript, 20 pages, Published in final edited form as: J. Am. Chem. Soc., vol. 130, No. 51, pp. 17584-17592 (Dec. 24, 2008).
Hoffbrand et al., "Role of deferiprone in chelation therapy for transfusional iron overload," Blood, vol. 102, pp. 17-24 (2003).
Holmes et al., "Siderocalin (Lcn 2) Also Binds Carboxymycobactins, Potentially Defending against Mycobacterial Infections through Iron Sequestration," Structure, vol. 13, pp. 29-41 (2005).
Horowitz et al., "Lipophilic siderophores of *Mycobacterium tuberculosis* prevent cardiac reperfusion injury," Proc. Natl. Acad. Sci. USA, vol. 95, pp. 5263-5268 (Apr. 1998).
Howard et al., "Urinary albumin, transferrin and iron excretion in diabetic patients," Kidney Int., vol. 40, pp. 923-926 (1991).
Hunsicker et al., "Predictors of the progression of renal disease in the Modification of Diet in Renal Disease Study," Kidney Int., vol. 51, pp. 1908-1919 (1997).
Huynh et al., "Reference Values of Urinary Neutrophil Gelatinase-Associated Lipocalin in Very Low Birth Weight Infants," Author Manuscript, 5 pages, Published in final edited form as: Pediatr. Res. vol. 66, pp. 528-532 (2009).
Hvidberg et al., "The endocytic receptor megalin binds the iron transporting neutrophil-gelatinase-associated lipocalin with high affinity and mediates its cellular uptake," FEBS Letters, vol. 579, pp. 773-777 (2005).
Iannetti et al., "The neutrophil gelatinase-associated lipocalin (NGAL), a NF-κB-regulated gene, is a survival factor for thyroid neoplastic cells," Proc. Natl. Acad. Sci. USA, vol. 105, No. 37, pp. 14058-14063 (2008).
Ichimura et al., "Kidney Injury Molecule-1 (KIM-1), a Putative Epithelial Cell Adhesion Molecule Containing a Novel Immunoglobulin Domain, Is Up-regulated in Renal Cells after Injury," J. Biol. Chem., vol. 273, pp. 4135-4142 (1998).
International Search Report and Written Opinion for Application No. PCT/US2010/054811 issued Dec. 23, 2010 (10 pages).
International Search Report and Written Opinion for International Application No. PCT/US09/61050 issued May 25, 2010 (8 pages).
International Search Report and Written Opinion for International Application No. PCT/US10/39018 issued Aug. 17, 2010 (8 pages).
International Search Report and Written Opinion for International Application No. PCT/US2005/015799 issued Nov. 17, 2005 (7 pages).
International Search Report and Written Opinion for International Application No. PCT/US2011/035757 issued Jul. 27, 2011 (10 pages).

(56) References Cited

OTHER PUBLICATIONS

International Search Report and Written Opinion for International Application No. PCT/US2011/037774 Issued Sep. 8, 2011 (7 pages).
International Search Report and Written Opinion for International Application No. PCT/US2013/071344 issued May 12, 2014 (14 pages).
International Search Report and Written Opinion for International Patent Application No. PCT/US09/36972 issued Feb. 24, 2010 (10 pages).
Jewett et al., "Novel Method to Examine the Formation of Unstable 2:1 and 3:1 Complexes of Catecholamines and Iron(III)," Journal of Inorganic Biochemistry, vol. 66, pp. 165-173 (1997).
Johnson et al., "Parenteral iron formulations differentially affect MCP-1, HO-1, and NGAL gene expression and renal responses to injury," Am. J. Physiol. Renal Physiol., vol. 299, pp. F426-F435 (2010).
Jones et al., "Low Molecular Weight Iron-Binding Factor from Mammalian Tissue That Potentiates Bacterial Growth," J. Exp. Med., vol. 151, pp. 418-428 (1980).
Kaiser et al., "Interactions between NKG2x Immunoreceptors and HLA-E Ligands Display Overlapping Affinities and Thermodynamics," J. Immunol., vol. 174, pp. 2878-2884 (2005).
Kalinowski and Richardson, "The Evolution of Iron Chelators for the Treatment of Iron Overload Disease and Cancer," Pharmacol. Rev., vol. 57, No. 4, pp. 547-583 (2005.
Kamijo et al., "Urinary liver-type fatty acid binding protein as a useful biomarker in chronic kidney disease," Molecular and Cellular Biochemistry, vol. 284, pp. 175-182 (2006).
Karpishin, R. B., et al., "Spectroscopic Studies of the Electronic Structure of Iron(III) Tris(catecholates)," J. Am. Chem. Soc., vol. 113, pp. 2977-2984 (1991).
Keberle, "The Biochemistry of Desferrioxamine and Its Relation to Iron Metabolism," Annals of the New York Academy of Sciences, vol. 119, Issue 2, pp. 758-768 (1964).
Kjeldsen et al., "Characterization of two ELISAs for NGAL, a newly described lipocalin in human neutrophils," Journal of Immunological Methods, vol. 198, 155-164 (1996).
Kjeldsen et al., "Human neutrophil gelatinase-associated lipocalin and homologous proteins in rat and mouse," Biochim. Biophys. Acta, vol. 1482, pp. 272-283 (2000).
Kjeldsen et al., "Isolation and Primary Structure of NGAL, a Novel Protein Associated with Human Neutrophil Gelatinase," J. Biol. Chem. 268, No. 14, pp. 10425-10432 (1993).
Klotman, "Pathogenesis and Treatment of HIV-Associated Nephropathy," Topics in HIV Medicine, vol. 9, Issue 2, pp. 27-29 (Jun. 2001).
Kok et al., "Renal Drug Delivery With Low-Molecular-Weight Proteins: The Effect of Charge Modifications on the Body Distribution of Drug-Lysozyme Conjugates," Drug Delivery 6, pp. 1-8 (1999).
Kowdley and Kaplan, "Iron-chelation therapy with oral deferiprone—toxicity or lack of efficacy," New England Journal of Medicine, vol. 339, No. 7, pp. 468-469 (Aug. 13, 1998).
Kozyraki and Gofflot, "Multiligand Endocytosis and Congenital Defects: Roles of Cubilin, Megalin and Amnionless," Current Pharmaceutical Design, vol. 13, pp. 3038-3046 (2007).
Kribben et al., "Pathophysiology of Acute Renal Failure," J. Nephrol., vol. 12 (suppl 2), pp. S142-S151 (1999).
Kubes et al., "Therapeutic Potential of Inhibiting Leukocyte Rolling in Ischemia/Reperfusion," J. Clin. Invest., vol. 95, pp. 2510-2519 (Jun. 1995).
Kuzmi, "Program DYNAFIT for the Analysis of Enzyme Kinetic Data: Application to HIV Proteinase," Anal. Biochem., vol. 237, pp. 260-273 (1996).
Lang et al., "Development of a Stable Isotope Dilution Analysis with Liquid Chromatography-Tandem Mass Spectrometry Detection for The Quantitative Analysis of Di- and Trihydroxybenzenes in Foods and Model Systems," J. Agric. Food Chem., vol. 54, pp. 5755-5762 (2006).
Lasko et al., "The use of receiver operating characteristic curves in biomedical informatics," Journal of Biomedical Informatics, vol. 38, pp. 404-415 (2005).
Laskowski et al., "Procheck: a program to check the stereochemical quality of protein structures," J. Appl. Cryst., vol. 26, pp. 283-291 (1993).
Lazar et al., "Transforming Growth Factor □: Mutation of Aspartic Acid 47 and Leucine 48 Results in Different Biological Activities," Mol. Cell. Biol., vol. 8, No. 3, pp. 1247-1252 (1988).
Leheste et al., "Hypocalcemia and osteopathy in mice with kidney-specific megalin gene defect," FASEB J., vol. 17, pp. 247-249 (2003).
Leheste et al., "Megalin Knockout Mice as an Animal Model of Low Molecular Weight Proteinuria," Am. J. Pathol., vol. 155, No. 4, pp. 1361-1370 (1999).
Lerma et al., "Current Diagnosis & Treatment Nephrology & Hypertension," McGraw Hill Education, Chapter 36, pp. 313-319, (2009).
Levey et al, "A More Accurate Method to Estimate Glomerular Filtration Rate from Serum Creatinine: A New Prediction Equation," Ann. Intern. Med. vol. 130, No. 6, pp. 461-470 (1999).
Lewis et al., "Renoprotective effect of the angiotensin receptor antagonist irbesartan in patients with nephropathy due to type 2 diabetes," N. Engl. J. Med., vol. 345, No. 12, pp. 851-860 (Sep. 20, 2001).
Li et al., "Crystal Structures of RAE-1β and Its Complex with the Activating Immunoreceptor NKG2D," Immunity, vol. 16, pp. 77-86 (Jan. 2002).
Li et al., "Detection of intracellular iron by its regulatory effect," Am. J. Physiol. Cell Physiol., vol. 287, pp. C1547-C1559 (2004).
Li et al., "Scara5 Is a Ferritin Receptor Mediating Non-Transferrin Iron Delivery," Author Manuscript, 22 pages, Published in final edited form as: Dev. Cell, vol. 16, pp. 35-46 (2009).
Liang et al., "WebFEATURE: An interactive web tool for identifying and visualizing functional sites on macromolecular structures," Nucleic Acids Res. vol. 31, No. 13, pp. 3324-3327 (2003).
Liangos et al., "Urinary N-Acetyl-β-(D)-Glucosaminidase Activity and Kidney Injury Molecule-1 Level are Associated with Adverse Outcomes in Acute Renal Failure," J. Am. Soc. Nephrol., vol. 18, pp. 904-912 (2007).
Loomis and Raymond, "Solution Equilibria of Enterobactin and Metal-Enterobactin Complexes," Inorganic Chemistry, vol. 30, pp. 906-911 (1991).
Lorenz et al., "Iron overload in kidney transplants: Prospective analysis of biochemical and genetic markers," Kidney Int, vol. 67, pp. 691-697 (2005).
Mackensen-Haen et al., "The consequences for renal function of widening of the interstitium and changes in the tubular epithelium of the renal cortex and outer medulla in various renal diseases," Clin. Nephrol., vol. 37, No. 2, pp. 70-77 (1992).
Magil, A.B., "Tubulointerstitial Lesions in Human Membranous Glomerulonephritis: Relationship to Proteinuria," Am. J. Kidney Dis., vol. 25, No. 3, pp. 375-379 (Mar. 1995).
Makris et al., "Urinary neutrophil gelatinase-associated lipocalin (NGAL) as an early marker of acute kidney injury in critically ill multiple trauma patients," Clin. Chem. Lab. Med., vol. 47, No. 1, pp. 79-82 (2009).
Mandalunis et al., "Experimental Renal Failure and Iron Overload: A Histomorphometric Study in Rat Tibia," Toxicol. Pathol., vol. 33, pp. 398-403 (2005).
Matsuo et al., "Crucial roles of binding sites for NF-κB and C/EBPs in IκB-ζ-mediated transcriptional activation," Biochem. J., vol. 405, pp. 605-615, 2007.
Matthaeus et al., "Acute Ischemic Renal Failure Induces Expression of Neutrophil Gelatinase-Associated Lipocalin and Matrix Metalloproteinase-9 in Damaged Tubuli," Kidney Blood Press. Res., vol. 24, Congress of Nephrology, p. 342 (2001).
Matthaeus et al., "Co-Regulation of Neutrophil Gelatinase-Associated Lipocalin and Matrix Metalloproteinase-9 in the Postischemic Rat Kidney," J. Am. Soc. Nephrol., vol. 12, p. 787A (2001).
Mayo Clinic, "Hemochromatosis", www.mayoclinic.org/diseases-conditions/hemochromatosis/diagnosis-treatment/drc-20351448, 2019 (9 pages).

(56) References Cited

OTHER PUBLICATIONS

McBeth et al., "A New Twist in TCR Diversity Revealed by a Forbidden αβ TCR," J. Mol. Biol., vol. 375, No. 5, pp. 1306-1319 (2008).
McFarland et al., "Thermodynamic Analysis of Degenerate Recognition by the NKG2D Immunoreceptor: Not Induced Fit but Rigid Adaptation," Immunity, vol. 19, pp. 803-812 (2003).
Meneghini, "Iron Homeostasis, Oxidative Stress, and DNA Damage," Free Radical Biology & Medicine, vol. 23, No. 5, pp. 783-792 (1997).
Metcalfe "How does early chronic kidney disease progress? A Background Paper prepared for the UK Consensus Conference on Early Chronic Kidney Disease," Nephrol. Dial. Transplant., 22 (Suppl. 9), ix26ix-30 (2007).
Mishra et al., "Amelioration of Ischemic Acute Renal Injury by Neutrophil Gelatinase-Associated Lipocalin," J. Am. Soc. Nephrol., vol. 15, pp. 3073-3082 (2004).
Mishra et al., "Identification of Neutrophil Gelatinase-Associated Lipocalin as a Novel Early Urinary Biomarker for Ischemic Renal Injury," J. Am. Soc. Nephrol., vol. 14, pp. 2534-2543 (2003).
Mishra et al., "Neutrophil gelatinase-associated lipocalin (NGAL) as a biomarker for acute renal injury after cardiac surgery," Lancet, vol. 365, pp. 1231-1238 (2005).
Mishra et al., "Neutrophil Gelatinase-Associated Lipocalin: A Novel Early Urinary Biomarker for Cisplatin Nephrotoxicity," Am. J. Nephrol., vol. 24, pp. 307-315 (2004).
Mishra J. et al., "Kidney NGAL is a Novel Early Marker of Acute Injury Following Transplantation," Pediatr. Nephrol., vol. 21, pp. 856-863 (2006).
Mitsnefes MM et al., "Serum neutrophil gelatinase-associated lipocalin as a marker of renal function in children with chronic kidney disease," Pediatr. Nephrol., vol. 22, pp. 101-108 (2006).
Moestrup and Verroust, "Megalin- and Cubilin-Mediated Endocytosis of Protein-Bound Vitamins, Lipids, and Hormones in Polarized Epithelia," Annual Review of Nutrition, vol. 21, pp. 407-428 (2001).
Moestrup et al., "Analysis of Ligand Recognition by the Purified β2-Macroglobulin Receptor (low Density Lipoprotein Receptor-related Protein). Evidence that high affinity of β2-macroglobulin-proteinase complex is achieved by binding to adjacent receptors," J. Biol. Chem., vol. 266, pp. 14011-14017 (1991).
Monier et al., "Gelatinase isoforms in urine from bladder cancer patients," Clinica Chimica Acta, vol. 299, pp. 11-23 (2000).
Mori and Nakao, "Neutrophil gelatinase associated lipocalin as the real time indicator of active kidney damage," Kidney Int., vol. 71, pp. 967-970 (2007).
Mori et al., "Endocytic delivery of lipocalin-siderophore-iron complex rescues the kidney from ischemia-reperfusion injury," J. Clin. Invest., vol. 115, No. 3, pp. 610-621 (Mar. 2005).
Murshudov et al., "Refinement of Macromolecular Structures by the Maximum-Likelihood Method," Acta Cryst., vol. D53, Part 3, pp. 240-255 (1997).
Nankivell et al., "Iron Accumulation in Human Chronic Renal Disease," Am. J. Kidney Dis., vol. 20, pp. 580-584 (1992).
National Kidney Foundation, "K/DOQI clinical practice guidelines for chronic kidney disease: evaluation, classification, and stratification," Am. J. Kidney Dis., vol. 39 (suppl 1), pp. SI-S266 (2002).
Nelson et al., "Bacterial colonization of nasal mucosa induces expression of siderocalin, an iron-sequestering component of innate immunity," Cell Microbiol., vol. 7, pp. 1404-1417 (2005).
Nguyen et al., "Novel Early Biomarkers of Acute Kidney Injury," [Abstract] J. Am. Soc. Nephrol., vol. 17, p. 49A (2006).
Nickolas et al., "Diagnostic and Prognostic Stratification in the Emergency Department Using Urinary Biomarkers of Nephron Damage," Journal of the American College of Cardiology, vol. 59, No. 3, pp. 246-255 (2012).
Nickolas, T. L., et al., "Monomeric neutrophil gelatinase associated lipocalin is associated with tubulointerstitial damage in chronic kidney disease," Author Manuscript, 10 pages, Published in final edited form as: Kidney International, vol. 82, No. 6, pp. 718-722 (Sep. 2012).
Nickolas, T.L., et al., "Sensitivity and specificity of a single emergency department measurement of urinary neutrophil gelatinase-associated lipocalin for diagnosing acute kidney injury," Ann. Intern. Med., vol. 148, pp. 810-819 (2008).
Olivieri et al., "Visual and Auditory Neurotoxicity in Patients Receiving Subcutaneous Deferoxamine Infusions," N. Engl. J. Med., vol. 314, No. 14, pp. 869-873 (1986).
Otwinowski, "Processing of X-ray Diffraction Data Collected in Oscillation Mode," Methods in Enzymology, vol. 276: Macromolecular Crystallography, part A, C.W. Carter, Jr. & R. M. Sweet, Eds. (Academic Press New York), pp. 307-326, 62 pages total (1997).
Paller and Hedlund, "Extracellular iron chelators protect kidney cells from hypoxia/reoxygenation," Free Radical Biology and Medicine, vol. 17, No. 6, pp. 597-603 (1994).
Paller and Hedlund, "Role of iron in postischemic renal injury in the rat," Kidney Int., vol. 34, pp. 474-480 (1988).
Paller and Jacob, "Cytochrome P-450 mediates tissue-damaging hydroxyl radical formation during reoxygenation of the kidney," Proc. Natl. Acad. Sci. USA., vol. 91, pp. 7002-7006 (Jul. 1994).
Paragas et al., "NGAL-Siderocalin in Kidney Disease," Author Manuscript, 20 pages, Published in final edited form as: Biochimica et Biophysica Acta, vol. 1823, No. 9, pp. 1451-1458 (2012).
Paragas et al., "The Ngal Reporter Mouse Detects the Response of the Kidney to Injury in Real Time," Author Manuscript, 18 pages, Published in final edited form as: Nat. Med., vol. 17, No. 2, pp. 216-222 (Feb. 2011).
Paragas et al., "Urinary NGAL Marks Cystic Disease in HIV-Associated Nephropathy," J. Am. Soc. Nephrol., vol. 20(8), pp. 1687-1692 (Aug. 2009).
Parikh et al., "Urinary IL-18 is an early predictive biomarker of acute kidney injury after cardiac surgery," Kidney Int., vol. 70, pp. 199-203 (2006).
Parikh et al., "Urinary Interleukin-18 is a Marker of Human Acute Tubular Necrosis," Am. J. Kidney Dis., vol. 43, No. 3, pp. 405-414 (Mar. 2004).
Parikh et al., "Urine IL-18 Is an Early Diagnostic Marker for Acute Kidney Injury and Predicts Mortality in the Intensive Care Unit," J. Am. Soc. Nephrol., vol. 16, pp. 3046-3052 (2005).
Parikh et al., "Urine NGAL and IL-18 are Predictive Biomarkers for Delayed Graft Function Following Kidney Transplantation," Am. J. Transplant, vol. 6, pp. 1639-1645 (2006).
Parravicini et al., "Reference Range of Urinary Neutrophil Gelatinase-Associated Lipocalin in Very Low-Birth-Weight Infants: Preliminary Data," Am. J. Perinatol., vol. 26, No. 6, pp. 437-440 (2009).
Perron et al., "Predicting How Polyphenol Antioxidants Prevent DNA Damage by Binding to Iron," Inorganic Chemistry, vol. 47, No. 14, pp. 6153-6161 (2008).
Perrone et al., "Serum Creatinine as an Index of Renal Function: New Insights into Old Concepts," Clin. Chem., vol. 38, No. 10, pp. 1933-1953 (1992).
Playford et al., "Effects of Mouse and Human Lipocalin Homologues 24p3/Lcn2 and Neutrophil Gelatinase-Associated Lipocalin on Gastrointestinal Mucosal Integrity and Repair," Gastroenterology, vol. 131, pp. 809-817 (2006).
Prinsen et al., "Transferrin Synthesis Is Increased in Nephrotic Patients Insufficiently to Replace Urinary Losses," J. Am. Soc. Nephrol., vol. 12, pp. 1017-1025 (2001).
Remuzzi et al., "Understanding the Nature of Renal Disease Progression," Kidney Int., vol. 51, pp. 2-15 (1997).
Rennick and Quebbemann, "Site of excretion of catechol and catecholamines: renal metabolism of catechol," Am. J. Physiol., vol. 218, No. 5, pp. 1307-1312 (1970).
Rubinstein et al., "The novel role of neutrophil gelatinase-b associated lipocalin (NGAL)/Lipocalin-2 as a biomarker for lupus nephritis," Autoimmunity Reviews, vol. 7, pp. 229-234 (2008).
Russo et al., "IroN Functions as a Siderophore Receptor and Is a Urovirulence Factor in an Extraintestinal Pathogenic Isolate of *Escherichia coli*," Infection and Immunity, vol. 70, No. 12, pp. 7156-7160 (Dec. 2002).

(56) References Cited

OTHER PUBLICATIONS

Russo et al., "The Siderophore Receptor IroN of Extraintestinal Pathogenic *Escherichia coli* Is a Potential Vaccine Candidate," Infection and Immunity, vol. 71, No. 12, pp. 7164-7169 (Dec. 2003).
Saad et al., "The preventive role of deferoxamine against acute doxorubicin-induced cardiac, renal and hepatic toxicity in rats," Pharmacological Research, vol. 43, No. 3, pp. 211-218 (2001).
Sawahata et al., "Biotransformation of Phenol to Hydroquinone and Catechol by Rat Liver Microsomes," Mol. Pharmacol., vol. 23, No. 2, pp. 453-460 (Mar. 1983).
Saweirs and Goddard, "What are the best treatments for early chronic kidney disease? A Background Paper prepared for the UK Consensus Conference on Early Chronic Kidney Disease," Nephrol. Dial. Transplant., vol. 22 (Suppl. 9), pp. ix31-ix38 (2007).
Schmidt-Ott et al., "Dual Action of Neutrophil Gelatinase-Associated Lipocalin," J. Am. Soc. Nephrol., vol. 18, pp. 407-413 (2007).
Schmidt-Ott et al., "Neutrophil gelatinase-associated lipocalin-mediated iron traffic in kidney epithelia," Curr. Opin. Nephrol. Hypertens., vol. 15, pp. 442-449 (2006).
Schmitt et al., "Tubulo Interstitial Alterations in Type I Membranoproliferative Glomerulonephritis, An Investigation of 259 Cases," Path. Res. Pract., vol. 182, pp. 6-10 (1987).
Schwartz et al., "Earliest cardiac toxicity induced by iron overload selectively inhibits electrical conduction," J. Appl. Physiol., vol. 93, pp. 746-751 (2002).
Singbartl et al., "Blocking P-selectin protects from ischemia/reperfusion-induced acute renal failure," FASEB J., vol. 14, pp. 48-54 (Jan. 2000).
Sise et al., "Urine neutrophil gelatinase-associated lipocalin identifies unilateral and bilateral urinary tract obstruction," Nephrol. Dial. Transplant., vol. 26, pp. 4132-4135 (2011).
Smith and Martell et al., "Critical Stability Constants, vol. 4: Inorganic Complexes," Plenum Press, New York, Table of Contents, 3 pages (1976).
Smith, "Origin of urinary pyrocatechol," Nature, vol. 190, pp. 167 (1961).
Soler-García et al., "Iron-Related Proteins: Candidate Urine Biomarkers in Childhood HIV-Associated Renal Diseases" Clin. J. Am. Soc. Nephrol., vol. 4, pp. 763-771 (2009).
Stone et al., "PJ34, a poly-ADP-ribose polymerase inhibitor, modulates renal injury after thoracic aortic ischemia/reperfusion," Surgery, vol. 138, pp. 368-374 (2005).
Strong et al., "Expression, purification, crystallization and crystallographic characterization of dimeric and monomeric human neutrophil gelatinase associated lipocalin (NGAL)," Acta Crystallographica, vol. D54, pp. 93-95 (1998).
Supplemental European Search Report mailed Sep. 6, 2016 for European Patent Application No. 13856275.6 (8 pages).
Supplementary European Search Report mailed on Oct. 4, 2011 for European Application No. EP 09720017.4 (6 pages).
Supplementary European Search Report mailed on Oct. 7, 2014 for European Application No. EP 11787264.8 (5 pages).
Sánchez et al., "Catechol releases iron(III) from ferritin by direct chelation without iron(II) production," Dalton Trans., No. 4, pp. 811-813 (Feb. 21, 2005).
Trinder et al., "Molecular pathogenesis of iron overload," Gut, vol. 51, pp. 290-295 (2002).
Vaidya et al., "Biomarkers of Acute Kidney Injury," Author Manuscript, 29 pages, Published in final edited form as: Ann. Rev. Pharmacol. Toxicol., vol. 48, pp. 463-493 (2008).
Vera et al., "Protective Effect of Carbon Monoxide-Releasing Compounds in Ischemia-Induced Acute Renal Failure," J. Am. Soc. Nephrol., vol. 16, pp. 950-958 (2005).
Vigdorovich et al., "Expression and Characterization of a Soluble, Active Form of the Jaagsiekte Sheep Retrovirus Receptor Hyal2," J. Virol., vol. 79, No. 1, pp. 79-86 (2005).
Volpe et al., "NGAL Controls the Metastatic Potential of Anaplastic Thyroid Carcinoma Cells," The Journal of Clinical Endocrinology & Metabolism, vol. 98, No. 1, pp. 228-235 (Jan. 2013).
Wagener et al., "Association between Increases in Urinary Neutrophil Gelatinase-associated Lipocalin and Acute Renal Dysfunction After Adult Cardiac Surgery," Anesthesiology, vol. 105, pp. 485-491 (2006).
Wagener et al., "Increased Incidence of Acute Kidney Injury with Aprotinin Use during Cardiac Surgery Detected with Urinary NGAL," Am. J. Nephrol., vol. 28, pp. 576-582 (2008).
Walker and Shah, "Evidence Suggesting a Role for Hydroxyl Radical in Gentamicin-induced Acute Renal Failure in Rats," J. Clin. Invest., vol. 81, pp. 334-341 (1988).
Wang et al., "Iron Deposition in Renal Biopsy Specimens from Patients With Kidney Diseases," Am. J. Kidney Dis., vol. 38, No. 5, pp. 1038-1044 (Nov. 2001).
Ward et al., "An Iron-Based Molecular Redox Switch as a Model for Iron Release from Enterobactin via the Salicylate Binding Mode," Inorg. Chem., vol. 38, pp. 5007-5017 (1999).
Wehrmann, et al., "Long-term prognosis of focal sclerosing glomerulonephritis. An analysis of 250 cases with particular regard to tubulointerstitial changes," Clin, Nephrol., vol. 33, pp. 115-122 (1990).
Wei et al., "Neutrophil gelatinase-associated lipocalin suppresses cyst growth by Pkd1 null cells in vitro and in vivo," Author Manuscript, 16 pages, Published in final edited form as: Kidney Int., vol. 74, pp. 1310-1318 (2008).
Windus et al., "Fatal Rhizopus Infections in Hemodialysis Patients Receiving Deferoxamine," Annals of Internal Medicine, vol. 107, pp. 678-680 (1987).
Wu and Paller, "Iron Loading Enhances Susceptibility to Renal Ischemia in Rats," Ren. Fail., vol. 16, No. 4, pp. 471-480 (1994).
Wyatt and Klotman, "HIV-1 and HIV-Associated Nephropathy 25 Years Later," Clin. J. Am. Soc. Nephrol., vol. 2, pp. S20-S24 (2007).
Wyatt et al., "Acute renal failure in hospitalized patients with HIV: risk factors and impact on in-hospital mortality," AIDS, vol. 20, pp. 561-565 (2006).
Xu et al., "Interactions between Lipids and Human Anti-HIV Antibody 4E10 Can Be Reduced without Ablating Neutralizing Activity," J. Virol., vol. 84, No. 2, pp. 1076-1088 (Jan. 2010).
Xu et al., "Serum measurements of human neutrophil lipocalin (HNL) discriminate between acute bacterial and viral infections," Scand. J. Clin. Lab Invest., vol. 55, pp. 125-131 (1995).
Yan et al., "The High Molecular Weight Urinary Matrix Metalloproteinase (MMP) Activity is a complex of Gelatinase B/MMP-9 and Neutrophil Gelatinase-associated Lipocalin (NGAL): Modulation of MMP-9ACTIVITY By NGAL," The Journal of Biological Chemistry, vol. 276, pp. 37258-37265 (2001).
Yang et al., "An Iron Delivery Pathway Mediated by a Lipocalin," Mol. Cell, vol. 10, pp. 1045-1056 (Nov. 2002).
Yang et al., "Iron, Lipocalin, and Kidney Epithelia," Am. J. Physiol. Renal Physiol., vol. 285, pp. F9-F18. Review (2003).
Zager, "Combined Mannitol and Deferoxamine Therapy for Myohemoglobinuric Renal Injury and Oxidant Tubular Stress, Mechanistic and Therapeutic Implications," J. Clin. Invest., vol. 90, pp. 711-719 (1992).
Zappitelli et al., "Urine neutrophil gelatinase-associated lipocalin is an early marker of acute kidney injury in critically ill children: a prospective cohort study," Crit. Care vol. 11:R84, 11 pages (2007).
Zhao et al., "Structural characterization of glycoprotein NGAL, an early predictive biomarker for acute kidney injury," Carbohydr. Res., vol. 345, pp. 2252-2261 (2010).
Zweig and Campbell, "Receiver-Operating Characteristic (ROC) Plots: A Fundamental Evaluation Tool in Clinical Medicine," Clin. Chem., vol. 39, No. 4, pp. 561-577 (1993).
Åkerstrom et al., "Lipocalins: unity in diversity," Biochim. Biophys. Acta., vol. 1482, pp. 1-8, 2000 (8 pages).
NCBI Reference Sequence NP_005555.2, "Neutrophil gelatinase-associated lipocalin precursor [*Homo sapiens*]". https://www.ncbi.nlm.nih.gov/protein/NP_005555.2?report=genbank&log$=protalign&blast_rank=10&RID=D44AY149013, accessed Jul. 15, 2022 (3 pages).

(56) References Cited

OTHER PUBLICATIONS

Zou et al., "Receiver-Operating Characteristic Analysis for Evaluating Diagnostic Tests and Predictive Models," Circulation, vol. 115, pp. 654-657, 2007 (5 pages).

* cited by examiner

```
HsMegalin      MDRGPAAVACTLLLALVACLAPASGQECDSAHFRCGSGHCIPADWRCDGTKDCSDDADEI  60
MmMegalin      MERGAAAAAWMLLLAIAACLAPVSGQECGSGNFRCDNGYCIPASWRCDGTRDCLDDTDEI  60
               *:**.**.*   ****:.*****.*****.*.:***..*:****.******:** **:***

HsMegalin      GCAVVTCQQGYFKCQSEGQCIPNSWVCDQDQDCDDGSDERQDCSQSTCSSHQITCSNGQC 120
MmMegalin      GCPPRSCGSGFFLCPAEGTCIPSSWVCDQDKDCSDGADEQQNCPGTTCSSQQLTCSNGQC 120
               **.  :* .*:* * :** ***.*******:**.**:**:*:*. :****:*:*******

HsMegalin      IPSEYRCDHVRDCPDGADENDCQYPTCEQLTCDNGACYNTSQKCDWKVDCRDSSDEINCT 180
MmMegalin      VPIEYRCDHVSDCPDGSDERNCYYPTCDQLTCANGACYNTSQKCDHKVDCRDSSDEANCT 180
               :* ******* *****:**.:* ****:**** ************ ********** ***

HsMegalin      EICLHNEFSCGNGECIPRAYVCDHDNDCQDGSDEHACNYPTCGGYQFTCPSGRCIYQNWV 240
MmMegalin      TLCSQKEFQCGSGECILRAYVCDHDNDCEDNSDEHNCNYDTCGGHQFTCSNGQCINQNWV 240
               :* ::**.**.**** ***********:*.**** *** ****:****..*:** ****
                                    Ligand Binding Domain 1

HsMegalin      CDGEDDCKDNGDEDGCESGPHDVHKCSPREWSCPESGRCISIYKVCDGILDCPGREDENN 300
MmMegalin      CDGDDDCQDSGDEDGCESN-QRHHTCYPREWACPGSGRCISMDKVCDGVPDCPEGEDENN 299
               ***:***:*.********.  :   *.* ****:** ******: *****: ***  *****

HsMegalin      TSTGKYCSMTLCSALNCQYQCHETPYGGACFCPPGYIINHNDSRTCVEFDDCQIWGICDQ 360
MmMegalin      ATSGRYCGTGLCSILNCEYQCHQTPYGGECFCPPGHIINSNDSRTCIDFDDCQIWGICDQ 359
               ::*:**.   *** ***:****:***** ******:*** ******::***********

HsMegalin      KCESRPGRHLCHCEEGYILERGQYCKANDSFGEASIIFSNGRDLLIGDIHGRSFRILVES 420
MmMegalin      KCESRQGRHQCLCEEGYILERGQHCKSNDSFSAASIIFSNGRDLLVGDLHGRNFRILAES 419
               ***** *** * ***********:**:****. ************:**:***.****.**

HsMegalin      QNRGVAVGVAFHYHLQRVFWTDTVQNKVFSVDINGLNIQEVLNVSVETPENLAVDWVNNK 480
MmMegalin      KNRGIVMGVDFHYQKHRVFWTDPMQAKVFSTDINGLNTQEILNVSIDAPENLAVDWINNK 479
               :***:.:** ***: :******.:* ****.****** **:****::*********:***

HsMegalin      IYLVETKVNRIDMVNLDGSYRVTLITENLGHPRGIAVDPTVGYLFFSDWESLSGEPKLER 540
MmMegalin      LYLVETRVNRIDVVNLEGNQRVTLITENLGHPRGIALDPTVGYLFFSDWGSLSGQPKVER 539
               :*****:*****:****:*.  ***************:************ ****:**:**

HsMegalin      AFMDGSNRKDLVKTKLGWPAGVTLDMISKRVYWVDSRFDYIETVTYDGIQRKTVVHGGSL 600
MmMegalin      AFMDGSNRKDLVTTKLGWPAGITLDLVSKRVYWVDSRYDYIETVTYDGIQRKTVARGGSL 599
               ************.********:***::**********:*****************.:****

HsMegalin      IPHPFGVSLFEGQVFFTDWTKMAVLKANKFTETNPQVYYQASLRPYGVTVYHSLRQPYAT 660
MmMegalin      VPHPFGISLFEEHVFFTDWTKMAVMKANKFTDTNPQVYHQSSLIPFGVTVYHALRQPNAT 659
               :*****:**** :***********:******:******:*:** *:*******:**** **

HsMegalin      NPCKDNNGGCEQVCVLSHRTDNDGLGFRCKCTFGFQLDTDERHCIAVQNFLIFSSQVAIR 720
MmMegalin      NPCGNNNGGCAQICVLSHRTDNGGLGYRCKCEFGFELDADEHHCVAVKNFLLFSSQTAVR 719
               *** :***** *:*********.***:**** ***:**:**:**:**:***:****.*:*

HsMegalin      GIPFTLSTQEDVMVPVSGNPSFFVGIDFDAQDSTIFFSDMSKHMIFKQKIDGTGREILAA 780
MmMegalin      GIPFTLSTQEDVMVPVTGSPSFFVGIDFDAQHSTIFYSDLSKNIIYQQKIDGTGKEVITA 779
               ****************:*.************.****:**:**::*::*******:*::*

HsMegalin      NRVENVESLAFDWISKNLYWTDSHYKSISVMRLADKTRRTVVQYLNNPRSVVVHPFAGYL 840
MmMegalin      NRLQNVECLSFDWISRNLYWTDGGSKSVTVMKLADKSRRQIISNLNNPRSIVVHPAAGYM 839
               **::***.*:*****:******.  **::**:****:** ::. ******:**** ***:

HsMegalin      FFTDWFRPAKIMRAWSDGSHLLPVINTTLGWPNGLAIDWAASKLYWVDAYFDKIEHSTFD 900
MmMegalin      FLSDWFRPAKIMRAWSDGSHLMPIVNTSLGWPNGLAIDWSTSRLYWVDAFFDKIEHSNLD 899
               *::******************:*::**:***********::*********:*******.:*

HsMegalin      GLDRRRLGHIEQMTHPFGLAIFGEHLFFTDWRLGAIIRVRKADGGEMTVIRSGIAYILHL 960
MmMegalin      GLDRKRLGHVDQMTHPFGLTVFKDNVFLTDWRLGAIIRVRKSDGGDMTVVRRGISSIMHV 959
               ****:****::*********::* :::*:*************:***:***:* **: *:*:
```

FIG. 2

```
HsMegalin     KSYDVNIQTGSNACNQPTHPNGDCSHFCFPVPNFQRVCGCPYGMRLASNHLICEGDPTNE 1020
MmMegalin     KAYDADLQTGTNYCSQTTHPNGDCSHFCFPVPNFQRVCGCPYGMKLQRDQMTCEGDPARE 1019
              *:**.::***:* *.*.****************************:*  :::******:.*

HsMegalin     PPTEQCGLFSFPCKNGRCVPNYYLCDGVDDCHDNSDEQLCGTLNNTCSSSAFTCGHG-EC 1079
MmMegalin     PPTQQCGSSSFPCNNGKCVPSIFRCDGVDDCHDNSDEHQCGALNNTCSSSAFTCVHGGQC 1079
              ***:***   ****:**:***. : **************: **:************* ** :*

HsMegalin     IPAHWRCDKRNDCVDGSDEHNCPTHAPAS-CLDTQYTCDNHQCISKNWVCDTDNDCGDGS 1138
MmMegalin     IPGQWRCDKQNDCLDGSDEQNCPTRSPSSTCPPTSFTCDNHMCIPKEWVCDTDNDCSDGS 1139
              **.:*****:***:*****:****::*:* *  *.:***** **.*:**********.***

HsMegalin     DEKNCNSTETCQPSQFNCPNHRCIDLSFVCDGDKDCVDGSDEVGCVLNCTASQFKCASGD 1198
MmMegalin     DEKNCQASGTCHPTQFRCPDHRCISPLYVCDGDKDCVDGSDEAGCVLNCTSSQFKCADGS 1199
              *****::: **:*:**.**:****.  :***************.*******:******.*.

HsMegalin     KCIGVTNRCDGVFDCSDNSDEAGCPTRPPGMCHSDEFQCQEDGICIPNFWECDGHPDCLY 1258
MmMegalin     SCINSRYRCDGVYDCKDNSDEAGCPTRPPGMCHPDEFQCQGDGTCIPNTWECDGHPDCIQ 1259
              .**.    *****:**.******************.****** ** **** *********:
                                  Ligand Binding Domain 2

HsMegalin     GSDEHNACVPKTCPSSYFHCDNGNCIHRAWLCDRDNDCGDMSDEKDCPTQPFRCPSWQWQ 1318
MmMegalin     GSDEHNGCVPKTCSPSHFLCDNGNCIYNSWVCDGDNDCRDMSDEKDCPTQPFHCPSSQWQ 1319
              ******.******..*:* *******:.:*:** **** ***************:*** ***

HsMegalin     CLGHNICVNLSVVCDGIFDCPNGTDESPLCNGNSCSDFNGGCTHECVQEPFGAKCLCPLG 1378
MmMegalin     CPGYSICVNLSALCDGVFDCPNGTDESSLCNQDSCLHFNGGCTHRCIQGPFGATCVCPIG 1379
              * *:.******.:***:*************** :** .*******.*:* ****.*:**:*

HsMegalin     FLLANDSKTCEDIDECDILGSCSQHCYNMRGSFRCSCDTGYMLESDGRTCKVTASESLLL 1438
MmMegalin     YQLANDTKTCEDVNECDIPGFCSQHCVNMRGSFRCACDPEYTLESDGRTCKVTASENLLL 1439
              : ****:*****::**** * ***** ********:**. * ****************.***

HsMegalin     LVASQNKIIADSVTSQVHNIYSLVENGSYIVAVDFDSISGRIFWSDATQGKTWSAFQNGT 1498
MmMegalin     VVASRDKIIMDNITAHTHNIYSLVQDVSFVVALDFDSVTGRVFWSDLLEGKTWSAFQNGT 1499
              :***::*** *.:*::.*******:: *::**:****::**:****:::*:****   :***********

HsMegalin     DRRVVFDSSIILTETIAIDWVGRNLYWTDYALETIEVSKIDGSHRTVLISKNLTNPRGLA 1558
MmMegalin     DRRVVHDSGLSLTEMIAVDWIGRNIYWTDYTLETIEVSKIDGSHRTVLISKNVTKPRGLA 1559
              *:***.**.: *** **:**:***:***:*****:**********************:*:*****

HsMegalin     LDPRMNEHLLFWSDWGHHPRIEPASMDGSMRTVIVQDKIFWPCGLTIDYPNRLLYFMDSY 1618
MmMegalin     LDPRMGDNVMFWSDWGHHPRIEPASMDGTMRTVIVQEKIYWPCGLSIDYPNRLIYFMDAY 1619
              *****.::::*******************:*******:**:*****:*******:****:*

HsMegalin     LDYMDFCDYNGHHRRQVIASDLIIRHPYALTLFEDSVYWTDRATRRVMRANKWHGGNQSV 1678
MmMegalin     LDYIEFCDYDGQNRRQVIASDLVLHHPHALTLFEDSVFWTDRGTHQVMQANKWHGRNQSV 1679
              ***::*****:*::**********:::**:*********:****.*::**:****** ****

HsMegalin     VMYNIQWPLGIVAVHPSKQPNSVNPCAFSRCSHLCLLSSQGPHFYSCVCPSGWSLSPDLL 1738
MmMegalin     VMYSVPQPLGIIAIHPSRQPSSPNPCASAICSHLCLLSAQEPRHYSCACPSGWNLSDDSV 1739
              ***.:  ****:*:***:**.* **** : ********:* *:.***.*****.** * :

HsMegalin     NCLRDDQPFLITVRQHIIFGISLNPEVKSNDAMVPIAGIQNGLDVEFDDAEQYIYWVENP 1798
MmMegalin     NCVRGDQPFLISVRENVIFGISLDPEVKSNDAMVPISGIQHGYDVEFDDSEQFIYWVENP 1799
              **:*.******:**::********:*************:****:***:* *******:**:*******

HsMegalin     GEIHRVKTDGTNRTVFASISMVGPSMNLALDWISRNLYSTNPRTQSIEVLTLHGDIRYRK 1858
MmMegalin     GEIHRVKTDGSNRTAFAPLSLLGSSLGLALDWVSRNIYYTTPASRSIEVLTLRGDIRYGK 1859
              **********:***.**.:*::*.*:.*****:***:* *.* ::*********:** ** *

HsMegalin     TLIANDGTALGVGFPIGITVDPARGKLYWSDQGTDSGVPAKIASANMDGTSVKILFTGNL 1918
MmMegalin     TLITNDGTPLGVGFPVGIAVDPARGKLYWSDHGTDSGVPAKIASANMDGTSLKILFTGNM 1919
              ***:****.******:**:************:*****************:* *****:
```

FIG. 2 (cont.)

```
HsMegalin    EHLECVTLDIEEQKLYWAVTGRGVIERGNVDGTDRMILVHQLSHPWGIAVHDSFLYYTDE 1978
MmMegalin    EHLEVVTLDIQEQKLYWAVISRGVIERGNVDGTERMILVHHLAHPWGLVVHGSFLYYSDE 1979
             **** *****:*********.************:******:*:****:.**.*****:**

HsMegalin    QYEVIERVDKATGANKIVLRDNVPNLRGLQVYHRRNAAESSNGCSNNMNACQQICLPVPG 2038
MmMegalin    QYEVIERVDKSSGSNKVVFRDNIPYLRGLRVYHHRNAADSSNGCSNNPNACQQICLPVPG 2039
             **********:;*:**:*:***:* ****:***:****:******** ***********

HsMegalin    GLFSCACATGFKLNPDNRSCSPYNSFIVVSMLSAIRGFSLELSDHSETMVPVAGQGRNAL 2098
MmMegalin    GMFSCACASGFKLSPDGRSCSPYNSFIVVSMLPAVRGFSLELSDHSEAMVPVAGQGRNVL 2099
             *:******:****.**.***************.*:************:**********.*

HsMegalin    HVDVDVSSGFIYWCDFSSSVASDNAIRRIKPDGSSLMNIVTHGIGENGVRGIAVDWVAGN 2158
MmMegalin    HADVDVANGFIYWCDFSSSVRSSNGIRRIKPNGSNFTNIVTYGIGANGIRGVAVDWVAGN 2159
             *.****:.************ *.*.******:**.: ****:*** **:**:********

HsMegalin    LYFTNAFVSETLIEVLRINTTYRRVLLKVTVDMPRHIVVDPKNRYLFWADYGQRPKIERS 2218
MmMegalin    LYFTNAFVYETLIEVIRINTTYRRVLLKVSVDMPRHIVVDPKHRYLFWADYGQKPKIERS 2219
             ******** ******:*************:************:***********:******

HsMegalin    FLDCTNRTVLVSEGIVTPRGLAVDRSDGYVYWVDDSLDIIARIRINGENSEVIRYGSRYP 2278
MmMegalin    FLDCTNRTVLVSEGIVTPRGLAVDHDTGYIYWVDDSLDIIARIHRDGGESQVVRYGSRYP 2279
             ************************:. **:**************: :* :*:*:*******

HsMegalin    TPYGITVFENSIIWVDRNLKKIFQASKEPENTEPPTVIRDNINWLRDVTIFDKQVQPRSP 2338
MmMegalin    TPYGITVFGESIIWVDRNLRKVFQASKQPGNTDPPTVIRDSINLLRDVTIFDEHVQPLSP 2339
             ******** :**********:*:******:* **:*******.** ********::*** **

HsMegalin    AEVNNNPCLENNGGCSHLCFALPGLHTPKCDCAFGTLQSDGKNCAISTENFLIFALSNSL 2398
MmMegalin    AELNNNPCLQSNGGCSHFCFALPELPTPKCGCAFGTLEDDGKNCATSREDFLIYSLNNSL 2399
             **:*******:.******:***** * ****.*******:.****** * *:****::*.***

HsMegalin    RSLHLDPENHSPPFQTINVERTVMSLDYDSVSDRIYFTQNLASGVGQISYATLSSGIHTP 2458
MmMegalin    RSLHFDPQDHNLPFQAISVEGMAIALDYDRRNNRIFFTQKLNPIRGQISYVNLYSGASSP 2459
             *****:***:*. ***:*.** .::**** .:**:***:* . *****..* ** :*

HsMegalin    TVIASGIGTADGIAFDWITRRIYYSDYLNQMINSMAEDGSNRTVIARVPKPRAIVLDPCQ 2518
MmMegalin    TILLSNIGVTDGIAFDWINRRIYYSDFSNQTINSMAEDGSNRAVIARVSKPRAIVLDPCR 2519
             *:: *.**.:*********.*******: ** ***********:*****.**********:

HsMegalin    GYLYWADWDTHAKIERATLGGNFRVPIVNSSLVMPSGLTLDYEEDLLYWVDASLQRIERS 2578
MmMegalin    GYMYWTDWGTNAKIERATLGGNFRVPIVNTSLVWPNGLTLDLETDLLYWADASLQKIERS 2579
             **:**:**.*:*******************:*** *.***** * *****.*****:****

HsMegalin    TLTGVDREVIVNAAVHAFGLTLYGQYIYWTDLYTQRIYRANKYDGSGQIAMTTNLLSQPR 2638
MmMegalin    TLTGSNREVVISTAFHSFGLTVYGQYIYWTDFYTKKIYRANKYDGSDLIAMTTRLPTQPS 2639
             **** :****::.:*.*:*****:***********:**::***********. *****.* :**

HsMegalin    GINTVVKNQKQQCNNPCEQFNGGCSHICAPGPNGAECQCPHEGNWYLANNRKHCIVDNGE 2698
MmMegalin    GISTVVKTQQQQCSNPCDQFNGGCSHICAPGPNGAECQCPHEGSWYLANDNKYCVVDTGA 2699
             **.****.*:***.***:**************************.*****:.*:*:**.*

HsMegalin    RCGASSFTCSNGRCISEEWKCDNDNDCGDGSDEMESVCALHTCSPTAFTCANGRCVQYSY 2758
MmMegalin    RCNQFQFTCLNGRCISQDWKCDNDNDCGDGSDELPTVCAFHTCRSTAFTCANGRCVPYHY 2759
             **.   .*** ******::*****************: :***:*** .*********** * *

HsMegalin    RCDYYNDCGDGSDEAGCLFRDCNATTEFMCNNRRCIPREFICNGVDNCHDNNTSDEKNCP 2818
MmMegalin    RCDFYNDCGDNSDEAGCLFRSCNSTTEFTCSNGRCIPLSYVCNGINNCHDNDTSDEKNCP 2819
             ***:******.**********.**:**** *.* **** .::***::*****:********

HsMegalin    DRTCQSGYTKCHNSNICIPRVYLCDGDNDCGDNSDENPTYCTTHTCSSSEFQCAS-GRCI 2877
MmMegalin    PITCQPDFAKCQTTNICVPRAFLCDGDNDCGDGSDENPIYCASHTCRSNEFQCVSPHRCI 2879
              ***..::**:.:***:**.:**********.***** **::*** *.****.* ***
```

FIG. 2 (cont.)

```
HsMegalin    FQHWYCDQETDCFDASDEPASCGHSERTCLADEFKCDGGRCIPSEWICDGDNDCGDMSDE 2937
MmMegalin    PSYWFCDGEADCVDSSDEPDTCGHSLNSCSANQFHCDNGRCISSSWVCDGDNDCGDMSDE 2939
             *.:*:** *:**.*:**** :**** .:* *::*:**.****.*.*:*************

HsMegalin    DKRHQCQNQNCSDSEFLCVNDRPPDRRCIPQSWVCDGDVDCTDGYDENQNCTRRTCSENE 2997
MmMegalin    DQRHHCELQNCSSTEFTCINSRPPNRRCIPQHWVCDGDADCADALDELQNCIMRACSTGE 2999
             *:**:*: ****.:** *:*.***:****** ******.**:*. ** **** *:** .*
                              Ligand Binding Domain 3

HsMegalin    FTCGYGLCIPKIFRCDRHNDCGDYSDERGCLYQTCQQNQFTCQNGRCISKTFVCDEDNDC 3057
MmMegalin    FSCANGRCIRQSFRCDRRNDCGDYSDERGCSYPPCRDDQFTCQNGQCITKLYVCDEDNDC 3059
             *:*. * ** : *****:*********** * .*::******:**:* :********

HsMegalin    GDGSDELMHLCHTPEPTCPPHEFKCDNGRCIEMMKLCNHLDDCLDNSDEKGCGINECHDP 3117
MmMegalin    GDGSDEQEHLCHTPEPTCPPHQFRCDNGHCIEMGTVCNHVDDCSDNSDEKGCGINECQDS 3119
             ******  ************:*:****:**** .:***:*** *************:*.

HsMegalin    SISGCDHNCTDTLISFYCSCRPGYKLMSDKRTCVDIDECTEMPFVCSQKCENVIGSYICK 3177
MmMegalin    SISHCDHNCTDTITSFYCSCLPGYKLMSDKRTCVDIDECKETPQLCSQKCENVIGSYICK 3179
             *** ********:******* ******************.* * :**************

HsMegalin    CAPGYLREPDGKTCRQNSNIEPYLIFSNRYYLRNLTIDGYFYSLILEGLDNVVALDFDRV 3237
MmMegalin    CAPGYIREPDGKSCRQNSNIEPYLVFSNRYYIRNLTIDGTSYSLILQGLGNVVALDFDRV 3239
             *****:******:***********:******:*******  ******:**.*********

HsMegalin    EKRLYWIDTQRQVIERMFLNKTNKETIINHRLPAAESLAVDWVSRKLYWLDARLDGLFVS 3297
MmMegalin    EERLYWIDAEKQIIERMFLNKTNQETIISHRLRRAESLAVDWVSRKLYWLDAILDCLFVS 3299
             *:******:::*:**********:****.***  ***************** ** ****

HsMegalin    DLNGGHRRMLAQHCVDANNTFCFDNPRGLALHPQYGYLYWADWGHRAYIGRVGMDGTNKS 3357
MmMegalin    DLEGRQRKMLAQHCVDANNTFCFENPRGIVLHPQRGYVYWADWGDHAYIARIGMDGTNKT 3359
             **:* .:*:**************:*****:.**** **:*******.:***.*:*******:

HsMegalin    VIISTKLEWPNGITIDYTNDLLYWADAHLGYIEYSDLEGHHRHTVYDGALPHPFAITIFE 3417
MmMegalin    VIISTKIEWPNAITIDYTNDLLYWADAHLGYIEFSDLEGHHRHTVYDGTLPHPFALTIFE 3419
             ******:****.*********************:**************:******:****

HsMegalin    DTIYWTDWNTRTVEKGNKYDGSNRQTLVNTTHRPFDIHVYHPYRQPIVSNPCGTNNGGCS 3477
MmMegalin    DTVFWTDWNTRTVEKGNKYDGSGRVVLVNTTHKPFDIHVLHPYRQPIMSNPCATNNGGCS 3479
             **::******************.* .******:****** *******:****.*******

HsMegalin    HLCLIKPGGKGFTCECPDDFRTLQLSGSTYCMPMCSSTQFLCANNEKCIPIWWKCDGQKD 3537
MmMegalin    HLCLIKAGGRGFTCECPDDFQTVQLRDRILCMPMCSSTQFLCGNNEKCIPIWWKCDGQKD 3539
             ******.**:*********:*:**  .  * ************.*****************

HsMegalin    CSDGSDELALCPQRKCRLGQFQCSDGNCTSPQTLCNAHQNCPDGSDEDRLLCENHHCDSN 3597
MmMegalin    CSDGSDESDLCPHRKCRLGQFQCRDGNCTSPQALCNARQDCADGSDEDRVLCEHHRCEAN 3599
             *******  ***:********** ********:****:*:*.*******:***:*:*::*

HsMegalin    EWQCANKRCIPESWQCDTFNDCEDNSDEDSSHCASRTCRPGQFRCANGRCIPQAWKCDVD 3657
MmMegalin    EWQCANKRCIPEYWQCDSVDDCLDNSDEDPSHCASRTCRPGQFKCNNGRCIPQSWKCDVD 3659
             ************ ****:..:** ******.**************:* ******:******

HsMegalin    NDCGDHSDEPIEECMSSAHLCDNFTEFSCKTNYRCIPKWAVCNGVDDCRDNSDEQGCEER 3717
MmMegalin    NDCGDYSDEPIHECMTAAYNCDNHTEFSCKTNYRCIPQWAVCNGFDDCRDNSDEQGCESV 3719
             *****:*****.***::*: ***.************:******.*************.
                              Ligand Binding Domain 4

HsMegalin    TCHPVGDFRCKNHHCIPLRWQCDGQNDCGDNSDEENCAPRECTESEFRCVNQQCIPSRWI 3777
MmMegalin    PCHPSGDFRCGNHHCIPLRWKCDGIDDCGDNSDEESCVPRECTESEFRCADQQCIPSRWV 3779
             .*** ***** *********:*** :*********.*.***********.:*********:
```

FIG. 2 (cont.)

```
HsMegalin       CDHYNDCGDNSDERDCEMRTCHPEYFQCTSGHCVHSELKCDGSADCLDASDEADCPTRFP 3837
MmMegalin       CEQENDCGDNSDERDCEMKTCHPEHFQCTSGHCVPKALACDGRADCLDASDESACPTRFP 3839
                **: **************:*****:**********  . * *** *********: ******

HsMegalin       DGAYCQAIMFECKNHVCIPPYWKCDGDDDCGDGSDEELHLCLDVPCNSPNRFRCDNNRCI 3897
MmMegalin       NGTYCPAAMFECKNHVCIQSFWICDGENDCVDGSDEEIHLCFNVPCESPQRFRCDNSRCI 3899
                :*:** *:********** .:* ***::** ******:***::***:**:****** .***

HsMegalin       YSHEVCNGVDDCGDGTDETEEHCRKPTPKPCTEYEYKCGNGHCIPHDNVCDDADDCGDWS 3957
MmMegalin       YGHQLCNGVDDCGDGSDEKEEHCRKPTHKPCTDTEYKCSNGNCVSQHYVCDNVDDCGDLS 3959
                *.*::**********:**.********* ****: ****.**:*:.:. ***:.***** *

HsMegalin       DELGCNHGKERTCAENICEQNCTQLNEGGFICSCTAGFETNVFDRTSCLDINECEQFGTC 4017
MmMegalin       DETGCNLGENRTCAEKICEQNCTQLSNGGFICSCRPGFKPSTLDKNSCQDINECEEFGIC 4019
                ** *** *::*****:*********.:******* .**:...:*:.** *******:** *

HsMegalin       PQHCRNTKGSYECVCADGFTSMSDRPGKRCAAEGSSPLLLLPDNVRIRKYNLSSERFSEY 4077
MmMegalin       PQSCRNSKGSYECFCVDGFKSMSTHYGERCAADGSPPLLLLPENVRIRKYNISSEKFSEY 4079
                ** ***:******.*.***.***.*** : *:****:**.******:********:***:****

HsMegalin       LQDEEYIQAVDYDWDPKDIGLSVVYYTVRGEGSRFGAIKRAYIPNFESGRNNLVQEVDLK 4137
MmMegalin       LEEEEHIQAIDYDWDPEGIGLSVVYYTVLSQGSQFGAIKRAYLPDFESGSNNPVREVDLG 4139
                *::**:***:******:.**********  .::*:*********:*:**** ** *:****

HsMegalin       LKYVMQPDGIAVDWVGRHIYWSDVKNKRIEVAKLDGRYRKWLISTDLDQPAAIAVNPKLG 4197
MmMegalin       LKYLMQPDGLAVDWVGRHIYWSDAKSQRIEVATLDGRYRKWLITTQLDQPAAIAVNPKLG 4199
                ***:*****:**************.*.:******.***********:*:**************

HsMegalin       LMFWTDWGKEPKIESAWMNGEDRNILVFEDLGWPTGLSIDYLNNDRIYWSDFKEDVIETI 4257
MmMegalin       LMFWTDQGKQPKIESAWMNGEHRSVLASANLGWPNGLSIDYLNGDRIYWSDSKEDVIESI 4259
                ****** **:***********.*.:*.   :****.*********.*******  *****:*

HsMegalin       KYDGTDRRVIANEAMNPYSLDIFEDQLYWISKEKGEVWKQNKFGQGKKEKTLVVNPWLTQ 4317
MmMegalin       KYDGTDRRLIINDAMKPFSLDIFEDQLYWVAKEKGEVWRQNKFGKGNKEKLLVVNPWLTQ 4319
                ********:* :::**:*:************::*******:*****:*:***  *********

HsMegalin       VRIFHQLRYNKSVPNLCKQICSHLCLLRPGGYSCACPQGSSFIEGSTTECDAAIELPINL 4377
MmMegalin       VRIFHQLRYNQSVSNPCKQVCSHLCLLRPGGYSCACPQGSDFVTGSTVECDAASELPITM 4379
                **********:**.* ***:***********************.*: ***.***** ****.:

HsMegalin       PPPCRCMHGGNCYFDETDLPKCKCPSGYTGKYCEMAFSKGISPGTTAVAVLLTILLIVVI 4437
MmMegalin       PSPCRCMHGGSCYFDENDLPKCKCSSGYSGEYCEIGLSKGIPPG-TTMALLLTFAMVIIV 4438
                *.********.*****.*******.***:*:***:.:**:**.** *::*:***: :::::

HsMegalin       GALAIAGFFHYRRTGSLLPALPKLPSLSSLVKPSENGNGVTFRSGADLNMDIGVSGFGPE 4497
MmMegalin       GALVLVGFFHYRKTGSLLPSLPKLPSLSSLAKPSENGNGVTFRSGADVNMDIGVSPFGPE 4498
                ***.:.*******:*******:**********.*********************:******** ****

HsMegalin       TAIDRSMAMSEDFVMEMGKQPIIFENPMYSARDSAVKVVQPIQ-------VTVSENVDNK 4550
MmMegalin       TIIDRSMAMNEQFVMEVGKQPVIFENPMYAAKDSTSKVGLAVQGPSVSSQVTVPENVENQ 4558
                * *******.*:*****:****:*******:*:**: **  .:*        ***.***:*:

HsMegalin       NYGSPINPSEIVPETNPTSPAADGTQVTKWNLFKRKSKQTTNFENPIYAQMENEQKESVA 4610
MmMegalin       NYGRSIDPSEIVPEPKPASPGADETQGTKWNIFKRKPKQTTNFENPIYAEMDTEQKEAVA 4618
                *** .*:********..*:**.** ** ****:****:***.*************:*:.*:**:**

HsMegalin       ATPPPSPSLPAKPKPPSRRDPTPTYSATEDTFKDTANLVKEDSEV 4655
MmMegalin       VAPPPSPSLPAK---ASKRSSTPGYTATEDTFKDTANLVKEDSDV 4660
                .:**********    .*:*..** *:*******************:*
```

FIG. 2 (cont.)

Wild type K3 mutant

Wild type K3 mutant

```
>K3 Ngal mutant  (SEQ ID NO: 2)
QDSTSDLIPAPPLSSVPLQQNFQDNQFQGKWYVVGLAGNA
ILREDEDPQKMYATIYELKEDKSYNVTSVLFRDDGCDYWI
RTFVPGCQPGEFTLGNIQSYPGLTSYLVRVVSTNYNQFAM
VFFKKVSQNQEYFKITLYGRTKELTSELQENFIRFSKSLG
LPENNIVFPVPIDQCIDG

>Wild-type Ngal protein  (SEQ ID NO: 1)
QDSTSDLIPAPPLSKVPLQQNFQDNQFQGKWYVVGLAGNA
ILREDKDPQKMYATIYELKEDKSYNVTSVLFRKKKCDYWI
RTFVPGCQPGEFTLGNIKSYPGLTSYLVRVVSTNYNQHAM
VFFKKVSQNREYFKITLYGRTKELTSELKENFIRFSKSLG
LPENHIVFPVPIDQCIDG

K3          QDSTSDLIPAPPLSSVPLQQNFQDNQFQGKWYVVGLAGNAILREDEDPQKMYATIYELKE
60
Wild-type   QDSTSDLIPAPPLSKVPLQQNFQDNQFQGKWYVVGLAGNAILREDKDPQKMYATIYELKE
60
            **************.******************************:**************

K3          DKSYNVTSVLFRDDGCDYWIRTFVPGCQPGEFTLGNIQSYPGLTSYLVRVVSTNYNQFAM
120
Wild-type   DKSYNVTSVLFRKKKCDYWIRTFVPGCQPGEFTLGNIKSYPGLTSYLVRVVSTNYNQHAM
120
            ************.. ***********************:*****************.**

K3          VFFKKVSQNQEYFKITLYGRTKELTSELQENFIRFSKSLGLPENNIVFPVPIDQCIDG
178
Wild-type   VFFKKVSQNREYFKITLYGRTKELTSELKENFIRFSKSLGLPENHIVFPVPIDQCIDG
178
            *********:******************:***************:*************
```

FIG. 19

- <u>K3 Ngal + second C mutated to S</u>

QDSTSDLIPAPPLSSVPLQQNFQDNQFQGKWYVVGLAGNA
ILREDEDPQKMYATIYELKEDKSYNVTSVLFRDDGCDYWI
RTFVPGSQPGEFTLGNIQSYPGLTSYLVRVVSTNYNQFAM
VFFKKVSQNQEYFKITLYGRTKELTSELQENFIRFSKSLG
LPENNIVFPVPIDQCIDG

Fig. 21

MUTANT 1=K3
MUTANT 2=K3CYS

SEQUENCE LISTING

```
Sequence total quantity: 252
SEQ ID NO: 1            moltype = AA  length = 178
FEATURE                 Location/Qualifiers
source                  1..178
                        mol_type = protein
                        organism = Homo sapiens
SEQUENCE: 1
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 2            moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 2
QDSTSDLIPA PPLSSVPLQQ NFQDNQFQGK WYVVGLAGNA ILREDEDPQK MYATIYELKE  60
DKSYNVTSVL FRDDGCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 3            moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 3
QDSTSDLIPA PPLSSVPLQQ NFQDNQFQGK WYVVGLAGNA ILREDKDPQK MYATIYELKE  60
DKSYNVTSVL FRDDGCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 4            moltype = AA  length = 178
FEATURE                 Location/Qualifiers
REGION                  1..178
                        note = Description of Artificial Sequence: Synthetic
                         polypeptide
source                  1..178
                        mol_type = protein
```

```
                          organism = synthetic construct
SEQUENCE: 4
QDSTSDLIPA PPLSKVPLQQ NFQDNQFQGK WYVVGLAGNA ILREDKDPQK MYATIYELKE  60
DGSYNVTSVL FRDDGCDYWI RTFVPGCQPG EFTLGNIQSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 5              moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
SEQUENCE: 5
QDSTSDLIPA PPLSSVPLQQ NFQDNQFQGK WYVVGLAGNA ILREDKDPQK MYATIYELKE  60
DKSYNVTSVL FRDDGCDYWI RTFVPGCQPG EFTLGNIKSY PGLTSYLVRV VSTNYNQHAM  120
VFFKKVSQNQ EYFKITLYGR TKELTSELKE NFIRFSKSLG LPENHIVFPV PIDQCIDG    178

SEQ ID NO: 6              moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
SEQUENCE: 6
QDSTSDLIPA PPLSSVPLQQ NFQDNQFQGK WYVVGLAGNA ILREDEDPQK MYATIYELKE  60
DKSYNVTSVL FRKKKCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 7              moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
SEQUENCE: 7
QDSTSDLIPA PPLSSVPLQQ NFQDNQFQGK WYVVGLAGNA ILREDEDPQK MYATIYELQE  60
DKSYNVTSVL FRKKKCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 8              moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
SEQUENCE: 8
QDSTSDLIPA PPLSSVPLQQ NFQDNQFQGK WYVVGLAGNA ILREDEDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELQE NFIRFSKSLG LPENHIVFPV PIDQCIDG    178

SEQ ID NO: 9              moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
SEQUENCE: 9
QDSTSDLIPA PPLSSVPLQQ NFQDNQFQGK WYVVGLAGNA ILREDEDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELQE NFIRFSKSLG LPENNIVFPV PIDQCIDG    178

SEQ ID NO: 10             moltype = AA  length = 178
FEATURE                   Location/Qualifiers
REGION                    1..178
                          note = Description of Artificial Sequence: Synthetic
                           polypeptide
source                    1..178
                          mol_type = protein
                          organism = synthetic construct
```

```
SEQUENCE: 10
QDSTSDLIPA PPLSSVPLQQ NFQDNQFQGK WYVVGLAGNA ILREDEDPQK MYATIYELKE  60
DKSYNVTSVL FRKKKCDYWI RTFVPGCQPG EFTLGNIKSY PGLTSYLVRV VSTNYNQFAM  120
VFFKKVSQNR EYFKITLYGR TKELTSELKE NFIRFSKSLG LPENNIVFPV PIDQCIDG    178

SEQ ID NO: 11          moltype = AA  length = 179
FEATURE                Location/Qualifiers
source                 1..179
                       mol_type = protein
                       organism = Equus caballus
SEQUENCE: 11
RDPAPKLIPA PPLDRVPLQP DFKDDQFQGK WYVVGVAGNA FKKEEQGQFT MYTTTYELKE  60
DHSYNVTSIL LRDQNCDHWI RTFIPSSQPG QFNLGDIKRY FGVQSYIVRV ADTDYNQFAI  120
VFFRKVYKNQ EYFKTTLYRR TKELTPELRE KFISFAKSLG LTDDHIIFPV PIDQCIDEE   179

SEQ ID NO: 12          moltype = AA  length = 178
FEATURE                Location/Qualifiers
source                 1..178
                       mol_type = protein
                       organism = Canis lupus
                       note = Canis familiaris
SEQUENCE: 12
QDSTPSLIPA PPPLKVPLQP DFQHDQFQGK WYVIGIAGNI LKKEGHGQLK MYTTTYELKD  60
DQSYNVTSTL LRNERCDYWN RDFVPSFQPG QFSLGDIQLY PGVQSYLVQV VATNYNQYAL  120
VYFRKVYKSQ EYFKITLYGR TKELPLELKK EFIRFAKSIG LTEDHIIFPV PIDQCIDE    178

SEQ ID NO: 13          moltype = AA  length = 179
FEATURE                Location/Qualifiers
source                 1..179
                       mol_type = protein
                       organism = Sus scrofa
SEQUENCE: 13
QGTIPNWIPA PPLSKVPLQP NFQADQFQGK WYVVGLAGNA VKKEEQGRFK MYTTTYELKE  60
DGSYNVISTL LRGQLCDNWI RTFVPSLQPG QFKLGDIKKY SGLQSYVVRV VSTNYSQFAI  120
VFFKKVSNNQ EYFKTTLYGR TKVLSPELKE NFVRFAKSLG LSDDNIIFPV AIDQCIDGQ   179

SEQ ID NO: 14          moltype = AA  length = 178
FEATURE                Location/Qualifiers
source                 1..178
                       mol_type = protein
                       organism = Pan troglodytes
SEQUENCE: 14
QDSTSDLIPA PPLSKVPLQQ NFQDNQFQGK WYVVGLAGNA ILREDKDPQK MYATIYELKE  60
DKSYNVTSVL FRKKKCDYWI RTFVPGRQPG EFTLGNIKSY PGLTSYLVRV VSTNYNQHAM  120
VFFKKVSQNR EYFKITLYGR TKELTSELQE NFIRFSKSLG LPENHIVFPV PIDQCIDG    178

SEQ ID NO: 15          moltype = AA  length = 178
FEATURE                Location/Qualifiers
source                 1..178
                       mol_type = protein
                       organism = Macaca mulatta
SEQUENCE: 15
QDSSSDLIPA PPLSKVPLQQ NFQDNQFQGK WYVVGLSGNA VGRKDEAPLK MYATIYELKE  60
DKSYNVTSIL FRKEKCDYWI RTFVPGSQPG EFTLGNIQNH PGLTSYVVRV VSTNYKQYAM  120
VFFKKVSQNK EYFKITLYGR TKELTSELKE NFIRFSKSLG LPENHIVFSV PIDQCING    178

SEQ ID NO: 16          moltype = AA  length = 179
FEATURE                Location/Qualifiers
source                 1..179
                       mol_type = protein
                       organism = Bos taurus
SEQUENCE: 16
RSSSSRLLRA PPLSRIPLQP NFQADQFQGK WYTVGVAGNA IKKEEQDPLK MYSSNYELKE  60
DGSYNVTSIL LKDDLCDYWI RTFVPSSQPG QFTLGNIKSY RGIRSYTVRV VNTDYNQFAI  120
VYFKKVQRKK TYFKITLYGR TKELTPEVRE NFINFAKSLG LTDDHIVFTV PIDRCIDDQ   179

SEQ ID NO: 17          moltype = AA  length = 180
FEATURE                Location/Qualifiers
source                 1..180
                       mol_type = protein
                       organism = Mus musculus
SEQUENCE: 17
QDSTQNLIPA PSLLTVPLQP DFRSDQFRGR WYVVGLAGNA VQKKTEGSFT MYSTIYELQE  60
NNSYNVTSIL VRDQDQGCRY WIRTFVPSSR AGQFTLGNMH RYPQVQSYNV QVATTDYNQF  120
AMVFFRKTSE NKQYFKITLY GRTKELSPEL KERFTRFAKS LGLKDDNIIF SVPTDQCIDN  180

SEQ ID NO: 18          moltype = AA  length = 178
FEATURE                Location/Qualifiers
source                 1..178
```

```
                         mol_type = protein
                         organism = Rattus norvegicus
SEQUENCE: 18
QDSTQNLIPA PPLISVPLQP GFWTERFQGR WFVVGLAGNA VQKERQSRFT MYSTIYELQE  60
DNSYNVTSIL VRGQGCRYWI RTFVPSSRPG QFTLGNIHSY PQIQSYDVQV ADTDYDQFAM  120
VFFQKTSENK QYFKVTLYGR TKGLSDELKE RFVSFAKSLG LKDNNIVFSV PTDQCIDN    178

SEQ ID NO: 19            moltype = AA  length = 4655
FEATURE                  Location/Qualifiers
source                   1..4655
                         mol_type = protein
                         organism = Homo sapiens
SEQUENCE: 19
MDRGPAAVAC TLLLALVACL APASGQECDS AHFRCGSGHC IPADWRCDGT KDCSDDADEI  60
GCAVVTCQQG YFKCQSEGQC IPNSWVCDQD QDCDDGSDER QDCSQSTCSS HQITCSNGQC  120
IPSEYRCDHV RDCPDGADEN DCQYPTCEQL TCDNGACYNT SQKCDWKVDC RDSSDEINCT  180
EICLHNEFSC GNGECIPRAY VCDHDNDCQD GSDEHACNYP TCGGYQFTCP SGRCIYQNWV  240
CDGEDDCKDN GDEDGCESGP HDVHKCSPRE WSCPESGRCI SIYKVCDGIL DCPGREDENN  300
TSTGKYCSMT LCSALNCQYQ CHETPYGGAC FCPPGYIINH NDSRTCVEFD DCQIWGICDQ  360
KCESRPGRHL CHCEEGYILE RGQYCKANDS FGEASIIFSN GRDLLIGDIH GRSFRILVES  420
QNRGVAVGVA FHYHLQRVFW TDTVQNKVFS VDINGLNIQE VLNVSVETPE NLAVDWVNNK  480
IYLVETKVNR IDMVNLDGSY RVTLITENLG HPRGIAVDPT VGYLFFSDWE SLSGEPKLER  540
AFMDGSNRKD LVKTKLGWPA GVTLDMISKR VYWVDSRFDY IETVTYDGIQ RKTVVHGGSL  600
IPHPFGVSLF EGQVFFTDWT KMAVLKANKF TETNPQVYYQ ASLRPYGVTV YHSLRQPYAT  660
NPCKDNNGGC EQVCVLSHRT DNDGLGFRCK CTFGFQLDTD ERHCIAVQNF LIFSSQVAIR  720
GIPFTLSTQE DVMVPVSGNP SFFVGIDFDA QDSTIFFSDM SKHMIFKQKI DGTGREILAA  780
NRVENVESLA FDWISKNLYW TDSHYKSISV MRLADKTRRT VVQYLNNPRS VVVHPFAGYL  840
FFTDWFRPAK IMRAWSDGSH LLPVINTTLG WPNGLAIDWA ASRLYWVDAY FDKIEHSTFD  900
GLDRRRLGHI EQMTHPFGLA IFGEHLFFTD WRLGAIIRVR KADGGEMTVI RSGIAYILHL  960
KSYDVNIQTG SNACNQPTHP NGDCSHFCFP VPNFQRVCGC PYGMRLASNH LTCEGDPTNE  1020
PPTEQCGLFS FPCKNGRCVP NYYLCDGVDD CHDNSDEQLC GTLNNTCSSS AFTCGHGECI  1080
PAHWRCDKRN DCVDGSDEHN CPTHAPASCL DTQYTCDNHQ CISKNWVCDT DNDCGDGSDE  1140
KNCNSTETCQ PSQFNCPNHR CIDLSFVCDG DKDCVDGSDE VGCVLNCTAS QFKCASGDKC  1200
IGVTNRCDGV FDCSDNSDEA GCPTRPPGMC HSDEFQCQED GICIPNFWEC DGHPDCLYGS  1260
DEHNACVPKT CPSSYFHCDN GNCIHRAWLC DRDNDCGDMS DEKDCPTQPF RCPSWQWQCL  1320
GHNICVNLSV VCDGIFDCPN GTDESPLCNG NSCSDFNGGC THECVQEPFG AKCLCPLGFL  1380
LANDSKTCED IDECDILGSC SQHCYNMRGS FRCSCDTGYM LESDGRTCKV TASESLLLLV  1440
ASQNKIIADS VTSQVHNIYS LVENGSYIVA VDFDSISGRI FWSDATQGKT WSAFQNGTDR  1500
RVVFDSSIIL TETIAIDWVG RNLYWTDYAL ETIEVSKIDG SHRTVLISKN LTNPRGLALD  1560
PRMNEHLLFW SDWGHHPRIE RASMDGSMRT VIVQDKIFWP CGLTIDYPNR LLYFMDSYLD  1620
YMDFCDYNGH HRRQVIASDL IIRHPYALTL FEDSVYWTDR ATRRVMRANK WHGGNQSVVM  1680
YNIQWPLGIV AVHPSKQPNS VNPCAFSRCS HLCLLSSQGP HFYSCVCPSG WSLSPDLLNC  1740
LRDDQPFLIT VRQHIIFGIS LNPEVKSNDA MVPIAGIQNG LDVEFDDAEQ YIYWVENPGE  1800
IHRVKTDGTN RTVFASISMV GPSMNLALDW ISRNLYSTNP RTQSIEVLTL HGDIRYRKTL  1860
IANDGTALGV GFPIGITVDP ARGKLYWSDQ GTDSGVPAKI ASANMDGTSV KTLFTGNLEH  1920
LECVTLDIEE QKLYWAVTGR GVIERGNVDG TDRMILVHQL SHPWGIAVHD SFLYYTDEQY  1980
EVIERVDKAT GANKIVLRDN VPNLRGLQVY HRRNAAESSN GCSNNMNACQ QICLPVPGGL  2040
FSCACATGFK LNPDNRSCSP YNSFIVVSML SAIRGFSLEL SDHSETMVPV AGQGRNALHV  2100
DVDVSSGFIY WCDFSSSVAS DNAIRRIKPD GSSLMNIVTH GIGENGVRGI AVDWVAGNLY  2160
FTNAFVSETL IEVLRINTTY RRVLLKVTVD MPRHIVVDPK NRYLFWADYG QRPKIERSFL  2220
DCTNRTVLVS EGIVTPRGLA VDRSDGYVYW VDDSLDIIAR IRINGENSEV IRYGSRYPTP  2280
YGITVFENSI IWVDRNLKKI FQASKEPENT EPPTVIRDNI NWLRDVTIFD KQVQPRSPAE  2340
VNNNPCLENN GGCSHLCFAL PGLHTPKCDC AFGTLQSDGK NCAISTENFL IFALSNSLRS  2400
LHLDPENHSP PFQTINVERT VMSLDYDSVS DRIYFTQNLA SGVGQISYAT LSSGIHTPTV  2460
IASGIGTADG IAFDWITRRI YYSDYLNQMI NSMAEDGSNR TVIARVPKPR AIVLDPCQGY  2520
LYWADWDTHA KIERATLGGN FRVPIVNSSL VMPSGLTLDY EEDLLYWVDA SLQRIERSTL  2580
TGVDREVIVN AAVHAFGLTL YGQYIYWTDL YTQRIYRANK YDGSGQIAMT TNLLSQPRGI  2640
NTVVKNQKQQ CNNPCEQFNG GCSHICAPGP NGAECQCPHE GNWYLANNRK HCIVDNGERC  2700
GASSFTCSNG RCISEEWKCD NDNDCGDGSD EMESVCALHT CSPTAFTCAN GRCVQYSYRC  2760
DYYNDCGDGS DEAGCLFRDC NATTEFMCNN RRCIPREFIC NGVDNCHDNN TSDEKNCPDR  2820
TCQSGYTKCH NSNICIPRVY LCDGDNDCGD NSDENPTYCT THTCSSSEFQ CASGRCIPQH  2880
WYCDQETDCF DASDEPASCG HSERTCLADE FKCDGGRCIP SEWICDGDND CGDMSDEDKR  2940
HQCQNQNCSD SEFLCVNDRP PDRRCIPQSW VCDGDVDCTD GYDENQNCTR RTCSENEFTC  3000
GYGLCIPKIF RCDRHNDCGD YSDERGCLYQ TCQQNQFTCQ NGRCISKTFV CDEDNDCGDG  3060
SDELMHLCHT PEPTCPPHEF KCDNGRCIEM MKLCNHLDDC LDNSDEKGCG INECHDPSIS  3120
GCDHNCTDTL TSFYCSCRPG YKLMSDKRTC VDIDECTEMP FVCSQKCENV IGSYICKCAP  3180
GYLREPDGKT CRQNSNIEPY LIFSNRYYLR NLTIDGYFYS LILEGLDNVV ALDFDRVEKR  3240
LYWIDTQRQV IERMFLNKTN KETIINHRLP AAESLAVDWV SRKLYWLDAR LDGLFVSDLN  3300
GGHRRMLAQH CVDANNTFCF DNPRGLALHP QYGYLYWADW GHRAYIGRVG MDGTNKSVII  3360
STKLEWPNGI TIDYTNDLLY WADAHLGYIE YSDLEGHHRH TVYDGALPHP FAITIFEDTI  3420
YWTDWNTRTV EKGNKYDGSN RQTLVNTTHR PFDIHVYHPY RQPIVSNPCG TNNGGCSHLC  3480
LIKPGGKGFT CECPDDFRTL QLSGSTYCMP MCSSTQFLCA NNEKCIPIWW KCDGQKDCSD  3540
GSDELALCPQ RFCRLGQFQC SDGNCTSPQT LCNAHQNCPD GSDEDRLLCE NHHCDSNEWQ  3600
CANKRCIPES WQCDTFNDCE DNSDEDSSHC ASRTCRPGQF RCANGRCIPQ AWKCDVDNDC  3660
GDHSDEPIEE CMSSAHLCDN FTEFSCKTNY RCIPKWAVCN GVDDCRDNSD EQGCEERTCH  3720
PVGDFRCKNH HCIPLRWQCD GQNDCGDNSD EENCAPRECT ESEFRCVNQQ CIPSRWICDH  3780
YNDCGDNSDE RDCEMRTCHP EYFQCTSGHC VHSELKCDGS ADCLDASDEA DCPTRFPDGA  3840
YCQATMFECK NHVCIPPYWK CDGDDDCGDG SDEELHLCLD VPCNSPNRFR CDNNRCIYSH  3900
EVCNGVDDCG DGTDETEEHC RKPTPKPCTE YEYKCGNGHC IPHDNVCDDA DDCGDWSDEL  3960
```

-continued

```
GCNKGKERTC AENICEQNCT QLNEGGFICS CTAGFETNVF DRTSCLDINE CEQFGTCPQH  4020
CRNTKGSYEC VCADGFTSMS DRPGKRCAAE GSSPLLLLPD NVRIRKYNLS SERFSEYLQD  4080
EEYIQAVDYD WDPKDIGLSV VYYTVRGEGS RFGAIKRAYI PNFESGRNNL VQEVDLKLKY  4140
VMQPDGIAVD WVGRHIYWSD VKNKRIEVAK LDGRYRKWLI STDLDQPAAI AVNPKLGLMF  4200
WTDWGKEPKI ESAWMNGEDR NILVFEDLGW PTGLSIDYLN NDRIYWSDFK EDVIETIKYD  4260
GTDRRVIAKE AMNPYSLDIF EDQLYWISKE KGEVWKQNKF GQGKKEKTLV VNPWLTQVRI  4320
FHQLRYNKSV PNLCKQICSH LCLLRPGGYS CACPQGSSFI EGSTTECDAA IELPINLPPP  4380
CRCMHGGNCY FDETDLPKCK CPSGYTGKYC EMAFSKGISP GTTAVAVLLT ILLIVVIGAL  4440
AIAGFFHYRR TGSLLPALPK LPSLSSLVKP SENGNGVTFR SGADLNMDIG VSGFGPETAI  4500
DRSMAMSEDF VMEMGKQPII FENPMYSARD SAVKVVQPIQ VTVSENVDNK NYGSPINPSE  4560
IVPETNPTSP AADGTQVTKW NLFKRKSKQT TNFENPIYAQ MENEQKESVA ATPPPSPSLP  4620
AKPKPPSRRD PTPTYSATED TFKDTANLVK EDSEV                            4655

SEQ ID NO: 20          moltype = AA  length = 4660
FEATURE                Location/Qualifiers
source                 1..4660
                       mol_type = protein
                       organism = Mus musculus
SEQUENCE: 20
MERGAAAAAW MLLLAIAACL APVSGQECGS GNFRCDNGYC IPASWRCDGT RDCLDDTDEI  60
GCPPRSCGSG FFLCPAEGTC IPSSWVCDQD KDCSDGADEQ QNCPGTTCSS QQLTCSNGQC  120
VPIEYRCDHV SDCPDGSDER NCYYPTCDQL TCANGACYNT SQKCDHKVDC RDSSDEANCT  180
TLCSQKEFQC GSGECILRAY VCDHDNDCED NSDEHNCNYD TCGGHQFTCS NGQCINQNWV  240
CDGDDDCQDS GDEDGCESNQ RHHTCYPREW ACPGSGRCIS MDKVCDGVPD CPEGEDENNA  300
TSGRYCGTGL CSILNCEYQC HQTPYGGECF CPPGHIINSN DSRTCIDFDD CQIWGICDQK  360
CESRQGRHQC LCEEGYILER GQHCKSNDSF SAASIIFSNG RDLLVGDLHG RNFRILAESK  420
NRGIVMGVDF HYQKHRVFWT DPMQAKVFST DINGLNTQEI LNVSIDAPEN LAVDWINNKL  480
YLVETRVNRI DVVNLEGNQR VTLITENLGH PRGIALDPTV GYLFFSDWGS LSGQPKVERA  540
FMDGSNRKDL VTTKLGWPAG ITLDLVSKRV YWVDSRYDYI ETVTYDGIQR KTVARGGSLV  600
PHPFGISLFE EHVFFTDWTK MAVMKANKFT DTNPQVYHQS SLTPFGVTVY HALRQPNATN  660
PCGNNNGGCA QICVLSHRTD NGGLGYRCKC EFGFELDADE HHCVAVKNFL LFSSQTAVRG  720
IPFTLSTQED VMVPVTGSPS FFVGIDFDAQ HSTIFYSDLS KNIIYQQKID GTGKEVITAN  780
RLQNVECLSF DWISRNLYWT DGGSKSVTVM KLADKSRRQI ISNLNNPRSI VVHPAAGYMF  840
LSDWFRPAKI MRAWSDGSHL MPIVNTSLGW PNGLAIDWST SRLYWVDAFF DKIEHSNLDG  900
LDRKRLGHVD QMTHPFGLTV FKDNVFLTDW RLGAIIRVRK SDGGDMTVVR RGISSIMHVK  960
AYDADLQTGT NYCSQTTHPN GDCSHFCFPV PNFQRVCGCP YGMKLQRDQM TCEGDPAREP  1020
PTQQCGSSSF PCNNGKCVPS IFRCDGVDDC HDNSDEHQCG ALNNTCSSSA FTCVHGGQCI  1080
PGQWRCDKQN DCLDGSDEQN CPTRSPSSTC PPTSFTCDNH MCIPKEWVCD TDNDCSDGSD  1140
EKNCQASGTC HPTQFRCPDH RCISPLYVCD GDKDCVDGSD EAGCVLNCTS SQFKCADGSS  1200
CINSRYRCDG VYDCKDNSDE AGCPTRPPGM CHPDEFQCQG DGTCIPNTWE CDGHPDCIQG  1260
SDEHNGCVPK TCSPSHFLCD NGNCIYNSWV CDGDNDCRDM SDEKDCPTQP FHCPSSQWQC  1320
PGYSICVNLS ALCDGVFDCP NGTDESPLCN QDSCLHFNGG CTHRCIQGPF GATCVCPIGY  1380
QLANDTKTCE DVNECDIPGF CSQHCVNMRG SFRCACDPEY TLESDGRTCK VTASENLLLV  1440
VASRDKIIMD NITAHTHNIY SLVQDVSFVV ALDFDSVTGR VFWSDLLEGK TWSAFQNGTD  1500
KRVVHDSGLS LTEMIAVDWI GRNIYWTDYT LETIEVSKID GSHRTVLISK NVTKPRGLAL  1560
DPRMGDNVMF WSDWGHHPRI ERASMDGTMR TVIVQEKIYW PCGLSIDYPN RLIYFMDAYL  1620
DYIEFCDYDG QNRRQVIASD LVLHHPHALT LFEDSVFWTD RGTHQVMQAN KWHGRNQSVV  1680
MYSVPQPLGI IAIHPSRQPS SPNPCASATC SHLCLLSAQE PRHYSCACPS GWNLSDDSVN  1740
CVRGDQPFLI SVRENVIFGI SLDPEVKSND AMVPISGIQH GYDVEFDDSE QFIYWVENPG  1800
EIHRVKTDGS NRTAFAPLSL LGSSLGLALD WVSRNIYYTT PASRSIEVLT LRGDTRYGKT  1860
LITNDGTPLG VGFPVGIAVD PARGKLYWSD HGTDSGVPAK IASANMDGTS LKILFTGNME  1920
HLEVVTLDIQ EQKLYWAVTS RGVIERGNVD GTERMILVHH LAHPWGLVVH GSFLYYSDEQ  1980
YEVIERVDKS SGSNKVVFRD NIPYLRGLRV YHHRNAADSS NGCSNNPNAC QQICLPVPGG  2040
MFSCACASGF KLSPDGRSCS PYNSFIVVSM LPAVRGFSLE LSDHSEAMVP VAGQGRNVLH  2100
ADVDVANGFI YWCDFSSSVR SSNGIRRIKP NGSNFTNIVT YGIGANGIRG VAVDWVAGNL  2160
YFTNAFVYET LIEVIRINTT YRRVLLKVSV DMPRHIVVDP KHRYLFWADY GQKPKIERSF  2220
LDCTNRTVLV SEGIVTPRGL AVDHDTGYIY WVDDSLDIIA RIHRDGGESQ VVRYGSRYPT  2280
PYGITVFGES IIWVDRNLRK VFQASKQPGN TDPPTVIRDS INLLRDVTIF DEHVQPLSPA  2340
ELNNNPCLQS NGGCSHFCFA LPELPTPKCG CAFGTLEDDG KNCATSREDF LIYSLNNSLR  2400
SLHFDPQDHN LPFQAISVEG MAIALDYDRR NNRIFFTQKL NPIRGQISYV NLYSGASSPT  2460
ILLSNIGVTD GIAFDWINRR IYYSDFSNQT INSMAEDGSN RAVIARVSKP RAIVLDPCRG  2520
YMYWTDWGTN AKIERATLGG NFRVPIVNTS LVWPNGLTLD LETDLLYWAD ASLQKIERST  2580
LTGSNREVVI STAFHSFGLT VYGQYIYWTD FYTKKIYRAN KYDGSDLIAM TTRLPTQPSG  2640
ISTVVKTQQQ QCSNPCDQFN GGCSHICAPG PNGAECQCPH EGSWYLANDN KYCVVDTGAR  2700
CNQFQFTCLN GRCISQDWKC DNDNDCGDGS DELPTVCAFH TCRSTAFTCA NGRCVPYHYR  2760
CDFYNDCGDN SDEAGCLFRS CNSTTEFTCS NGRCIPLSYV CNGINNCHDN DTSDEKNCPP  2820
ITCQPDFAKC QTTNICVPRA FLCDGDNDCG DGSDENPIYC ASHTCRSNEF QCVSPHRCIP  2880
SYWFCDGEAD CVDSSDEPDT CGHSLNSCSA NQFHCDNGRC ISSSWVCDGD NDCGDMSDED  2940
QRHHCELQNC SSTEFTCINS RPPNRRCIPQ HWVCDGDADC ADALDELQNC TMRACSTGEF  3000
SCANGRCIRQ SFRCDRRNDC GDYSDERGCS YPPCRDDQFT CQNGQCITKL YVCDEDNDCG  3060
DGSDEQEHLC HTPEPTCPPH QFRCDNGHCI EMGTVCNHVD DCSDNSDEKG CGINECQDSS  3120
ISHCDHNCTD TITSFYCSCL PGYKLMSDKR TCVDIDECKE TPQLCSQKCE NVIGSYICKC  3180
APGYIREPDG KSCRQNSNIE PYLVFSNRYY IRNLTIDGTS YSLILQGLGN VVALDFDRVE  3240
ERLYWIDAEK QIIERMFLNK TNQETIISHR LRRAESLAVD WVSRKLYWLD AILDCLFVSD  3300
LEGRQRKMLA QHCVDANNTF CFENPRGIVL HPQRGYVYWA DWGDHAYIAR IGMDGTNKTV  3360
IISTKIEWPN AITIDYTNDL LYWADAHLGY IEFSDLEGHH RHTVYDGTLP HPFALTIFED  3420
TVFWTDWNTR TVEKGNKYDG SGRVVLVNTT HKPFDIHVLH PYRQPIMSNP CATNNGGCSH  3480
LCLIKAGGRG FTCECPDDFQ TVQLRDRTLC MPMCSSTQFL CGNNEKCIPI WWKCDGQKDC  3540
SDGSDESDLC PHRFCRLGQF QCRDGNCTSP QALCNARQDC ADGSDEDRVL CEHHRCEANE  3600
```

-continued

```
WQCANKRCIP EYWQCDSVDD CLDNSDEDPS HCASRTCRPG QFKCNNGRCI PQSWKCDVDN  3660
DCGDYSDEPI HECMTAAYNC DNHTEFSCKT NYRCIPQWAV CNGFDDCRDN SDEQGCESVP  3720
CHPSGDFRCG NHHCIPLRWK CDGIDDCGDN SDEESCVPRE CTESEFRCAD QQCIPSRWVC  3780
DQENDCGDNS DERDCEMKTC HPEHFQCTSG HCVPKALACD GRADCLDASD ESACPTRFPN  3840
GTYCPAAMFE CKNHVCIQSF WICDGENDCV DGSDEEIHLC FNVPCESPQR FRCDNSRCIY  3900
GHQLCNGVDD CGDGSDEKEE HCRKPTHKPC TDTEYKCSNG NCVSQHYVCD NVDDCGDLSD  3960
ETGCNLGENR TCAEKICEQN CTQLSNGGFI CSCRPGFKPS TLDKNSCQDI NECEEFGICP  4020
QSCRNSKGSY ECFCVDGFKS MSTHYGERCA ADGSPPLLLL PENVRIRKYN ISSEKFSEYL  4080
EEEEHIQAID YDWDPEGIGL SVVYYTVLSQ GSQFGAIKRA YLPDFESGSN NPVREVDLGL  4140
KYLMQPDGLA VDWVGRHIYW SDAKSQRIEV ATLDGRYRKW LITTQLDQPA AIAVNPKLGL  4200
MFWTDQGKQP KIESAWMNGE HRSVLASANL GWPNGLSIDY LNGDRIYWSD SKEDVIESIK  4260
YDGTDRRLII NDAMKPFSLD IFEDQLYWVA KEKGEVWRQN KFGKGNKEKL LVVNPWLTQV  4320
RIFHQLRYNQ SVSNPCKQVC SHLCLLRPGG YSCACPQGSD FVTGSTVECD AASELPITMP  4380
SPCRCMHGGS CYFDENDLPK CKCSSGYSGE YCEIGLSRGI PPGTTMALLL TFAMVIIVGA  4440
LVLVGFFHYR KTGSLLPSLP KLPSLSSLAK PSENGNGVTF RSGADVNMDI GVSPFGPETI  4500
IDRSMAMNEQ FVMEVGKQPV IFENPMYAAK DSTSKVGLAV QGPSVSSQVT VPENVENQNY  4560
GRSIDPSEIV PEPKPASPGA DETQGTKWNI FKRKPKQTTN FENPIYAEMD TEQKEAVAVA  4620
PPPSPSLPAK ASKRSSTPGY TATEDTFKDT ANLVKEDSDV                        4660

SEQ ID NO: 21           moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 21
QDSTSDLIPA PPLSSVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 22           moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 22
QDSTSDLIPA PPLSSVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGQ TQELTSELKE NFIRFSKSLG LPENHIVFPV PIDQCIDG    178

SEQ ID NO: 23           moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 23
QDSTSDLIPA PPLSKVPLQQ NFQDNQFQGK WYVVGLAGNA ILQEDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 24           moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 24
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIQSY PGLTSYLVRV VSTNYNQFAM  120
VFFKKVSQNR EYFKITLYGR TKELTSELKE NFIRFSKSLG LPENNIVFPV PIDQCIDG    178

SEQ ID NO: 25           moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
```

```
SEQUENCE: 25
QDSTSDLIPA PPLSKVPLQQ NFQDNQFQGK WYVVGLAGNA ILREDEDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENNIVFPV PIDQCIDG    178

SEQ ID NO: 26          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 26
QDSTSDLIPA PPLSKVPLQQ NFQDNQFQGK WYVVGLAGNA ILREDEDPQK MYATIYELKE  60
DKSYNVTSVL FRKKKCDYWI RTFVPGCQPG EFTLGNIQSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 27          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 27
QDSTSDLIPA PPLSKVPLQQ NFQDNQFQGK WYVVGLAGNA ILREDEDPQK MYATIYELKE  60
DGSYNVTSVL FRKKKCDYWI RTFVPGCQPG EFTLGNIQSY PGLTSYLVRV VSTNYNQFAM  120
VFFKKVSQNR EYFKITLYGR TKELTSELQE NFIRFSKSLG LPENNIVFPV PIDQCIDG    178

SEQ ID NO: 28          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 28
QDSTSDLIPA PPLSKVPLQQ NFQDNQFQGK WYVVGLAGNA ILREDKDPQT MYATIYELKE  60
DKSYNVTSVL FQKKKCDYWI RTFVPGCQPG EFTLGNIKSY PGLTSYLVRV VSTNYNQHAM  120
VFFKKVSQNQ EYFKITLYGR TKELTSELQE NFIRFSQSLG LPENHIVFPV PIDQCIDG    178

SEQ ID NO: 29          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 29
QDSTSDLIPA PPLSSVPLQQ NFQDNQFQGK WYVVGLAGNA ILREDKDPQT MYATIYELKE  60
DKSYNVTSVL FQKKKCDYWI RTFVPGCQPG EFTLGNIKSY PGLTSYLVRV VSTNYNQHAM  120
VFFKKVSQNR EYFKITLYGR TKELTSELQE NFIRFSQSLG LPENHIVFPV PIDQCIDG    178

SEQ ID NO: 30          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 30
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNQ EYFKITLYGR TKELTSELKE NFIRFSQSLG LPENHIVFPV PIDQCIDG    178

SEQ ID NO: 31          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 31
```

```
QDSTSDLIPA PPLSKVPLQQ NFQDNQFQGK WYVVGLAGNA ILREDKDPQK MYATIYELKE  60
DKSYNVTSVL FQKKKCDYWI RTFVPGCQPG EFTLGNIKSY PGLTSYLVRV VSTNYNQHAM  120
VFFKKVSQNR EYFKITLYGR TKELTSELKE NFIRFSQSLG LPENHIVFPV PIDQCIDG    178

SEQ ID NO: 32          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 32
QDSTSDLIPA PPLSKVPLQQ NFQDNQFQGK WYVVGLAGNA ILREDKDPQK MYATIYELKE  60
DKSYNVTSVL FRDDGCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 33          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 33
QDSTSDLIPA PPLSKVPLQQ NFQDNQFQGK WYVVGLAGNA ILREDKDPQK MYATIYELKE  60
DGSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 34          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 34
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGQ TQELTSELKE NFIRFSKSLG LPENHIVFPV PIDQCIDG    178

SEQ ID NO: 35          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 35
QDSTSDLIPA PPLSSVPLQQ NFQDNQFQGK WYVVGLAGNA ILREDEDPQK MYATIYELQE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 36          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 36
QDSTSDLIPA PPLSKVPLQQ NFQDNQFQGK WYVVGLAGNA ILREDEDPQK MYATIYELQE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 37          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 37
QDSTSDLIPA PPLSSVPLQQ NFQDNQFQGK WYVVGLAGNA ILQEDKDPQK MYATIYELKE  60
```

```
DKSYNVTSVL FRKKKCDYWI RTFVPGCQPG EFTLGNIKSY PGLTSYLVRV VSTNYNQHAM  120
VFFKKVSQNR EYFKITLYGR TKELTSELQE NFIRFSKSLG LPENHIVFPV PIDQCIDG    178

SEQ ID NO: 38          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 38
QDSTSDLIPA PPLSKVPLQQ NFQDNQFQGK WYVVGLAGNA ILQEDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGQ TQELTSELKE NFIRFSKSLG LPENHIVFPV PIDQCIDG    178

SEQ ID NO: 39          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 39
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSQSLG LPENHIVFPV PIDQCIDG    178

SEQ ID NO: 40          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 40
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENNIVFPV PIDQCIDG    178

SEQ ID NO: 41          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 41
QDSTSDLIPA PPLSSVPLQQ NFQDNQFQGK WYVVGLAGNA ILREDKDPQK MYATIYELKE  60
DKSYNVTSVL FRKKKCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 42          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 42
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQFAM  120
VFFKKVSQNR EYFKITLYGR TKELTSELQE NFIRFSKSLG LPENNIVFPV PIDQCIDG    178

SEQ ID NO: 43          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 43
QDSTSDLIPA PPLSSVPLQQ NFQDNQFQGK WYVVGLAGNA ILREDKDPQK MYATIYELKE  60
DKSYNVTSVL FRKKKCDYWI RTFVPGCQPG EFTLGNIQSY PGLTSYLVRV VSTNYNQHAM  120
```

```
VFFKKVSQNR EYFKITLYGR TKELTSELKE NFIRFSKSLG LPENNIVFPV PIDQCIDG    178

SEQ ID NO: 44          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 44
QDSTSDLIPA PPLSSVPLQQ NFQDNQFQGK WYVVGLAGNA ILREDKDPQK MYATIYELKE  60
DKSYNVTSVL FRDDGCDYWI RTFVPGCQPG EFTLGNIQSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 45          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 45
QDSTSDLIPA PPLSSVPLQQ NFQDNQFQGK WYVVGLAGNA ILREDKDPQK MYATIYELKE  60
DGSYNVTSVL FRDDGCDYWI RTFVPGCQPG EFTLGNIKSY PGLTSYLVRV VSTNYNQHAM  120
VFFKKVSQNQ EYFKITLYGR TKELTSELKE NFIRFSKSLG LPENHIVFPV PIDQCIDG    178

SEQ ID NO: 46          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 46
QDSTSDLIPA PPLSKVPLQQ NFQDNQFQGK WYVVGLAGNA ILQEDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGQ TQELTSELKE NFIRFSQSLG LPENHIVFPV PIDQCIDG    178

SEQ ID NO: 47          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 47
QDSTSDLIPA PPLSSVPLQQ NFQDNQFQGK WYVVGLAGNA ILQEDKDPQK MYATIYELKE  60
DKSYNVTSVL FQKKKCDYWI RTFVPGCQPG EFTLGNIKSY PGLTSYLVRV VSTNYNQHAM  120
VFFKKVSQNR EYFKITLYGQ TQELTSELKE NFIRFSQSLG LPENHIVFPV PIDQCIDG    178

SEQ ID NO: 48          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 48
QDSTSDLIPA PPLSKVPLAP DFQDNQFQGK WYVVGLAGNA ILREDEDPQK MYATIYELKE  60
DGSYNVTSVL FRKKKCDYWI RTFVPGCQPG EFTLGNIQSY PGLTSYLVRV VSTNYNQFAM  120
VFFKKVSQNR EYFKITLYGR TKELTSELQE NFIRFSKSLG LPENNIVFPV PIDQCIDG    178

SEQ ID NO: 49          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 49
QDSTSDLIPA PPLSKVPLAP DFQDNQFQGK WYVVGLAGNA ILREDEDPQK MYATIYELAE  60
DGSYNVTSVL FRKKKCDYWI RTFVPGCQPG EFTLGNIQSY PGLTSYLVRV VSTNYNQFAM  120
VFFKKVSQNR EYFKITLYGR TKELTSELQE NFIRFSKSLG LPENNIVFPV PIDQCIDG    178
```

```
SEQ ID NO: 50          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 50
QDSTSDLIPA PPLSKVPLQQ NFQDNQFQGK WYVVGLAGNA ILREDEDPQK MYATIYELKE  60
DGSYNVTSVL FRKKKCDYWI RTFVPGCQPG EFTLGNIQSY PGLTSYLVRV VSTDYNQFAM  120
VFFKKVSQNR EYFKITLYGR TKELTSELQE NFIRFSKSLG LPENNIVFPV PIDQCIDG    178

SEQ ID NO: 51          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 51
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGA TAELTSELKE NFIRFSKSLG LPENHIVFPV PIDQCIDG    178

SEQ ID NO: 52          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 52
QDSTSDLIPA PPLSKVPLQQ NFQDNQFQGK WYVVGLAGNA ILAEDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGA TAELTSELKE NFIRFSASLG LPENHIVFPV PIDQCIDG    178

SEQ ID NO: 53          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 53
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGA TAELTSELKE NFIRFSASLG LPENHIVFPV PIDQCIDG    178

SEQ ID NO: 54          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 54
QDSTSDLIPA PPLSKVPLQQ NFQDNQFQGK WYVVGLAGNA ILREDKDPQK MYATIYELKE  60
DKSYNVTSVL FAKKKCDYWI RTFVPGCQPG EFTLGNIKSY PGLTSYLVRV VSTNYNQHAM  120
VFFKKVSQNR EYFKITLYGA TAELTSELKE NFIRFSASLG LPENHIVFPV PIDQCIDG    178

SEQ ID NO: 55          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 55
QDSTSDLIPA PPLSKVPLQQ NFQDNQFQGK WYVVGLAGNA ILAEDKDPQK MYATIYELKE  60
DKSYNVTSVL FAKKKCDYWI RTFVPGCQPG EFTLGNIKSY PGLTSYLVRV VSTNYNQHAM  120
VFFKKVSQNR EYFKITLYGA TAELTSELKE NFIRFSASLG LPENHIVFPV PIDQCIDG    178
```

-continued

```
SEQ ID NO: 56          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 56
QDSTSDLIPA PPLSKVPLAP DFQDNQFQGK WYVVGLAGNA ILREDKDPQK MYATIYELKE  60
DKSYNVTSVL FRDDGCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 57          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 57
QDSTSDLIPA PPLSKVPLQQ NFQDNQFQGK WYVVGLAGNA ILREDKDPQK MYATIYELKE  60
DGSYNVTSVL FRDDGCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 58          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 58
QDSTSDLIPA PPLSKVPLQQ NFQDNQFQGK WYVVGLAGNA ILREDKDPQK MYATIYELAE  60
DGSYNVTSVL FRDDGCDYWI RTFVPGCQPG EFTLGNIKSY PGLTSYLVRV VSTNYNQHAM  120
VFFKKVSQNR EYFKITLYGR TKELTSELKE NFIRFSKSLG LPEDAIVFPV PIDQCIDG    178

SEQ ID NO: 59          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 59
QDSTSDLIPA PPLSKVPLQQ NFQDNQFQGK WYVVGLAGNA ILREDKDPQK MYATIYELAE  60
DGSYNVTSVL FRDDGCDYWI RTFVPGCQPG EFTLGNIASY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 60          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 60
QDSTSDLIPA PPLSKVPLQQ NFQDNQFQGK WYVVGLAGNA ILREDEDPQK MYATIYELAE  60
DGSYNVTSVL FRDDGCDYWI RTFVPGCQPG EFTLGNIASY PGLTSYLVRV VSTNYNQHAM  120
VFFKKVSESA EYFKITLYGR TKELTSELKE NFIRFSKSLG LPENHIVFPV PIDQCIDG    178

SEQ ID NO: 61          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 61
QDSTSDLIPA PPLSKVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTNYNQHAM  120
VFFKKVSESA EYFKITLYGR TKELTSELKE NFIRFSKSLG LPENHIVFPV PIDQCIDG    178

SEQ ID NO: 62          moltype = AA  length = 178
```

```
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 62
QDSTSDLIPA PPLSKVPLQQ NFQDNQFQGK WYVVGLAGNA ILREDEDPQK MYATIYELAE  60
DGSYNVTSVL FRDDGCDYWI RTFVPGCQPG EFTLGNIASY PGLTSYLVRV VSTDYNQHAM  120
VFFKKVSESA EYFKITLYGR TKELTSELKE NFIRFSKSLG LPENHIVFPV PIDQCIDG    178

SEQ ID NO: 63          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 63
QDSTSDLIPA PPLSKVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTDYNQHAM  120
VFFKKVSESA EYFKITLYGR TKELTSELKE NFIRFSKSLG LPENHIVFPV PIDQCIDG    178

SEQ ID NO: 64          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 64
QDSTSDLIPA PPLSSVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTNYNQHAM  120
VFFKKVSESA EYFKITLYGR TKELTSELAE NFIRFSKSLG LPENHIVFPV PIDQCIDG    178

SEQ ID NO: 65          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 65
QDSTSDLIPA PPLSKVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTNYNQHAM  120
VFFKKVSESA EYFKITLYGR TKELTSELAE NFIRFSKSLG LPENHIVFPV PIDQCIDG    178

SEQ ID NO: 66          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 66
QDSTSDLIPA PPLSSVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTNYNQHAM  120
VFFKKVSESA EYFKITLYGR TKELTSELKE NFIRFSKSLG LPENHIVFPV PIDQCIDG    178

SEQ ID NO: 67          moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 67
QDSTSDLIPA PPLSSVPLQQ NFQDNQFQGK WYVVGLAGNA ILREDEDPQT MYATIYELKE  60
DKSYNVTSVL FADDGCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 68          moltype = AA  length = 178
FEATURE                Location/Qualifiers
```

```
REGION                  1..178
                        note = Description of Artificial Sequence: Synthetic
                         polypeptide
source                  1..178
                        mol_type = protein
                        organism = synthetic construct
SEQUENCE: 68
QDSTSDLIPA PPLSSVPLQQ NFQDNQFQGK WYVVGLAGNA ILREDEDPQK MYATIYELKE  60
DKSYNVTSVL FADDGCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 69           moltype = AA  length = 178
FEATURE                 Location/Qualifiers
REGION                  1..178
                        note = Description of Artificial Sequence: Synthetic
                         polypeptide
VARIANT                 1
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 69
XDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 70           moltype = AA  length = 178
FEATURE                 Location/Qualifiers
REGION                  1..178
                        note = Description of Artificial Sequence: Synthetic
                         polypeptide
VARIANT                 2
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 70
QXSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 71           moltype = AA  length = 178
FEATURE                 Location/Qualifiers
REGION                  1..178
                        note = Description of Artificial Sequence: Synthetic
                         polypeptide
VARIANT                 3
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 71
QDXTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 72           moltype = AA  length = 178
FEATURE                 Location/Qualifiers
REGION                  1..178
                        note = Description of Artificial Sequence: Synthetic
                         polypeptide
VARIANT                 4
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 72
QDSXSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 73           moltype = AA  length = 178
FEATURE                 Location/Qualifiers
REGION                  1..178
                        note = Description of Artificial Sequence: Synthetic
```

```
                         polypeptide
VARIANT                 5
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 73
QDSTXDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 74           moltype = AA  length = 178
FEATURE                 Location/Qualifiers
REGION                  1..178
                        note = Description of Artificial Sequence: Synthetic
                         polypeptide
VARIANT                 6
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 74
QDSTSXLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 75           moltype = AA  length = 178
FEATURE                 Location/Qualifiers
REGION                  1..178
                        note = Description of Artificial Sequence: Synthetic
                         polypeptide
VARIANT                 7
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 75
QDSTSDXIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 76           moltype = AA  length = 178
FEATURE                 Location/Qualifiers
REGION                  1..178
                        note = Description of Artificial Sequence: Synthetic
                         polypeptide
VARIANT                 8
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 76
QDSTSDLXPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 77           moltype = AA  length = 178
FEATURE                 Location/Qualifiers
REGION                  1..178
                        note = Description of Artificial Sequence: Synthetic
                         polypeptide
VARIANT                 9
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 77
QDSTSDLIXA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 78           moltype = AA  length = 178
FEATURE                 Location/Qualifiers
REGION                  1..178
```

```
                        note = Description of Artificial Sequence: Synthetic
                         polypeptide
VARIANT                 10
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 78
QDSTSDLIPX PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 79           moltype = AA  length = 178
FEATURE                 Location/Qualifiers
REGION                  1..178
                        note = Description of Artificial Sequence: Synthetic
                         polypeptide
VARIANT                 11
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 79
QDSTSDLIPA XPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 80           moltype = AA  length = 178
FEATURE                 Location/Qualifiers
REGION                  1..178
                        note = Description of Artificial Sequence: Synthetic
                         polypeptide
VARIANT                 12
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 80
QDSTSDLIPA PXLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 81           moltype = AA  length = 178
FEATURE                 Location/Qualifiers
REGION                  1..178
                        note = Description of Artificial Sequence: Synthetic
                         polypeptide
VARIANT                 13
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 81
QDSTSDLIPA PPXSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 82           moltype = AA  length = 178
FEATURE                 Location/Qualifiers
REGION                  1..178
                        note = Description of Artificial Sequence: Synthetic
                         polypeptide
VARIANT                 14
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 82
QDSTSDLIPA PPLXKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 83           moltype = AA  length = 178
FEATURE                 Location/Qualifiers
```

```
REGION                  1..178
                        note = Description of Artificial Sequence: Synthetic
                         polypeptide
VARIANT                 15
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 83
QDSTSDLIPA PPLSXVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 84           moltype = AA  length = 178
FEATURE                 Location/Qualifiers
REGION                  1..178
                        note = Description of Artificial Sequence: Synthetic
                         polypeptide
VARIANT                 16
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 84
QDSTSDLIPA PPLSKXPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 85           moltype = AA  length = 178
FEATURE                 Location/Qualifiers
REGION                  1..178
                        note = Description of Artificial Sequence: Synthetic
                         polypeptide
VARIANT                 17
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 85
QDSTSDLIPA PPLSKVXLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 86           moltype = AA  length = 178
FEATURE                 Location/Qualifiers
REGION                  1..178
                        note = Description of Artificial Sequence: Synthetic
                         polypeptide
VARIANT                 18
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 86
QDSTSDLIPA PPLSKVPXQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 87           moltype = AA  length = 178
FEATURE                 Location/Qualifiers
REGION                  1..178
                        note = Description of Artificial Sequence: Synthetic
                         polypeptide
VARIANT                 19
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 87
QDSTSDLIPA PPLSKVPLXQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 88           moltype = AA  length = 178
```

```
FEATURE                 Location/Qualifiers
REGION                  1..178
                        note = Description of Artificial Sequence: Synthetic
                         polypeptide
VARIANT                 20
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 88
QDSTSDLIPA PPLSKVPLQX NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 89           moltype = AA  length = 178
FEATURE                 Location/Qualifiers
REGION                  1..178
                        note = Description of Artificial Sequence: Synthetic
                         polypeptide
VARIANT                 21
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 89
QDSTSDLIPA PPLSKVPLQQ XFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 90           moltype = AA  length = 178
FEATURE                 Location/Qualifiers
REGION                  1..178
                        note = Description of Artificial Sequence: Synthetic
                         polypeptide
VARIANT                 22
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 90
QDSTSDLIPA PPLSKVPLQQ NXQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 91           moltype = AA  length = 178
FEATURE                 Location/Qualifiers
REGION                  1..178
                        note = Description of Artificial Sequence: Synthetic
                         polypeptide
VARIANT                 23
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 91
QDSTSDLIPA PPLSKVPLQQ NFXDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 92           moltype = AA  length = 178
FEATURE                 Location/Qualifiers
REGION                  1..178
                        note = Description of Artificial Sequence: Synthetic
                         polypeptide
VARIANT                 24
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 92
QDSTSDLIPA PPLSKVPLQQ NFQXNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178
```

```
SEQ ID NO: 93          moltype = AA  length = 178
FEATURE                Location/Qualifiers
REGION                 1..178
                       note = Description of Artificial Sequence: Synthetic
                        polypeptide
VARIANT                25
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 93
QDSTSDLIPA PPLSKVPLQQ NFQDXQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 94          moltype = AA  length = 178
FEATURE                Location/Qualifiers
REGION                 1..178
                       note = Description of Artificial Sequence: Synthetic
                        polypeptide
VARIANT                26
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 94
QDSTSDLIPA PPLSKVPLQQ NFQDNXFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 95          moltype = AA  length = 178
FEATURE                Location/Qualifiers
REGION                 1..178
                       note = Description of Artificial Sequence: Synthetic
                        polypeptide
VARIANT                27
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 95
QDSTSDLIPA PPLSKVPLQQ NFQDNQXQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 96          moltype = AA  length = 178
FEATURE                Location/Qualifiers
REGION                 1..178
                       note = Description of Artificial Sequence: Synthetic
                        polypeptide
VARIANT                28
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 96
QDSTSDLIPA PPLSKVPLQQ NFQDNQFXGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 97          moltype = AA  length = 178
FEATURE                Location/Qualifiers
REGION                 1..178
                       note = Description of Artificial Sequence: Synthetic
                        polypeptide
VARIANT                29
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 97
QDSTSDLIPA PPLSKVPLQQ NFQDNQFQXK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178
```

```
SEQ ID NO: 98          moltype = AA  length = 178
FEATURE                Location/Qualifiers
REGION                 1..178
                       note = Description of Artificial Sequence: Synthetic
                        polypeptide
VARIANT                30
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 98
QDSTSDLIPA PPLSKVPLQQ NFQDNQFQGX WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 99          moltype = AA  length = 178
FEATURE                Location/Qualifiers
REGION                 1..178
                       note = Description of Artificial Sequence: Synthetic
                        polypeptide
VARIANT                31
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 99
QDSTSDLIPA PPLSKVPLQQ NFQDNQFQGK XYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 100         moltype = AA  length = 178
FEATURE                Location/Qualifiers
REGION                 1..178
                       note = Description of Artificial Sequence: Synthetic
                        polypeptide
VARIANT                32
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 100
QDSTSDLIPA PPLSKVPLQQ NFQDNQFQGK WXVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 101         moltype = AA  length = 178
FEATURE                Location/Qualifiers
REGION                 1..178
                       note = Description of Artificial Sequence: Synthetic
                        polypeptide
VARIANT                33
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 101
QDSTSDLIPA PPLSKVPLQQ NFQDNQFQGK WYXVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 102         moltype = AA  length = 178
FEATURE                Location/Qualifiers
REGION                 1..178
                       note = Description of Artificial Sequence: Synthetic
                        polypeptide
VARIANT                34
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 102
QDSTSDLIPA PPLSKVPLQQ NFQDNQFQGK WYVXGLAGNA ILREDKDPQK MYATIYELKE  60
DKSYNVTSVL FRKKKCDYWI RTFVPGCQPG EFTLGNIKSY PGLTSYLVRV VSTNYNQHAM  120
```

```
VFFKKVSQNR EYFKITLYGR TKELTSELKE NFIRFSKSLG LPENHIVFPV PIDQCIDG    178

SEQ ID NO: 103         moltype = AA  length = 178
FEATURE                Location/Qualifiers
REGION                 1..178
                       note = Description of Artificial Sequence: Synthetic
                        polypeptide
VARIANT                35
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 103
QDSTSDLIPA PPLSKVPLQQ NFQDNQFQGK WYVVXLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 104         moltype = AA  length = 178
FEATURE                Location/Qualifiers
REGION                 1..178
                       note = Description of Artificial Sequence: Synthetic
                        polypeptide
VARIANT                36
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 104
QDSTSDLIPA PPLSKVPLQQ NFQDNQFQGK WYVVGXAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 105         moltype = AA  length = 178
FEATURE                Location/Qualifiers
REGION                 1..178
                       note = Description of Artificial Sequence: Synthetic
                        polypeptide
VARIANT                37
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 105
QDSTSDLIPA PPLSKVPLQQ NFQDNQFQGK WYVVGLXGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 106         moltype = AA  length = 178
FEATURE                Location/Qualifiers
REGION                 1..178
                       note = Description of Artificial Sequence: Synthetic
                        polypeptide
VARIANT                38
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 106
QDSTSDLIPA PPLSKVPLQQ NFQDNQFQGK WYVVGLAXNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 107         moltype = AA  length = 178
FEATURE                Location/Qualifiers
REGION                 1..178
                       note = Description of Artificial Sequence: Synthetic
                        polypeptide
VARIANT                39
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 107
QDSTSDLIPA PPLSKVPLQQ NFQDNQFQGK WYVVGLAGXA ILREDKDPQK MYATIYELKE  60
```

```
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 108         moltype = AA  length = 178
FEATURE                Location/Qualifiers
REGION                 1..178
                       note = Description of Artificial Sequence: Synthetic
                        polypeptide
VARIANT                40
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 108
QDSTSDLIPA PPLSKVPLQQ NFQDNQFQGK WYVVGLAGNX ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 109         moltype = AA  length = 178
FEATURE                Location/Qualifiers
REGION                 1..178
                       note = Description of Artificial Sequence: Synthetic
                        polypeptide
VARIANT                41
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 109
QDSTSDLIPA PPLSKVPLQQ NFQDNQFQGK WYVVGLAGNA XLREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 110         moltype = AA  length = 178
FEATURE                Location/Qualifiers
REGION                 1..178
                       note = Description of Artificial Sequence: Synthetic
                        polypeptide
VARIANT                42
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 110
QDSTSDLIPA PPLSKVPLQQ NFQDNQFQGK WYVVGLAGNA IXREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 111         moltype = AA  length = 178
FEATURE                Location/Qualifiers
REGION                 1..178
                       note = Description of Artificial Sequence: Synthetic
                        polypeptide
VARIANT                43
                       note = MOD_RES - Gln, Ala, Asn, Asp, Cys, Glu, Gly, Ile,
                        Leu, Met, Phe, Pro, Ser, Thr, Trp, Tyr, Val, or Arg
source                 1..178
                       mol_type = protein
                       organism = synthetic construct
SEQUENCE: 111
QDSTSDLIPA PPLSKVPLQQ NFQDNQFQGK WYVVGLAGNA ILXEDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 112         moltype = AA  length = 178
FEATURE                Location/Qualifiers
REGION                 1..178
                       note = Description of Artificial Sequence: Synthetic
                        polypeptide
VARIANT                44
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 112
```

```
QDSTSDLIPA PPLSKVPLQQ NFQDNQFQGK WYVVGLAGNA ILRXDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 113         moltype = AA  length = 178
FEATURE                Location/Qualifiers
REGION                 1..178
                       note = Description of Artificial Sequence: Synthetic
                        polypeptide
VARIANT                45
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 113
QDSTSDLIPA PPLSKVPLQQ NFQDNQFQGK WYVVGLAGNA ILREXKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 114         moltype = AA  length = 178
FEATURE                Location/Qualifiers
REGION                 1..178
                       note = Description of Artificial Sequence: Synthetic
                        polypeptide
VARIANT                46
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 114
QDSTSDLIPA PPLSKVPLQQ NFQDNQFQGK WYVVGLAGNA ILREDXDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 115         moltype = AA  length = 178
FEATURE                Location/Qualifiers
REGION                 1..178
                       note = Description of Artificial Sequence: Synthetic
                        polypeptide
VARIANT                47
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 115
QDSTSDLIPA PPLSKVPLQQ NFQDNQFQGK WYVVGLAGNA ILREDKXPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 116         moltype = AA  length = 178
FEATURE                Location/Qualifiers
REGION                 1..178
                       note = Description of Artificial Sequence: Synthetic
                        polypeptide
VARIANT                48
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 116
QDSTSDLIPA PPLSKVPLQQ NFQDNQFQGK WYVVGLAGNA ILREDKDXQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 117         moltype = AA  length = 178
FEATURE                Location/Qualifiers
REGION                 1..178
                       note = Description of Artificial Sequence: Synthetic
                        polypeptide
VARIANT                49
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
```

```
SEQUENCE: 117
QDSTSDLIPA PPLSKVPLQQ NFQDNQFQGK WYVVGLAGNA ILREDKDPXK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 118         moltype = AA  length = 178
FEATURE                Location/Qualifiers
REGION                 1..178
                       note = Description of Artificial Sequence: Synthetic
                        polypeptide
VARIANT                50
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 118
QDSTSDLIPA PPLSKVPLQQ NFQDNQFQGK WYVVGLAGNA ILREDKDPQX MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 119         moltype = AA  length = 178
FEATURE                Location/Qualifiers
REGION                 1..178
                       note = Description of Artificial Sequence: Synthetic
                        polypeptide
VARIANT                51
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 119
QDSTSDLIPA PPLSKVPLQQ NFQDNQFQGK WYVVGLAGNA ILREDKDPQK XYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 120         moltype = AA  length = 178
FEATURE                Location/Qualifiers
REGION                 1..178
                       note = Description of Artificial Sequence: Synthetic
                        polypeptide
VARIANT                52
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 120
QDSTSDLIPA PPLSKVPLQQ NFQDNQFQGK WYVVGLAGNA ILREDKDPQK MXATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 121         moltype = AA  length = 178
FEATURE                Location/Qualifiers
REGION                 1..178
                       note = Description of Artificial Sequence: Synthetic
                        polypeptide
VARIANT                53
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 121
QDSTSDLIPA PPLSKVPLQQ NFQDNQFQGK WYVVGLAGNA ILREDKDPQK MYXTIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 122         moltype = AA  length = 178
FEATURE                Location/Qualifiers
REGION                 1..178
                       note = Description of Artificial Sequence: Synthetic
                        polypeptide
VARIANT                54
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
```

```
                         organism = synthetic construct
SEQUENCE: 122
QDSTSDLIPA PPLSKVPLQQ NFQDNQFQGK WYVVGLAGNA ILREDKDPQK MYAXIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 123           moltype = AA  length = 178
FEATURE                  Location/Qualifiers
REGION                   1..178
                         note = Description of Artificial Sequence: Synthetic
                          polypeptide
VARIANT                  55
                         note = MOD_RES - Gln, Ala, Asn, Asp, Cys, Glu, Gly, Ile,
                          Leu, Met, Phe, Pro, Ser, Thr, Trp, Tyr, or Val
source                   1..178
                         mol_type = protein
                         organism = synthetic construct
SEQUENCE: 123
QDSTSDLIPA PPLSKVPLQQ NFQDNQFQGK WYVVGLAGNA ILREDKDPQK MYATXYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 124           moltype = AA  length = 178
FEATURE                  Location/Qualifiers
REGION                   1..178
                         note = Description of Artificial Sequence: Synthetic
                          polypeptide
VARIANT                  56
                         note = MOD_RES - Gln, Ala, Asn, Asp, Cys, Glu, Gly, Ile,
                          Leu, Met, Phe, Pro, Ser, Thr, Trp, Tyr, or Val
source                   1..178
                         mol_type = protein
                         organism = synthetic construct
SEQUENCE: 124
QDSTSDLIPA PPLSKVPLQQ NFQDNQFQGK WYVVGLAGNA ILREDKDPQK MYATIXELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 125           moltype = AA  length = 178
FEATURE                  Location/Qualifiers
REGION                   1..178
                         note = Description of Artificial Sequence: Synthetic
                          polypeptide
VARIANT                  57
                         note = MOD_RES - Gln, Ala, Asn, Asp, Cys, Glu, Gly, Ile,
                          Leu, Met, Phe, Pro, Ser, Thr, Trp, Tyr, or Val
source                   1..178
                         mol_type = protein
                         organism = synthetic construct
SEQUENCE: 125
QDSTSDLIPA PPLSKVPLQQ NFQDNQFQGK WYVVGLAGNA ILREDKDPQK MYATIYXLKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 126           moltype = AA  length = 178
FEATURE                  Location/Qualifiers
REGION                   1..178
                         note = Description of Artificial Sequence: Synthetic
                          polypeptide
VARIANT                  58
                         note = MOD_RES - Gln, Ala, Asn, Asp, Cys, Glu, Gly, Ile,
                          Leu, Met, Phe, Pro, Ser, Thr, Trp, Tyr, or Val
source                   1..178
                         mol_type = protein
                         organism = synthetic construct
SEQUENCE: 126
QDSTSDLIPA PPLSKVPLQQ NFQDNQFQGK WYVVGLAGNA ILREDKDPQK MYATIYEXKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 127           moltype = AA  length = 178
FEATURE                  Location/Qualifiers
REGION                   1..178
                         note = Description of Artificial Sequence: Synthetic
                          polypeptide
VARIANT                  59
                         note = MOD_RES - Gln, Ala, Asn, Asp, Cys, Glu, Gly, Ile,
                          Leu, Met, Phe, Pro, Ser, Thr, Trp, Tyr, Val, or Lys
source                   1..178
```

```
                        mol_type = protein
                        organism = synthetic construct
SEQUENCE: 127
QDSTSDLIPA PPLSKVPLQQ NFQDNQFQGK WYVVGLAGNA ILREDKDPQK MYATIYELXE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 128          moltype = AA  length = 178
FEATURE                 Location/Qualifiers
REGION                  1..178
                        note = Description of Artificial Sequence: Synthetic
                         polypeptide
VARIANT                 60
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 128
QDSTSDLIPA PPLSKVPLQQ NFQDNQFQGK WYVVGLAGNA ILREDKDPQK MYATIYELKX  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 129          moltype = AA  length = 178
FEATURE                 Location/Qualifiers
REGION                  1..178
                        note = Description of Artificial Sequence: Synthetic
                         polypeptide
VARIANT                 61
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 129
QDSTSDLIPA PPLSKVPLQQ NFQDNQFQGK WYVVGLAGNA ILREDKDPQK MYATIYELKE  60
XKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 130          moltype = AA  length = 178
FEATURE                 Location/Qualifiers
REGION                  1..178
                        note = Description of Artificial Sequence: Synthetic
                         polypeptide
VARIANT                 62
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 130
QDSTSDLIPA PPLSKVPLQQ NFQDNQFQGK WYVVGLAGNA ILREDKDPQK MYATIYELKE  60
DXSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 131          moltype = AA  length = 178
FEATURE                 Location/Qualifiers
REGION                  1..178
                        note = Description of Artificial Sequence: Synthetic
                         polypeptide
VARIANT                 63
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 131
QDSTSDLIPA PPLSKVPLQQ NFQDNQFQGK WYVVGLAGNA ILREDKDPQK MYATIYELKE  60
DKXYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 132          moltype = AA  length = 178
FEATURE                 Location/Qualifiers
REGION                  1..178
                        note = Description of Artificial Sequence: Synthetic
                         polypeptide
VARIANT                 64
                        note = MOD_RES - Gln, Ala, Asn, Asp, Cys, Glu, Gly, Ile,
                         Leu, Met, Phe, Pro, Ser, Thr, Trp, Tyr, or Val
```

```
source                 1..178
                       mol_type = protein
                       organism = synthetic construct
SEQUENCE: 132
QDSTSDLIPA PPLSKVPLQQ NFQDNQFQGK WYVVGLAGNA ILREDKDPQK MYATIYELKE  60
DKSXNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 133         moltype = AA  length = 178
FEATURE                Location/Qualifiers
REGION                 1..178
                       note = Description of Artificial Sequence: Synthetic
                        polypeptide
VARIANT                65
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 133
QDSTSDLIPA PPLSKVPLQQ NFQDNQFQGK WYVVGLAGNA ILREDKDPQK MYATIYELKE  60
DKSYXVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 134         moltype = AA  length = 178
FEATURE                Location/Qualifiers
REGION                 1..178
                       note = Description of Artificial Sequence: Synthetic
                        polypeptide
VARIANT                66
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 134
QDSTSDLIPA PPLSKVPLQQ NFQDNQFQGK WYVVGLAGNA ILREDKDPQK MYATIYELKE  60
DKSYNXTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 135         moltype = AA  length = 178
FEATURE                Location/Qualifiers
REGION                 1..178
                       note = Description of Artificial Sequence: Synthetic
                        polypeptide
VARIANT                67
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 135
QDSTSDLIPA PPLSKVPLQQ NFQDNQFQGK WYVVGLAGNA ILREDKDPQK MYATIYELKE  60
DKSYNVXSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 136         moltype = AA  length = 178
FEATURE                Location/Qualifiers
REGION                 1..178
                       note = Description of Artificial Sequence: Synthetic
                        polypeptide
VARIANT                68
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 136
QDSTSDLIPA PPLSKVPLQQ NFQDNQFQGK WYVVGLAGNA ILREDKDPQK MYATIYELKE  60
DKSYNVTXVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 137         moltype = AA  length = 178
FEATURE                Location/Qualifiers
REGION                 1..178
                       note = Description of Artificial Sequence: Synthetic
                        polypeptide
VARIANT                69
                       note = MOD_RES - Gln, Ala, Asn, Asp, Cys, Glu, Gly, Ile,
```

```
                         Leu, Met, Phe, Pro, Ser, Thr, Trp, Tyr, or Val
source                  1..178
                        mol_type = protein
                        organism = synthetic construct
SEQUENCE: 137
QDSTSDLIPA PPLSKVPLQQ NFQDNQFQGK WYVVGLAGNA ILREDKDPQK MYATIYELKE  60
DKSYNVTSXL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 138          moltype = AA  length = 178
FEATURE                 Location/Qualifiers
REGION                  1..178
                        note = Description of Artificial Sequence: Synthetic
                         polypeptide
VARIANT                 70
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 138
QDSTSDLIPA PPLSKVPLQQ NFQDNQFQGK WYVVGLAGNA ILREDKDPQK MYATIYELKE  60
DKSYNVTSVX FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 139          moltype = AA  length = 178
FEATURE                 Location/Qualifiers
REGION                  1..178
                        note = Description of Artificial Sequence: Synthetic
                         polypeptide
VARIANT                 71
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 139
QDSTSDLIPA PPLSKVPLQQ NFQDNQFQGK WYVVGLAGNA ILREDKDPQK MYATIYELKE  60
DKSYNVTSVL XRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 140          moltype = AA  length = 178
FEATURE                 Location/Qualifiers
REGION                  1..178
                        note = Description of Artificial Sequence: Synthetic
                         polypeptide
VARIANT                 72
                        note = MOD_RES - Gln, Ala, Asn, Asp, Cys, Glu, Gly, Ile,
                         Leu, Met, Phe, Pro, Ser, Thr, Trp, Tyr, Val, or Arg
source                  1..178
                        mol_type = protein
                        organism = synthetic construct
SEQUENCE: 140
QDSTSDLIPA PPLSKVPLQQ NFQDNQFQGK WYVVGLAGNA ILREDKDPQK MYATIYELKE  60
DKSYNVTSVL FXKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 141          moltype = AA  length = 178
FEATURE                 Location/Qualifiers
REGION                  1..178
                        note = Description of Artificial Sequence: Synthetic
                         polypeptide
VARIANT                 73
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 141
QDSTSDLIPA PPLSKVPLQQ NFQDNQFQGK WYVVGLAGNA ILREDKDPQK MYATIYELKE  60
DKSYNVTSVL FRXKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 142          moltype = AA  length = 178
FEATURE                 Location/Qualifiers
REGION                  1..178
                        note = Description of Artificial Sequence: Synthetic
                         polypeptide
VARIANT                 74
```

```
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 142
QDSTSDLIPA PPLSKVPLQQ NFQDNQFQGK WYVVGLAGNA ILREDKDPQK MYATIYELKE  60
DKSYNVTSVL FRKXKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 143          moltype = AA  length = 178
FEATURE                 Location/Qualifiers
REGION                  1..178
                        note = Description of Artificial Sequence: Synthetic
                         polypeptide
VARIANT                 75
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 143
QDSTSDLIPA PPLSKVPLQQ NFQDNQFQGK WYVVGLAGNA ILREDKDPQK MYATIYELKE  60
DKSYNVTSVL FRKKXCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 144          moltype = AA  length = 178
FEATURE                 Location/Qualifiers
REGION                  1..178
                        note = Description of Artificial Sequence: Synthetic
                         polypeptide
VARIANT                 76
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 144
QDSTSDLIPA PPLSKVPLQQ NFQDNQFQGK WYVVGLAGNA ILREDKDPQK MYATIYELKE  60
DKSYNVTSVL FRKKKXDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 145          moltype = AA  length = 178
FEATURE                 Location/Qualifiers
REGION                  1..178
                        note = Description of Artificial Sequence: Synthetic
                         polypeptide
VARIANT                 77
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 145
QDSTSDLIPA PPLSKVPLQQ NFQDNQFQGK WYVVGLAGNA ILREDKDPQK MYATIYELKE  60
DKSYNVTSVL FRKKKCXYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 146          moltype = AA  length = 178
FEATURE                 Location/Qualifiers
REGION                  1..178
                        note = Description of Artificial Sequence: Synthetic
                         polypeptide
VARIANT                 78
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 146
QDSTSDLIPA PPLSKVPLQQ NFQDNQFQGK WYVVGLAGNA ILREDKDPQK MYATIYELKE  60
DKSYNVTSVL FRKKKCDXWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 147          moltype = AA  length = 178
FEATURE                 Location/Qualifiers
REGION                  1..178
                        note = Description of Artificial Sequence: Synthetic
                         polypeptide
```

```
VARIANT                 79
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 147
QDSTSDLIPA PPLSKVPLQQ NFQDNQFQGK WYVVGLAGNA ILREDKDPQK MYATIYELKE  60
DKSYNVTSVL FRKKKCDYXI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 148          moltype = AA  length = 178
FEATURE                 Location/Qualifiers
REGION                  1..178
                        note = Description of Artificial Sequence: Synthetic
                         polypeptide
VARIANT                 80
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 148
QDSTSDLIPA PPLSKVPLQQ NFQDNQFQGK WYVVGLAGNA ILREDKDPQK MYATIYELKE  60
DKSYNVTSVL FRKKKCDYWX RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 149          moltype = AA  length = 178
FEATURE                 Location/Qualifiers
REGION                  1..178
                        note = Description of Artificial Sequence: Synthetic
                         polypeptide
VARIANT                 81
                        note = MOD_RES - Gln, Ala, Asn, Asp, Cys, Glu, Gly, Ile,
                         Leu, Met, Phe, Pro, Ser, Thr, Trp, Tyr, Val, or Arg
source                  1..178
                        mol_type = protein
                        organism = synthetic construct
SEQUENCE: 149
QDSTSDLIPA PPLSKVPLQQ NFQDNQFQGK WYVVGLAGNA ILREDKDPQK MYATIYELKE  60
DKSYNVTSVL FRKKKCDYWI XTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 150          moltype = AA  length = 178
FEATURE                 Location/Qualifiers
REGION                  1..178
                        note = Description of Artificial Sequence: Synthetic
                         polypeptide
VARIANT                 82
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 150
QDSTSDLIPA PPLSKVPLQQ NFQDNQFQGK WYVVGLAGNA ILREDKDPQK MYATIYELKE  60
DKSYNVTSVL FRKKKCDYWI RXFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 151          moltype = AA  length = 178
FEATURE                 Location/Qualifiers
REGION                  1..178
                        note = Description of Artificial Sequence: Synthetic
                         polypeptide
VARIANT                 83
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 151
QDSTSDLIPA PPLSKVPLQQ NFQDNQFQGK WYVVGLAGNA ILREDKDPQK MYATIYELKE  60
DKSYNVTSVL FRKKKCDYWI RTXVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 152          moltype = AA  length = 178
FEATURE                 Location/Qualifiers
REGION                  1..178
                        note = Description of Artificial Sequence: Synthetic
```

```
                        polypeptide
VARIANT                 84
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 152
QDSTSDLIPA PPLSKVPLQQ NFQDNQFQGK WYVVGLAGNA ILREDKDPQK MYATIYELKE  60
DKSYNVTSVL FRKKKCDYWI RTFXPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 153          moltype = AA  length = 178
FEATURE                 Location/Qualifiers
REGION                  1..178
                        note = Description of Artificial Sequence: Synthetic
                         polypeptide
VARIANT                 85
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 153
QDSTSDLIPA PPLSKVPLQQ NFQDNQFQGK WYVVGLAGNA ILREDKDPQK MYATIYELKE  60
DKSYNVTSVL FRKKKCDYWI RTFVXGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 154          moltype = AA  length = 178
FEATURE                 Location/Qualifiers
REGION                  1..178
                        note = Description of Artificial Sequence: Synthetic
                         polypeptide
VARIANT                 86
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 154
QDSTSDLIPA PPLSKVPLQQ NFQDNQFQGK WYVVGLAGNA ILREDKDPQK MYATIYELKE  60
DKSYNVTSVL FRKKKCDYWI RTFVPXCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 155          moltype = AA  length = 178
FEATURE                 Location/Qualifiers
REGION                  1..178
                        note = Description of Artificial Sequence: Synthetic
                         polypeptide
VARIANT                 87
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 155
QDSTSDLIPA PPLSKVPLQQ NFQDNQFQGK WYVVGLAGNA ILREDKDPQK MYATIYELKE  60
DKSYNVTSVL FRKKKCDYWI RTFVPGXQPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 156          moltype = AA  length = 178
FEATURE                 Location/Qualifiers
REGION                  1..178
                        note = Description of Artificial Sequence: Synthetic
                         polypeptide
VARIANT                 88
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 156
QDSTSDLIPA PPLSKVPLQQ NFQDNQFQGK WYVVGLAGNA ILREDKDPQK MYATIYELKE  60
DKSYNVTSVL FRKKKCDYWI RTFVPGCXPG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 157          moltype = AA  length = 178
FEATURE                 Location/Qualifiers
REGION                  1..178
```

```
                          note = Description of Artificial Sequence: Synthetic
                           polypeptide
VARIANT                   89
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 157
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQXG EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 158            moltype = AA  length = 178
FEATURE                   Location/Qualifiers
REGION                    1..178
                          note = Description of Artificial Sequence: Synthetic
                           polypeptide
VARIANT                   90
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 158
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPX EFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 159            moltype = AA  length = 178
FEATURE                   Location/Qualifiers
REGION                    1..178
                          note = Description of Artificial Sequence: Synthetic
                           polypeptide
VARIANT                   91
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 159
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG XFTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 160            moltype = AA  length = 178
FEATURE                   Location/Qualifiers
REGION                    1..178
                          note = Description of Artificial Sequence: Synthetic
                           polypeptide
VARIANT                   92
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 160
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EXTLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 161            moltype = AA  length = 178
FEATURE                   Location/Qualifiers
REGION                    1..178
                          note = Description of Artificial Sequence: Synthetic
                           polypeptide
VARIANT                   93
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 161
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFXLGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 162            moltype = AA  length = 178
FEATURE                   Location/Qualifiers
```

```
REGION                  1..178
                        note = Description of Artificial Sequence: Synthetic
                         polypeptide
VARIANT                 94
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 162
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTXGNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 163          moltype = AA  length = 178
FEATURE                 Location/Qualifiers
REGION                  1..178
                        note = Description of Artificial Sequence: Synthetic
                         polypeptide
VARIANT                 95
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 163
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLXNIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 164          moltype = AA  length = 178
FEATURE                 Location/Qualifiers
REGION                  1..178
                        note = Description of Artificial Sequence: Synthetic
                         polypeptide
VARIANT                 96
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 164
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGXIKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 165          moltype = AA  length = 178
FEATURE                 Location/Qualifiers
REGION                  1..178
                        note = Description of Artificial Sequence: Synthetic
                         polypeptide
VARIANT                 97
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 165
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNXKSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 166          moltype = AA  length = 178
FEATURE                 Location/Qualifiers
REGION                  1..178
                        note = Description of Artificial Sequence: Synthetic
                         polypeptide
VARIANT                 98
                        note = MOD_RES - Gln, Ala, Asn, Asp, Cys, Glu, Gly, Ile,
                         Leu, Met, Phe, Pro, Ser, Thr, Trp, Tyr, Val, or Lys
source                  1..178
                        mol_type = protein
                        organism = synthetic construct
SEQUENCE: 166
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIXSY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 167          moltype = AA  length = 178
```

```
FEATURE                Location/Qualifiers
REGION                 1..178
                       note = Description of Artificial Sequence: Synthetic
                        polypeptide
VARIANT                99
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 167
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKXY PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 168         moltype = AA  length = 178
FEATURE                Location/Qualifiers
REGION                 1..178
                       note = Description of Artificial Sequence: Synthetic
                        polypeptide
VARIANT                100
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 168
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSX PGLTSYLVRV VSTNYNQHAM  120
VFFKKVSQNR EYFKITLYGR TKELTSELKE NFIRFSKSLG LPENHIVFPV PIDQCIDG    178

SEQ ID NO: 169         moltype = AA  length = 178
FEATURE                Location/Qualifiers
REGION                 1..178
                       note = Description of Artificial Sequence: Synthetic
                        polypeptide
VARIANT                101
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 169
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY XGLTSYLVRV VSTNYNQHAM  120
VFFKKVSQNR EYFKITLYGR TKELTSELKE NFIRFSKSLG LPENHIVFPV PIDQCIDG    178

SEQ ID NO: 170         moltype = AA  length = 178
FEATURE                Location/Qualifiers
REGION                 1..178
                       note = Description of Artificial Sequence: Synthetic
                        polypeptide
VARIANT                102
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 170
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PXLTSYLVRV VSTNYNQHAM  120
VFFKKVSQNR EYFKITLYGR TKELTSELKE NFIRFSKSLG LPENHIVFPV PIDQCIDG    178

SEQ ID NO: 171         moltype = AA  length = 178
FEATURE                Location/Qualifiers
REGION                 1..178
                       note = Description of Artificial Sequence: Synthetic
                        polypeptide
VARIANT                103
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 171
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGXTSYLVRV VSTNYNQHAM  120
VFFKKVSQNR EYFKITLYGR TKELTSELKE NFIRFSKSLG LPENHIVFPV PIDQCIDG    178
```

```
SEQ ID NO: 172         moltype = AA  length = 178
FEATURE                Location/Qualifiers
REGION                 1..178
                       note = Description of Artificial Sequence: Synthetic
                        polypeptide
VARIANT                104
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 172
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLXSYLVRV VSTNYNQHAM  120
VFFKKVSQNR EYFKITLYGR TKELTSELKE NFIRFSKSLG LPENHIVFPV PIDQCIDG    178

SEQ ID NO: 173         moltype = AA  length = 178
FEATURE                Location/Qualifiers
REGION                 1..178
                       note = Description of Artificial Sequence: Synthetic
                        polypeptide
VARIANT                105
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 173
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTXYLVRV VSTNYNQHAM  120
VFFKKVSQNR EYFKITLYGR TKELTSELKE NFIRFSKSLG LPENHIVFPV PIDQCIDG    178

SEQ ID NO: 174         moltype = AA  length = 178
FEATURE                Location/Qualifiers
REGION                 1..178
                       note = Description of Artificial Sequence: Synthetic
                        polypeptide
VARIANT                106
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 174
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSXLVRV VSTNYNQHAM  120
VFFKKVSQNR EYFKITLYGR TKELTSELKE NFIRFSKSLG LPENHIVFPV PIDQCIDG    178

SEQ ID NO: 175         moltype = AA  length = 178
FEATURE                Location/Qualifiers
REGION                 1..178
                       note = Description of Artificial Sequence: Synthetic
                        polypeptide
VARIANT                107
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 175
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYXVRV VSTNYNQHAM  120
VFFKKVSQNR EYFKITLYGR TKELTSELKE NFIRFSKSLG LPENHIVFPV PIDQCIDG    178

SEQ ID NO: 176         moltype = AA  length = 178
FEATURE                Location/Qualifiers
REGION                 1..178
                       note = Description of Artificial Sequence: Synthetic
                        polypeptide
VARIANT                108
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 176
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLXRV VSTNYNQHAM  120
VFFKKVSQNR EYFKITLYGR TKELTSELKE NFIRFSKSLG LPENHIVFPV PIDQCIDG    178
```

```
SEQ ID NO: 177         moltype = AA  length = 178
FEATURE                Location/Qualifiers
REGION                 1..178
                       note = Description of Artificial Sequence: Synthetic
                        polypeptide
VARIANT                109
                       note = MOD_RES - Gln, Ala, Asn, Asp, Cys, Glu, Gly, Ile,
                        Leu, Met, Phe, Pro, Ser, Thr, Trp, Tyr, Val, or Arg
source                 1..178
                       mol_type = protein
                       organism = synthetic construct
SEQUENCE: 177
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVXV VSTNYNQHAM  120
VFFKKVSQNR EYFKITLYGR TKELTSELKE NFIRFSKSLG LPENHIVFPV PIDQCIDG    178

SEQ ID NO: 178         moltype = AA  length = 178
FEATURE                Location/Qualifiers
REGION                 1..178
                       note = Description of Artificial Sequence: Synthetic
                        polypeptide
VARIANT                110
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 178
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRX VSTNYNQHAM  120
VFFKKVSQNR EYFKITLYGR TKELTSELKE NFIRFSKSLG LPENHIVFPV PIDQCIDG    178

SEQ ID NO: 179         moltype = AA  length = 178
FEATURE                Location/Qualifiers
REGION                 1..178
                       note = Description of Artificial Sequence: Synthetic
                        polypeptide
VARIANT                111
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 179
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV XSTNYNQHAM  120
VFFKKVSQNR EYFKITLYGR TKELTSELKE NFIRFSKSLG LPENHIVFPV PIDQCIDG    178

SEQ ID NO: 180         moltype = AA  length = 178
FEATURE                Location/Qualifiers
REGION                 1..178
                       note = Description of Artificial Sequence: Synthetic
                        polypeptide
VARIANT                112
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 180
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VXTNYNQHAM  120
VFFKKVSQNR EYFKITLYGR TKELTSELKE NFIRFSKSLG LPENHIVFPV PIDQCIDG    178

SEQ ID NO: 181         moltype = AA  length = 178
FEATURE                Location/Qualifiers
REGION                 1..178
                       note = Description of Artificial Sequence: Synthetic
                        polypeptide
VARIANT                113
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 181
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSXNYNQHAM  120
```

```
VFFKKVSQNR EYFKITLYGR TKELTSELKE NFIRFSKSLG LPENHIVFPV PIDQCIDG    178

SEQ ID NO: 182         moltype = AA  length = 178
FEATURE                Location/Qualifiers
REGION                 1..178
                       note = Description of Artificial Sequence: Synthetic
                        polypeptide
VARIANT                114
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 182
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTXYNQHAM  120
VFFKKVSQNR EYFKITLYGR TKELTSELKE NFIRFSKSLG LPENHIVFPV PIDQCIDG    178

SEQ ID NO: 183         moltype = AA  length = 178
FEATURE                Location/Qualifiers
REGION                 1..178
                       note = Description of Artificial Sequence: Synthetic
                        polypeptide
VARIANT                115
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 183
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNXNQHAM  120
VFFKKVSQNR EYFKITLYGR TKELTSELKE NFIRFSKSLG LPENHIVFPV PIDQCIDG    178

SEQ ID NO: 184         moltype = AA  length = 178
FEATURE                Location/Qualifiers
REGION                 1..178
                       note = Description of Artificial Sequence: Synthetic
                        polypeptide
VARIANT                116
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 184
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYXQHAM  120
VFFKKVSQNR EYFKITLYGR TKELTSELKE NFIRFSKSLG LPENHIVFPV PIDQCIDG    178

SEQ ID NO: 185         moltype = AA  length = 178
FEATURE                Location/Qualifiers
REGION                 1..178
                       note = Description of Artificial Sequence: Synthetic
                        polypeptide
VARIANT                117
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 185
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNXHAM  120
VFFKKVSQNR EYFKITLYGR TKELTSELKE NFIRFSKSLG LPENHIVFPV PIDQCIDG    178

SEQ ID NO: 186         moltype = AA  length = 178
FEATURE                Location/Qualifiers
REGION                 1..178
                       note = Description of Artificial Sequence: Synthetic
                        polypeptide
VARIANT                118
                       note = MOD_RES - Gln, Ala, Asn, Asp, Cys, Glu, Gly, Ile,
                        Leu, Met, Phe, Pro, Ser, Thr, Trp, Tyr, Val, or His
source                 1..178
                       mol_type = protein
                       organism = synthetic construct
SEQUENCE: 186
QDSTSDLIPA PPLSKVPLQQ NFQDNQFQGK WYVVGLAGNA ILREDKDPQK MYATIYELKE  60
```

```
DKSYNVTSVL FRKKKCDYWI RTFVPGCQPG EFTLGNIKSY PGLTSYLVRV VSTNYNQXAM  120
VFFKKVSQNR EYFKITLYGR TKELTSELKE NFIRFSKSLG LPENHIVFPV PIDQCIDG    178

SEQ ID NO: 187         moltype = AA  length = 178
FEATURE                Location/Qualifiers
REGION                 1..178
                       note = Description of Artificial Sequence: Synthetic
                        polypeptide
VARIANT                119
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 187
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHXM  120
VFFKKVSQNR EYFKITLYGR TKELTSELKE NFIRFSKSLG LPENHIVFPV PIDQCIDG    178

SEQ ID NO: 188         moltype = AA  length = 178
FEATURE                Location/Qualifiers
REGION                 1..178
                       note = Description of Artificial Sequence: Synthetic
                        polypeptide
VARIANT                120
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 188
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAX  120
VFFKKVSQNR EYFKITLYGR TKELTSELKE NFIRFSKSLG LPENHIVFPV PIDQCIDG    178

SEQ ID NO: 189         moltype = AA  length = 178
FEATURE                Location/Qualifiers
REGION                 1..178
                       note = Description of Artificial Sequence: Synthetic
                        polypeptide
VARIANT                121
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 189
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
XFFKKVSQNR EYFKITLYGR TKELTSELKE NFIRFSKSLG LPENHIVFPV PIDQCIDG    178

SEQ ID NO: 190         moltype = AA  length = 178
FEATURE                Location/Qualifiers
REGION                 1..178
                       note = Description of Artificial Sequence: Synthetic
                        polypeptide
VARIANT                122
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 190
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VXFKKVSQNR EYFKITLYGR TKELTSELKE NFIRFSKSLG LPENHIVFPV PIDQCIDG    178

SEQ ID NO: 191         moltype = AA  length = 178
FEATURE                Location/Qualifiers
REGION                 1..178
                       note = Description of Artificial Sequence: Synthetic
                        polypeptide
VARIANT                123
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 191
```

```
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFXKKVSQNR EYFKITLYGR TKELTSELKE NFIRFSKSLG LPENHIVFPV PIDQCIDG    178

SEQ ID NO: 192         moltype = AA  length = 178
FEATURE                Location/Qualifiers
REGION                 1..178
                       note = Description of Artificial Sequence: Synthetic
                        polypeptide
VARIANT                124
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 192
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFXKVSQNR EYFKITLYGR TKELTSELKE NFIRFSKSLG LPENHIVFPV PIDQCIDG    178

SEQ ID NO: 193         moltype = AA  length = 178
FEATURE                Location/Qualifiers
REGION                 1..178
                       note = Description of Artificial Sequence: Synthetic
                        polypeptide
VARIANT                125
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 193
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKXVSQNR EYFKITLYGR TKELTSELKE NFIRFSKSLG LPENHIVFPV PIDQCIDG    178

SEQ ID NO: 194         moltype = AA  length = 178
FEATURE                Location/Qualifiers
REGION                 1..178
                       note = Description of Artificial Sequence: Synthetic
                        polypeptide
VARIANT                126
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 194
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKXSQNR EYFKITLYGR TKELTSELKE NFIRFSKSLG LPENHIVFPV PIDQCIDG    178

SEQ ID NO: 195         moltype = AA  length = 178
FEATURE                Location/Qualifiers
REGION                 1..178
                       note = Description of Artificial Sequence: Synthetic
                        polypeptide
VARIANT                127
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 195
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVXQNR EYFKITLYGR TKELTSELKE NFIRFSKSLG LPENHIVFPV PIDQCIDG    178

SEQ ID NO: 196         moltype = AA  length = 178
FEATURE                Location/Qualifiers
REGION                 1..178
                       note = Description of Artificial Sequence: Synthetic
                        polypeptide
VARIANT                128
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
```

```
SEQUENCE: 196
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSXNR EYFKITLYGR TKELTSELKE NFIRFSKSLG LPENHIVFPV PIDQCIDG    178

SEQ ID NO: 197          moltype = AA  length = 178
FEATURE                 Location/Qualifiers
REGION                  1..178
                        note = Description of Artificial Sequence: Synthetic
                         polypeptide
VARIANT                 129
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 197
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQXR EYFKITLYGR TKELTSELKE NFIRFSKSLG LPENHIVFPV PIDQCIDG    178

SEQ ID NO: 198          moltype = AA  length = 178
FEATURE                 Location/Qualifiers
REGION                  1..178
                        note = Description of Artificial Sequence: Synthetic
                         polypeptide
VARIANT                 130
                        note = MOD_RES - Gln, Ala, Asn, Asp, Cys, Glu, Gly, Ile,
                         Leu, Met, Phe, Pro, Ser, Thr, Trp, Tyr, Val, or Arg
source                  1..178
                        mol_type = protein
                        organism = synthetic construct
SEQUENCE: 198
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNX EYFKITLYGR TKELTSELKE NFIRFSKSLG LPENHIVFPV PIDQCIDG    178

SEQ ID NO: 199          moltype = AA  length = 178
FEATURE                 Location/Qualifiers
REGION                  1..178
                        note = Description of Artificial Sequence: Synthetic
                         polypeptide
VARIANT                 131
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 199
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR XYFKITLYGR TKELTSELKE NFIRFSKSLG LPENHIVFPV PIDQCIDG    178

SEQ ID NO: 200          moltype = AA  length = 178
FEATURE                 Location/Qualifiers
REGION                  1..178
                        note = Description of Artificial Sequence: Synthetic
                         polypeptide
VARIANT                 132
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 200
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EXFKITLYGR TKELTSELKE NFIRFSKSLG LPENHIVFPV PIDQCIDG    178

SEQ ID NO: 201          moltype = AA  length = 178
FEATURE                 Location/Qualifiers
REGION                  1..178
                        note = Description of Artificial Sequence: Synthetic
                         polypeptide
VARIANT                 133
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
```

```
                          organism = synthetic construct
SEQUENCE: 201
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYXKITLYGR TKELTSELKE NFIRFSKSLG LPENHIVFPV PIDQCIDG    178

SEQ ID NO: 202            moltype = AA  length = 178
FEATURE                   Location/Qualifiers
REGION                    1..178
                          note = Description of Artificial Sequence: Synthetic
                           polypeptide
VARIANT                   134
                          note = MOD_RES - Gln, Ala, Asn, Asp, Cys, Glu, Gly, Ile,
                           Leu, Met, Phe, Pro, Ser, Thr, Trp, Tyr, Val, or Lys
source                    1..178
                          mol_type = protein
                          organism = synthetic construct
SEQUENCE: 202
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFXITLYGR TKELTSELKE NFIRFSKSLG LPENHIVFPV PIDQCIDG    178

SEQ ID NO: 203            moltype = AA  length = 178
FEATURE                   Location/Qualifiers
REGION                    1..178
                          note = Description of Artificial Sequence: Synthetic
                           polypeptide
VARIANT                   135
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 203
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKXTLYGR TKELTSELKE NFIRFSKSLG LPENHIVFPV PIDQCIDG    178

SEQ ID NO: 204            moltype = AA  length = 178
FEATURE                   Location/Qualifiers
REGION                    1..178
                          note = Description of Artificial Sequence: Synthetic
                           polypeptide
VARIANT                   136
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 204
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKIXLYGR TKELTSELKE NFIRFSKSLG LPENHIVFPV PIDQCIDG    178

SEQ ID NO: 205            moltype = AA  length = 178
FEATURE                   Location/Qualifiers
REGION                    1..178
                          note = Description of Artificial Sequence: Synthetic
                           polypeptide
VARIANT                   137
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 205
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITXYGR TKELTSELKE NFIRFSKSLG LPENHIVFPV PIDQCIDG    178

SEQ ID NO: 206            moltype = AA  length = 178
FEATURE                   Location/Qualifiers
REGION                    1..178
                          note = Description of Artificial Sequence: Synthetic
                           polypeptide
VARIANT                   138
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
```

```
                          mol_type = protein
                          organism = synthetic construct
SEQUENCE: 206
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLXGR TKELTSELKE NFIRFSKSLG LPENHIVFPV PIDQCIDG    178

SEQ ID NO: 207            moltype = AA  length = 178
FEATURE                   Location/Qualifiers
REGION                    1..178
                          note = Description of Artificial Sequence: Synthetic
                           polypeptide
VARIANT                   139
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 207
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYXR TKELTSELKE NFIRFSKSLG LPENHIVFPV PIDQCIDG    178

SEQ ID NO: 208            moltype = AA  length = 178
FEATURE                   Location/Qualifiers
REGION                    1..178
                          note = Description of Artificial Sequence: Synthetic
                           polypeptide
VARIANT                   140
                          note = MOD_RES - Gln, Ala, Asn, Asp, Cys, Glu, Gly, Ile,
                           Leu, Met, Phe, Pro, Ser, Thr, Trp, Tyr, Val, or Arg
source                    1..178
                          mol_type = protein
                          organism = synthetic construct
SEQUENCE: 208
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGX TKELTSELKE NFIRFSKSLG LPENHIVFPV PIDQCIDG    178

SEQ ID NO: 209            moltype = AA  length = 178
FEATURE                   Location/Qualifiers
REGION                    1..178
                          note = Description of Artificial Sequence: Synthetic
                           polypeptide
VARIANT                   141
                          note = MOD_RES - Gln, Ala, Asn, Asp, Cys, Glu, Gly, Ile,
                           Leu, Met, Phe, Pro, Ser, Thr, Trp, Tyr, or Val
source                    1..178
                          mol_type = protein
                          organism = synthetic construct
SEQUENCE: 209
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR XKELTSELKE NFIRFSKSLG LPENHIVFPV PIDQCIDG    178

SEQ ID NO: 210            moltype = AA  length = 178
FEATURE                   Location/Qualifiers
REGION                    1..178
                          note = Description of Artificial Sequence: Synthetic
                           polypeptide
VARIANT                   142
                          note = MOD_RES - Gln, Ala, Asn, Asp, Cys, Glu, Gly, Ile,
                           Leu, Met, Phe, Pro, Ser, Thr, Trp, Tyr, Val, or Lys
source                    1..178
                          mol_type = protein
                          organism = synthetic construct
SEQUENCE: 210
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TXELTSELKE NFIRFSKSLG LPENHIVFPV PIDQCIDG    178

SEQ ID NO: 211            moltype = AA  length = 178
FEATURE                   Location/Qualifiers
REGION                    1..178
                          note = Description of Artificial Sequence: Synthetic
                           polypeptide
VARIANT                   143
                          note = MOD_RES - Gln, Ala, Asn, Asp, Cys, Glu, Gly, Ile,
                           Leu, Met, Phe, Pro, Ser, Thr, Trp, Tyr, or Val
```

```
source                  1..178
                        mol_type = protein
                        organism = synthetic construct
SEQUENCE: 211
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKXLTSELKE NFIRFSKSLG LPENHIVFPV PIDQCIDG    178

SEQ ID NO: 212          moltype = AA  length = 178
FEATURE                 Location/Qualifiers
REGION                  1..178
                        note = Description of Artificial Sequence: Synthetic
                         polypeptide
VARIANT                 144
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 212
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKEXTSELKE NFIRFSKSLG LPENHIVFPV PIDQCIDG    178

SEQ ID NO: 213          moltype = AA  length = 178
FEATURE                 Location/Qualifiers
REGION                  1..178
                        note = Description of Artificial Sequence: Synthetic
                         polypeptide
VARIANT                 145
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 213
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELXSELKE NFIRFSKSLG LPENHIVFPV PIDQCIDG    178

SEQ ID NO: 214          moltype = AA  length = 178
FEATURE                 Location/Qualifiers
REGION                  1..178
                        note = Description of Artificial Sequence: Synthetic
                         polypeptide
VARIANT                 146
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 214
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTXELKE NFIRFSKSLG LPENHIVFPV PIDQCIDG    178

SEQ ID NO: 215          moltype = AA  length = 178
FEATURE                 Location/Qualifiers
REGION                  1..178
                        note = Description of Artificial Sequence: Synthetic
                         polypeptide
VARIANT                 147
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 215
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSXLKE NFIRFSKSLG LPENHIVFPV PIDQCIDG    178

SEQ ID NO: 216          moltype = AA  length = 178
FEATURE                 Location/Qualifiers
REGION                  1..178
                        note = Description of Artificial Sequence: Synthetic
                         polypeptide
VARIANT                 148
                        note = MOD_RES - Gln, Ala, Asn, Asp, Cys, Glu, Gly, Ile,
```

```
                        Leu, Met, Phe, Pro, Ser, Thr, Trp, Tyr, or Val
source                 1..178
                       mol_type = protein
                       organism = synthetic construct
SEQUENCE: 216
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSEXKE NFIRFSKSLG LPENHIVFPV PIDQCIDG    178

SEQ ID NO: 217         moltype = AA  length = 178
FEATURE                Location/Qualifiers
REGION                 1..178
                       note = Description of Artificial Sequence: Synthetic
                        polypeptide
VARIANT                149
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 217
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELXE NFIRFSKSLG LPENHIVFPV PIDQCIDG    178

SEQ ID NO: 218         moltype = AA  length = 178
FEATURE                Location/Qualifiers
REGION                 1..178
                       note = Description of Artificial Sequence: Synthetic
                        polypeptide
VARIANT                150
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 218
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKX NFIRFSKSLG LPENHIVFPV PIDQCIDG    178

SEQ ID NO: 219         moltype = AA  length = 178
FEATURE                Location/Qualifiers
REGION                 1..178
                       note = Description of Artificial Sequence: Synthetic
                        polypeptide
VARIANT                151
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 219
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE XFIRFSKSLG LPENHIVFPV PIDQCIDG    178

SEQ ID NO: 220         moltype = AA  length = 178
FEATURE                Location/Qualifiers
REGION                 1..178
                       note = Description of Artificial Sequence: Synthetic
                        polypeptide
VARIANT                152
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 220
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NXIRFSKSLG LPENHIVFPV PIDQCIDG    178

SEQ ID NO: 221         moltype = AA  length = 178
FEATURE                Location/Qualifiers
REGION                 1..178
                       note = Description of Artificial Sequence: Synthetic
                        polypeptide
VARIANT                153
```

```
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 221
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFXRFSKSLG LPENHIVFPV PIDQCIDG    178

SEQ ID NO: 222         moltype = AA  length = 178
FEATURE                Location/Qualifiers
REGION                 1..178
                       note = Description of Artificial Sequence: Synthetic
                        polypeptide
VARIANT                154
                       note = MOD_RES - Gln, Ala, Asn, Asp, Cys, Glu, Gly, Ile,
                        Leu, Met, Phe, Pro, Ser, Thr, Trp, Tyr, Val, or Arg
source                 1..178
                       mol_type = protein
                       organism = synthetic construct
SEQUENCE: 222
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIXFSKSLG LPENHIVFPV PIDQCIDG    178

SEQ ID NO: 223         moltype = AA  length = 178
FEATURE                Location/Qualifiers
REGION                 1..178
                       note = Description of Artificial Sequence: Synthetic
                        polypeptide
VARIANT                155
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 223
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRXSKSLG LPENHIVFPV PIDQCIDG    178

SEQ ID NO: 224         moltype = AA  length = 178
FEATURE                Location/Qualifiers
REGION                 1..178
                       note = Description of Artificial Sequence: Synthetic
                        polypeptide
VARIANT                156
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 224
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFXKSLG LPENHIVFPV PIDQCIDG    178

SEQ ID NO: 225         moltype = AA  length = 178
FEATURE                Location/Qualifiers
REGION                 1..178
                       note = Description of Artificial Sequence: Synthetic
                        polypeptide
VARIANT                157
                       note = MOD_RES - Gln, Ala, Asn, Asp, Cys, Glu, Gly, Ile,
                        Leu, Met, Phe, Pro, Ser, Thr, Trp, Tyr, Val, or Lys
source                 1..178
                       mol_type = protein
                       organism = synthetic construct
SEQUENCE: 225
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSXSLG LPENHIVFPV PIDQCIDG    178

SEQ ID NO: 226         moltype = AA  length = 178
FEATURE                Location/Qualifiers
REGION                 1..178
                       note = Description of Artificial Sequence: Synthetic
                        polypeptide
```

```
VARIANT                 158
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 226
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKXLG LPENHIVFPV PIDQCIDG    178

SEQ ID NO: 227          moltype = AA  length = 178
FEATURE                 Location/Qualifiers
REGION                  1..178
                        note = Description of Artificial Sequence: Synthetic
                         polypeptide
VARIANT                 159
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 227
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSXG LPENHIVFPV PIDQCIDG    178

SEQ ID NO: 228          moltype = AA  length = 178
FEATURE                 Location/Qualifiers
REGION                  1..178
                        note = Description of Artificial Sequence: Synthetic
                         polypeptide
VARIANT                 160
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 228
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLX LPENHIVFPV PIDQCIDG    178

SEQ ID NO: 229          moltype = AA  length = 178
FEATURE                 Location/Qualifiers
REGION                  1..178
                        note = Description of Artificial Sequence: Synthetic
                         polypeptide
VARIANT                 161
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 229
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG XPENHIVFPV PIDQCIDG    178

SEQ ID NO: 230          moltype = AA  length = 178
FEATURE                 Location/Qualifiers
REGION                  1..178
                        note = Description of Artificial Sequence: Synthetic
                         polypeptide
VARIANT                 162
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 230
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LXENHIVFPV PIDQCIDG    178

SEQ ID NO: 231          moltype = AA  length = 178
FEATURE                 Location/Qualifiers
REGION                  1..178
                        note = Description of Artificial Sequence: Synthetic
```

```
                         polypeptide
VARIANT                 163
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 231
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPXNHIVFPV PIDQCIDG    178

SEQ ID NO: 232          moltype = AA  length = 178
FEATURE                 Location/Qualifiers
REGION                  1..178
                        note = Description of Artificial Sequence: Synthetic
                         polypeptide
VARIANT                 164
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 232
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPEXHIVFPV PIDQCIDG    178

SEQ ID NO: 233          moltype = AA  length = 178
FEATURE                 Location/Qualifiers
REGION                  1..178
                        note = Description of Artificial Sequence: Synthetic
                         polypeptide
VARIANT                 165
                        note = MOD_RES - Gln, Ala, Asn, Asp, Cys, Glu, Gly, Ile,
                         Leu, Met, Phe, Pro, Ser, Thr, Trp, Tyr, Val, or His
source                  1..178
                        mol_type = protein
                        organism = synthetic construct
SEQUENCE: 233
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENXIVFPV PIDQCIDG    178

SEQ ID NO: 234          moltype = AA  length = 178
FEATURE                 Location/Qualifiers
REGION                  1..178
                        note = Description of Artificial Sequence: Synthetic
                         polypeptide
VARIANT                 166
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 234
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHXVFPV PIDQCIDG    178

SEQ ID NO: 235          moltype = AA  length = 178
FEATURE                 Location/Qualifiers
REGION                  1..178
                        note = Description of Artificial Sequence: Synthetic
                         polypeptide
VARIANT                 167
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 235
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIXFPV PIDQCIDG    178

SEQ ID NO: 236          moltype = AA  length = 178
FEATURE                 Location/Qualifiers
REGION                  1..178
```

```
                        note = Description of Artificial Sequence: Synthetic
                         polypeptide
VARIANT                 168
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 236
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVXPV PIDQCIDG    178

SEQ ID NO: 237          moltype = AA  length = 178
FEATURE                 Location/Qualifiers
REGION                  1..178
                        note = Description of Artificial Sequence: Synthetic
                         polypeptide
VARIANT                 169
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 237
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFXV PIDQCIDG    178

SEQ ID NO: 238          moltype = AA  length = 178
FEATURE                 Location/Qualifiers
REGION                  1..178
                        note = Description of Artificial Sequence: Synthetic
                         polypeptide
VARIANT                 170
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 238
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPX PIDQCIDG    178

SEQ ID NO: 239          moltype = AA  length = 178
FEATURE                 Location/Qualifiers
REGION                  1..178
                        note = Description of Artificial Sequence: Synthetic
                         polypeptide
VARIANT                 171
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 239
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV XIDQCIDG    178

SEQ ID NO: 240          moltype = AA  length = 178
FEATURE                 Location/Qualifiers
REGION                  1..178
                        note = Description of Artificial Sequence: Synthetic
                         polypeptide
VARIANT                 172
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 240
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PXDQCIDG    178

SEQ ID NO: 241          moltype = AA  length = 178
FEATURE                 Location/Qualifiers
```

```
REGION                  1..178
                        note = Description of Artificial Sequence: Synthetic
                         polypeptide
VARIANT                 173
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 241
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIXQCIDG    178

SEQ ID NO: 242          moltype = AA  length = 178
FEATURE                 Location/Qualifiers
REGION                  1..178
                        note = Description of Artificial Sequence: Synthetic
                         polypeptide
VARIANT                 174
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 242
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDXCIDG    178

SEQ ID NO: 243          moltype = AA  length = 178
FEATURE                 Location/Qualifiers
REGION                  1..178
                        note = Description of Artificial Sequence: Synthetic
                         polypeptide
VARIANT                 175
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 243
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQXIDG    178

SEQ ID NO: 244          moltype = AA  length = 178
FEATURE                 Location/Qualifiers
REGION                  1..178
                        note = Description of Artificial Sequence: Synthetic
                         polypeptide
VARIANT                 176
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 244
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCXDG    178

SEQ ID NO: 245          moltype = AA  length = 178
FEATURE                 Location/Qualifiers
REGION                  1..178
                        note = Description of Artificial Sequence: Synthetic
                         polypeptide
VARIANT                 177
                        note = MOD_RES - Gln, Ala, Asn, Asp, Cys, Glu, Gly, Ile,
                         Leu, Met, Phe, Pro, Ser, Thr, Trp, Tyr, or Val
source                  1..178
                        mol_type = protein
                        organism = synthetic construct
SEQUENCE: 245
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIXG    178

SEQ ID NO: 246          moltype = AA  length = 178
```

```
FEATURE                Location/Qualifiers
REGION                 1..178
                       note = Description of Artificial Sequence: Synthetic
                        polypeptide
VARIANT                178
                       note = MOD_RES - Gln, Ala, Asn, Asp, Cys, Glu, Gly, Ile,
                        Leu, Met, Phe, Pro, Ser, Thr, Trp, Tyr, or Val
source                 1..178
                       mol_type = protein
                       organism = synthetic construct
SEQUENCE: 246
QDSTSDLIPA PPLSKVPLQQ NFQDNQFQGK WYVVGLAGNA ILREDKDPQK MYATIYELKE  60
DKSYNVTSVL FRKKKCDYWI RTFVPGCQPG EFTLGNIKSY PGLTSYLVRV VSTNYNQHAM  120
VFFKKVSQNR EYFKITLYGR TKELTSELKE NFIRFSKSLG LPENHIVFPV PIDQCIDX    178

SEQ ID NO: 247         moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 247
QDSTSDLIPA PPLSKVPLQQ NFQDNQFQGK WYVVGLAGNA ILREDEDPQT MYATIYELAE  60
DGSYNVTSVL FADDGCDYWI RTFVPGCQPG EFTLGNIASY PGLTSYLVRV VSTDYNQHAM  120
VFFKKVSESA EYFKITLYGR TKELTSELKE NFIRFSKSLG LPENHIVFPV PIDQCIDG    178

SEQ ID NO: 248         moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 248
QDSTSDLIPA PPLSSVPLQQ NFQDNQFQGK WYVVGLAGNA ILREDEDPQT MYATIYELAE  60
DGSYNVTSVL FRDDGCDYWI RTFVPGCQPG EFTLGNIASY PGLTSYLVRV VSTDYDEFAM  120
VFFKKVSESA EYFKITLYGR TKELTSELKE NFIRFSKSLG LPENHIVFPV PIDQCIDG    178

SEQ ID NO: 249         moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 249
QDSTSDLIPA PPLSSVPLQQ NFQDNQFQGK WYVVGLAGNA ILREDEDPQT MYATIYELKE  60
DGSYNVTSVL FADDGCDYWI RTFVPGCQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178

SEQ ID NO: 250         moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 250
QDSTSDLIPA PPLSSVPLQQ NFQDNQFQGK WYVVGLAGNA ILAEDEDPQK MYATIYELKE  60
DKSYNVTSVL FRDDGCDYWI RTFVPGCQPG EFTLGNIQSY PGLTSYLVRV VSTNYNQFAM  120
VFFKKVSQNQ EYFKITLYGA TAELTSELQE NFIRFSASLG LPENNIVFPV PIDQCIDG    178

SEQ ID NO: 251         moltype = AA  length = 178
FEATURE                Location/Qualifiers
REGION                 1..178
                       note = Description of Artificial Sequence: Synthetic
                        polypeptide
source                 1..178
                       mol_type = protein
                       organism = synthetic construct
SEQUENCE: 251
QDSTSDLIPA PPLSSVPLQQ NFQDNQFQGK WYVVGLAGNA ILAEDEDPQK MYATIYELKE  60
DKSYNVTSVL FRDDGCDYWI RTFVPGCQPG EFTLGNIQSY PGLTSYLVRV VSTNYNQFAM  120
VFFKKVSQNQ EYFKITLYGR TKELTSELQE NFIRFSASLG LPENNIVFPV PIDQCIDG    178
```

-continued

```
SEQ ID NO: 252          moltype = AA  length = 178
FEATURE                 Location/Qualifiers
REGION                  1..178
                        note = Description of Artificial Sequence: Synthetic
                         polypeptide
source                  1..178
                        mol_type = protein
                        organism = synthetic construct
SEQUENCE: 252
QDSTSDLIPA PPLSSVPLQQ NFQDNQFQGK WYVVGLAGNA ILREDEDPQK MYATIYELKE  60
DKSYNVTSVL FRDDGCDYWI RTFVPGSQPG EFTLGNIQSY PGLTSYLVRV VSTNYNQFAM  120
VFFKKVSQNQ EYFKITLYGR TKELTSELQE NFIRFSKSLG LPENNIVFPV PIDQCIDG    178
```

MUTANT NGAL PROTEINS AND USES THEREOF

This application is a continuation application of U.S. patent application Ser. No. 16/819,891, filed Mar. 16, 2020, which is a continuation application to U.S. patent application Ser. No. 15/376,327, filed Dec. 12, 2016, now U.S. Pat. No. 10,588,937, which is a divisional application of U.S. patent application Ser. No. 13/684,060, filed Nov. 21, 2012, now U.S. Pat. No. 9,534,027, which is a continuation-in-part of International Application No. PCT/US2011/037774, filed on May 24, 2011, which claims the benefit of U.S. Provisional Patent Application No. 61/347,587, filed May 24, 2010, and U.S. Provisional Patent Application No. 61/354,973, filed Jun. 15, 2010, the contents of each of which are hereby incorporated by reference.

GOVERNMENT SUPPORT

This invention was made with government support under DK073462 awarded by the National Institutes of Health. The government has certain rights in the invention.

SEQUENCE LISTING

The instant application contains a Sequence Listing which has been submitted electronically in XML file format and is hereby incorporated by reference in its entirety. Said XML copy, created on Jun. 28, 2023, is named 0019240_00895US6_SL.xml and is 453,066 bytes in size.

All patents, patent applications and publications cited herein are hereby incorporated by reference in their entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

NGAL (Lipocalin 2) is a small protein with a molecular weight of about 22 kD. NGAL binds to iron-binding siderophores, such as enterochelin, with high affinity and thus chelates and traffics iron. Once produced in cells, NGAL is secreted into the extracellular space and transported to the kidney where it passes the filtration barrier of the glomerulus and enters the primary urine. However, NGAL is then efficiently reabsorbed by megalin receptors localized on the apical side of the epithelia of the proximal tubules. Once NGAL is reabsorbed and endocytosed, it is trafficked to lysosomes and degraded. Once degraded, any iron which NGAL transported to the kidney is reabsorbed.

SUMMARY OF THE INVENTION

The present invention is based, in part, on the development of mutant versions of the NGAL protein that are not reabsorbed in the kidney and thus, unlike wild-type NGAL, are excreted in significant amounts in the urine. Like wild-type NGAL, these mutant forms of NGAL have the ability to bind to iron-binding siderophores, such as enterochelin. Thus, these NGAL mutants can be used to traffic iron out of the body by facilitating its excretion in the urine. As such, the mutant NGAL proteins of the invention can be used in the treatment of iron overload and diseases and disorders associated with iron overload. In addition, the mutant NGAL proteins of the invention have bacteriostatic activity and can be used to treat bacterial infections of the urinary tract. These and other aspects of the present invention are described in more detail below, and in other sections of this application.

In one embodiment the present invention provides a mutant NGAL protein comprising an amino acid sequence that is at least 70% identical to the sequence of wild-type human NGAL (SEQ ID NO. 1), or a fragment thereof, wherein one or more residues from among Lys 15, Lys 46, Lys 50, Lys 59, Lys 62, Lys 73, Lys 74, Lys 75, Lys 98, His 118, Arg 130, Lys 149, and His 165 is mutated by deletion or by substitution with a non-positively charged amino acid residue, and wherein one or more of, or preferably all of, residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the mutant NGAL protein is able to bind to a siderophore and/or to a siderophore-iron complex, and/or is excreted in the urine, and/or has bacteriostatic activity.

In preferred embodiments five, six, seven, eight, nine, ten, or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In some embodiments the % of the mutant NGAL protein that accumulates in the urine following systemic administration of the mutant NGAL protein to a subject is greater than the % of WT NGAL protein that accumulates in the urine following systemic administration of WT NGAL protein to a subject. In some embodiments the % of the mutant NGAL protein that accumulates in the urine following systemic administration of the mutant NGAL protein to a subject is greater than 10-fold or greater than 100-fold more than the % of WT NGAL protein that accumulates in the urine following systemic administration of WT NGAL protein to a subject. In one embodiment the % of the mutant NGAL protein that accumulates in the urine three hours after systemic administration of the mutant NGAL protein to a subject is 1% or more, or 2% or more, or 5% or more, or 10% or more, or 20% or more. This is significantly higher than the % of WT NGAL protein that accumulates in the urine—typically only about 0.1% of WT NGAL that is administered to a subject systemically accumulates in the urine over the same time period.

In some embodiments the present invention provides a nucleic acid sequence that encodes a mutant NGAL protein. In some embodiments the present invention provides an expression vector comprising such a nucleic acid sequence operatively linked to a promoter. The present invention also provides bacterial cells and mammalian cells that stably express such nucleic acids and that may be useful for the production of recombinant mutant NGAL proteins.

The present invention also provides pharmaceutical compositions comprising the mutant NGAL proteins of the invention and pharmaceutical compositions comprising complexes of such mutant NGAL proteins together with a siderophore, such as enterochelin, pyrogallol, carboxymycobactin, catechol, or variants thereof.

In one embodiment, the siderophore is pH insensitive. In another embodiment, the siderophore binds to the mutant NGAL protein and iron at urinary pH. In another embodiment, the siderophore binds to the mutant NGAL protein and iron in the urine.

In one embodiment, the siderophore binds to the mutant NGAL protein and iron at blood pH. In another embodiment, the siderophore binds to the mutant NGAL protein and iron in the blood. In one embodiment, the mutant NGAL protein and the siderophore are present in a 1:1 molar ratio. In one embodiment, the mutant NGAL protein and the siderophore are present in a 1:3 molar ratio.

The present invention also provides methods for treating iron overload in a subject in need thereof, comprising administering to the subject an effect amount of a pharmaceutical composition comprising a mutant NGAL protein.

The present invention also provides methods for treating iron overload in a subject in need thereof, comprising administering to the subject an effect amount of a pharmaceutical composition comprising a mutant NGAL protein and a siderophore.

The present invention also provides methods for treating bacterial urinary tract infections in a subject in need thereof, comprising administering to the subject an effect amount of a pharmaceutical composition comprising a mutant NGAL protein.

The present invention also provides methods for treating bacterial urinary tract infections in a subject in need thereof, comprising administering to the subject an effect amount of a pharmaceutical composition comprising a mutant NGAL protein and a siderophore.

The present invention provides for a polypeptide that encodes a K3 NGAL protein and comprises an amino acid sequence that is identical to SEQ ID NO. 2.

The present invention also provides for a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a nucleic acid encoding a polypeptide that encodes a K3 NGAL protein and comprises an amino acid sequence that is identical to SEQ ID NO. 2. The present invention also provides for a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a pharmaceutical composition comprising a polypeptide that encodes a K3 NGAL protein and comprises an amino acid sequence that is identical to SEQ ID NO. 2. The present invention also provides for a pharmaceutical composition comprising a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a K3 NGAL protein comprising an amino acid sequence that is identical to SEQ ID NO: 2, or a fragment thereof, wherein the K3 NGAL protein (a) is able to bind to a siderophore, and (b) is excreted in the urine.

The present invention also provides for a polypeptide that encodes a K3Cys protein and comprises an amino acid sequence that is identical to SEQ ID NO. 252.

The present invention also provides for a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a nucleic acid encoding a polypeptide that encodes a K3Cys protein and comprises an amino acid sequence that is identical to SEQ ID NO. 252. The present invention also provides for a nucleic acid encoding a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a pharmaceutical composition comprising a polypeptide that encodes a K3Cys protein and comprises an amino acid sequence that is identical to SEQ ID NO. 252. The present invention also provides for a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

In another aspect, the present invention provides for a K3Cys protein comprising an amino acid sequence that is identical to SEQ ID NO: 252, or a fragment thereof, wherein the K3Cys protein (a) is able to bind to a siderophore, and (b) is excreted in the urine.

In one embodiment, the K3Cys protein has bacteriostatic activity.

In one embodiment, the % of the K3Cys protein that accumulates in the urine at a certain time following systemic administration of the K3Cys protein to a subject is greater than the % of WT NGAL protein that accumulates in the urine following systemic administration of the WT NGAL protein to a subject over the same time period.

In another embodiment, the % of the K3Cys protein that accumulates in the urine at a certain time following systemic administration of the K3Cys protein to a subject is about 1-fold, 2-fold, 5-fold, 10-fold, 20-fold, 30-fold, 50-fold, 60-fold, 70-fold, 80-fold, 90-fold or more greater than the % of WT NGAL protein that accumulates in the urine following systemic administration of WT NGAL protein to a subject over the same time period.

In another embodiment, the % of the K3Cys protein that accumulates in the urine at a certain time following systemic administration of the K3Cys protein to a subject is 10-fold or more greater than the % of WT NGAL protein that accumulates in the urine following systemic administration of WT NGAL protein to a subject over the same time period.

In another embodiment, the % of the K3Cys protein that accumulates in the urine at a certain time following systemic administration of the K3Cys protein to a subject is 100-fold or more greater than the % of WT NGAL protein that accumulates in the urine following systemic administration of WT NGAL protein to a subject over the same time period.

In one embodiment, the % of K3Cys protein that accumulates in the urine three hours after systemic administration of the K3Cys protein to a subject is about 1%, 2%, 5% or more. In another embodiment, the % of K3Cys protein that accumulates in the urine three hours after systemic administration of the K3Cys protein to a subject is about 10%, 20%, 30%, 40%, 50%, 60%, 70%, 80%, 90% or more. In one embodiment, the % of K3Cys protein that accumulates in the urine three hours after systemic administration of the K3Cys protein to a subject is about 15%, 25%, 35%, 45%, 55%, 65%, 75%, 85%, 95% or more.

In one embodiment, the % of K3Cys protein that accumulates in the urine three hours after systemic administration of the K3Cys protein to a subject is about 50% or more. In another embodiment, the % of K3Cys protein that accumulates in the urine three hours after systemic administration of the K3Cys protein to a subject is about 70% or more. In another embodiment, the % of K3Cys protein that accumulates in the urine three hours after systemic administration of the K3Cys protein to a subject is about 85% or more.

In one embodiment, the % of the K3Cys protein that accumulates in the kidney at a certain time following systemic administration of the K3Cys protein to a subject is lower than the % of WT NGAL protein that accumulates in the kidney following systemic administration of the WT NGAL protein to a subject over the same time period.

In another embodiment, the % of the K3Cys protein that accumulates in the kidney at a certain time following systemic administration of the K3Cys protein to a subject is about 1-fold, 2-fold, 5-fold, 10-fold, 20-fold, 30-fold, 50-fold, 60-fold, 70-fold, 80-fold, 90-fold or more lower than the % of WT NGAL protein that accumulates in the kidney following systemic administration of the WT NGAL protein to a subject over the same time period.

In one embodiment, the % of the K3Cys protein that accumulates in the kidney at a certain time following systemic administration of the K3Cys protein to a subject is 10-fold or more lower than the % of WT NGAL protein that accumulates in the kidney following systemic administration of WT NGAL protein to a subject over the same time period.

In another embodiment, the % of the K3Cys protein that accumulates in the kidney at a certain time following systemic administration of the K3Cys protein to a subject is 100-fold or more lower than the % of WT NGAL protein that accumulates in the kidney following systemic administration of WT NGAL protein to a subject over the same time period.

In one embodiment, the % of K3Cys protein that accumulates in the kidney three hours after systemic administration of the K3Cys protein to a subject is about 1% or less. In another embodiment, the % of K3Cys protein that accumulates in the kidney three hours after systemic administration of the K3Cys protein to a subject is about 2% or less. In another embodiment, the % of K3Cys protein that accumulates in the kidney three hours after systemic administration of the K3Cys protein to a subject is about 3% or less. In another embodiment, the % of K3Cys protein that accumulates in the kidney three hours after systemic administration of the K3Cys protein to a subject is about 4% or less. In another embodiment, the % of K3Cys protein that accumulates in the kidney three hours after systemic administration of the K3Cys protein to a subject is about 5% or less.

In another embodiment, the % of K3Cys protein that accumulates in the kidney three hours after systemic administration of the K3Cys protein to a subject is about 10%, 20%, 30%, 40%, 50%, 60%, 70%, 80%, 90% or less. In one embodiment, the % of K3Cys protein that accumulates in the kidney three hours after systemic administration of the K3Cys protein to a subject is about 15%, 25%, 35%, 45%, 55%, 65%, 75%, 85%, 95% or less.

In another aspect, the present invention provides for a pharmaceutical composition comprising a K3Cys protein comprising an amino acid sequence that is identical to SEQ ID NO: 252, or a fragment thereof, wherein the K3Cys protein (a) is able to bind to a siderophore, and (b) is excreted in the urine.

In another aspect, the present invention provides for a pharmaceutical composition comprising a complex of a K3Cys protein comprising an amino acid sequence that is identical to SEQ ID NO: 252, or a fragment thereof, and a siderophore, wherein the K3Cys protein (a) is able to bind to a siderophore, and (b) is excreted in the urine.

In one embodiment, the siderophore is selected from the group consisting of enterochelin, pyrogallol, carboxymycobactin, catechol, and variants thereof. In another embodiment, the siderophore is pH insensitive. In one embodiment, the siderophore binds to the K3Cys protein and iron at urinary pH. In another embodiment, the siderophore binds to the K3Cys protein and iron in the urine. In one embodiment, the siderophore binds to the K3Cys protein and iron at blood pH. In another embodiment, the siderophore binds to the K3Cys protein and iron in the blood.

In one embodiment, the K3Cys protein and the siderophore are present in a 1:1 molar ratio. In another embodiment, the K3Cys protein and the siderophore are present in a 1:3 molar ratio.

The present invention provides for a method for treating iron overload in a subject in need thereof, the method comprising administering to the subject an effective amount of a pharmaceutical composition comprising a polypeptide that encodes a K3Cys protein and comprises an amino acid sequence that is identical to SEQ ID NO. 252.

The present invention provides for a method for treating iron overload in a subject in need thereof, the method comprising administering to the subject an effective amount of a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a method for treating iron overload in a subject in need thereof, the method comprising administering to the subject an effective amount of a pharmaceutical composition comprising a K3Cys protein comprising an amino acid sequence that is identical to SEQ ID NO: 252, or a fragment thereof, wherein the K3Cys protein (a) is able to bind to a siderophore, and (b) is excreted in the urine.

The present invention provides for a method for treating iron overload in a subject in need thereof, the method comprising administering to the subject an effective amount of a pharmaceutical composition comprising a complex of a K3Cys protein comprising an amino acid sequence that is identical to SEQ ID NO: 252, or a fragment thereof, and a siderophore, wherein the K3Cys protein (a) is able to bind to a siderophore, and (b) is excreted in the urine.

The present invention also provides for a method of treating a urinary tract infection in a subject in need thereof, the method comprising administering to the subject an effective amount of a pharmaceutical composition comprising a polypeptide that encodes a K3Cys protein and comprises an amino acid sequence that is identical to SEQ ID NO. 252.

The present invention provides for a method for treating a urinary tract infection in a subject in need thereof, the method comprising administering to the subject an effective amount of a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a method for treating a urinary tract infection in a subject in need thereof, the method comprising administering to the subject an effective amount of a pharmaceutical composition comprising a K3Cys protein comprising an amino acid sequence that is identical to SEQ ID NO: 252, or a fragment thereof, wherein the K3Cys protein (a) is able to bind to a siderophore, and (b) is excreted in the urine.

The present invention provides for a method for treating a urinary tract infection in a subject in need thereof, the method comprising administering to the subject an effective amount of a pharmaceutical composition comprising a complex of a K3Cys protein comprising an amino acid sequence that is identical to SEQ ID NO: 252, or a fragment thereof, and a siderophore, wherein the K3Cys protein (a) is able to bind to a siderophore, and (b) is excreted in the urine.

In another aspect, the present invention provides for a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In one embodiment, six or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid. In another embodiment, seven or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, eight or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid. In another embodiment, nine or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, ten or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, the K3Cys mutant protein has bacteriostatic activity.

In one embodiment, the % of the K3Cys mutant protein that accumulates in the urine at a certain time following systemic administration of the K3Cys mutant protein to a subject is greater than the % of K3Cys protein that accumulates in the urine following systemic administration of the K3Cys protein to a subject over the same time period.

In another embodiment, the % of the K3Cys mutant protein that accumulates in the urine at a certain time following systemic administration of the K3Cys mutant protein to a subject is about 1-fold, 2-fold, 5-fold, 10-fold, 20-fold, 30-fold, 50-fold, 60-fold, 70-fold, 80-fold, 90-fold or more greater than the % of K3Cys protein that accumulates in the urine following systemic administration of K3Cys protein to a subject over the same time period.

In another embodiment, the % of the K3Cys mutant protein that accumulates in the urine at a certain time following systemic administration of the K3Cys mutant protein to a subject is 10-fold or more greater than the % of K3Cys protein that accumulates in the urine following systemic administration of K3Cys protein to a subject over the same time period.

In another embodiment, the % of the K3Cys mutant protein that accumulates in the urine at a certain time following systemic administration of the K3Cys mutant protein to a subject is 100-fold or more greater than the % of K3Cys protein that accumulates in the urine following systemic administration of K3Cys protein to a subject over the same time period.

In one embodiment, the % of K3Cys mutant protein that accumulates in the urine three hours after systemic administration of the K3Cys mutant protein to a subject is about 1%, 2%, 5% or more. In another embodiment, the % of K3Cys mutant protein that accumulates in the urine three hours after systemic administration of the K3Cys mutant protein to a subject is about 10%, 20%, 30%, 40%, 50%, 60%, 70%, 80%, 90% or more. In one embodiment, the % of K3Cys mutant protein that accumulates in the urine three hours after systemic administration of the K3Cys mutant protein to a subject is about 15%, 25%, 35%, 45%, 55%, 65%, 75%, 85%, 95% or more.

In one embodiment, the % of the K3Cys mutant protein that accumulates in the kidney at a certain time following systemic administration of the K3Cys mutant protein to a subject is lower than the % of K3Cys protein that accumulates in the kidney following systemic administration of the K3Cys protein to a subject over the same time period.

In another embodiment, the % of the K3Cys mutant protein that accumulates in the kidney at a certain time following systemic administration of the K3Cys mutant protein to a subject is about 1-fold, 2-fold, 5-fold, 10-fold, 20-fold, 30-fold, 50-fold, 60-fold, 70-fold, 80-fold, 90-fold or more lower than the % of K3Cys protein that accumulates in the kidney following systemic administration of the K3Cys protein to a subject over the same time period.

In one embodiment, the % of the K3Cys mutant protein that accumulates in the kidney at a certain time following systemic administration of the K3Cys mutant protein to a subject is 10-fold or more lower than the % of K3Cys protein that accumulates in the kidney following systemic administration of K3Cys protein to a subject over the same time period.

In one embodiment, the % of the K3Cys mutant protein that accumulates in the kidney at a certain time following systemic administration of the K3Cys mutant protein to a subject is 100-fold or more lower than the % of K3Cys protein that accumulates in the kidney following systemic administration of K3Cys protein to a subject over the same time period.

In one embodiment, the % of K3Cys mutant protein that accumulates in the kidney three hours after systemic administration of the K3Cys mutant protein to a subject is about 1% or less. In another embodiment, the % of K3Cys mutant protein that accumulates in the kidney three hours after systemic administration of the K3Cys mutant protein to a subject is about 2% or less. In another embodiment, the % of K3Cys mutant protein that accumulates in the kidney three hours after systemic administration of the K3Cys mutant protein to a subject is about 3% or less. In another embodiment, the % of K3Cys mutant protein that accumulates in the kidney three hours after systemic administration of the K3Cys mutant protein to a subject is about 4% or less. In another embodiment, the % of K3Cys mutant protein that accumulates in the kidney three hours after systemic administration of the K3Cys mutant protein to a subject is about 5% or less.

In another embodiment, the % of K3Cys mutant protein that accumulates in the kidney three hours after systemic administration of the K3Cys mutant protein to a subject is about 10%, 20%, 30%, 40%, 50%, 60%, 70%, 80%, 90% or less. In one embodiment, the % of K3Cys mutant protein that accumulates in the kidney three hours after systemic administration of the K3Cys mutant protein to a subject is about 15%, 25%, 35%, 45%, 55%, 65%, 75%, 85%, 95% or less.

In another aspect, the present invention provides for a nucleic acid sequence that encodes a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for an expression vector comprising a nucleic acid sequence that encodes a K3Cys mutant protein comprising an amino acid sequence that is at least 70% identical to the sequence of the K3Cys protein of SEQ ID NO: 252, or a fragment thereof, operatively linked to a promoter, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a bacterial cell that stably expresses a nucleic acid sequence that encodes a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a mammalian cell that stably expresses a nucleic acid sequence that encodes a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a pharmaceutical composition comprising a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a pharmaceutical composition comprising a complex of a K3Cys mutant protein comprising an amino acid sequence that is at least 70% identical to the sequence of the K3Cys protein of SEQ ID NO: 252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In one embodiment, the siderophore is selected from the group consisting of enterochelin, pyrogallol, carboxymycobactin, catechol, and variants thereof. In another embodiment, the siderophore is pH insensitive. In one embodiment, the siderophore binds to the K3Cys mutant protein and iron at urinary pH. In another embodiment, the siderophore binds to the K3Cys mutant protein and iron in the urine. In one embodiment, the siderophore binds to the K3Cys mutant protein and iron at blood pH. In another embodiment, the siderophore binds to the K3Cys mutant protein and iron in the blood.

In one embodiment, the K3Cys mutant protein and the siderophore are present in a 1:1 molar ratio. In another embodiment, the K3Cys mutant protein and the siderophore are present in a 1:3 molar ratio.

In another aspect, the present invention provides for a method for treating iron overload in a subject in need thereof, the method comprising administering to the subject an effective amount of a pharmaceutical composition comprising a K3Cys mutant protein.

In another aspect, the present invention provides for a method for treating iron overload in a subject in need thereof, the method comprising administering to the subject an effective amount of a pharmaceutical composition comprising a complex of a K3Cys mutant protein and a siderophore.

In another aspect, the present invention provides for a method for treating a urinary tract infection in a subject in need thereof, the method comprising administering to the subject an effective amount of a pharmaceutical composition comprising a K3Cys mutant protein.

In another aspect, the present invention provides for a method for treating a urinary tract infection in a subject in need thereof, the method comprising administering to the subject an effective amount of a pharmaceutical composition comprising a complex of a K3Cys mutant protein and a siderophore.

In another aspect, the present invention provides for a method for treating iron overload in a subject in need thereof, the method comprising administering to the subject an effective amount of a pharmaceutical composition comprising a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating iron overload in a subject in need thereof, the method comprising administering to the subject an effective amount of a pharmaceutical composition comprising a complex of a K3Cys mutant protein comprising an amino acid sequence that is at least 70% identical to the sequence of the K3Cys protein of SEQ ID NO: 252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating a urinary tract infection in a subject in need thereof, the method comprising administering to the subject an effective amount of a pharmaceutical composition comprising a K3Cys mutant protein comprising an amino acid sequence that is at least 70% identical to the sequence of the K3Cys protein of SEQ ID NO: 252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating a urinary tract infection in a subject in need thereof, the method comprising administering to the subject an effective amount of a pharmaceutical composition comprising a complex of a K3Cys mutant protein comprising an amino acid sequence that is at least 70% identical to the sequence of the K3Cys protein of SEQ ID NO: 252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

These and other embodiments of the invention are further described in the following sections of the application, including the Detailed Description, Examples, Claims, and Drawings.

BRIEF DESCRIPTION OF THE FIGURES

FIG. 2. Comparison of human (SEQ ID NO: 19) and mouse (SEQ ID NO: 20) megalin proteins. The sequences of the human and mouse megalin proteins were aligned by using ClustalW2 (www.ebi.ac.uk/Tools/clustalw2/), and were shown to share 76% identity and 87% similarity, respectively.

FIG. 3A. NGAL mutants bind to enterochelin (Ent) and $^{55}Fe^{3+}$ to form a complex. Apo NGAL mutant protein (4 nmol) was mixed with equal molar Ent and $^{55}Fe^{3+}$, and incubated at room temperature (RT) for 30 minutes. The mixture was then washed for 4×5 minutes in a filter column with a 10K cutoff, and the NGAL-bound Ent-$^{55}Fe^{3+}$ was calculated as percentage of the starting total $^{55}Fe^{3+}$. FIGS. 3A-3D. The prepared NGAL-Ent-$^{55}Fe^{3+}$ complex was intraperitoneally injected into mice (female, 4 weeks), and the urine, FIG. 3B, was collected for 3 hours in a metabolic cage. Liver, FIG. 3C, and kidneys, FIG. 3D, were dissected and solubilized in 1MNaOH and 2% SDS for examination of $^{55}Fe^{3+}$ accumulation, expressed as a percentage of total NGAL-Ent-$^{55}Fe^{3+}$ complex.

FIG. 4A. Crystal structure of wild-type NGAL protein (Accession number: 1nglA.pdb) was used to predict the 3D structure of the K3 mutant protein by using Swissmodel (www.swissmodel.expasy.org). The organization of the Ent-iron binding pocket in the K3 protein is predicted to be very similar to that in wild-type NGAL. FIG. 4B. The K3 mutant protein has less positively charged residues (arginine, lysine or histidine) on its surface in comparison to wild-type NGAL according to the modeled 3D structure. Positive charged residues are shown as ball-and-stick molecules, and the yellow color indicates the solvent accessible surface of the NGAL protein.

FIG. 6A. Left Enterochelin:Fe. The essential siderophore of gram negative organisms. It is composed of three catechol groups bound together by a backbone. Iron (red) is bound with affinity 10-49M. FIG. 6B. Right Enterochelin:Fe bound within the calyx of the Ngal protein with an affinity of 0.4 nM.

represent Wild Type and actual Mutants K1, K2, D1-4-2-1-1, K5, D1-4-2-1-1-4, K3, WT-3 and WT4.

Figure 14:
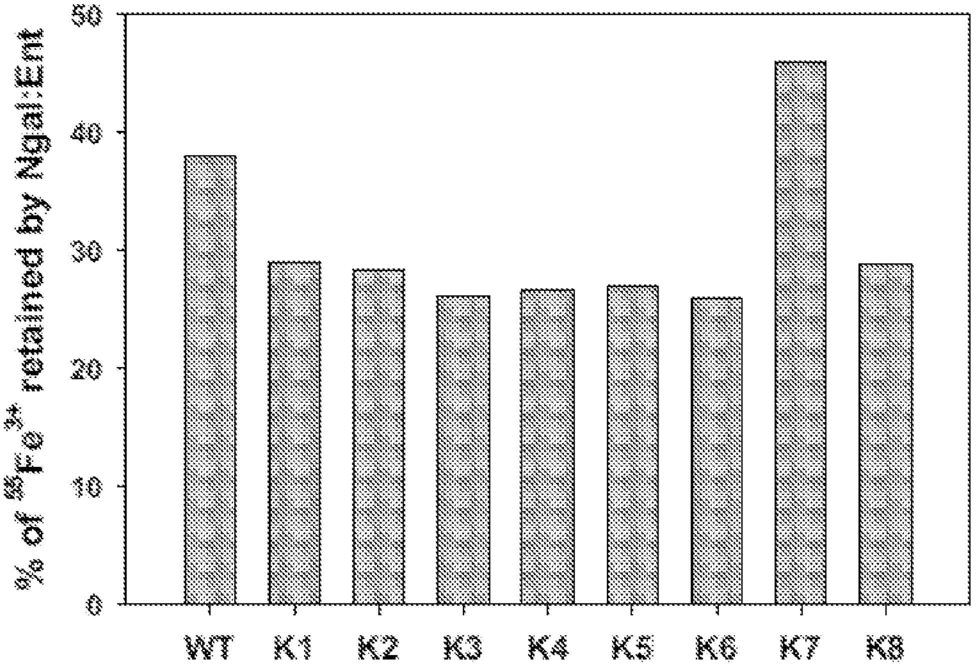

FIG. 14. 55Fe3+ retaining activity of wild-type and mutant Ngal:Ent. The designations "WT" and "K numbers 1-8" represent Wild Type and actual Mutants K1, K2, D1-4-2-1-1, K5, D1-4-2-1-1-4, K3, WT-3 and WT4.

Figure 15A:
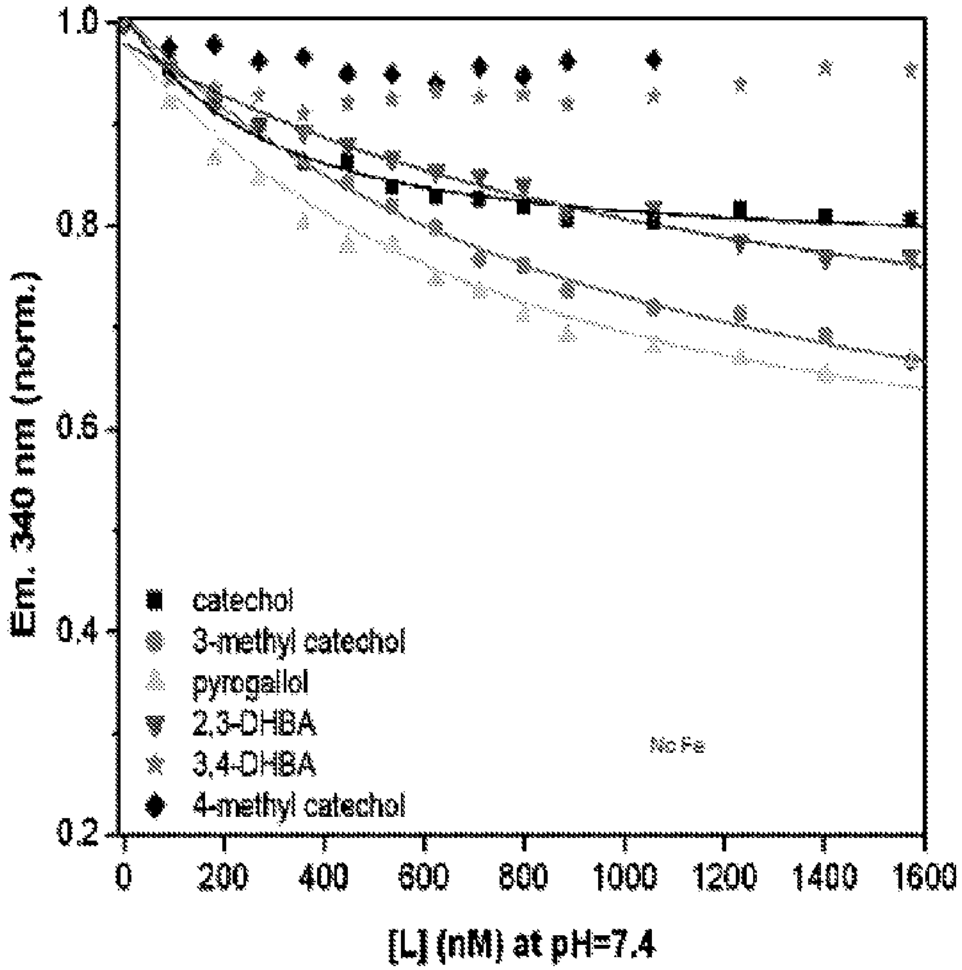
Figure 15B:
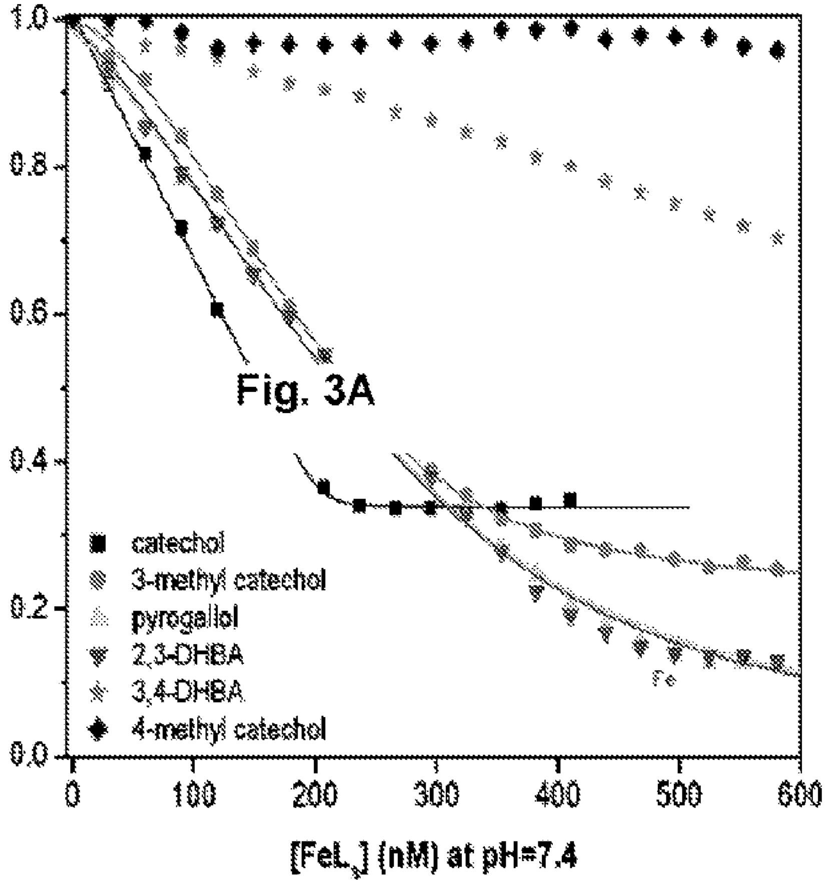

FIGS. 15A-15B. Determination of the affinity of siderophore:iron in complex with wild type Ngal. FIG. 15A. Fluorescence quenching analysis of Ngal with siderophores ("L") FIG. 15B. or Ngal with FeIII-siderophores ("FeL3"). Note that FeIII dramatically enhanced the affinity of Ngal for different catechols. 2,3DHBA=Ent.

Figure 16:
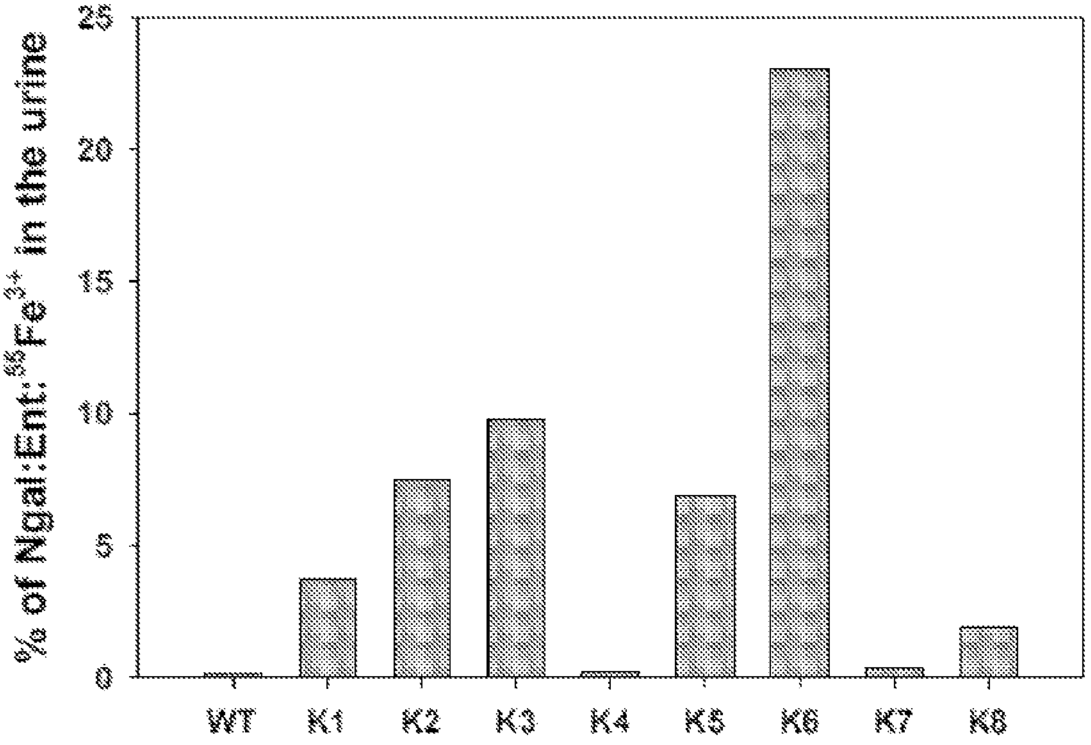

FIG. 16. Analysis of 55Fe3+ which was delivered by wild-type or mutant Ngal:Ent into mouse urine. The designations "WT" and "K numbers 1-8" represent Wild Type and actual Mutants K1, K2, D1-4-2-1-1, K5, D1-4-2-1-1-4, K3, WT-3 and WT4.

Figure 17:
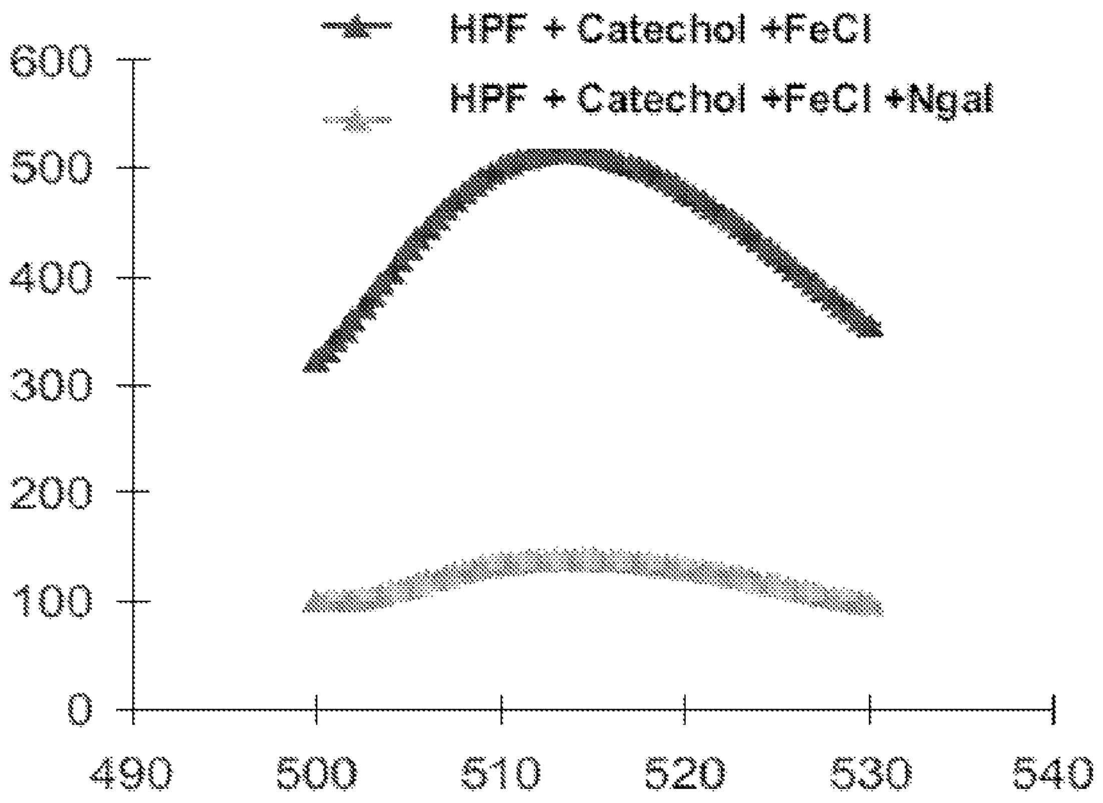

FIG. 17. Ngal effectively chelates FeIII. Conversion of HPF to fluorescein (Ex 490 nm, Em 515 nm) was detected in the presence of catechol, ironIII and $H_2O_2$ (black line), but the addition of Ngal blocked this reaction (grey line); P<10-5.

Figure 18:
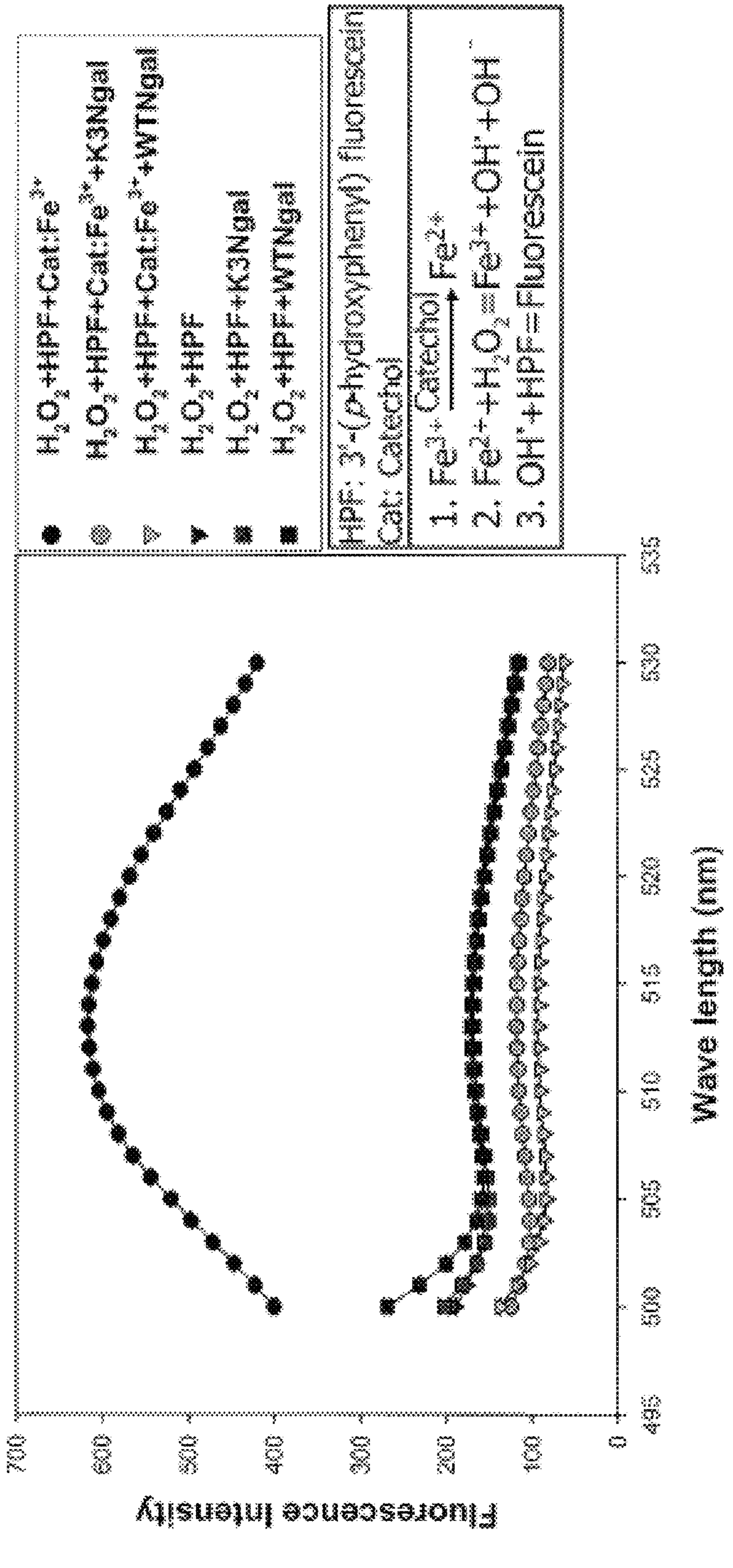

FIG. 18. K3 Ngal mutant inhibits the Redox Activity of Iron. Oxidative radicals produced by Fe(III), catechol and $H_2O_2$ was detected by a fluorescent probe, 3'-(p-hydroxyphenyl) fluorescein (HPF), and the production of the Oxidative radicals was completely inhibited by wild-type (WT) and K3 Ngal proteins.

FIG. 19. Shows sequences and amino acid alignment of WT NGAL (SEQ ID NO: 1) and K3 NGAL (SEQ ID NO: 2).

Figure 20:
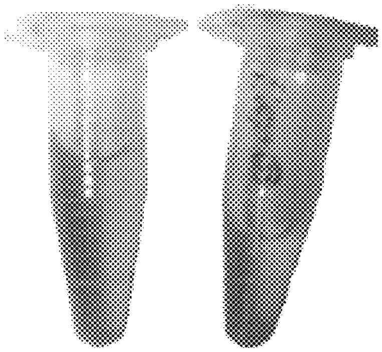

FIG. 20. Left tube shows that NGAL binds Catechol:Fe found in the urine, generating a bright red color. The tube contains the K3 mutant form of NGAL which can bypass the proximal tubule and deliver Iron or Apo-NGAL to the urine. Right tube: Apo-Ngal. These data show that the K3 NGAL is capable of binding to siderophores such as Ent:Fe and therefore are predicted to transport iron from the blood into the urine.

FIG. 21. Amino acid sequence of K3Cys protein (Seq ID NO: 252).

Figures 22A, 22B:
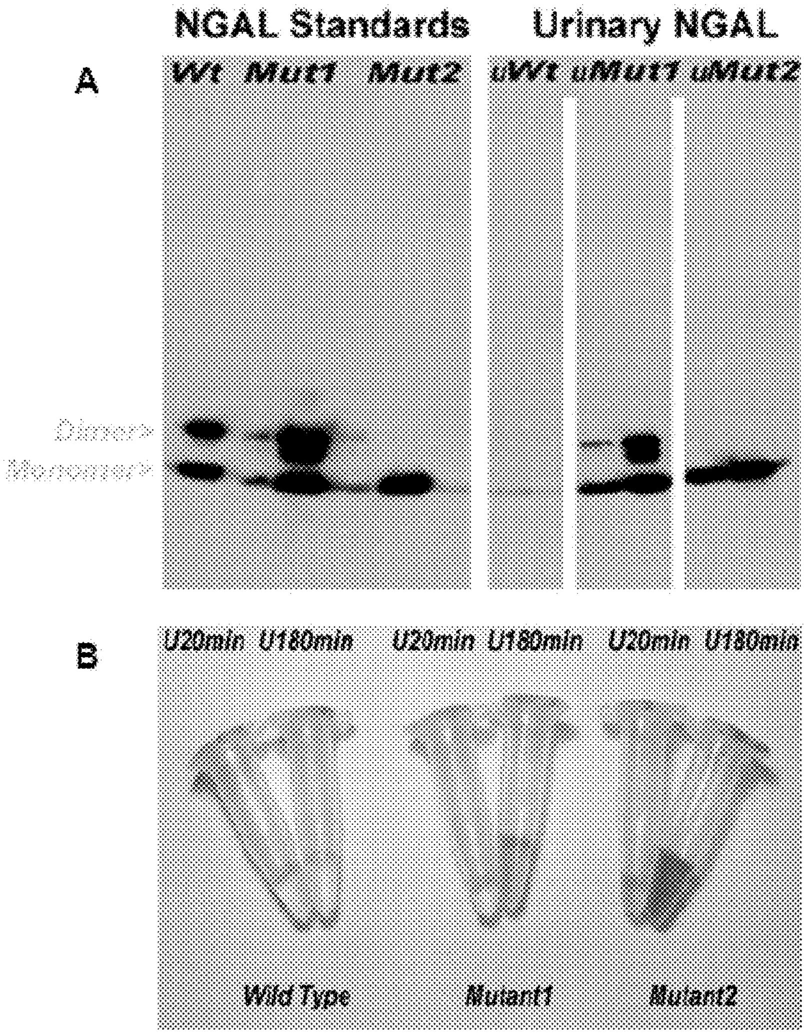

FIGS. 22A-22B. FIG. 22A. Left: Western blot of different species of NGAL. Wild type NGAL forms protein dimers (46-50 KDa) from monomers (at 23-25 KDa). Similarly the Mutant1 (K3 NGAL) forms dimers from monomers. However, Mutant2 (K3Cys) only forms monomers. Right. NGAL proteins (Wt, Mut1 and Mut2) were injected into mice, and the NGAL proteins in the urine (uWt=urinary wild-type protein; uMut1=urinary Mut1 K3 and uMut2=urinary Mut2 K3Cys) were collected at two different time points, and analyzed by Western Blot. For each protein (uWt, uMut1 and uMut2), the 1st lane on the Western blot represents proteins that were collected in the urine 20 min. after the injection and the 2nd lane on the Western blot represents proteins that were collected from the mouse at 180 min. after the injection. Very low levels of uWt appear in urine, whereas higher levels of both uMut1 and uMut2 appear in urine. uMut1 forms both monomers and dimers, whereas uMut2 only forms monomers. FIG. 22B. Mice were injected with NGAL proteins (Wt, Mut1 and Mut2) that were labeled with the dye Alexa Fluor™ 568 (Molecular Probes-Invitrogen), which covalently attaches to the proteins. The urinary NGAL proteins (uWt, uMut1 and uMut2) were subsequently collected from the urine, and tested for by color at either 20 min or 180 min after collection (see tubes from left to right: 1st tube: uWt; at 20 min; 2nd tube: uWt at 180 min. 3rd tube: uMut1 at 20 min; 4th tube: uMut1 at 180 min; 5th tube: uMut2 at 20 min; 6th tube: uMut2 at 180 min tube). The darker the color, the higher the amount of protein present in the urine. These data demonstrate that both K3 and K3Cys can traffic to the urine but K3Cys appears more efficient.

Figure 23:
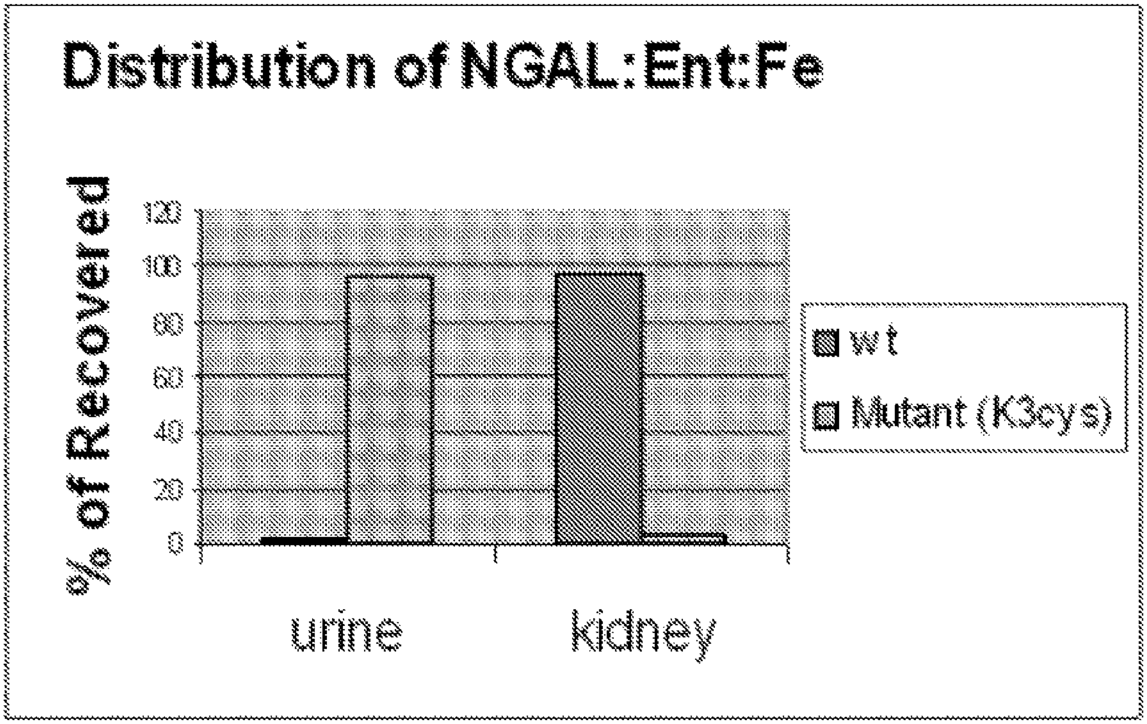
Figure 24:
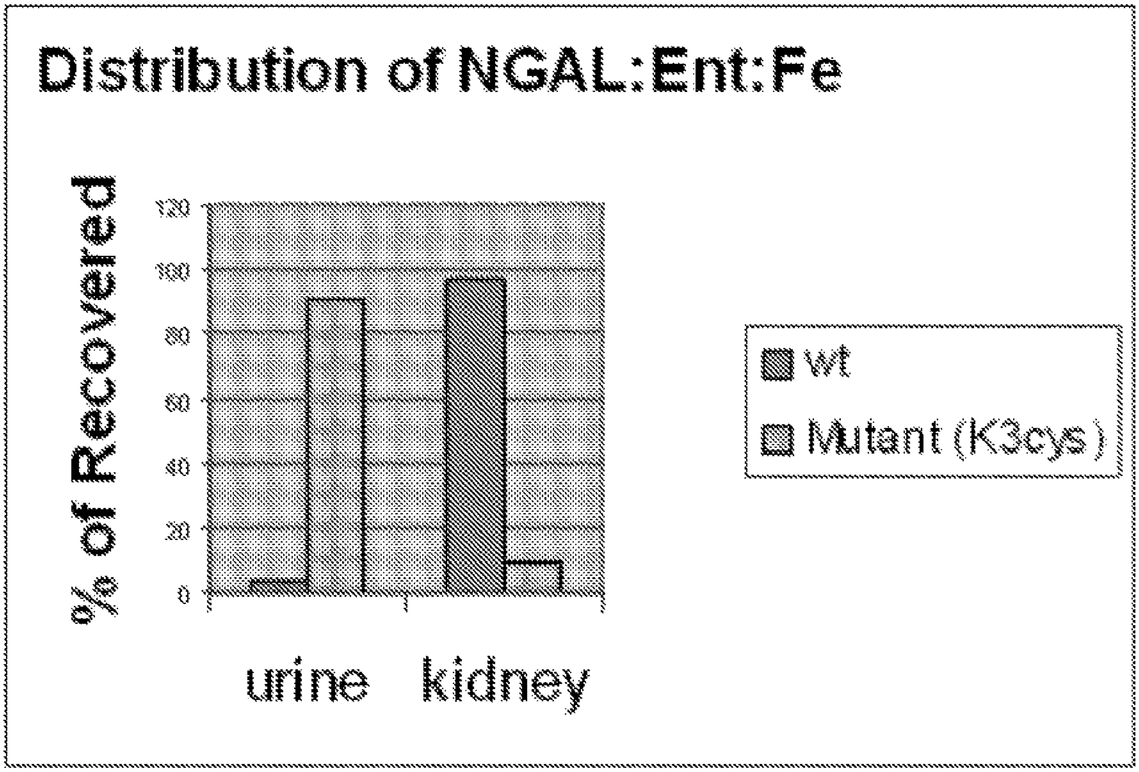

FIG. 23 and FIG. 24. Distribution of NGAL:Ent:Fe in kidney and urine 180 minutes after their introduction in mice. Either wild-type NGAL protein (Wt) or K3Cys protein (Mutant (K3cys)) was introduced in mice and the percentage of iron recovered in either the urine or the kidney of the injected mouse was determined. The Y-axis represents the percentage of recovered iron. FIG. 23 and FIG. 24 are different mice. Note that iron associated with wild type NGAL remains in the kidney, while iron associated with the K3Cys is found in the urine, rather than in the kidney.

Figure 25:
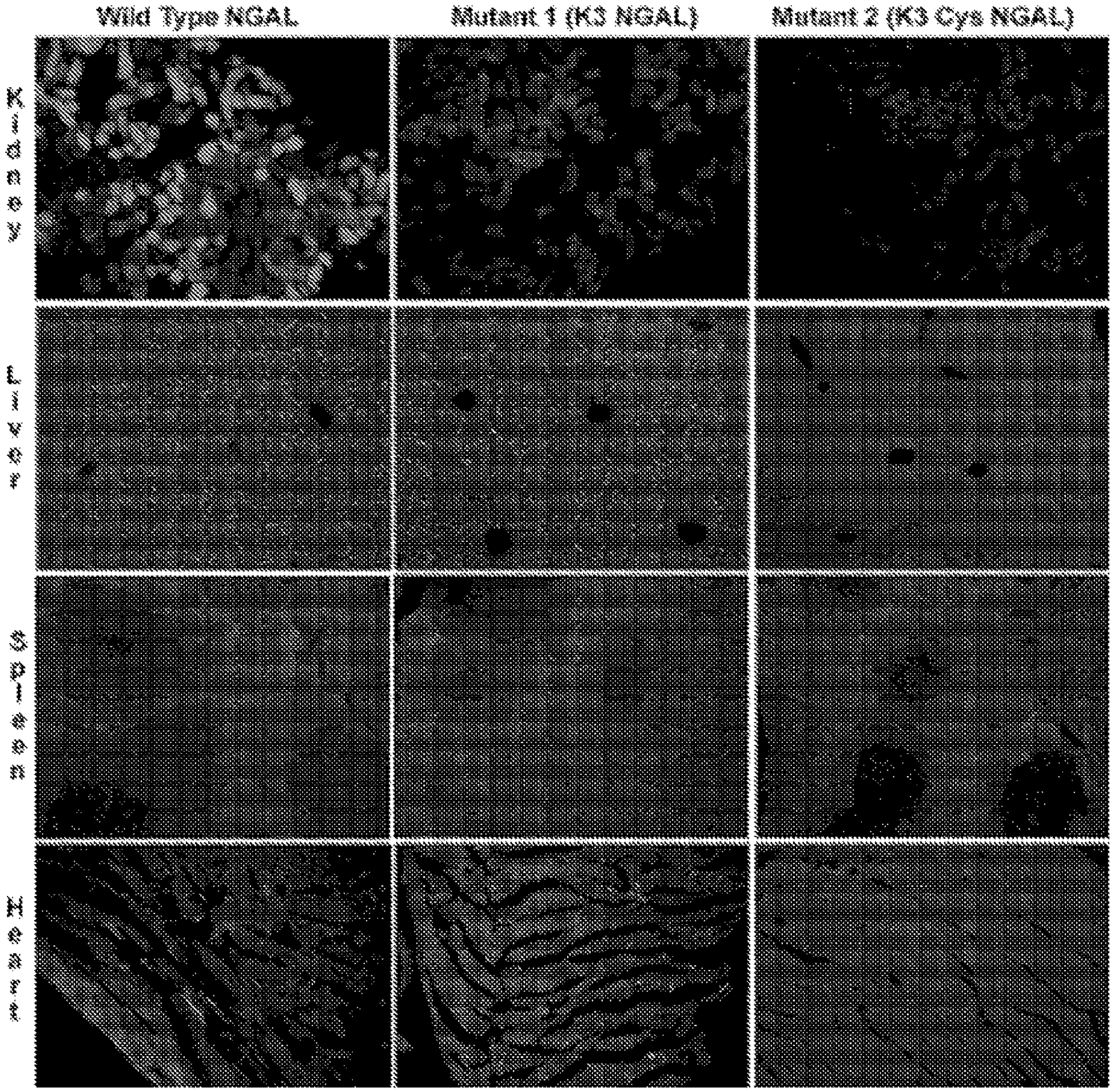

FIG. 25. Distribution of NGAL (Wt, K3 or K3Cys) labeled with the dye Alexa Fluor™ 568 (Molecular Probes-Invitrogen) in the mouse. Note that Wt NGAL is taken up by the kidney's proximal tubule, but limited uptake by K3 and K3Cys. Even more striking is the fact that K3Cys is essentially not found in the body (it is all excreted into the urine) whereas K3 is found in the liver's Kupffer cells (bright red staining).

Figure 26:
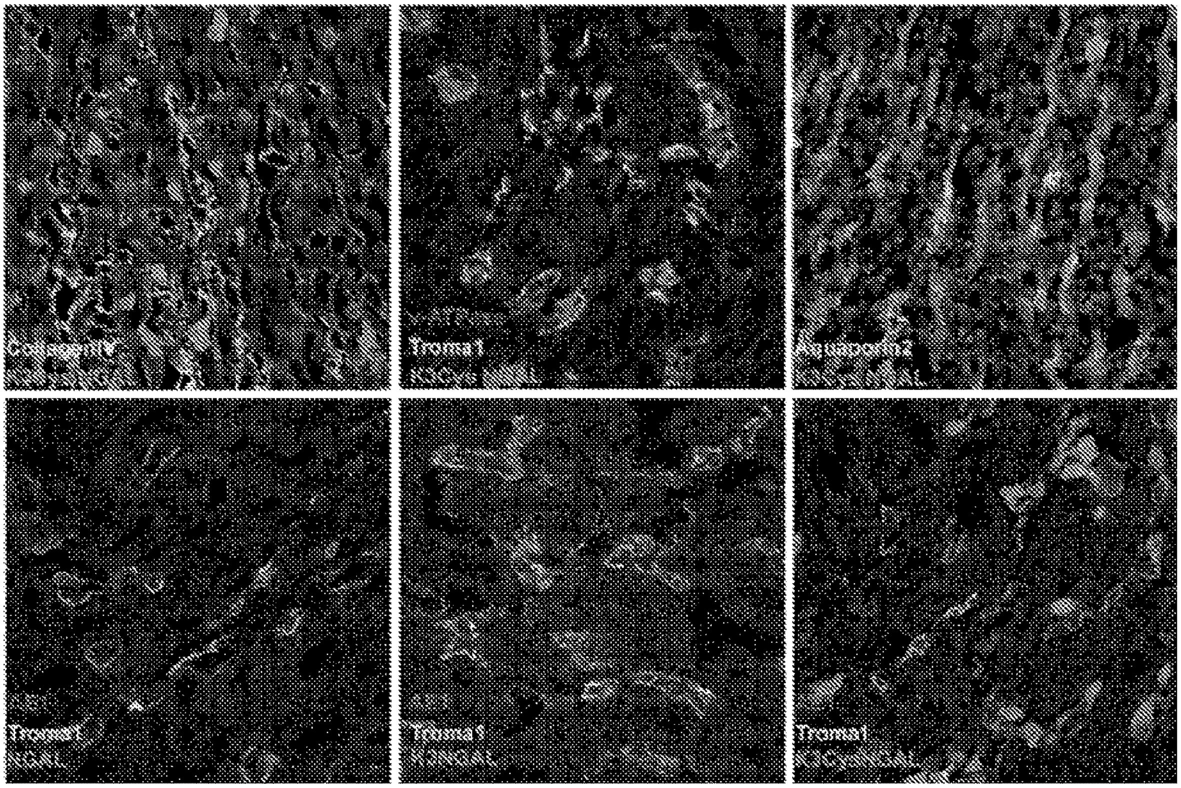

FIG. 26. Top row Alexa Fluor™ 568-mutant NGAL is captured in scattered cells in the collecting ducts outlined by collagen, including ATPase+ intercalated cells and Aquaporin2+ collecting ducts. Bottom row: Comparison wt, mutT, mut2 uptake in AE1+ cells.

Figure 27:
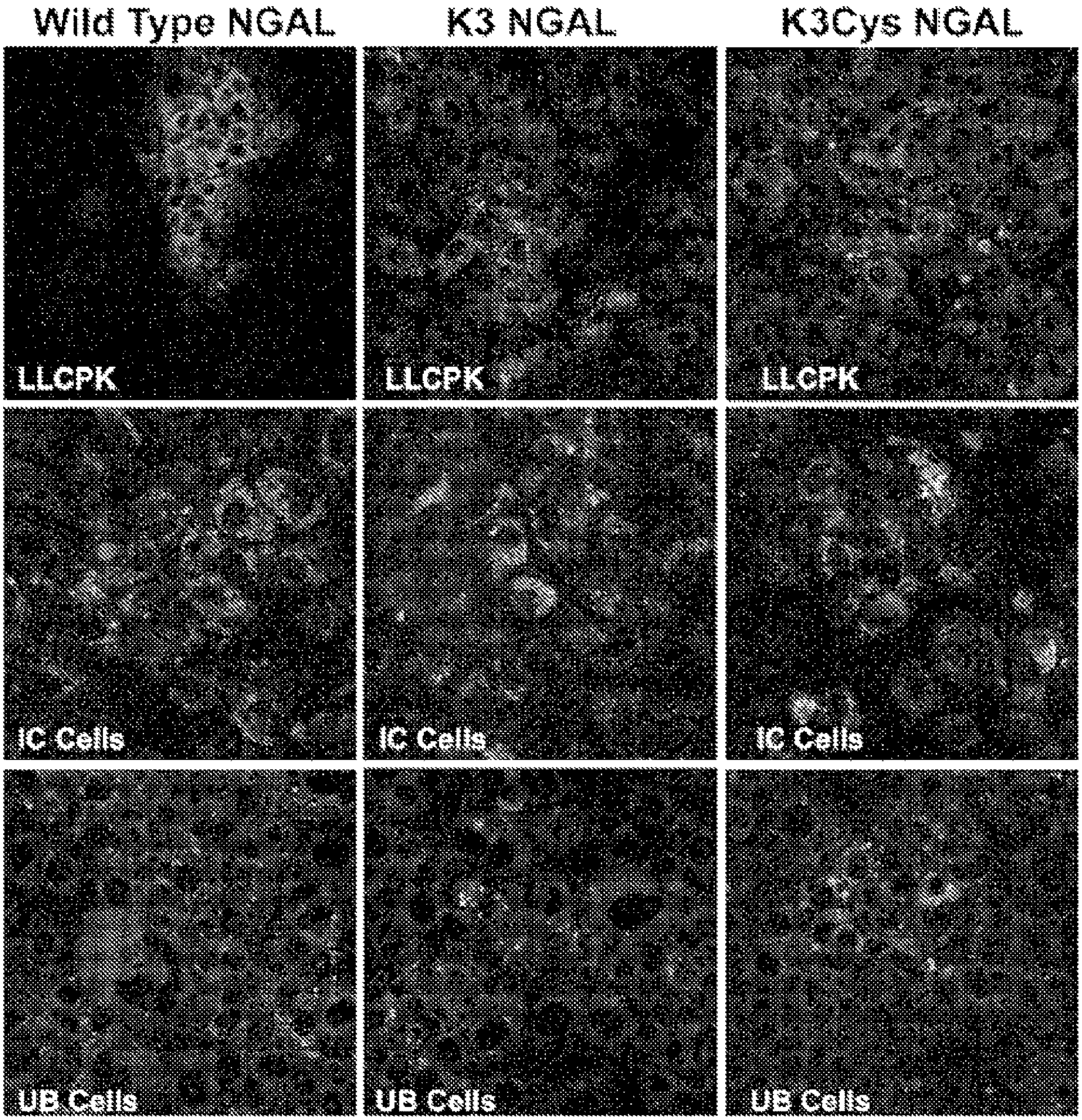

FIG. 27. Three cell lines. LLCPK distinguishes wt and mutant Ngal and takes up only wt Ngal (red uptake), Intercalated cells take up both wild type and mutant Ngal, whereas UB cells take up neither wt nor mutant Ngal Green=fluorescent dextran which demonstrates that all of the cell lines have active endocytosis and highlights the fact that each have distinct NGAL uptake profiles.

Figure 28:
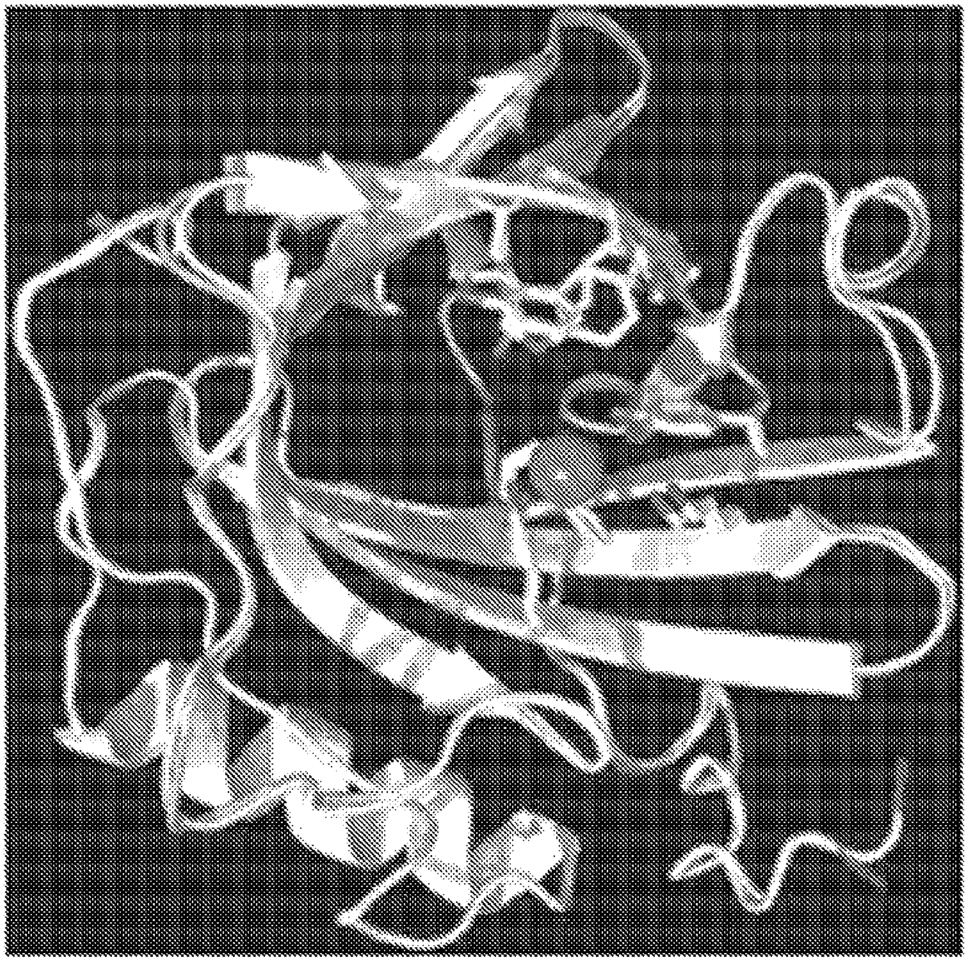

FIG. 28. Superimposed structures of wild type and mutant 1 of Ngal demonstrating nearly identical structures with the potential to bind siderophores and iron (red sphere). Mutant amino acids are indicated in yellow.

Figure 29A:
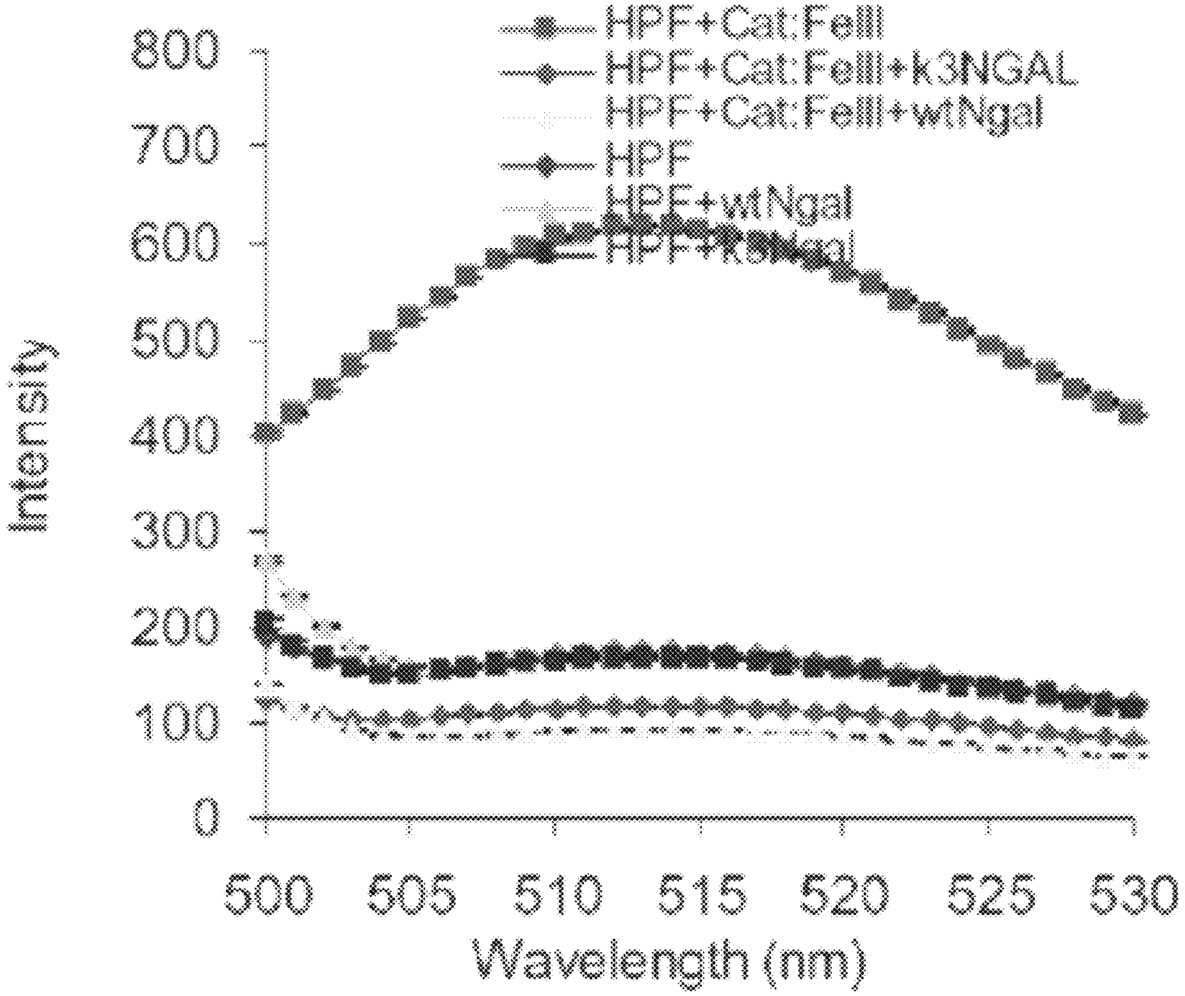
Figure 29B:
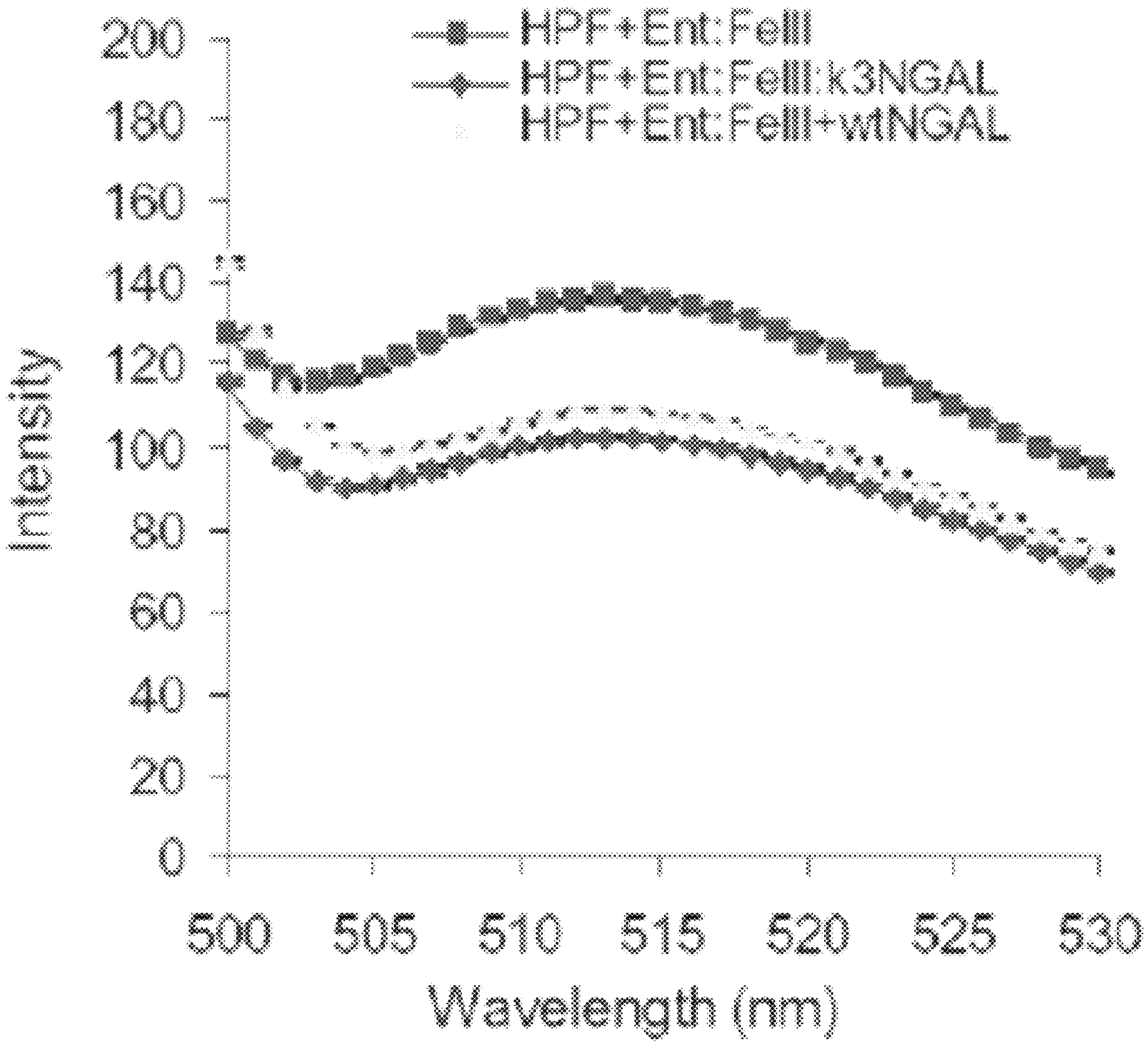
Figure 29C:
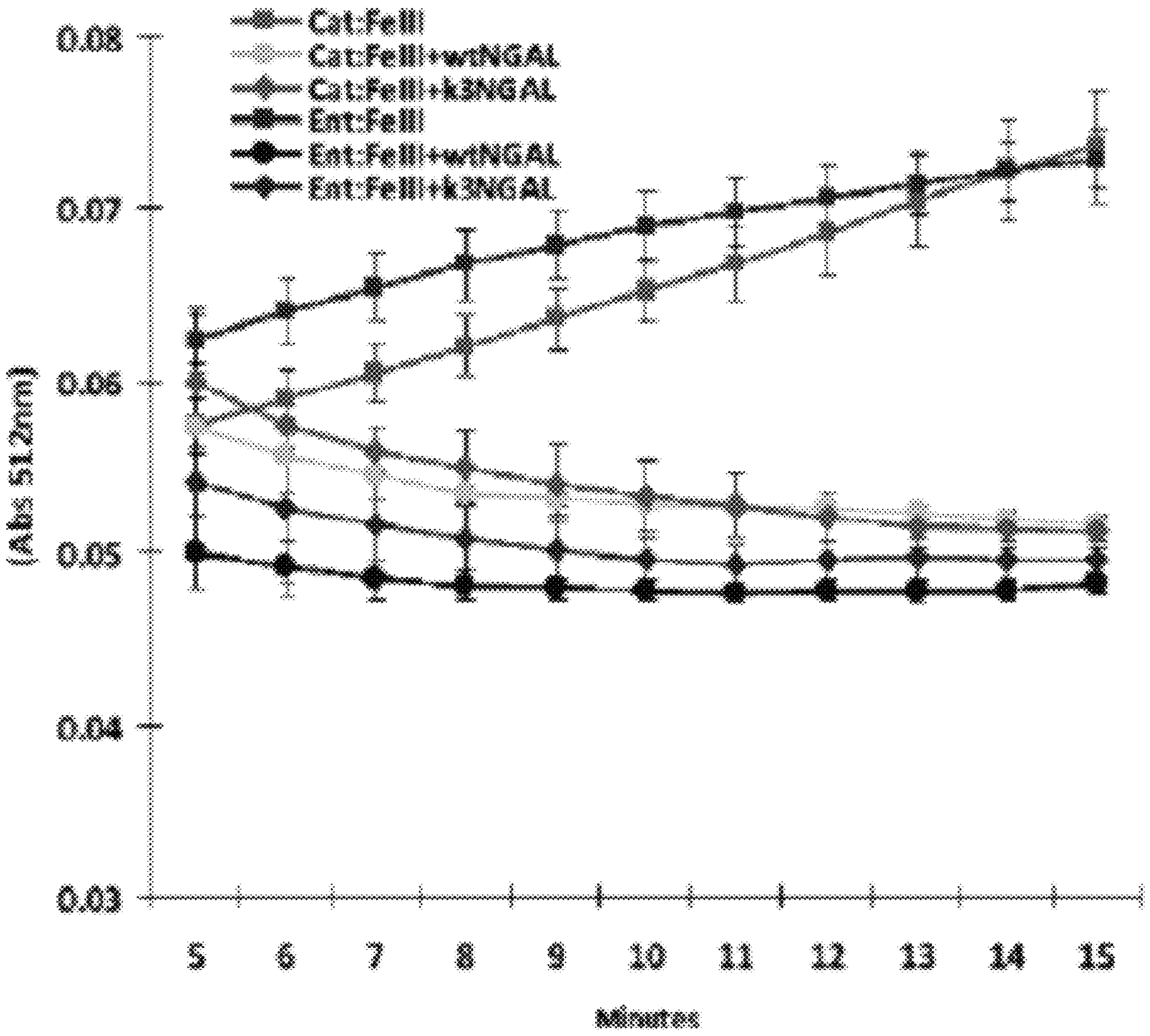

FIGS. 29A-29C. Redox measurements of mutant Ngal. FIG. 29A. The conversion of HPF to fluorescein is detected in the presence of catechol and iron. When Ngal species are added, the activity is suppressed. Similarly when conversion of ferric to ferrous iron is detected (due to the intrinsic reductase activity of catechol groups), Ngal species suppressed the activity. Mutant Ngal was as effective as wt NGAL. FIG. 29B. The conversion of HPF to Fluorescin is detected in the presence of Ent and iron. The Ngal species are added, the activity is suppressed. Mutant Ngal was as effective as wt NGAL.

FIG. 29C. The conversion of HPF to fluorescein is detected in the presence of catechol or Ent and iron. When Ngal species are added, the activity is suppressed. Similarly when conversion of ferric to ferrous iron is detected (due to the intrinsic reductase activity of catechol groups), Ngal species suppressed the activity. Mutant Ngal was as effective as wt NGAL.

Figure 30:
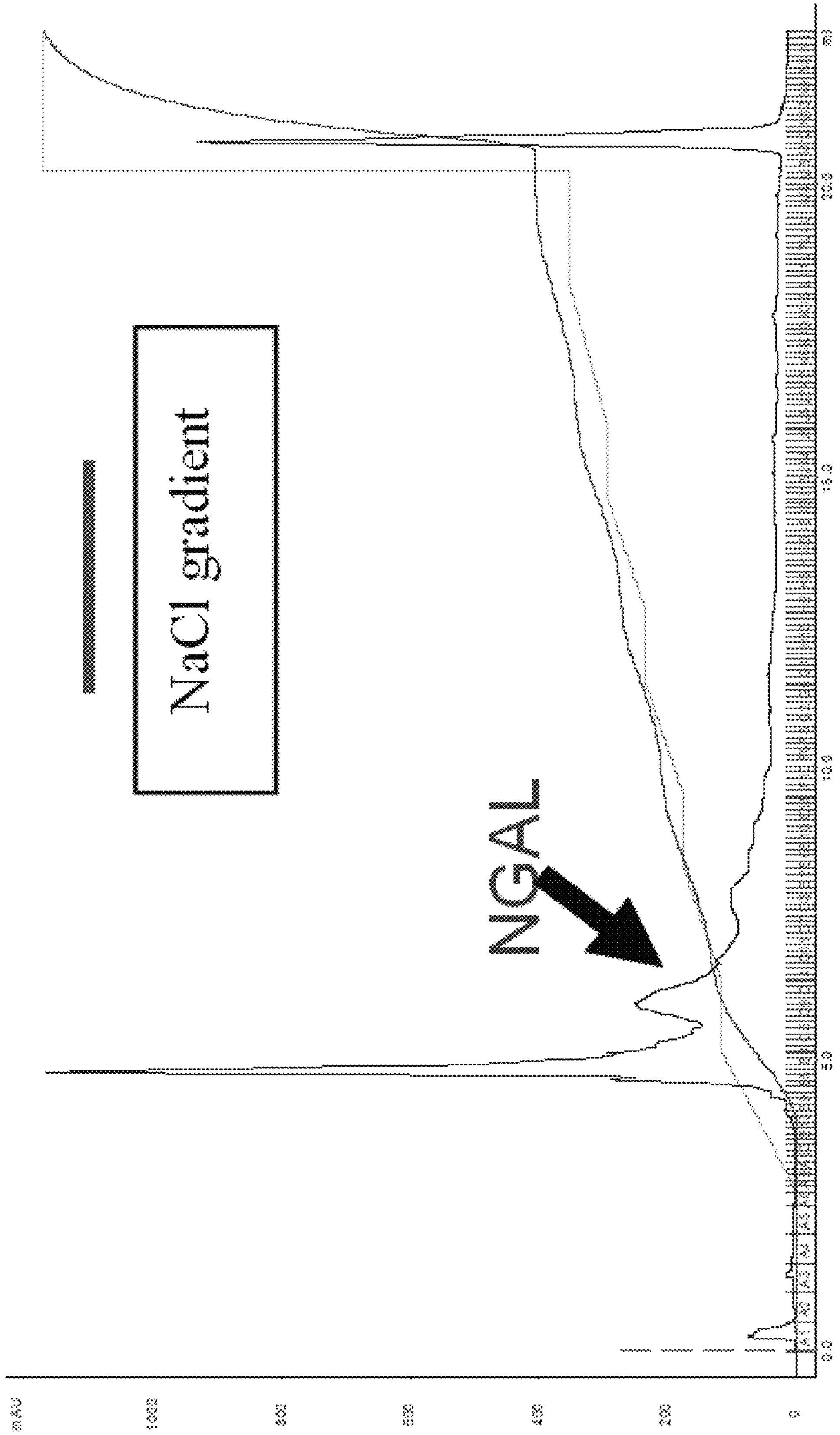

FIG. 30. Purification of NGAL protein. NaCL gradient showing that the small peak contains the majority of the NGAL protein.

DETAILED DESCRIPTION

The present invention is based, in part, on the development of mutant versions of the NGAL protein that are not reabsorbed in the kidney and thus, unlike wild-type NGAL, are excreted in the urine. These mutant forms of NGAL have the ability to bind to iron-binding siderophores, such as enterochelin, and can be used to traffic iron out of the body by excretion in the urine. As such, the mutant NGAL proteins of the invention can be used in the treatment of iron overload and diseases and disorders associated with iron overload. In addition, the mutant NGAL proteins of the invention have bacteriostatic activity and can be used to treat infections of the urinary tract. Thus, the present invention provides mutant NGAL proteins, pharmaceutical compositions comprising such mutant NGAL proteins, either alone or complexed with siderophores, and the use of such mutant NGAL proteins and compositions in the treatment of various disorders and diseases, such as in the treatment of disorders associated with iron overload and in the treatment of bacterial infections of the urinary tract. These and other aspects of the present invention are described more fully below, and also in other sections of this application.

As discussed herein, a series of defined mutations in the positive surface residues of Ngal were made and clones that traffic into the urine (i.e. bypassing megalin) were identified. A mutation in the unpaired cysteine was introduced to block the homodimerization of the NGAL mutant referred to as a "K3" NGAL. In the resultant new NGAL protein, called K3Cys, the cysteine residue at position 87 in K3 NGAL is substituted with a serine residue. This substitution resulted in the loss of dimerization of the K3Cys protein, which forms monomers. This K3Cys protein appeared earlier in the urine than K3 NGAL protein which was still capable of dimerization. This nearly complete loss of NGAL from the mouse by filtration and urinary excretion is most likely a result of the lower molecular weight of the monomeric-non dimerizable species.

Abbreviations and Definitions

The abbreviation "NGAL" refers to Neutrophil Gelatinase Associated Lipocalin. NGAL is also referred to in the art as human neutrophil lipocalin, siderocalin, a-micro-globulin related protein, Scn-NGAL, lipocalin 2, 24p3, superinducible protein 24 (SIP24), uterocalin, and neu-related lipocalin. These alternative names for NGAL may be used interchangeably herein. Unless stated otherwise, the term "NGAL", as used herein, includes any NGAL protein, fragment, or mutant. In some embodiments the NGAL protein is wild-type human NGAL. In other embodiments the NGAL protein is a mutant NGAL protein.

The abbreviation hNGAL refers to human NGAL.

The abbreviation "WT" refers to wild-type, such as a wild-type nucleotide or amino acid sequence.

The abbreviation "K3Cys" refers to a mutant K3 NGAL protein (SEQ ID NO: 2) that contains a cysteine residue at position 87. The amino acid sequence of K3Cys is represented by SEQ ID NO: 252. The designation "K3Cys" is used interchangeably with the designations "K3 Cys", "K3Cys protein", "K3 Cys NGAL" and "K3Cys NGAL".

The phrase "K3Cys mutant" refers to a K3Cys protein that contains one or more amino acid mutations, including, but not limited to, substitutions, deletions and insertions. The designation "K3Cys mutant" is used interchangeably with the designation "K3Cys mutant protein".

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

NGAL

NGAL is a small protein with a molecular weight of about 22 kD and is a siderophore binding protein. A siderophore is an organic molecule that binds to and chelates iron. Bacteria produce the siderophore enterochelin, and mammals endogenously express a similar type, but simpler molecule called catechol. Enterochelin has an extremely high affinity for iron, and wild type NGAL has a high affinity for the enterochelin-iron complex. The enterochelin-iron-NGAL complex is pH insensitive and the bound iron is redox inactive. Thus the iron bound by such NGAL complexes is not available to catalyze oxygen radical formation, making NGAL an ideal iron chelator for in vivo use.

NGAL, and once produced in cells, is secreted into extracellular space and quickly cleared by kidney with a half-life of 10 minutes. Serum and urine levels of the protein can become very high in a number of disease models. The NGAL protein is transported into the kidney of healthy humans and can pass the filtration barrier of the glomerulus (the cut-off size of filtration is about 70 kD) to enter the primary urine, but then NGAL is efficiently reabsorbed by megalin or megalin-cubilin-cubilin receptors localized on the apical side of the epithelia of the proximal tubules. Megalin is a universal receptor with broad substrate specificity and is expressed at the apical surface of the proximal tubules of the kidney where it is involved in protein reabsorption. The binding of megalin to its substrates is mediated by ionic interactions, and its negative charged substrate binding domains can efficiently bind to the positively charged surfaces of proteins in the urinary filtrate. Once absorbed and endocytosed, NGAL is trafficked to lysosomes, where it is degraded. Once degraded, the iron which NGAL transported to the kidney is reabsorbed.

K3 NGAL

The present invention provides mutant NGAL proteins, including, but not limited to those which have been mutated to remove positively charged residues that may be involved in the megalin interaction.

Figure 1:
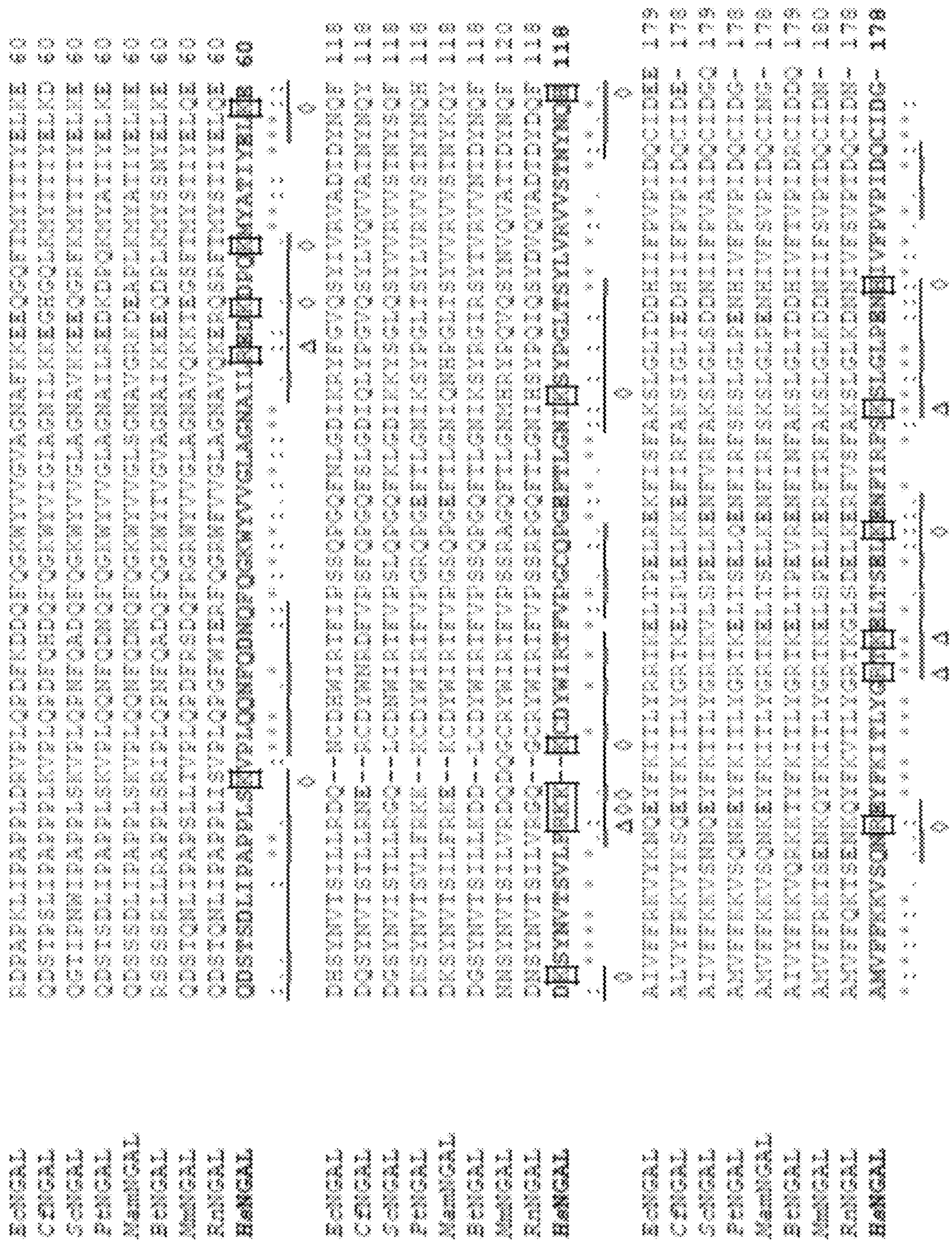
FIG. 1. Alignment of Ngal protein from human (HsNgal; NP_005555-WT Human NGAL-SEQ ID NO: 1), mouse (MmNgal; NP_032517, SEQ ID NO: 17), rat (RnNgal; NP_570097, SEQ ID NO: 18), Chimpanzee (PtNgal, XP_001153985, SEQ ID NO: 14), bovine (BtNgal; XP_605012; SEQ ID NO: 16), dog (CfNgal; SEQ ID NO: 12), wild boar (SsNgal; SEQ ID NO: 13), Rhesus Monkey (MamNgal, SEQ ID NO: 15), and horse (*Equus caballus* (Ec) NGAL, SEQ ID NO: 11). Human NGAL protein sequence is Bold, and the amino acid residues on the surface of NGAL proteins are underlined. Δ and ◇ indicate the conserved and the non-conserved positively charged residues (Arginine [R], Lysine [K] and Histidine [H]) on the surface of functional Ngal protein, respectively. Magenta: positive charged residues; Blue: negative charged residues; red: nonpolar and hydrophobic residues; Green: polar and hydrophilic residues.

The terms "mutant NGAL protein" and "NGAL mutant" as used herein, refer to a protein or an amino acid sequence that differs by one or more amino acids from the amino acid sequence of WT human NGAL (SEQ ID NO. 1, see sequence of HsNGAL in FIG. 1).

The invention provides for a mutant NGAL protein, K3 (or K3 NGAL, or K3 NGAI protein), that has an amino acid sequence identical to SEQ ID NO: 2 (Table 2).

Like WT NGAL, K3 NGAL has high affinity for enterochelin-iron complexes but appear to have significantly reduced affinity for megalin. Thus, rather than being reabsorbed by a megalin receptor mediated mechanism in the kidney, K3 NGAL of the invention, and complexes of K3 NGAL with enterochelin and iron, are not efficiently reabsorbed in the kidney and are instead excreted in the urine. The K3 NGAL protein of the invention can thus be used to efficiently remove excessive iron from the body and traffic it into the urine in a safe redox inactive form. Furthermore, previous reports have shown that NGAL-enterochelin-iron has little or no chemical or cellular toxicity, suggesting that it could be safely used therapeutically, for example in the therapeutic treatment of diseases and disorders associated with iron overload, such as hemochromatosis.

K3Cys

The present invention provides a mutant K3 NGAL protein, "K3Cys", which comprises a K3 NGAL protein (SEQ ID NO: 2) in which the cysteine residue at position 87 (Cysteine 87) was substituted with a serine residue. The amino acid sequence of K3Cys is identical to SEQ ID NO:

252. Thus, rather than being reabsorbed by a megalin receptor mediated mechanism in the kidney, K3Cys, and complexes of this mutant with enterochelin and iron, are not efficiently reabsorbed in the kidney and are instead excreted in the urine. K3Cys can thus be used to efficiently remove excessive iron from the body and traffic it into the urine in a safe redox inactive form. Furthermore, previous reports have shown that NGAL-enterochelin-iron has little or no chemical or cellular toxicity, indicating that it could be safely used therapeutically, for example in the therapeutic treatment of diseases and disorders associated with iron overload, such as hemochromatosis.

In one aspect, the present invention provides a K3Cys protein that comprises, consists essentially of, or consists of an amino acid sequence that is identical to SEQ ID NO. 252, and wherein the K3Cys protein: (a) is excreted in the urine or exhibits a greater level of excretion in the urine than the WT NGAL protein, and/or (b) is not reabsorbed in the proximal tubule of the kidney or exhibits a lower level of reabsorption in the proximal tubule of the kidney as compared to the WT NGAL protein, and/or (c) is not a substrate for reabsorption in the kidney by a megalin-cubilin-cubilin-receptor mediated mechanism, and/or (d) has reduced affinity for the megalin-cubilin-receptor as compared to the WT NGAL protein, and/or (e) has fewer positively charged residues on its solvent accessible surface as compared to the WT NGAL protein, and wherein the K3Cys protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity.

In another aspect, the present invention provides a K3Cys protein that comprises, consists essentially of, or consists of an amino acid sequence that is at least 70%, or at least 75%, or at least 80%, or at least 85%, or at least 90%, or at least 95%, or at least 98%, or at least 99% identical to SEQ ID NO. 252, and wherein the K3Cys protein: (a) is excreted in the urine or exhibits a greater level of excretion in the urine than the WT NGAL protein, and/or (b) is not reabsorbed in the proximal tubule of the kidney or exhibits a lower level of reabsorption in the proximal tubule of the kidney as compared to the WT NGAL protein, and/or (c) is not a substrate for reabsorption in the kidney by a megalin-cubilin-cubilin-receptor mediated mechanism, and/or (d) has reduced affinity for the megalin-cubilin-receptor as compared to the WT NGAL protein, and/or (e) has fewer positively charged residues on its solvent accessible surface as compared to the WT NGAL protein, and wherein the K3Cys protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity.

K3Cys Mutants

The present invention also provides for K3Cys mutants, which comprise K3Cys proteins that contain one or more amino acid mutations, including, but not limited to, substitutions, deletions and insertions.

K3Cys mutants may have one or more "non conservative" changes, as compared to K3Cys, wherein a given amino acid is substituted with another amino acid that has different structural or chemical properties. In several embodiments of the invention basic/positively charged lysine, arginine, and/or histidine residues on the surface of K3Cys mutants, such as those that interact with megalin, are mutated by substituting these residues with non-basic/non-positively charged residues. These are non-conservative changes. For example, in several embodiments of the invention basic/positively charged lysine (Lys—K), arginine (Arg—R), and/or histidine (His—H), residues, such as those on the surface of K3Cys mutants that may be involved in the megalin interaction, are substituted with non-basic/non-positively charged residues such as alanine (Ala—A), asparagine (Asn—N), aspartic acid (Asp—D), cysteine (Cys—C), glutamine (Gln—Q), glutamic acid (glu—E), glycine (Gly—G), isoleucine (Ile—I), leucine (Leu—L), methionine (Met—M), phenylalanine (Phe—F), proline (Pro—P), serine (Ser—S), threonine (thr—T), tryptophan (Trp—W), tyrosine (Tyr—Y), and valine (Val—V). In some embodiments, basic/positively charged lysine, arginine, and/or histidine residues are substituted with negatively charged residues such as aspartic acid (Asp—D) and glutamic acid (Glu—E).

In some embodiments, the K3Cys mutant may have one or more "conservative" changes, as compared to K3Cys, wherein a given amino acid is substituted for another amino acid that has similar structural or chemical properties. For example, in some embodiments it is desirable to either leave the residues of the K3Cys mutant that are involved in the siderophore interaction intact or to only make conservative changes at those residues. Various other conservative amino acid substitutions may be made throughout the K3Cys mutant, such as conservative amino acid substitutions that do not destroy the ability of the K3Cys mutant to transport iron out of the body. One type of conservative amino acid substitution refers to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side chains is cysteine and methionine. Useful conservative amino acids substitution groups are: valine leucine isoleucine, phenylalanine tyrosine, lysine arginine, alanine valine, and asparagine glutamine.

The K3Cys mutant may contain various mutations (including additions, deletions, and substitutions), including, for example, additions to or deletions from the N- and/or C-termini of the K3Cys mutant. Any such mutations can be made to the extent that they do not adversely affect the ability of the K3Cys mutant to bind to a siderophore, to transport iron, and/or to be excreted in the urine.

In further embodiments, the K3Cys mutant may comprise one or more non-naturally occurring amino acids. Non-natural amino acids, such as those that contain unique side chain functional groups including halogens, unsaturated hydrocarbons, heterocycles, silicon, and organometallic units, can offer advantages in improving the stability of proteins. Many such non-naturally occurring amino acids are known. Such non-naturally occurring amino acids can be used in the K3Cys mutant.

In one embodiment the cysteine 87 residue of the K3Cys mutant is deleted. In another embodiment, the cysteine 87 residue of the K3Cys mutant is substituted with a non-positively charged amino acid (i.e. a non-conservative substitution). In another embodiment the cysteine 87 residue of the K3Cys mutant, is substituted with a negatively charged amino acid (i.e. a non-conservative substitution). In another embodiment, the cysteine 87 residue of the K3Cys mutant is substituted with an alanine residue. In another embodiment, the K3Cys mutant may comprise any combination of such mutations, i.e. any combination of deletions, substitutions for non-positively charged amino acids, or substitutions for negatively charged amino acids may be present at any one, two, three, four, five, six, seven, eight nine, ten, eleven, twelve, or all thirteen of the above listed amino acid residues. In preferred embodiments, the K3Cys mutant is not mutated (i.e. has the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one preferred embodiment the present invention provides a K3Cys mutant in which Lys (K) 15 is substituted with an uncharged amino acid, including, but not limited to, Ser (S). In one preferred embodiment the present invention provides a K3Cys mutant in which Lys (K) 46 is substituted with a negatively charged amino acid, including, but not limited to, Glu (E). In one preferred embodiment the present invention provides a K3Cys mutant in which Lys (K) 50 is substituted with an uncharged amino acid, including, but not limited to, Thr (T). In one preferred embodiment the present invention provides a K3Cys mutant in which Lys (K) 59 is substituted with an uncharged amino acid, including, but not limited to, Gln (Q). In one preferred embodiment the present invention provides a K3Cys mutant in which Lys (K) 62 is substituted with an uncharged amino acid, including, but not limited to, Gly (G). In one preferred embodiment the present invention provides a K3Cys mutant in which Lys (K) 73 is substituted with a negatively charged amino acid, including, but not limited to, Asp (D). In one preferred embodiment the present invention provides a K3Cys mutant in which Lys (K) 74 is substituted with a negatively charged amino acid, including, but not limited to, Asp (D). In one preferred embodiment the present invention provides a K3Cys mutant in which Lys (K) 75 is substituted with an aliphatic amino acid, including, but not limited to, Gly (G). In one preferred embodiment the present invention provides a K3Cys mutant in which Lys (K) 98 is substituted with an uncharged amino acid, including, but not limited to, Gln (Q). In one preferred embodiment the present invention provides a K3Cys mutant in which His (H) 118 is substituted with a non-polar amino acid, including, but not limited to, Phe (F). In one preferred embodiment the present invention provides a K3Cys mutant in which Arg (R) 130 is substituted with an uncharged amino acid, including, but not limited to, Gln (Q). In one preferred embodiment the present invention provides a K3Cys mutant in which Lys (K) 149 is substituted with an uncharged amino acid, including, but not limited to, Gln (Q). In one preferred embodiment the present invention provides a K3Cys mutant in which His (H) 165 is substituted with an uncharged amino acid, including, but not limited to, Asn (N).

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO. 252), or a fragment thereof, wherein one, two, three, four, five, six, seven, eight, nine, ten, eleven, twelve, or all thirteen residues from among Lys 15, Lys 46, Lys 50, Lys 59, Lys 62, Lys 73, Lys 74, Lys 75, Lys 98, His 118, Arg 130, Lys 149, and His 165 is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the K3Cys mutant protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to the K3Cys protein. In some embodiments six or more of the thirteen listed amino acid positions are mutated as compared to the K3Cys protein. In some embodiments seven or more of the thirteen listed amino acid positions are mutated as compared to the K3Cys protein. In some embodiments eight or more of the thirteen listed amino acid positions are mutated as compared to the K3Cys protein. In some embodiments nine or more of the thirteen listed amino acid positions are mutated as compared to the K3Cys protein. In some embodiments ten or more of the thirteen listed amino acid positions are mutated as compared to the K3Cys protein. In preferred embodiments, such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In some embodiments, the K3Cys mutant has the amino acids specified in SEQ ID NO: 252 (Table 2) at residues 15, 46, 59, 62, 73, 74, 75, 98, 118, 130, 149, and 165, but other amino acid residues can differ from the specified sequences provided that the K3Cys mutant protein is at least 70%, or at least 75%, or at least 80%, or at least 85%, or at least 90%, or at least 95%, or at least 98% identical to the sequence of the K3Cys protein (SEQ ID NO.:252), or a fragment thereof, and provided that the K3Cys mutant protein: (a) is excreted in the urine or exhibits a greater level of excretion in the urine than K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to K3Cys protein and/or WT NGAL, and/or (e) has fewer positively charged residues on its solvent accessible surface as compared to the K3Cys protein and/or WT NGAL, and also provided that the K3Cys mutant protein (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to the K3Cys protein. In some embodiments six or more of the thirteen listed amino acid positions are mutated as compared to the K3Cys protein. In some embodiments seven or more of the thirteen listed amino acid positions are mutated as compared to the K3Cys protein. In some embodiments eight or more of the thirteen listed amino acid positions are mutated as compared to the K3Cys protein. In some embodiments nine or more of the thirteen listed amino acid positions are mutated as compared to the K3Cys protein. In some embodiments ten or more of the thirteen listed amino acid positions are mutated as compared to the K3Cys protein. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments, a K3Cys mutant protein described above that has mutations in one or more of the thirteen non-conserved positive/basic surface residues, can also have mutations in one or more of the five conserved positive/based surface residues below, or one or more of the other mutations described in other following sections of this Detailed Description.

Five Conserved Positive/Basic Surface Residues in NGAL

The K3Cys protein contains five basic/positive surface amino acid residues that are conserved among human, rat, mouse, chimpanzee, cow, dog, wild boar and rhesus monkey species, namely residues Arg(R) 43, Arg(R) 72, Arg(R) 140, Lys(K) 142, and Lys(K) 157. In one embodiment, the present invention provides K3Cys mutant proteins having one, two, three, four, or all five of these amino acid positions mutated as compared to the K3Cys protein. In one embodiment the mutated amino acid residue or residues are deleted. In another embodiment the mutated amino acid residue or residues are substituted with a non-positively charged amino acid (i.e. a non-conservative change). In another embodiment the mutated amino acid residue or residues are substituted with a negatively charged amino acid (i.e. a non-conservative change). In another embodiment the K3Cys mutant protein may comprise any combination of such mutations, i.e. any combination of deletions, substitutions for non-positively charged amino acids, or substitutions for negatively charged amino acids may be provided at one, two, three, four, or five of the above listed amino acid residues.

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO. 252), or a fragment thereof, wherein one, two, three, four, or all five residues from among (R) 43, Arg(R) 72, Arg(R) 140, Lys(K) 142, and Lys(K) 157 is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the K3Cys mutant protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments, the K3Cys mutant proteins described in this section that have mutations in one or more of the five conserved positive/basic surface residues, can also have mutations in one or more of the thirteen non-conserved positive/based surface residues described in the previous section of the Detailed Description, or one or more of the other mutations described in the following sections of this Detailed Description.

Additional Surface Residues in NGAL

The following amino acid residues are located on the surface of the K3Cys protein and can play a role in the interaction of the K3Cys protein with the megalin protein and/or in the reabsorption of the K3Cys protein in the kidney: amino acid residues 1-15, 17-26, 40-50, 57-62, 71-82, 84-89, 96-105, 114-118, 128-131, 134, 140-151, 157-165, and 170-174.

In one embodiment, the K3Cys mutant proteins of the invention comprise, consist of, or consist essentially of amino acid sequences that are based on the amino acid sequence of human K3Cys protein, or a fragment thereof, but that contain mutations at one or more of the individual amino acid residues located at residues 1-15, 17-26, 40-50, 57-62, 71-82, 84-89, 96-105, 114-118, 128-131, 134, 140-151, 157-165, and/or 170-174 of the K3Cys protein. In one embodiment one or more of the mutated amino acid residues can be deleted. In another embodiment one or more of the mutated amino acid residues can be substituted with a non-positively charged amino acid, including, but not limited to a negatively charged amino acid. In another embodiment the K3Cys mutant protein may comprise any combination of such mutations, i.e. any combination of deletions, substitutions for non-positively charged amino acids, and/or substitutions for negatively charged amino acids at any one or more of the above listed amino acid residues.

In some embodiments, K3Cys mutant proteins are mutated, at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134.

In other embodiments, K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO.:252), or a fragment thereof, wherein one or more of the individual amino acid residues located at residues 1-15, 17-26, 40-50, 57-62, 71-82, 84-89, 96-105, 114-118, 128-131, 134, 140-151, 157-165, and/or 170-174 of the K3Cys mutant is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the the K3Cys protein (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

NGAL Mutants

The present invention provides mutant NGAL proteins, including, but not limited to those which have been mutated to remove positively charged residues that may be involved in the megalin interaction. Like WT NGAL, the NGAL mutants of the invention have high affinity for enterochelin-iron complexes but appear to have significantly reduced affinity for megalin (Table 1). Thus, rather than being reabsorbed by a megalin receptor mediated mechanism in the kidney, the NGAL mutants of the invention, and complexes of these mutants with enterochelin and iron, are not efficiently reabsorbed in the kidney and are instead excreted in the urine. The mutant NGAL proteins of the invention can thus be used to efficiently remove excessive iron from the body and traffic it into the urine in a safe redox inactive form. Furthermore, previous reports have shown that NGAL-enterochelin-iron has little or no chemical or cellular toxicity, suggesting that it could be safely used therapeutically, for example in the therapeutic treatment of diseases and disorders associated with iron overload, such as hemochromatosis.

The terms "mutant NGAL protein" and "NGAL mutant" as used herein, refer to a protein or an amino acid sequence that differs by one or more amino acids from the amino acid sequence of WT human NGAL (SEQ ID NO. 1, see sequence of HsNGAL in FIG. 1).

The mutant NGAL proteins of the invention may have one or more "non conservative" changes, wherein a given amino acid is substituted with another amino acid that has different structural or chemical properties. In several embodiments of the invention basic/positively charged lysine, arginine, and/or histidine residues on the surface of the NGAL protein, such as those that interact with megalin, are mutated by substituting these residues with non-basic/non-positively charged residues. These are non-conservative changes. For example, in several embodiments of the invention basic/positively charged lysine (Lys—K), arginine (Arg—R), and/or histidine (His—H), residues, such as those on the surface of the NGAL protein that may be involved in the megalin interaction, are substituted with non-basic/non-positively charged residues such as alanine (Ala—A), asparagine (Asn—N), aspartic acid (Asp—D), cysteine (Cys—C), glutamine (Gln—Q), glutamic acid (glu—E), glycine (Gly—G), isoleucine (Ile—I), leucine (Leu—L), methionine (Met—M), phenylalanine (Phe—F), proline (Pro—P), serine (Ser—S), threonine (thr—T), tryptophan (Trp—W), tyrosine (Tyr—Y), and valine (Val—V). In some embodiments, basic/positively charged lysine, arginine, and/or histidine residues are substituted with negatively charged residues such as aspartic acid (Asp—D) and glutamic acid (Glu—E).

In some embodiments the mutant NGAL proteins of the invention may have one or more "conservative" changes, wherein a given amino acid is substituted for another amino acid that has similar structural or chemical properties. For example, in some embodiments it is desirable to either leave the residues of NGAL that are involved in the siderophore interaction intact or to only make conservative changes at those residues. Various other conservative amino acid substitutions may be made throughout the NGAL protein, such as conservative amino acid substitutions that do not destroy the ability of the NGAL mutants of the invention to transport iron out of the body. One type of conservative amino acid substitution refers to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side chains is cysteine and methionine. Useful conservative amino acids substitution groups are: valine leucine isoleucine, phenylalanine tyrosine, lysine arginine, alanine valine, and asparagine glutamine.

The mutant NGAL proteins of the invention may contain various mutations (including additions, deletions, and substitutions) in addition to the mutations of specific residues set forth herein (below), including, for example, additions to or deletions from the N- and/or C-termini of the NGAL mutants. Any such mutations can be made to the extent that they do not adversely affect the ability of the NGAL mutants to bind to a siderophore, to transport iron, and/or to be excreted in the urine.

In further embodiments, the NGAL mutants of the invention may comprise one or more non-naturally occurring amino acids. Non-natural amino acids, such as those that contain unique side chain functional groups including halogens, unsaturated hydrocarbons, heterocycles, silicon, and organometallic units, can offer advantages in improving the stability of proteins. Many such non-naturally occurring amino acids are known. Such non-naturally occurring amino acids can be used in the NGAL mutants of the invention.

In certain embodiments, the present invention provides NGAL mutants having a certain % identity to WT human NGAL or to some other NGAL mutant. The following terms are used to describe the sequence relationships between two or more polynucleotides or amino acid sequences: “sequence identity,” “percentage sequence identity” and “identity.” These terms are used in accordance with their usual meaning in the art. Percentage sequence identity is measured with reference to a reference sequence. The term “sequence identity” means that two polynucleotide or amino acid sequences are identical (i.e., on a nucleotide-by-nucleotide basis). The term “percentage of sequence identity” is calculated by comparing two optimally aligned sequences, determining the number of positions at which the identical nucleic acid base or amino acid occurs in both sequences to yield the number of matched positions, dividing the number of matched positions by the total number of positions, and multiplying the result by 100 to yield the percentage of sequence identity.

Thirteen Non-Conserved Positive Surface Residues in NGAL

The NGAL protein contains thirteen basic/positive surface amino acid residues that are not conserved among species, namely residues Lys 15, Lys 46, Lys 50, Lys 59, Lys 62, Lys 73, Lys 74, Lys 75, Lys 98, His 118, Arg 130, Lys 149, and His 165. Data presented in the present application demonstrate that mutations of various combinations of these thirteen amino acid residues results in the generation of NGAL mutants that, like WT NGAL, have the ability to bind to enterochelin-iron but, unlike WT NGAL, are not effectively reabsorbed in the kidney. Such NGAL mutants, when complexed with a siderophore such as enterochelin, can be used to transport excess iron out of the body by facilitating its excretion in the urine. Such NGAL mutants may also have bacteriostatic activity and can be used to treat bacterial infections of the urinary tract.

In one embodiment, the mutant NGAL proteins of the invention comprise, consist of, or consist essentially of amino acid sequences that are based on the amino acid sequence of WT human NGAL, or a fragment thereof, but that contain one or more mutations. In one embodiment, the present invention provides an NGAL mutant having one, two, three, four, five, six, seven, eight, nine, ten, eleven, twelve, or all thirteen of the following amino acid positions mutated as compared to WT human NGAL: Lys 15, Lys 46, Lys 50, Lys 59, Lys 62, Lys 73, Lys 74, Lys 75, Lys 98, His 118, Arg 130, Lys 149, and His 165. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL.

In one embodiment the mutated amino acid residues are deleted. In another embodiment the mutated amino acid residues are substituted with a non-positively charged amino acid (i.e. a non-conservative substitution). In another embodiment the mutated amino acid residues are substituted with a negatively charged amino acid (i.e. a non-conservative substitution). In another embodiment the NGAL mutant may comprise any combination of such mutations, i.e. any combination of deletions, substitutions for non-positively charged amino acids, or substitutions for negatively charged amino acids may be present at any one, two, three, four, five, six, seven, eight nine, ten, eleven, twelve, or all thirteen of the above listed amino acid residues. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one preferred embodiment the present invention provides an NGAL mutant in which Lys (K) 15 is substituted with an uncharged amino acid, including, but not limited to, Ser (S). In one preferred embodiment the present invention provides an NGAL mutant in which Lys (K) 46 is substituted with a negatively charged amino acid, including, but not limited to, Glu (E). In one preferred embodiment the present invention provides an NGAL mutant in which Lys (K) 50 is substituted with an uncharged amino acid, including, but not limited to, Thr (T). In one preferred embodiment the present invention provides an NGAL mutant in which Lys (K) 59 is substituted with an uncharged amino acid, including, but not limited to, Gln (Q). In one preferred embodiment the present invention provides an NGAL mutant in which Lys (K) 62 is substituted with an uncharged amino acid, including, but not limited to, Gly (G). In one preferred embodiment the present invention provides an NGAL mutant in which Lys (K) 73 is substituted with a negatively charged amino acid, including, but not limited to, Asp (D). In one preferred embodiment the present invention provides an NGAL mutant in which Lys (K) 74 is substituted with a negatively charged amino acid, including, but not limited to, Asp (D). In one preferred embodiment the present invention provides an NGAL mutant in which Lys (K) 75 is substituted with an aliphatic amino acid, including, but not limited to, Gly (G). In one preferred embodiment the present invention provides an NGAL mutant in which Lys (K) 98 is substituted with an uncharged amino acid, including, but not limited to, Gln (Q). In one preferred embodiment the present invention provides an NGAL mutant in which His (H) 118 is substituted with a non-polar amino acid, including, but not limited to, Phe (F). In one preferred embodiment the present invention provides an NGAL mutant in which Arg (R) 130 is substituted with an uncharged amino acid, including, but not limited to, Gln (Q). In one preferred embodiment the present invention provides an NGAL mutant in which Lys (K) 149 is substituted with an uncharged amino acid, including, but not limited to, Gln (Q). In one preferred embodiment the present invention provides an NGAL mutant in which His (H) 165 is substituted with an uncharged amino acid, including, but not limited to, Asn (N).

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO. 1), or a fragment thereof, wherein one, two, three, four, five, six, seven, eight, nine, ten, eleven, twelve, or all thirteen residues from among Lys 15, Lys 46, Lys 50, Lys 59, Lys 62, Lys 73, Lys 74, Lys 75, Lys 98, His 118, Arg 130, Lys 149, and His 165 is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

Exemplary NGAL mutants of the invention include those that comprise the sequence of mutants K1, K2, K3, K5, I1, I3, F4, F5, and B2 (see Table 2), or that comprise fragments or variants of such sequences. In some embodiments such variants have the amino acids specified in Table 2 at residues 15, 46, 59, 62, 73, 74, 75, 98, 118, 130, 149, and 165, but other amino acid residues can differ from the specified sequences provided that the NGAL mutant is at least 70%, or at least 75%, or at least 80%, or at least 85%, or at least 90%, or at least 95%, or at least 98% identical to the sequence of WT human NGAL (SEQ ID NO. 1), or a fragment thereof, and provided that the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and also provided that the NGAL mutant (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K3 NGAL mutant (SEQ ID NO. 2), wherein residues 15, 46, 73, 74, 75, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K2 NGAL mutant (SEQ ID NO. 3), wherein residues 15, 73, 74, 75, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the 13 NGAL mutant (SEQ ID NO. 4), wherein residues 62, 73, 74, 75, and 98 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the I1 NGAL mutant (SEQ ID NO. 5), wherein residues 15, 73, 74, 75, and 130 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also ((i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K5 NGAL mutant (SEQ ID NO. 6), wherein residues 15, 46, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the F4 NGAL mutant (SEQ ID NO. 8), wherein residues 15 and 46 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the F5 NGAL mutant (SEQ ID NO. 9), wherein residues 15, 46, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the B2 NGAL mutant (SEQ ID NO. 10), wherein residues 15, 46, 118, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K1 NGAL mutant (SEQ ID NO. 7), wherein residues 15, 46, 59, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments the NGAL mutants described above that have mutations in one or more of the thirteen non-conserved positive/basic surface residues, can also have mutations in one or more of the five conserved positive/based surface residues below, or one or more of the other mutations described in other following sections of this Detailed Description.

Five Conserved Positive/Basic Surface Residues in NGAL

The NGAL protein contains five basic/positive surface amino acid residues that are conserved among human, rat, mouse, chimpanzee, cow, dog, wild boar and rhesus monkey species, namely residues Arg(R) 43, Arg(R) 72, Arg(R) 140, Lys(K) 142, and Lys(K) 157. In one embodiment, the present invention provides an NGAL mutant having one, two, three, four, or all five of these amino acid positions mutated as compared to WT human NGAL. In one embodiment the mutated amino acid residue or residues are deleted. In another embodiment the mutated amino acid residue or residues are substituted with a non-positively charged amino acid (i.e. a non-conservative change). In another embodiment the mutated amino acid residue or residues are substituted with a negatively charged amino acid (i.e. a non-conservative change). In another embodiment the NGAL mutant may comprise any combination of such mutations, i.e. any combination of deletions, substitutions for non-positively charged amino acids, or substitutions for negatively charged amino acids may be provided at one, two, three, four, or five of the above listed amino acid residues.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO. 1), or a fragment thereof, wherein one, two, three, four, or all five residues from among (R) 43, Arg(R) 72, Arg(R) 140, Lys(K) 142, and Lys(K) 157 is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments the NGAL mutants described in this section that have mutations in one or more of the five conserved positive/basic surface residues, can also have mutations in one or more of the thirteen non-conserved positive/based surface residues described in the previous section of the Detailed Description, or one or more of the other mutations described in the following sections of this Detailed Description.

Additional Surface Residues in NGAL

The following amino acid residues are located on the surface of the NGAL protein and can play a role in the interaction of the NGAL protein with the megalin protein and/or in the reabsorption of NGAL in the kidney: amino acid residues 1-15, 17-26, 40-50, 57-62, 71-82, 84-89, 96-105, 114-118, 128-131, 134, 140-151, 157-165, and 170-174.

In one embodiment, the mutant NGAL proteins of the invention comprise, consist of, or consist essentially of amino acid sequences that are based on the amino acid sequence of human NGAL, or a fragment thereof, but that contain mutations as at one or more of the individual amino acid residues located at residues 1-15, 17-26, 40-50, 57-62, 71-82, 84-89, 96-105, 114-118, 128-131, 134, 140-151, 157-165, and/or 170-174 of WT human NGAL. In one embodiment one or more of the mutated amino acid residues can be deleted. In another embodiment one or more of the mutated amino acid residues can be substituted with a non-positively charged amino acid, including, but not limited to a negatively charged amino acid. In another embodiment the NGAL mutant may comprise any combination of such mutations, i.e. any combination of deletions, substitutions for non-positively charged amino acids, and/or substitutions for negatively charged amino acids at any one or more of the above listed amino acid residues. Table 2 provides details of all possible mutations of the surface residues of NGAL that are contemplated by the present invention. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO. 1), or a fragment thereof, wherein one or more of the individual amino acid residues located at residues 1-15, 17-26, 40-50, 57-62, 71-82, 84-89, 96-105, 114-118, 128-131, 134, 140-151, 157-165, and/or 170-174 of WT human NGAL is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Tryptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

Functional Properties of NGAL Mutants

In certain embodiments the mutant NGAL proteins of the invention have certain specified functions. For example, in some embodiments the mutant NGAL proteins of the invention have one or more of the following properties: (a) they are excreted in the urine or exhibit a greater level of excretion in the urine than WT human NGAL, and/or (b) they are not reabsorbed in the proximal tubule of the kidney or exhibit a lower level of reabsorption in the proximal tubule of the kidney than WT human NGAL, and/or (c) they are not a substrate for reabsorption in the kidney by a megalin-cubilin-receptor mediated mechanism. Similarly, in some embodiments the mutant NGAL proteins of the invention have one or more of the following properties: (i) they are able to bind to enterochelin-type siderophores, and/or (ii)

they are able to bind to enterochelin-type siderophores complexed with iron, and/or (iii) they have a preserved three-dimensional structure of the enterochelin binding pocket and/or (iv) they have bacteriostatic activity.

Each of the above properties of the mutant NGAL proteins of the invention can be tested for and/or quantified, and in some embodiments the mutant NGAL proteins of the invention have functional properties that fall within a certain numeric range.

Figure 5:
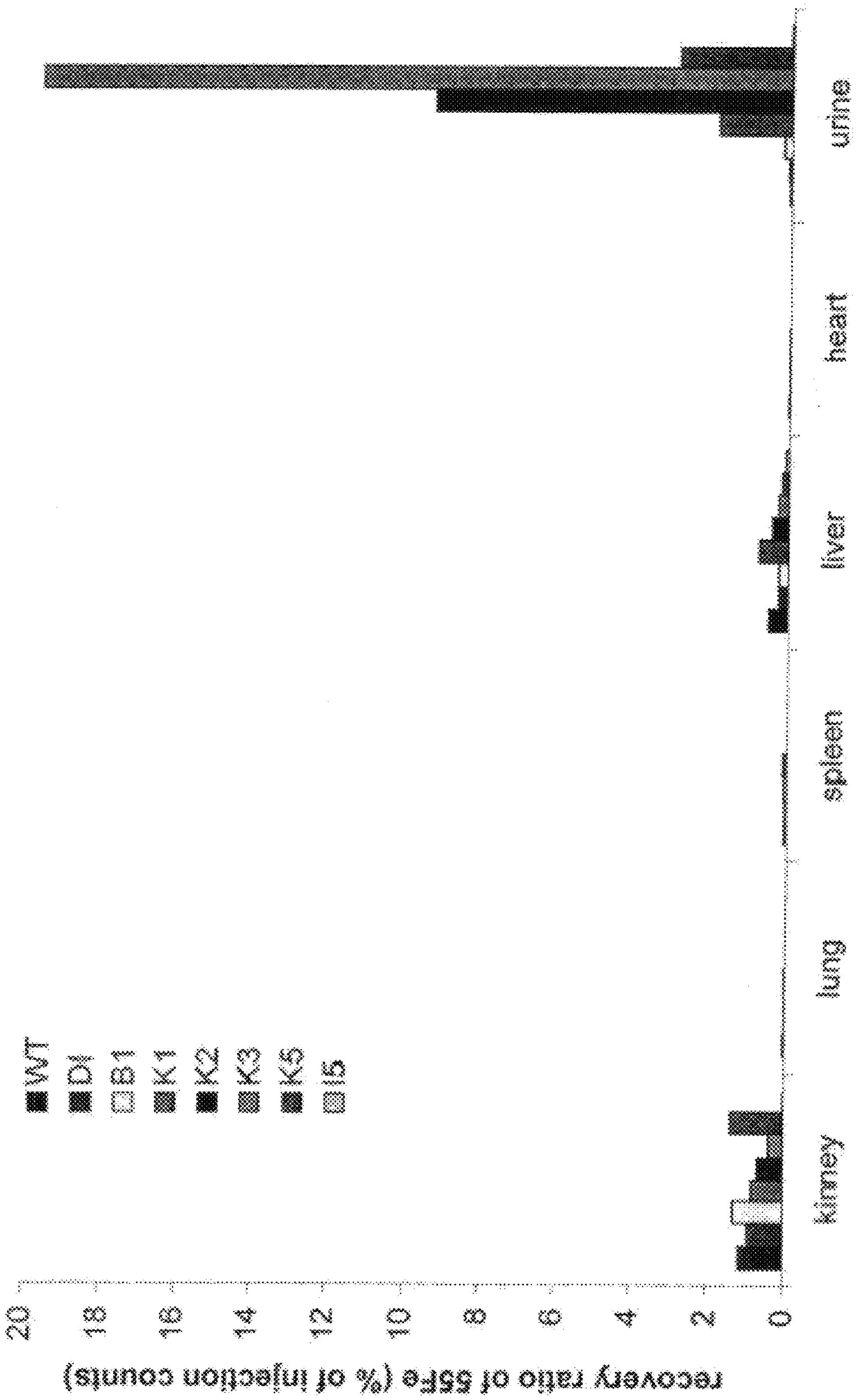
FIG. 5. Percentage recovery of $^{55}Fe^{3+}$ following injection of NGAL mutant proteins complexed with enterochelin and $^{55}Fe^{3+}$. The amount of NGAL-bound Ent-$^{55}Fe^{3+}$ was calculated as percentage of the starting total $^{55}Fe^{3+}$. Recovery in the urine, kidney, lung, spleen, liver, and heart is shown. D1 is SEQ ID NO: 32; B1 is SEQ ID NO: 24; K1 is SEQ ID NO: 7; K2 is SEQ ID NO: 3; K3 is SEQ ID NO: 2; K5 is SEQ ID NO: 6; I5 is SEQ ID NO: 45.

For example, in some embodiments the mutant NGAL proteins of the invention are excreted in the urine or exhibit a greater level of excretion in the urine than WT human NGAL. Excretion of the mutant NGAL proteins of the invention can be detected and quantified, for example using the methods described in the Examples section of this application. For example the amount of the mutant NGAL protein present in the urine a given time after its is administered to a subject, such as a mouse or a human subject, can be measured and can be expressed as a percentage of the total amount administered (see Examples and Table 1) to give a % accumulation in the urine. The % accumulation in the urine of a given NGAL mutant can be compared to that of other mutants or of WT NGAL. NGAL or an NGAL mutant or siderophore complex thereof can be radiolabeled (e.g. with radioactive iron) or labeled with some other detectable moiety in order to facilitate its detection and quantification. In some embodiments the present invention provides that the mutant NGAL proteins of the invention exhibit a greater level of excretion in the urine than does WT human NGAL. For example, the NGAL mutants can have a 6-fold, 7-fold, 8-fold, 9-fold, 10-fold, 15-fold, 20-fold, 25-fold, 30-fold, 40-fold, 50-fold, 100-fold or higher level of excretion in the urine than WT human NGAL. As seen in FIG. 5, WT NGAL can have a % accumulation in the urine (measured as a % of the amount administered intraperitoneally) of less than 0.2%. In contrast, as can be seen from FIG. 3, FIG. 5, and Table 1, the NGAL mutants of the invention can have a % accumulation in the urine (measured as a % of the amount administered intraperitoneally 3 hours after administration) of greater than 1%, or greater than 2%, or greater than 3%, or greater than 4%, or greater than 5%, or greater than 6%, or greater than 7%, or greater than 8%, or greater than 9%, or greater than 10%, or greater than 15%, or greater than 20%, or more.

In some embodiments the mutant NGAL proteins of the invention are able to bind to siderophores, such as enterochelin, and/or they are able to bind to siderophores complexed with iron. The ability of the NGAL mutants of the invention to bind to siderophores and siderophore-iron complexes can be tested and/or quantified, for example using the methods described in the Examples section of this application. For example NGAL (including the NGAL mutants of the invention) and siderophore molecules such as enterochelin and iron associate with each other in a 1:1:1 molar ratio and NGAL (including the NGAL mutants of the invention) and siderophore molecules such as catechol and iron associate with each other in a 1:3:1 molar ratio. Accordingly using a radiolabelled form of iron the binding of NGAL to siderophore molecules and iron can be measured or estimated by examining the % of radiolabelled iron that is retained by a given NGAL protein. The % of iron (iron-siderophore) that is retained can be compared between NGAL mutants or between an NGAL mutant and WT NGAL. In some embodiments the present invention provides that the mutant NGAL proteins of the invention exhibit a similar % of iron (iron-siderophore) retention as compared to WT NGAL. In some embodiments the present invention provides that the mutant NGAL proteins of the invention exhibit a higher % of iron (iron-siderophore) retention as compared to WT NGAL, such as a 1.5-fold, 2-fold, 2.5-fold or greater-fold higher % of iron (iron-siderophore) retention. In some embodiments, the mutant NGAL proteins of the invention exhibit a % iron (iron-siderophore) retention of about 20% or more, or about 30% or more, or about 40% or more.

In some embodiments the mutant NGAL proteins of the invention have anti-bacterial activity. Antibacterial activity of the NGAL mutants of the invention can be tested and/or quantified, for example using standard methodologies known in the art, for example by culturing bacteria in the presence of the NGAL mutants and assessing the effect of the NGAL mutants on bacterial growth, survival, numbers, etc. in comparison to control conditions in which no NGAL mutant is present.

In one embodiment, Ngal mutants bypass megalin. In another embodiment, Ngal mutants bind Ent:iron. Thus, the Ngal mutants of the invention comprise a therapeutic that can safely excrete NTBI in the urine.

Non-NGAL Lipocalins

In addition to mutants of NGAL, the present invention also contemplates that mutants of other lipocalins can be made that, like the NGAL mutants described herein, have the ability to bind to siderophore-iron complexes but that are not reabsorbed in the kidney. It is expected that such lipocalin mutants could be used similarly to the NGAL mutants described herein to traffic iron out of the body and could thus be used in the treatment of iron overload disorders. It is also expected that such lipocalin mutants could also be used to treat bacterial infections of the urinary tract.

There are about 20 known proteins in the lipocalin family. Any lipocalin protein, or homolog, variant, derivative, fragment, or mutant thereof, that binds to a siderophore-iron complex can be mutated in order to provide a lipocalin mutant of the invention. Examples of lipocalins that can be used in accordance with the present invention include, but are not limited to, retinol binding protein, lipocalin allergen, aphrodisin, alpha-2-microglobulin, prostaglandin D synthase, beta-lactoglobulin, bilin-binding protein, the nitrophorins, lipocalin 1, lipcalin 12, and lipocalin 13.

Siderophores

Siderophores are high affinity iron (e.g. $Fe^{3+}$) binding compounds. The vast majority of siderophores known are produced by bacteria. Bacteria release siderophores into the surrounding environment for the purpose of scavenging or chelating iron and transporting the iron to the bacteria—a process necessary for survival of bacteria. Siderophores that are known in the art include, but are not limited to heme, enterochelin, TRENCAM, MECAM, TRENCAM-3,2-HOPO, parabactin, carboxymycobactin, fusigen, triacetylfusarinine, feriichrome, coprogen, rhodotorulic acid, omibactin, exochelin, ferrioxamine, desferrioxamine B, aerobactin, ferrichrome, rhizoferrin, pyochelin, pyoverdin. The structures of these compounds are disclosed in Holmes et al., Structure, 2005, 13:29-41 and Flo et al., Nature, 2004, 432: 917-921, the contents of which are hereby incorporated by reference.

Several of the above siderophores are known to bind to lipocalins, including NGAL, and complexes of these siderophores and lipocalins are known to be able to sequester iron (see for example, Holmes et al., Structure, 2005, 13:29-41 and Flo et al., Nature, 2004, 432: 917-921; Goetz et al, Molecular Cell, 2002, 10: 1033-1043 and Mori, et al., "Endocytic delivery of lipocalin-siderophore-iron complex rescues the kidney from ischemia-reperfusion injury." J.

Clin Invest., 2005, 115, 610-621). The mutant NGAL proteins of the invention can also form complexes with siderophores and can thereby chelate and transport iron.

In some aspects the present invention provides complexes of a mutant NGAL protein of the invention and a siderophore, including, but not limited to, the siderophores listed herein. In preferred aspects the siderophore is selected from the group consisting of enterochelin, pyrogallol, carboxymycobactin, catechol, and variants or derivatives thereof. Any variant or derivative of such siderophores that retains the ability to bind to iron (ideally in a pH insensitive manner) and that retains the ability to bind to NGAL and/or one or more of the NGAL mutants of the invention may be used.

Manufacture of Mutant NGAL Proteins and Complexes with Siderophores

The mutant NGAL proteins of the invention can be manufactured by any suitable method known in the art for manufacture of protein drugs. For example the mutant NGAL proteins can be made using standard techniques known for the production of recombinant proteins, for example by delivering to a cell, such as a bacterial cell or a mammalian cell, an expression vector containing a nucleotide sequence that encodes an NGAL mutant under the control of a suitable promoter, and culturing the cell under conditions in which the protein will be expressed. Methods for the large scale culture, isolation, and purification of recombinant proteins are well known in the art and can be used in the manufacture of the NGAL mutants of the present invention. Similarly, methods of producing peptides and proteins synthetically are known in the art and can be used in the manufacture of the NGAL mutants of the present invention.

In certain embodiments, the present invention provides fusion proteins comprising the NGAL mutants of the invention and one or more additional "tags". Such additional tags can be fused to the N- or C-terminus of the NGAL mutants, or can in some instances be added at an internal location to the extent that the inclusion of the tag does not adversely affect the function of the NGAL mutant. Suitable tags include, but are not limited to glutathione-S-transferase (GST), poly-histidine (His), alkaline phosphatase (AP), horseradish peroxidase (HRP), and green fluorescent protein (GFP). Other suitable tags will also be apparent to those skilled in the art. The tags may be useful for several applications, including to assist in the isolation and/or purification of the NGAL mutants and/or to facilitate their detection.

Many chemical modifications of proteins are known in the art to be useful for improving the properties of protein-based drugs and such modifications can be used in accordance with the present invention to improve the stability and reduce the immunogenicity of the mutant NGAL proteins of the invention for therapeutic applications. For example, it is well known in the art that the process of covalent attachment of polyethylene glycol polymer chains to another molecule (i.e. PEGylation) can "mask" a proteinaceous agent from the host's immune system, and also increase the hydrodynamic size (size in solution), prolongs the circulatory half-life, and improve water solubility of protein-based drugs. Various other chemical modifications are also known and used in the art and can be used in conjunction with the mutant NGAL proteins of the invention.

Complexes containing a mutant NGAL protein of the invention and a siderophore, such as enterochelin or a derivative or variant thereof, can readily be prepared used standard methodologies known in the art, such as those provided in the Examples section of this application. For example, an NGAL-siderophore complex can be prepared by mixing NGAL (including mutant NGAL) and a siderophore together in a molar ratio of 1:1 (e.g. Ent) or 1:3 (e.g. catechol). The mixture can be incubated at room temperature for a suitable time, e.g. 30 minutes, to allow for complex formation. Unbound siderophore can then be removed/separated from the bound siderophore-NGAL complexes using standard separation techniques, such as centrifugation based techniques, filter-based techniques, or other size-based separation techniques.

Methods of Treatment—Iron Overload

In one embodiment, the mutant NGAL proteins of the invention, and complexes and compositions comprising such mutant NGAL proteins, can be used to treat conditions, diseases, or disorders associated with excessive iron levels or iron overload. In particular, complexes of the mutant NGAL proteins of the invention with a siderophore, such as enterochelin, and compositions comprising such complexes, can be used to chelate iron in the body and facilitate its excretion in the urine.

Large amounts of free iron in the bloodstream can lead to cell damage, especially in the liver, heart and endocrine glands. The causes of excess iron may be genetic, for example the iron excess may be caused by a genetic condition such as hemochromatosis type 1 (classical hemochromatosis), hemochromatosis type 2A or 2B (juvenile hemochromatosis), hemochromatosis type 3, hemochromatosis type 4 (African iron overload), neonatal hemochromatosis, aceruloplasminemia, or congenital atransferrinemia. Examples of non-genetic causes of iron excess include dietary iron overload, transfusional iron overload (due to a blood transfusion given to patients with thalassaemia or other congenital hematological disorders), hemodialysis, chronic liver disease (such as hepatitis C, cirrhosis, non-alcoholic steatohepatitis), porphyria cutanea tarda, post-portacaval shunting, dysmetabolic overload syndrome, iron tablet overdose (such as that caused by consumption by children of iron tablets intended for adults), or any other cause of acute or chronic iron overload.

The two common iron-chelating agents available for the treatment of iron overload are deferoxamine (DFO) and deferiprone (oral DFO). Due to its high cost and need for parenteral administration, the standard iron chelator deferoxamine is not used in many individuals with acute and/or chronic iron poisoning. Deferoxamine must be administered parenterally, usually as a continuous subcutaneous infusion over a 12-hour period, from three to seven times a week. Treatment is time consuming and can be painful. As a result compliance is often poor. Side-effects include local skin reactions, hearing loss, nephrotoxicity, pulmonary toxicity, growth retardation and infection. Deferiprone is the only orally active iron-chelating drug to be used therapeutically in conditions of transfusional iron overload. It is indicated as a second-line treatment in patients with thalassaemia major, for whom deferoxamine therapy is contraindicated, or in patients with serious toxicity to deferoxamine therapy. Deferiprone is an oral iron-chelating agent which removes iron from the heart, the target organ of iron toxicity and mortality in iron-loaded thalassaemia patients. However, although deferiprone offers the advantage of oral administration, it is associated with significant toxicity and there are questions about its long-term safety and efficacy. It is recommended to be used in patients who are unable to use desferrioxamine because of adverse effects, allergy, or lack of effectiveness. Deferiprone is associated with serious safety issues include genotoxicity, neutropenia and agranulocytosis. Weekly monitoring of neutrophils is recommended, Gastrointestinal and joint problems can occur and liver toxicity has been reported. Therefore, there is clearly a need for alternative convenient, safe, and effective iron chelation therapies, such as those provided by the present invention.

The mutant NGAL proteins of the invention, and in particular complexes thereof with siderophores, can be used to chelate free iron and clear the excess iron from the body via the kidneys, for example to reduce toxic circulating levels of iron to below toxic levels.

Methods of Treatment—Bacterial Infections of the Urinary Tract

WT NGAL is known to have bacteriostatic activity, in part due to its ability to tightly bind to bacterial siderophores, leading to depletion of bacterial iron and inhibition of bacterial growth (Goetz et al., Mol. Cell. (2002), 10(5) 1033-1043). The mutant NGAL proteins of the invention, like WT NGAL, have the ability to bind to bacterial siderophores, and thus can have anti-bacterial activity. Furthermore, because the mutant NGAL proteins of the invention are not reabsorbed by the kidney and accumulate in the urine, they are particularly well-suited to use in the treatment of bacterial infections of the urinary tract.

Pharmaceutical Compositions & Administration

The present invention also provides pharmaceuctical compositions, formulations, kits, and medical devices that comprise the mutant NGAL proteins described herein, and complexes thereof with siderophores, and which may be useful to treat various diseases, disorders, and conditions, including iron overload and bacterial infections. Pharmaceutical formulations include those suitable for oral or parenteral (including intramuscular, subcutaneous and intravenous) administration. Examples of medical devices provided by the invention include, but are not limited to, beads, filters, shunts, stents, and extracorporeal loops which are coated with or otherwise contain a mutant NGAL or complexes thereof, as described herein, such that the device is implanted in or otherwise administered to a subject in a manner which permits the mutant NGAL or complexes thereof to chelate or absorb excess iron in the subject.

Administration of a therapeutically effective amount of the mutant NGAL proteins, and complexes thereof can be accomplished via any mode of administration suitable for therapeutic agents. One of skill in the art can readily select mode of administration without undue experimentation. Suitable modes may include systemic or local administration such as oral, nasal, parenteral, transdermal, subcutaneous, vaginal, buccal, rectal, topical, intravenous (both bolus and infusion), intraperitoneal, or intramuscular administration modes. In preferred embodiments, oral or intravenous administration is used. In other preferred embodiments, the compositions of the invention are administered directly to the desired site of action, such as for example, the kidney, for example by local injection or local infusion or by use of (e.g. conjugation to) agents useful for targeting proteins or pharmaceuticals to specific tissues, such as antibodies etc.

Depending on the intended mode of administration, the mutant NGAL proteins and complexes of the invention, in a therapeutically effective amount, may be in solid, semi-solid or liquid dosage form, such as, for example, injectables, tablets, suppositories, pills, time-release capsules, elixirs, tinctures, emulsions, syrups, powders, liquids, suspensions, or the like. In one embodiment the mutant NGAL proteins and complexes of the invention may be formulated in unit dosage forms, consistent with conventional pharmaceutical practices. Liquid, particularly injectable, compositions can, for example, be prepared by dissolution or dispersion. For example, mutant NGAL proteins and complexes of the invention can be admixed with a pharmaceutically acceptable solvent such as, for example, water, saline, aqueous dextrose, glycerol, ethanol, and the like, to thereby form an injectable isotonic solution or suspension.

Parental injectable administration can be used for subcutaneous, intramuscular or intravenous injections and infusions. Injectables can be prepared in conventional forms, either as liquid solutions or suspensions or solid forms suitable for dissolving in liquid prior to injection. One embodiment, for parenteral administration, employs the implantation of a slow-release or sustained-released system, according to U.S. Pat. No. 3,710,795, incorporated herein by reference.

The mutant NGAL proteins and complexes of the invention can be sterilized and may contain any suitable adjuvants, preservatives, stabilizers, wetting agents, emulsifying agents, solution promoters, salts (e.g. for regulating the osmotic pressure), pH buffering agents, and/or other pharmaceutically acceptable substances, including, but not limited to, sodium acetate or triethanolamine oleate. In addition, the compositions of the invention may also contain other therapeutically useful substances, such as, for example, other iron chelators or other agents useful in the treatment of iron overload, or other agents useful in the treatment of any of the conditions described herein.

The compositions of the invention can be prepared according to conventional mixing, granulating or coating methods, respectively, and the present pharmaceutical compositions can contain from about 0.1% to about 99%, preferably from about 1% to about 70% of the compound or composition of the invention by weight or volume.

The dose and dosage regimen to be used can be determined in accordance with a variety of factors including the species, age, weight, sex and medical condition of the subject; the severity of the condition; the route of administration; the renal or hepatic function of the subject; and the particular mutant or complex employed. A person skilled in the art can readily determine and/or prescribe an effective amount of a mutant or complex of the invention useful for treating or preventing a condition, for example, taking into account the factors described above. Dosage strategies are also provided in L. S. Goodman, et al., The Pharmacological Basis of Therapeutics, 201-26 (5th ed. 1975), which is herein incorporated by reference in its entirety. In one embodiment, compositions of the invention are administered such that the NGAL component is administered at a dose range of about 1 to about 100 mg/kg body weight, and typically at a dosage of about 1 to about 10 mg/kg body weight is administered at a dose that results in a concentration in the range of about 0.1 ng/ml to about 100 ng/ml, e.g., in the range of about 1.0 ng/ml to about 20 ng/ml, in the blood. The amount of a siderophore component of a composition of the invention will be chosen accordingly, such that the desired stoichiometry, e.g. 1:1 or 1:3 binding with the mutant NGAL protein, is achieved.

In addition to the above methods of treatment, the mutant NGAL protein-siderophore complexes of the invention may be useful to chelate and/or remove iron from samples, wherein the samples are not in a subject's body. Thus, in one embodiment, the present invention provides a method for removing iron from a fluid, the method comprising admixing the fluid with a mutant NGAL protein-siderophore complex for a period of time sufficient for iron in the sample to bind to the mutant NGAL protein-siderophore complexes, wherein the mutant NGAL protein-siderophore complex can chelate iron from the sample. In one embodiment, the mutant NGAL protein-siderophore complexes having iron bound thereto may then be removed from the sample. In preferred embodiments, the sample is a biological fluid, such as blood, serum, plasma, or urine. In certain embodiments the mutant NGAL protein-siderophore complexes are admixed with the sample outside the body, e.g. in an extracorporeal device, and the sample is then delivered to or returned to the body. For example, such methods can be used to chelate and/or remove excess iron in blood samples for transfusion, or in a dialysis procedure. For example, blood or another bodily fluid from a subject may be removed from the body, treated with a compound or composition of the invention to chelate or remove excess iron, and then returned to the subject.

EXAMPLES

Example 1

Mutant NGAL Proteins and their Use as Therapeutic Iron Chelators and as Antimicrobial Agents Lipocalin 2 (Lcn2), also called Neutrophil Gelatinase-Associated Lipocalin (NGAL) is a protein that binds to iron with high affinity. To bind iron, NGAL binds a cofactor called a siderophore produced by bacteria (Binding constant $K_m=0.41\times10^{-9}$M for the NGAL:enterochelin-iron interaction; $K_m=10^{-49}$M for the enterochelin (enterobactin):iron interaction) or catechol containing compounds ($K_m=0.4\pm10^{-9}$M for catechol-iron; $K_m=10^{-45.9}$M for the catechol:iron interaction) produced by a combination of bacterial and mammalian enzymes. NGAL is also a secretory protein that is markedly upregulated by bacterial infection and acute kidney injury and is secreted into the blood and urine. During bacterial infection, NGAL sequesters iron from bacteria by binding enterochelin-iron, resulting in the inhibition of bacterial growth.

Serum NGAL with bound enterochelin:Fe is filtered by the glomerulus in the kidney, but then the majority of it is retained (reabsorbed) by kidney where it is degraded. Very little NGAL escapes to the urine and is excreted. For example, as demonstrated by recent research, when NGAL is injected intraperitoneally, more than 70% of the WT NGAL accumulates in kidney while less than 0.1% is found in the urine after 3 hours.

The capture and retention of serum NGAL in the kidney is achieved by the absorption of NGAL by megalin, a multi-ligand receptor also called low-density lipoprotein receptor-related protein 2 (LRP2). Megalin is located at the apical plasma membrane of proximal tubular epithelial cells where it contacts the glomerular filtrate. Megalin associates with cubilin. NGAL can transport iron by using cofactors such as enterochelin or catechol and deliver the iron specifically to the kidney.

Amnionless is another protein associated with the megalin-cubulin-receptor complex. In one embodiment, NGAL interacts with megalin, cubilin, amnionless, or a combination thereof. For additional information on the amnionless protein, see Kozyraki R, Gofflot F, (2007) *Curr Pharm Des.* 13(29):3038-46 and Nielsen R, Christensen E I., (2010) *Pediatr Nephrol.*, 25(5):813-22, both of which are incorporated by reference in their entireties.

Mutant NGAL as a Therapeutic Iron Chelator and Antimicrobial Agent

The molecular cutoff for glomerular filtration is about 70 kD. Recombinant or native NGAL protein with molecular weights of about 20.5 kD and 23-25 kD respectively can be filtered in the glomerulus, but is then efficiently reabsorbed into the proximal epithelia by megalin and/or by a megalin associated complex which includes cubilin. Megalin has a binding affinity for apo- and iron-loaded NGAL of about 60 nM (Hvidberg, et al., FEBS Letters, 2005, 579: 773-777)). Megalin is a multi-ligand, endocytic receptor, responsible for reabsorption of many proteins including NGAL, apoE, lipoprotein lipase, lactoferrin, approtinin, etc., after glomerular filtration (Christensen and Birn, Nature Reviews-Molecular Cell Biology, 2002, 3: 258-2682002). Electrostatic interactions between megalin's acidic regions of "type A repeats" in megalin protein and basic regions of ligands are involved in ligand-receptor recognition i.e. megalin recognizes positively charged surfaces of ligand proteins (Moestrup and Verrost, Annual Reviews of Nutrition, 2001, 21: 407-428. 2001). Some basic amino acid residues on the surface of human NGAL protein can therefore be involved in its high binding affinity to megalin, and mutation of these basic residues can disrupt the electrostatic interactions between NGAL and megalin while preserving the binding affinity for enterochelin-iron in its interior clayx. The disabled interaction between mutant NGAL and megalin can allow mutant NGAL:enterocalin:iron or apo-mutant NGAL to be filtered into the urine without being reabsorbed from the filtrate after glomerular filtration. In the former case, where enterochelin is present in the mutant NGAL complex, it can absorb iron from the blood and traffic it into the urine. This can allow removal of iron from the subject (e.g. animal or human) associated with the siderophore-iron. Alternatively, in the case of the mutant apo-NGAL, it can lead to an accumulation of NGAL in the urine which can inhibit bacterial growth in the urinary tract.

The mutant NGAL proteins of the invention have at least two potential applications in clinical therapeutics.

Firstly, the mutant NGAL proteins can be used as efficient iron chelators to remove excess iron from subjects, such as human subjects, with iron overload disorders. Iron overload patients (e.g. due to hemachromatosis, sickle cell disease, thalassemia, multiple transfusion of red blood cells or other biological products) are administered mutant NGAL bound to iron-free siderophore, such as enterochelin, by intravenous infusion. Enterochelin chelates serum iron to form an NGAL-enterochelin-iron complex. This complex is mostly transported to the kidney and subsequently filtered by glomerulus. It remains in the glomerular filtrate without being reabsorbed due to its inability to bind megalin in the proximal tubular epithelial cells. It then appears in the urine and is ultimately excreted together with the iron that it binds. Mutant NGAL can be an efficient tool to remove excessive iron from iron overloaded human subjects. The molar ratio for NGAL binding to enterochelin and iron is 1:1:1. If 10 g of mutant apo-NGAL, which equals about 500 μmoles, is given to an iron overloaded patient, about 500 μmoles or about 27.9 mg of iron can theoretically bind mutant NGAL and enterochelin and be delivered into the urine for excretion (assuming accumulation of mutant NGAL protein in urine is 100%). This is a very efficient way to remove excessive iron from a human patient with iron overload given that the human only loses 1-2 mg iron per day mainly via the shedding of intestinal cells and dead skin cells, and only gains 1-2 mg per day from food.

Secondly, the mutant NGAL protein can be used as an anti-microbial to treat patients with a urinary tract infection (UTI). Mutant apo-NGAL is given to human subjects with a UTI by infusion. The mutant NGAL is transported to the kidney and filtered into the urine without reabsorption due to its loss of binding affinity for megalin. Once inside the urine, the mutant apo-NGAL protein binds siderophores of UTI bacteria (e.g. enterochelin) and results in the inhibition of their growth.

Experimental Design and Experimental Procedures

Cloning of Human NGAL

Human NGAL cDNA (Ganbank accession number: NM_005564) is obtained from Open Biosystems, and the open reading frame encoding the secreted NGAL protein is PCR-amplified by using a PfuUltra™ DNA polymerase (Stratagene), and cloned into a pGEX-4T-3 plasmid vector (GE Healthcare) for site-directed mutagenesis.

Structure of Human NGAL Protein

Figure 4A:
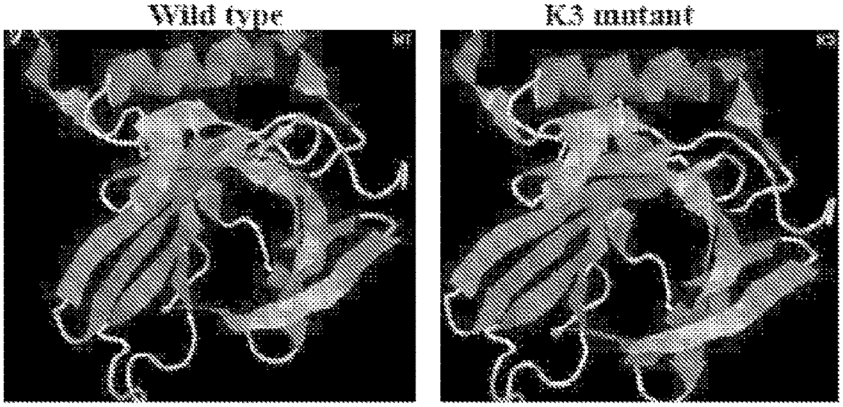
FIGS. 4A-4B. Comparison of structures of wild-type NGAL and the K3 mutant NGAL protein.

Based on the structure of the human NGAL protein, amino acid residues, especially basic residues (arginine, lysine and histidine), on the surface of the protein can mediate the electrostatic interaction with megalin for high affinity binding (FIG. 1 and FIG. 4A).

Designation of NGAL Mutants

There are five basic amino acid residues on the surface of NGAL protein which are conserved (R43, 72, 140, and K142, 157) among different mammalian species including human, mouse, rat, Chimpanzee, bovine, dog, wild boar, and Rhesus Monkey, while there are 13 non-conserved basic residues (R130; K15, 46, 50, 59, 62, 73, 74, 75, 97, 149; H118, 165). These basic residues can be mutated to other non-basic residues.

Generation of NGAL Mutants

A variety of different amino acid residues on the surface of NGAL protein were mutated by using a QuikChange™ Site-Directed Lightning Multi Mutagenesis Kit (Stratagene), and this resulted in the generation of many mutants with mutations at different sites of the NGAL protein. 57 NGAL mutants were made as shown in Table 2, SEQ ID NOS:2-10, 21-68, 247-251.

Production of NGAL Protein

Wild-type and mutant plasmid constructs are electroporated into BL21 *E. coli* (GE Healthcare), and expression of wild-type and mutant apo-NGAL proteins are induced by the addition of IPTG to a final concentration of 0.2 mM for 5 hours, and subsequently purified by a combination of GST-based pull-down and gel filtration in a FPLC system with a Sepharose™ column.

Binding Affinity of Mutant NGAL for Enterochelin and Iron

The NGAL mutant proteins are examined for their ability to bind enterochelin and iron by using a radioactive form of iron, $^{55}Fe^{3+}$. The binding affinity of NGAL for enterochelin and $^{55}Fe^{3+}$ was estimated by examining the percentage of $^{55}Fe^{3+}$ which was retained by mutant and wild type NGAL proteins, and the wild-type NGAL protein can be used as a positive control.

Preparation of NGAL-Enterochelin-Iron Complex

The NGAL-enterochelin-iron complex is prepared by mixing NGAL protein, enterochelin and $^{55}Fe^{3+}$ together in a molar ratio of 1:1:1 (4 nmole each). The mixture is incubated at RT for 30 minutes, and washed in a 10 K Microcon™ by centrifugation 4 times at 7000 rpm for 5 minutes to remove the unbound enterochelin and $^{55}Fe^{3+}$, and the NGAL-enterochelin-$^{55}Fe^{3+}$ complex is retained in the Microcon™.

Screening of NGAL Mutants in Mice

There is 76% amino acid identity and 87% amino acid similarity between human mouse megalin proteins, indicating that they likely have very similar binding properties. In the present experiments the binding of human NGAL protein to mouse megalin was tested. Due to the high degree of amino acid identity and similarity between human and mouse megalin protein, the mouse system provides a useful model to screen mutant NGAL proteins for their ability to escape megalin-cubilin-dependent renal reabsorption and ultimately to be delivered into urine.

The radiolabelled NGAL-enterocalin-$^{55}Fe^{3+}$ complex is intraperitoneally injected into female C57BL/6 mice (4 weeks), and urine is collected in metabolic cages. After urine collection for 3 hours, the mice are sacrificed and kidneys and liver are collected, weighed and solubilized in a solution of 0.5M NaOH and 1% SDS at 70° C. overnight. The radioactivity in urine, kidney and liver is examined in a scintillation counter, and the accumulation of the NGAL-enterochelin-iron complex will be calculated as the percentage of total injected complex.

Experimental Results

Figure 3A:
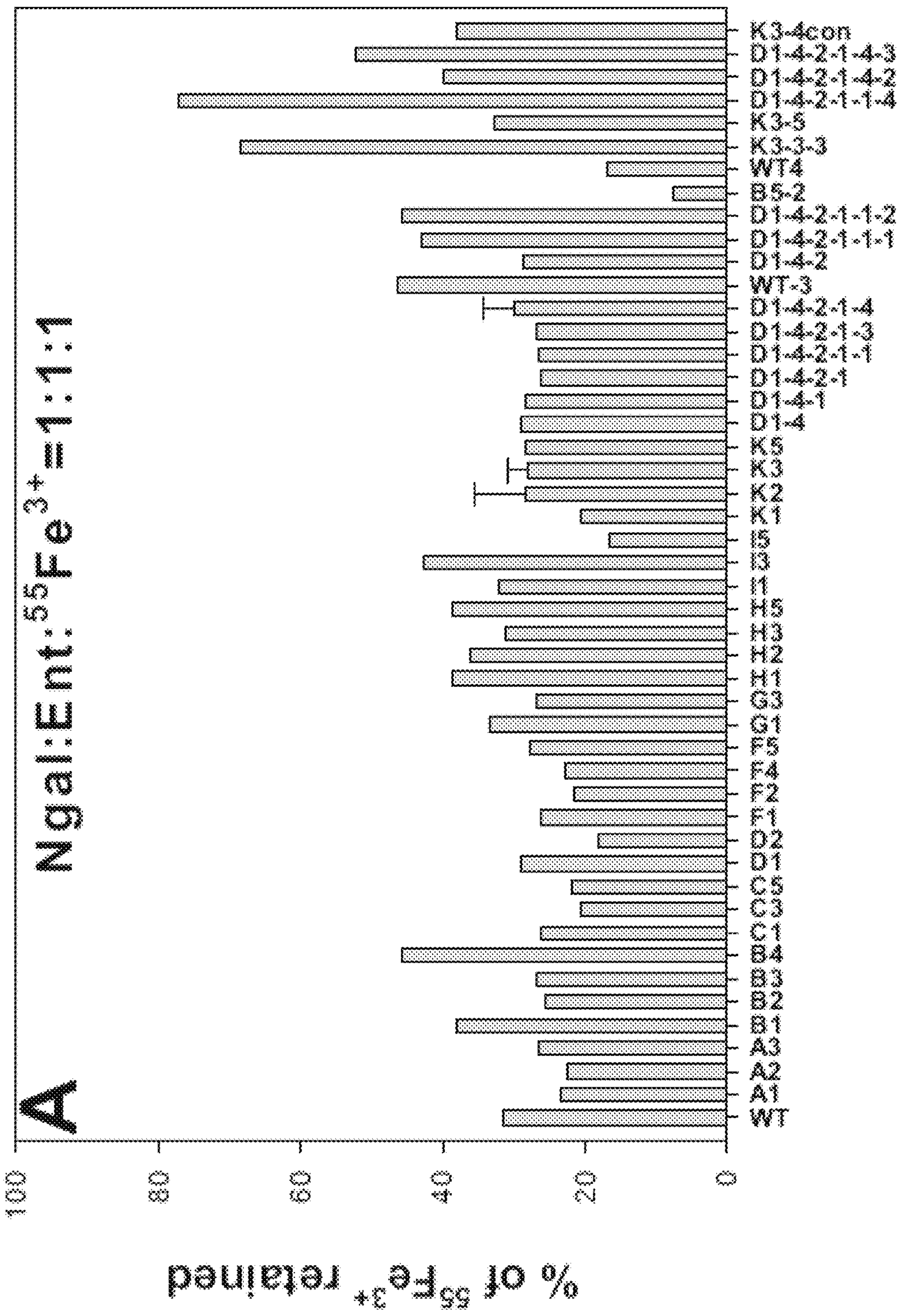
FIGS. 3A-3D. Screening for NGAL mutants exhibiting specific accumulation in urine.
Figure 3B:
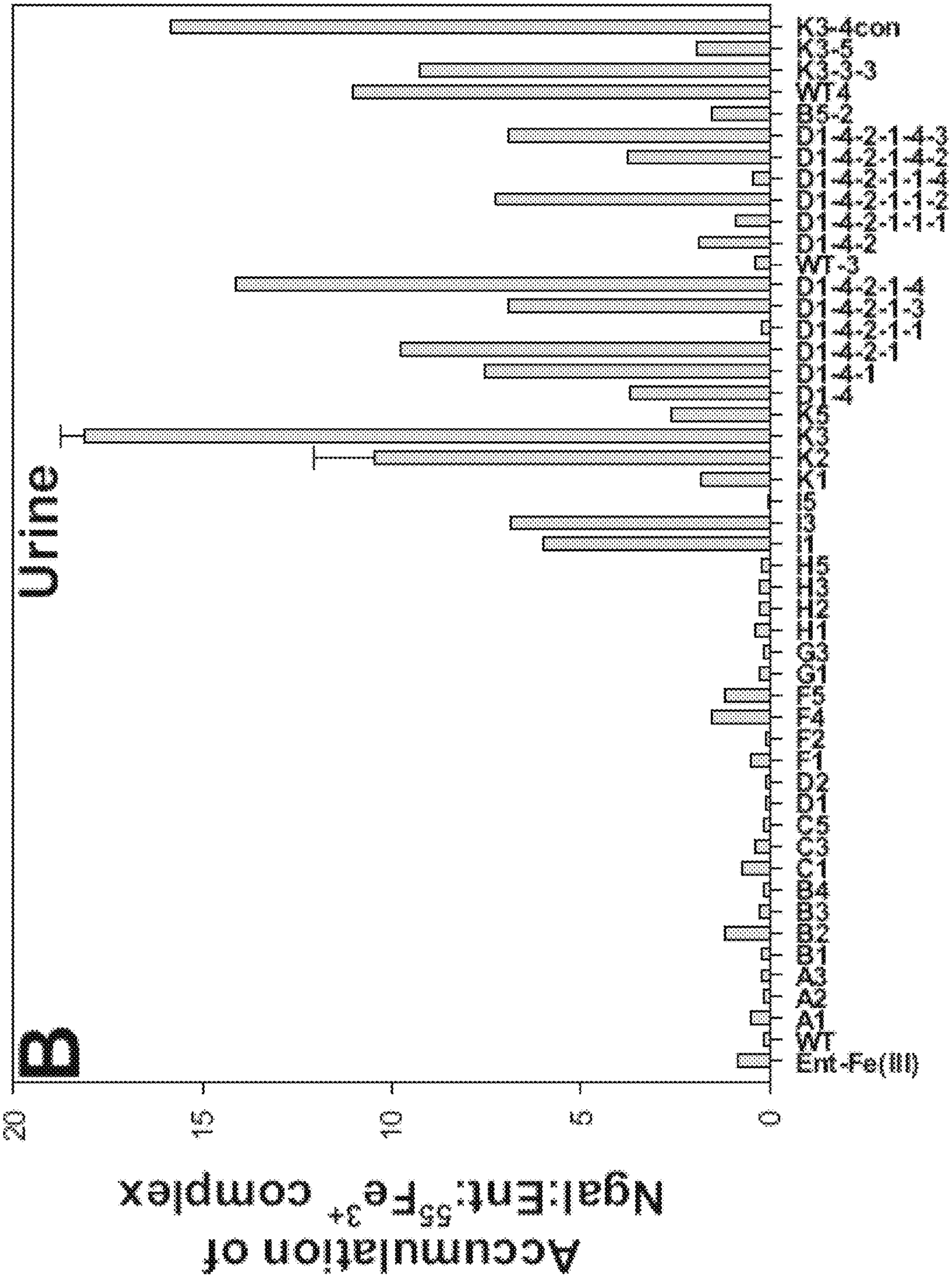
Figure 3C:
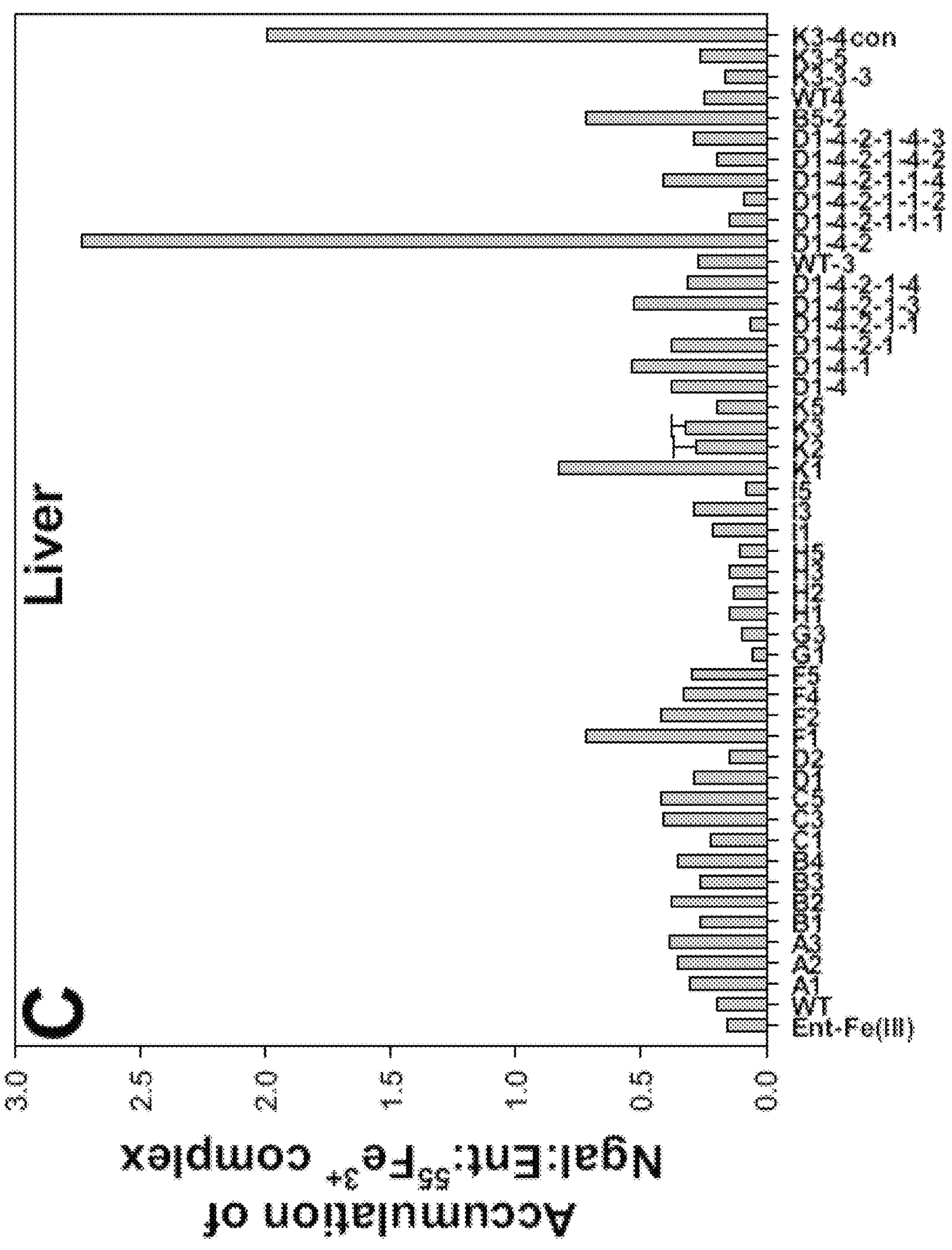
Figure 3D:
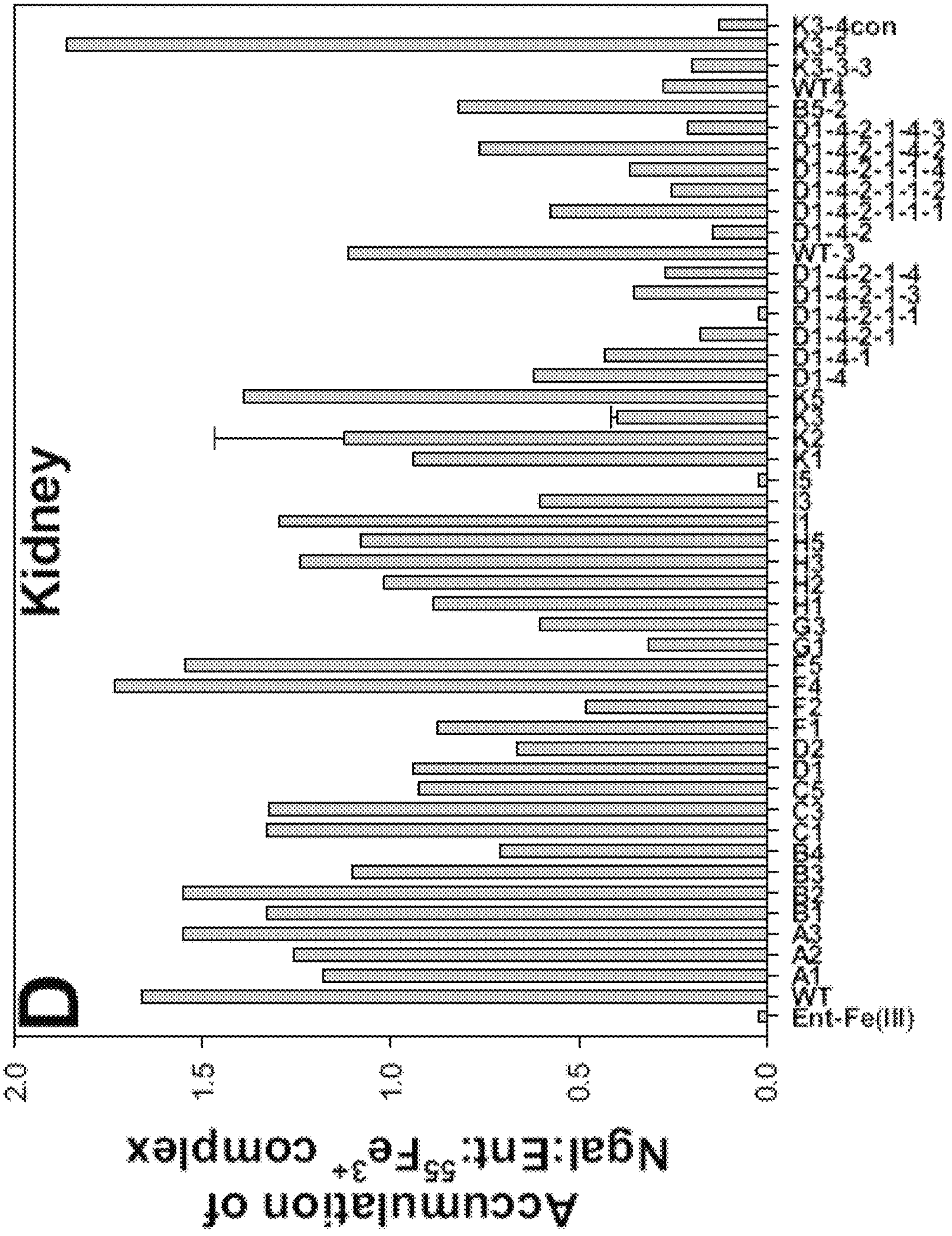

57 NGAL mutants were generated (Table 2; SEQ ID NOS:2-10, 21-68, 247-251). Twenty nine mutant apo-proteins were produced in BL21 *E. coli*, and were examined for their binding affinity to enterochelin and trafficking in C57B6L/6 mice after intraperitoneal (i.p.) injection. As shown in FIG. 3A, all mutant human NGAL proteins retained 16.7% to 45.7% of total iron after incubation with enterochelin-iron in a molar ratio of 1:1:1 (4 nmole each) for 30 minutes at room temperature, indicating their preserved binding affinity for enterochelin-iron (high amounts of enterochelin will increase loading of NGAL).

When administered by i.p. injection, six mutant NGAL-enterochelin-$^{55}Fe^{3+}$ complexes showed a markedly increased accumulation in urine compared with wild-type NGAL complex (mutants K3, K2, I3, I1, K5, and K1). Decreased accumulation in liver and kidney after 3 hours (FIG. 3B, C, D; Table 1) was also seen. There were 6%, 6.9%, 1.9%, 9.3%, 19.6% and 2.9% of I1, I3, K1, K2, K3 and K5 mutant NGAL complexes which were delivered to urine after 3 hours, respectively, while there were only 0.18%, 0.13%, 0.26%, 0.1%, 0.11%, 0.17%, 0.27% and 0.05% of A2, B4, C3, D1, F2, G3, H2 and 15 mutant NGAL complexes in urine.

Figure 4B:
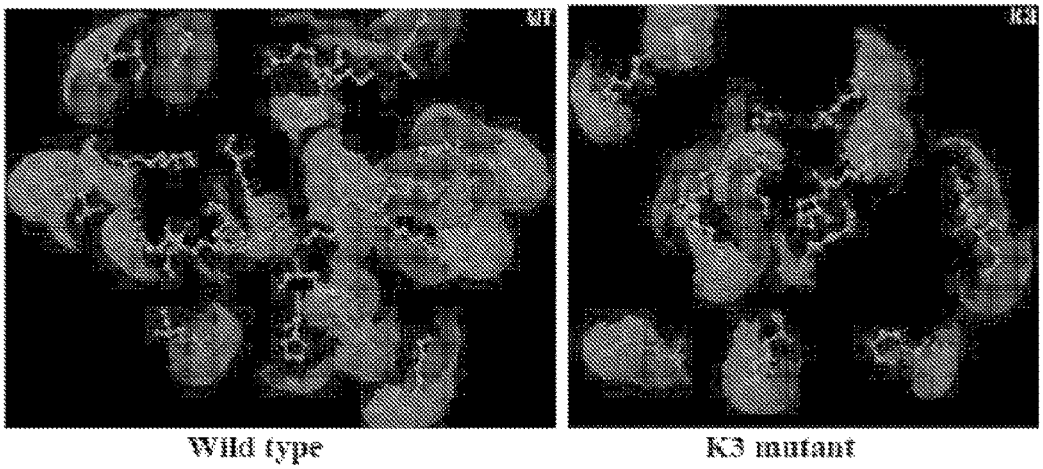

Using the crystal structure of wild-type NGAL (PDB accession number: 1nglA) as substrate, the structure of K3 mutant protein was predicted by using Swissmodel (www.swissmodel.expasy.org). As shown in FIG. 4A, the predicted 3D structure of K3 mutant protein contains a similar pocket as the wild type protein, supporting our finding that affinity for enterochelin-iron is preserved. However, K3 mutant protein exhibited fewer positive amino acids on the solvent accessible surface than wild-type NGAL protein (FIG. 4B), consistent with its decreased ability for electrostatic interaction with megalin, and increased accumulation in urine once introduced into mice.

TABLE 1

Binding of mutant Ngal proteins to enterochelin-$^{55}Fe^{3+}$ and accumulation of mutant Ngal-enterochelin-$^{55}Fe^{3+}$ in urine, kidney and liver 3 hours after i.p. injection into C57BL/6 mice.

| Ngal | Enterocalin-iron Binding | Accumulation 3 hours after i.p. injection (%) | | |
|---|---|---|---|---|
| Mutants | (%) | Urine | Kidney | Liver |
| A1 | 23.4 | 0.55 | 0.32 | 1.10 |
| A2 | 22.6 | 0.18 | 0.37 | 1.11 |
| A3 | 26.6 | 0.23 | 0.39 | 1.52 |
| B1 | 20.7 | 0.22 | 0.26 | 1.30 |
| B2 | 25.7 | 1.22 | 0.34 | 1.27 |

TABLE 1-continued

Binding of mutant Ngal proteins to enterochelin-$^{55}Fe^{3+}$ and accumulation of mutant Ngal-enterochelin-$^{55}Fe^{3+}$ in urine, kidney and liver 3 hours after i.p. injection into C57BL/6 mice.

| Ngal Mutants | Enterocalin-iron Binding (%) | Accumulation 3 hours after i.p. injection (%) Urine | Kidney | Liver |
|---|---|---|---|---|
| B3 | 26.9 | 0.30 | 0.26 | 1.01 |
| B4 | 45.7 | 0.13 | 0.32 | 0.71 |
| C1 | 26.2 | 0.72 | 0.21 | 1.15 |
| C3 | 20.6 | 0.44 | 0.33 | 1.22 |
| C5 | 21.9 | 0.26 | 0.44 | 0.85 |
| D1 | 29.1 | 0.10 | 0.26 | 0.94 |
| D2 | 18.1 | 0.11 | 0.16 | 0.60 |
| F1 | 26.1 | 0.51 | 0.69 | 0.79 |
| F2 | 21.5 | 0.11 | 0.40 | 0.51 |
| F4 | 22.8 | 1.65 | 0.43 | 1.68 |
| F5 | 27.7 | 1.23 | 0.29 | 1.61 |
| G1 | 33.5 | 0.28 | 0.05 | 0.33 |
| G3 | 26.9 | 0.17 | 0.58 | 0.30 |
| H1 | 38.7 | 0.37 | 0.15 | 0.89 |
| H2 | 36.1 | 0.27 | 0.12 | 1.06 |
| H3 | 31.1 | 0.30 | 0.15 | 1.25 |
| H5 | 38.6 | 0.24 | 0.09 | 1.07 |
| I1 | 32.1 | 6.00 | 0.20 | 1.21 |
| I3 | 42.8 | 6.90 | 0.27 | 0.55 |
| I5 | 16.7 | 0.05 | 0.10 | 0.02 |
| K1 | 21.2 | 1.90 | 0.76 | 0.82 |
| K2 | 31.4 | 9.60 | 0.43 | 0.68 |
| K3 | 22.9 | 19.60 | 0.27 | 0.40 |
| K5 | 28.4 | 2.90 | 0.18 | 1.37 |

Example 2

The superscripted numbers in this Example refer to the numbered references in the list of references that follows this Example. Ngal mutants "K numbers 1-8" represent actual Mutants K1, K2, D1-4-2-1-1, K5, D1-4-2-1-1-4, K3, WT-3 and WT4. The sequences of the mutants are provided herein in Table 2.

The transport of iron poses a significant problem because free ferric iron is insoluble (<10-18 M) in aerobic solutions at physiologic pH, while upon solubilization by some chelators, a reactive form of iron is created that can produce toxic oxygen species. Specialized mechanisms are consequently required to traffic iron and these specialized mechanisms are found in proteins which utilize conserved motifs to directly bind iron (transferrin and ferritin) or utilize embedded cofactors. While extracellular iron transport is largely mediated by transferrin, mice carrying deletions of these genes displayed surprisingly limited phenotypes (Barasch, Developmental Cell, 2009). It was found that a member of the lipocalin superfamily called Ngal acted as a high affinity iron carrier (Barasch, Molecular Cell, 2002) when binding a family of novel cofactors called the catechols or related bacterial siderophores constructed from catechol. In the presence of iron, formation of the Ngal:siderophore:FeIII complex occurred at subnanomolar affinity (Barasch, Nature Chemical Biology, 2010) forming a bright red protein, which was stable for many days in solution and stable in vivo for transport of its tightly bound iron. Ngal is expressed in vivo, but a number of "damage" stimuli raise its concentration by orders of magnitude. Thereafter, Ngal traffics in the serum and is thought to be captured by the kidney receptor megalin, where Ngal clears the siderophore:Fe complex. While a great deal is known about the metabolism of the urinary form of Ngal (it is expressed from the distal nephron and is excreted in the urine as a full length protein), much less is known about this clearance system and the role of the megalin receptor, which is the only confirmed receptor for Ngal. To study this process in depth a conditional mutant of megalin can be examined. Also, for studies in wild type mice a series of Ngal mutants can be tested. Some such mutants bypass the proximal tubule where megalin is located, resulting in their presence in the urine. These mutants can still bind to siderophore:FeIII at high affinity (and produce red colored proteins), and can definitely excrete iron, likely in a redox inactive manner. Indeed, rather than donate iron to micro-organisms, which is a major concern for small molecule chelators, the Ngal:siderophore:Fe complexes sequester iron from bacteria. The hypothesis that megalin is the key recycling receptor for Ngal can be tested. It is expected that when the megalin-Ngal complex is inhibited, Ngal can carry tightly bound iron in the urine, hence serving as a safe therapeutic for the common syndromes of iron overload diseases.

Iron overload diseases are common occurrences in clinical medicine, and their therapies have proved toxic to many cell lineages as well as inductive of bacterial growth. Iron overload is a common sequela of blood transfusions, but it is well known in hepatitis, chronic kidney disease as well as in common hereditary diseases such as hemachromatosis. The present invention involves the discovery of an iron trafficking pathway based on the protein Ngal, which is massively expressed in the human in different types of tissue damage. Our studies in Ngal metabolism provide proof of concept that Ngal can be used as a safe therapeutic iron chelator.

Iron is specifically bound by transferrin in circulation, which preserves its bioavailability and prevents its redox toxicity. However, non-transferrin-bound iron (NTBI) appears in patients with a variety of diseases[1-3] including both genetic causes and the non-genetic causes. NTBI damages liver[4-7], heart[8-12], endocrine glands[13-18] and kidney[19-21] and severe overload can be fatal[22,23] by catalyzing reactive oxygen species (ROS) via the Haber-Weiss and Fenton reactions[24-25].

To date, two small molecules, deferoxamine (DFO) and deferiprone are available for the chelation of NTBI and the treatment of iron overload[26-28]. However, these molecules demonstrate significant toxicity. DFO causes skin reactions, hearing loss, renal and pulmonary toxicity, and most interestingly fungal infection[29-32], which results because DFO (which is a derivative of a fungal "siderophore") can deliver iron to pathogens[32]. Deferiprone is also associated with genotoxicity, neutropenia and agranulocytosis and kidney disease[33,34]. Hence, new agents are required for non-toxic NTBI excretion, that do not deliver iron to microorganisms.

The present invention utilizes an endogenous mechanism of iron transport (*Molecular Cell,* 2002*; Nature N&V* 2005*; Nature Chemical Biology,* 2010)[35-38], which is manipulated to safely export iron from the body. The carrier is called Neutrophil Gelatinase-Associated Lipocalin (Ngal). The present invention involves Ngal mutants which allow Ngal to be safely excreted in urine, still tightly binding its iron.

Ngal is a small iron carrier protein (22 KDa) which is markedly expressed in the serum and in the urine when a human or an animal is exposed to a stimulus which typically causes acute kidney injury (AKI: *JASN,* 2003*; JCI,* 2005*; Lancet,* 2005*; Ann Int Med,* 2008)[39-42]. As a result, the protein is now well known as a "biomarker" of AKI, with well over 100 papers confirming its robust expression, yet only a few labs study its biology. We have found that once Ngal is expressed, it is rapidly secreted into circulation, where it can capture iron by binding cofactors such as endogenous catechols or related catecholate-type siderophores (Enterochelin, Ent)[36] which are synthesized by bacteria to capture iron (See FIG. 6A-6B). Hence, Ngal interrupts the nutrient supply of iron for bacteria, providing bacteriostasis.

Figure 7:
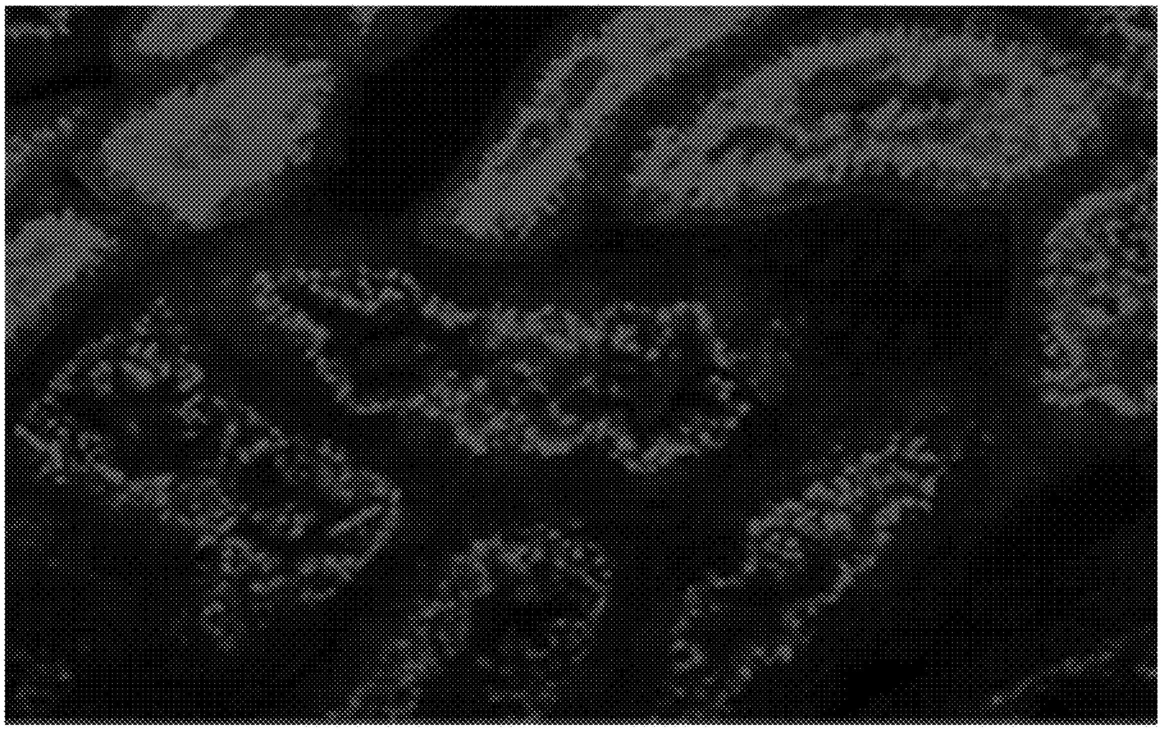
FIG. 7. Clearance of Ngal by the proximal tubule. F1-Ngal was introduced into the peritoneum, and after 1 hour the kidney harvested. Ngal was localized to proximal tubule lysosomes.

Ngal complexes are stable for transport, and they are filtered by the glomerulus and captured by the proximal tubule (FIG. 7), where Ngal is degraded and iron is released for recycling[38]. Ngal is thought to be endocytosed by megalin in proximal tubule cells and a direct interaction between Ngal-megalin has been characterized using surface plasmon resonance (SPR/Biacore™)[43]. The present invention involves Ngal mutants that may bypass megalin, yet still bind Ent:iron, hence providing a therapeutic that can safely excrete NTBI in the urine.

Evaluation of the Ngal-Megalin Interaction Using Ngal Mutants

Since megalin may be the major receptor mediating the reabsorption of filtered Ngal[43], 40 mutant Ngal proteins were produced, some of which are believed to target the Ngal-megalin interaction. The megalin hypothesis can be tested using one of these mutants (K6, i.e, K3) and its optimized derivatives, which partially bypass the proximal tubule and appear in the urine. This mutant can be used to study protein interactions, and cellular, and organ capture in wild type mice and in conditional megalin knockouts, to confirm that the interruption of megalin permits the excretion of iron. Additional mutants can also be tested using this system.

Evaluation of the Ngal:Ent:$Fe^{III}$ Interaction in Ngal Mutants

Figure 8:
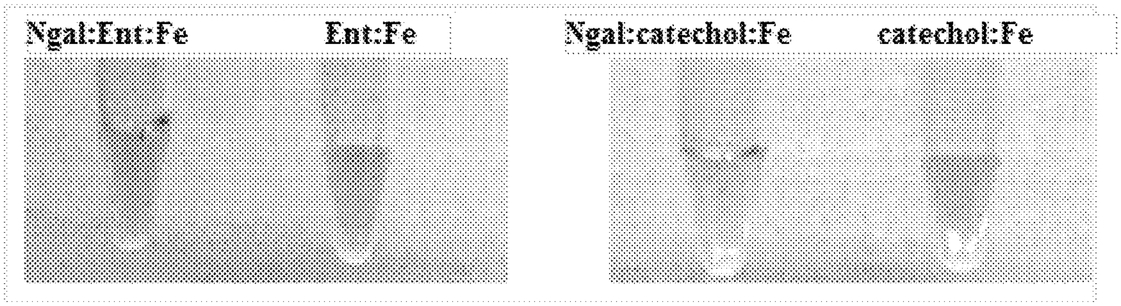
FIG. 8. While ligand-metal charge-transfers between Ent and Fe3+(lmax=498 nm) were not modified by the addition of Ngal protein (note red coloration in 2 left tubes), catechol: Fe3+ converted from a FeL complex (blue, lmax=575 nm) to a FeL3 complex (red, lmax=498 nm) when bound to Ngal (right tubes) and produced an identical spectrum as Ent:Fe.

Ngal contains a central calyx where, when Ent:$Fe^{III}$ is bound, a bright red protein[35] is produced (FIG. 8). Ngal mutants, engineered to reduce their interactions with megalin, were also brightly red colored when mixed with Ent:$Fe^{III}$, indicating retention of ligand affinity. The Ngal complexes can be quantitatively analyzed using Flourescence Quenching techniques and X-Ray Crystallography.

Safe Excretion of Iron by the Delivery of Mutant NGAL: Ent:$Fe^{III}$

K6 (i.e, K3) and optimized mutants can be administered to mice to test NTBI chelation and urinary excretion of $Fe^{III}$ in murine models of hereditary ($HFE^{-/-}$)[44,45] and acquired hemochromatosis[44]. Efficacy can be evaluated by measuring the depletion of NTBI from serum and liver, and toxicity can be ruled out by measuring oxidative stress and the expression of endogenous Ngal, which we previously discovered, indicates the onset of kidney damage.

Significance Iron overloaded patients demonstrate elevated serum transferrin saturation (>50%) and elevated serum ferritin levels (>1000 μg/L)[1-3]. They also demonstrate non-transferrin-bound iron in circulation (NTBI, e.g. 0.9-12.8 mol/L in thalassemic sera; 4-16.3 μM in hereditary hemachromatosis (HH) sera[2]), as well as a labile iron pool (LIP) within cells[46]. These abnormal pools of iron participate in Haber-Weiss and Fenton reactions which oxidize lipids and proteins and mutate nucleotides by forming hydroxyl, ferryl, or perferryl species[24-25,47]. Ultimately, cell death is found in a variety of sensitive organs, including liver (fibrosis/cirrhosis and hepatocellular carcinoma)[4-7], heart (congestive cardiomyopathy)[8-12], kidney (necrosis and apoptosis of proximal tubular cells)[19-21] and endocrine glands (diabetes, hypothyroidism, and hypogonadism)[13-18].

In general there are two types of iron overload disorders, hereditary hemachromatosis (HH) and acquired hemochromatosis (AH). HH is caused by loss of function of genes associated with the regulation of iron metabolism, such as HFE (type 1 HH), HJV (type 2A HH), HAMP (type 2B HH), TfR2 (type 3 HH), SLC40A1 (type 4 HH), CP (aceruloplasminaemia), TF (hypotransferrinaemia)[348]. In the most common entity, Type I HFE C282Y allele, 28% of males were iron overloaded[49]. AH in contrast is caused by blood transfusions, thalassaemia major, sideroblastic and hemolytic anemias, dietary iron overload, chronic kidney and liver diseases due to hepatitis C or alcohol or porphyria[34448]. The 5 million blood transfusions, >15 million units/yr in the US are the most common cause of AH[50]. Blood transfusions cause iron overload because while the human loses 1-2 mg iron per day, each unit of blood contains 250 mg of iron and clear evidence of toxicity appears after 20 transfusions[51-53]. Chronic kidney diseases can also produce a syndrome of excess iron deposition in the proximal tubule and in the urinary space. Iron is deposited in the kidney cortex in HIV associated nephropathy[54] as well as in other forms of nephrotic syndrome[55]. Urinary iron is also a common finding in AKI of various etiologies including hemoglobinuria and myoglobinuria[56], chemotherapy (cis-platin[57]; doxorubicin[58]), ischemia-reperfusion[59,60] and transplant ischemia[61]. It is believed that the release of iron into the urine is a critical step in cell damage[62-69]. In sum, both HH and AH patients suffer organ damage without iron chelation therapy[22,23].

Figure 9:
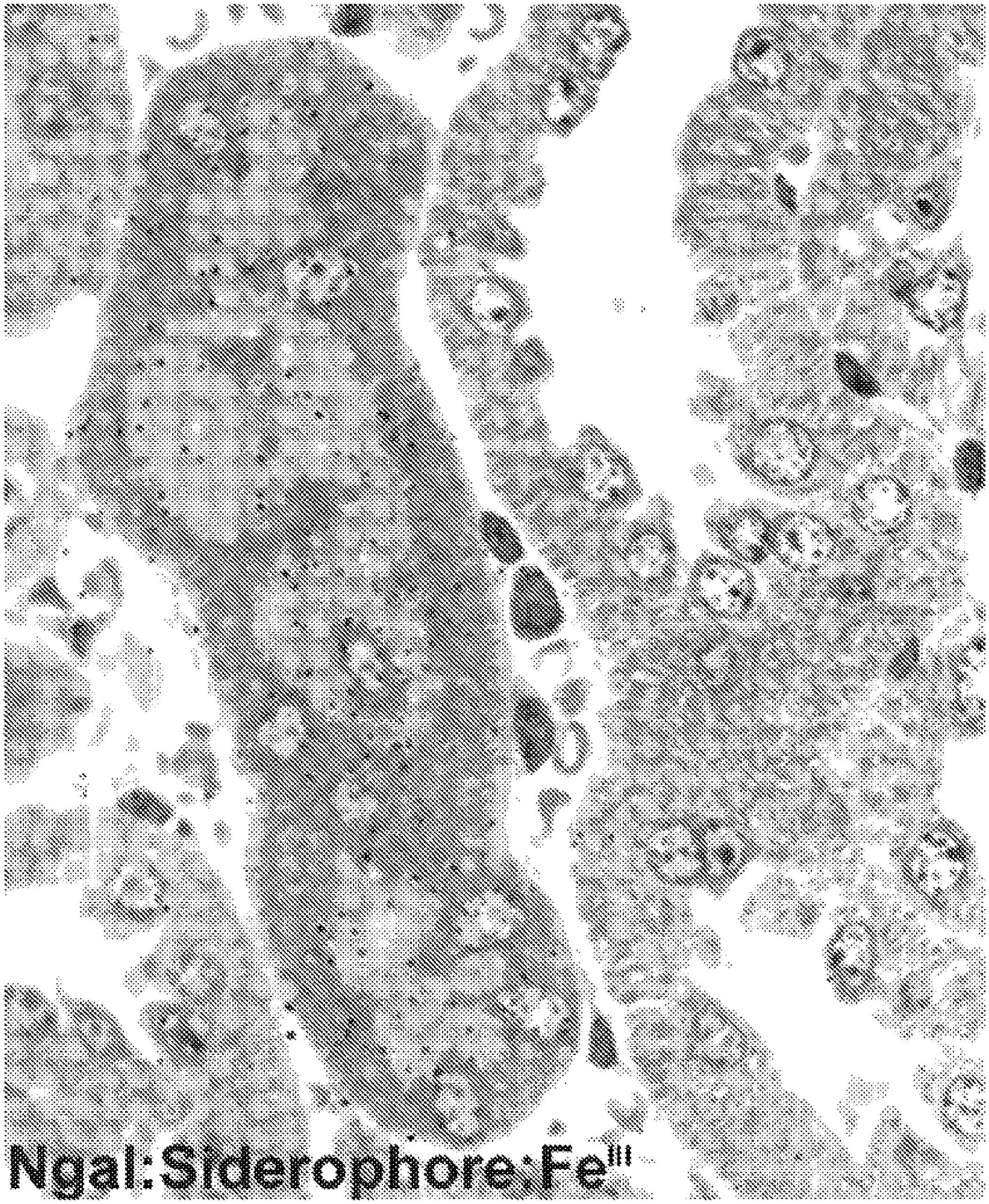
FIG. 9. Trafficking of 55Fe bound to Ngal through the serum to the kidney was visualized by radioautography. Note the black silver grains in proximal tubules but not in distal nephrons after introduction of Ngal:Ent:55Fe or Ngal: catechol:55Fe.
Figure 10:
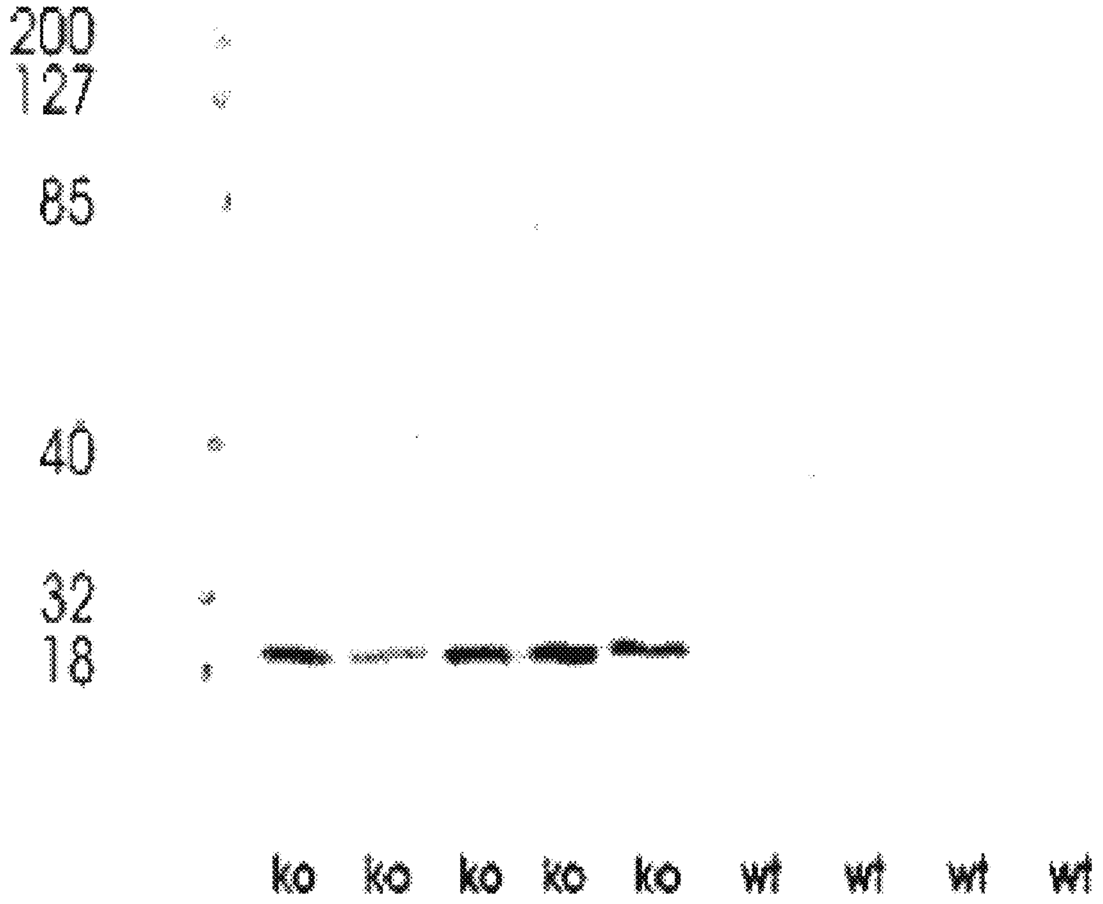
FIG. 10. Urine was collected from both wild type and megalin deleted mice. Ngal was detected by immunoblot using polyclonal anti-mouse Ngal antibodies.
Figure 11:
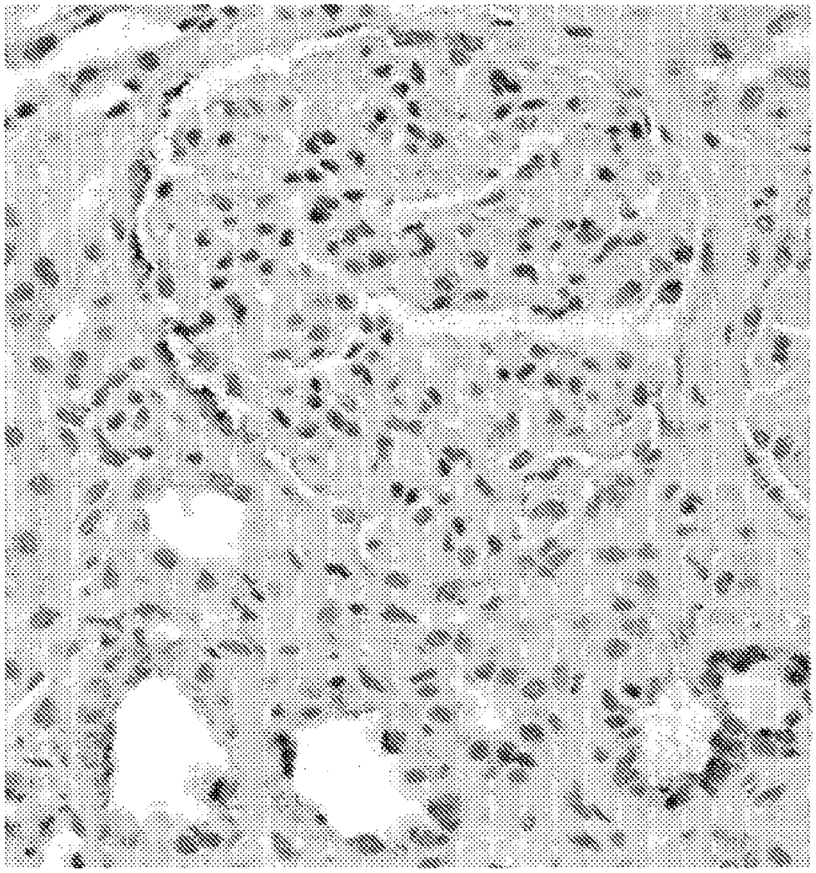
FIG. 11. Human kidney biopsy for AKI stained with anti-Ngal antibodies. Note the association of NGAL with Bowman's Capsule and with the proximal tubule (red-brown staining) apical endosomes.
Figure 12:
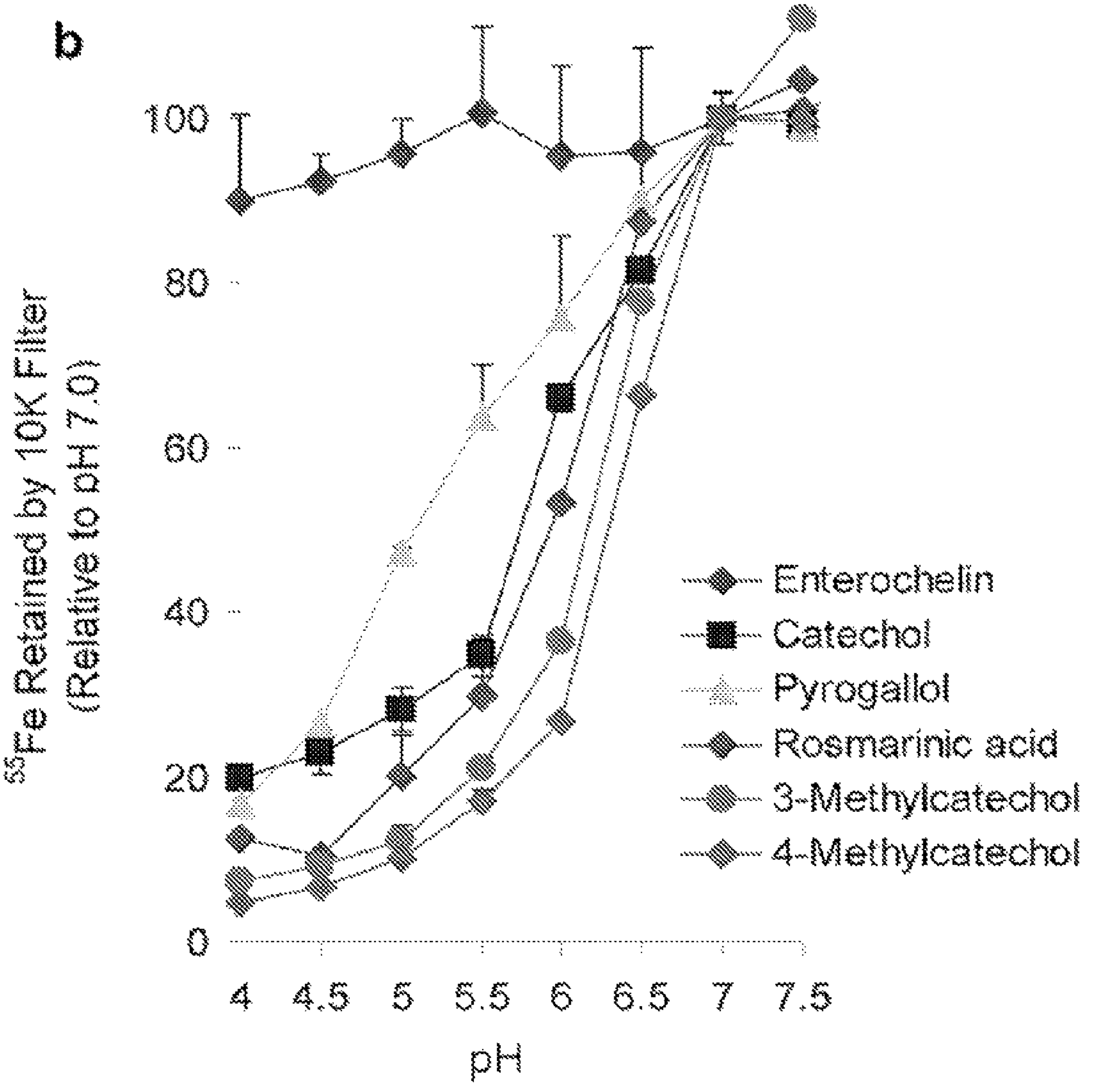
FIG. 12. Release of ligands from Ngal as a result of acidification. Low pH released 55Fe from Ngal:catechol: FeIII complexes but not from Ngal:Ent:FeIII. FeIII loading at pH 7.0 was defined as 100% of the assay. Catechol differed significantly from Ent (P=0.00012).

Two iron-chelating chemicals are currently in clinical use[26-28], but both are limited by toxicity and long-term safety concerns (e.g. "Deferasirox: Uncertain future following renal failure fatalities, agranulocytosis and other toxicities. Expert Opin Drug Saf. 2007 6:235-9)[29-34]. The present invention provides a novel strategy which takes advantage of the endogenous mechanisms of iron trafficking which is manipulated to develop a highly efficient, non-toxic iron chelator for the treatment of iron overload. Ngal is well suited to this approach because of the following characteristics. Ngal was first identified as an iron carrier and growth factor in kidney cells[35]. Second, Ngal binds iron (FIG. 6A-6B) by using bacterial siderophores (such as enterochelin [Ent] from Gram-negative bacteria, bacillibactin from Gram-positive bacteria and carboxymycobactins from mycobacteria[36,70]) or alternatively endogenous catechols found in mammals[38]. Ent and catechols have extremely high affinity for iron ($K_d$=$10^{-49}$M and $10^{-45.9}$M, respectively)[71,72], and Ngal strongly binds Ent:Fe and catechol:Fe ($K_d$=0.4 nM)[36,38], which allows these complexes to sequester iron. In fact, the chelation of bacterial siderophores by Ngal is a critical aspect of the innate immune response, given that the Ngall-mice do not clear bacterial inocula[37]. These data stand in contrast to the high affinity iron chelator DFO ($K_d$=$10^{-30}$ M)[73] which can deliver its iron to *Rhizopus* and induce fatal MucorMycosis[32]. Third, binding of iron to Ngal limited its reactivity as demonstrated by the suppression of phenanthroline and 3'-(p-hydroxyphenyl) fluorescein (HPF) tests of reactive $Fe^{2+}$; in other words, binding to Ngal blocked the Fenton reaction[38]. Fourth, Ngal can load with iron in vivo when it was presented with Ent:$^{55}$Fe or Catechol:$^{55}$Fe; the Ngal complex can then be recovered from the serum five minutes later. Fourth, Ngal loaded with iron traveled through the circulation and targeted the mouse kidney, as demonstrated by radioautography[38,40] (FIG. 9). This process most likely involved glomerular filtration of the Ngal complex, followed by megalin-mediated endocytosis at the apical membrane of the proximal tubule[43] since we found Ngal in the urine of megalin knock-out mice[74] (FIG. 10), and since Surface Plasmon Resonance Analysis (Biacore™) showed that Ngal and megalin interacted directly ($K_d$=60 nM[43]). Fifth, the same process was ongoing in humans, since Ngal was visualized in lysosomes of the proximal tubule of patients with AKI (FIG. 11). Sixth, Ent had a very high affinity for Ngal even in the absence of iron ($K_d$=3.57 nM)[75], while catechol itself bound to Ngal with poor affinity ($K_d$=200±6 nM)[38] meaning that Ent was even a better candidate for iron capture and transport than catechol. Finally, the Ngal:Ent:$Fe^{III}$ complex was pH insensitive, failing to dissociate even at pH 4.0, while Ngal:catechol:$Fe^{III}$ complexes were stable until pH6.5, but acidification progressively reversed catechol-dependent fluorescence quenching and resulted in the dissociation of iron by pH 6.0 (FIG. 12)[38]. Hence, because of its stability at acidic pH, Ngal:Ent:$Fe^{III}$ is not expected to dissociate in acidified urine.

In summary, Ngal:catechol/Ent can chelate NTBI in the circulation with high affinity and clear iron in the kidney. This pathway is active in humans in vivo and potentially traffics large amounts of Ngal and iron: if the GFR is 140 L/Day and the concentration of serum Ngal is 20 ng/ml, 2.8 mg/day of NGAL (0.14 μmole) and 8 μg iron are recycled in the proximal tubule, but in the setting of ischemia, renal failure, sepsis, the level of Ngal rises 100-1000 fold, meaning a very substantial mechanism of clearance may be ongoing (depending on the residual GFR). Therefore, to understand the capture of iron in the kidney and to create a new therapy, we have decided to disrupt the reabsorption of Ngal.

Innovation: A. The first area of innovation has to do with the treatment of iron overload diseases which for too long has relied on toxic chelators[29-34]. The present invention provides a strategy to develop high-efficacy, non-toxic NTBI chelators. This strategy has many advantages over current iron chelators in that (1) Ngal provides an endogenous pathway for delivering iron to the kidney[35,36,38,39]; (2) Ngal:Ent has higher affinity for iron than any other known substance[71,72]; (3) Ngal:Ent:$Fe^{III}$ is redox inactive[38]; (4) Ngal:Ent:$Fe^{III}$ is stable in acidified urine[38] and hence (5) may chelate urinary iron, perhaps alleviating damage in certain renal diseases. A second area of innovation is a description of the metabolism of Ngal-iron. A bioluminescent mouse can be used to compare the timing and intensity of Ngal gene expression in the kidney and in the urine, which has provided a clear understanding of the biosynthesis and excretion of this pool (Paragas et al, In Review). Ngal mutants can directly test the role of megalin in wild type mice and provide complimentary data for the analysis of megalin defective mice. This approach can also test the notion that a second NGAL receptor (24p3R)[76] may be present in the nephron.

Evaluation of the Ngal-Megalin Interaction by the Generation of Ngal Mutants

Figure 13:
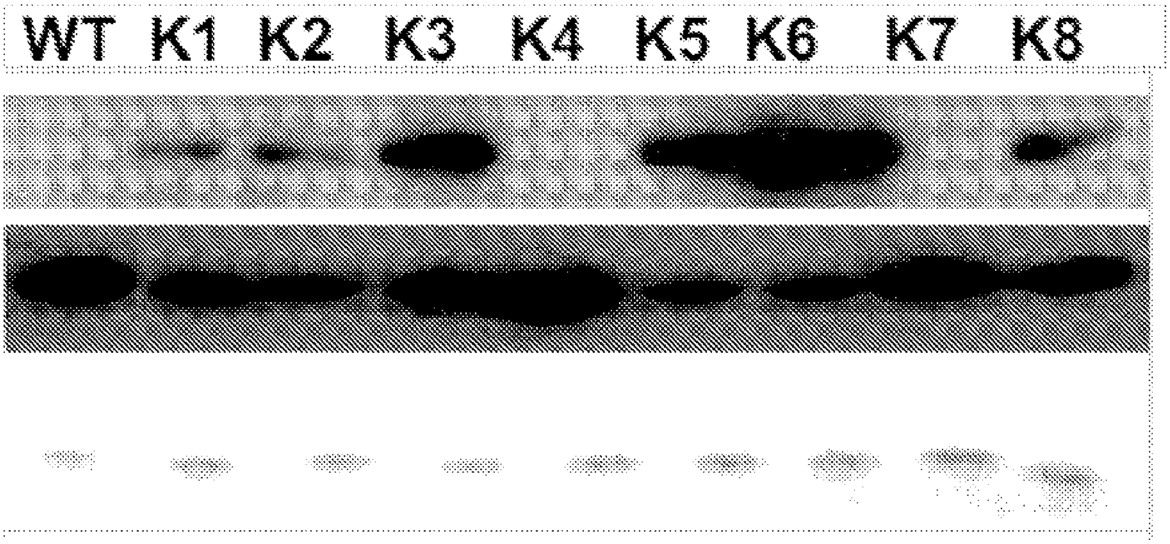
FIG. 13. Top Urine Immunodetection by Western Blot of WT and mutant Ngal species in the urine 3 hrs after i.p. injection (80 micrograms). Middle Starting Material shows immunoblot of purified WT and Mutant Ngal proteins (100 ng) and Bottom SDS-Page and Coomassie stain of each mutant. The designations "WT" and "K numbers 1-8"

Megalin is thought to bind its ligands using a series of electrostatic interactions between megalin's negatively-charged ligand-binding domains and the positively-charged surface-domains of the ligand[77]. Consequently, by mutating Ngal's positively charged surface residues the megalin-Ngal interaction can be disrupted. Surface domains of human Ngal were identified based on its crystal structure (R. Strong; PDB no. 1L6M) using the software Pymol[78]. The surface domains contained 18 positively charged amino acids (Lys 15, Lys 46, Lys 50, Lys 59, Lys 62, Lys 73, Lys 74, Lys 75, Lys 98, His 118, Arg 130, Lys 149, and His 165, R43, 72, 140, and K142, 157), 5 of which were conserved in mammalians[36], and these residues were chosen for site-directed mutagenesis. The human Ngal ORF (without signal peptide sequence) was cloned into pGEX-4T-3 bacterial expression plasmid (Amersham) to generate a GST-Ngal fusion to create a template for mutagenesis. The conserved positively charged surface residues were then mutated to alanine. Non-conserved amino acids were mutated to non-positively charged residues which occupied the same position in non-human Ngal proteins. For mutagenesis a single or a combined strategy with the QuikChange™ Site-Directed Mutagenesis kit (Stratagene) was used, producing 40 Ngal mutant clones. Wild-type and mutant Ngal proteins were then produced in BL21 *E. coli* by induction with 0.2 mM IPTG, and purification by GST-based affinity isolation and gel filtration chromatography using our established protocols[35,38]. We then functionally screened these Ngal proteins by introducing them (80 g/400 1) into C57BL/6 mice (4 weeks) to identify which mutants could bypass renal absorption and appear in urine within 3 hrs. Ngal mutants K1, K2, K3, K5, K6 (i.e, K3), and K8 were detected in the urine by SDS-PAGE as well as by immunoblot using a human Ngal-specific antibody developed in rat (R&D System) (recombinant Ngal=21 KDa; endogenous Ngal=25 KDa), suggesting that the mutations resulted in loss of affinity for the recycling receptors on the apical plasma membrane of proximal tubular epithelia. In contrast, wild-type, K4 and K7 mutants could not be detected in the urine and consequently were most likely reabsorbed (FIG. 13). These data provide valuable information about the Ngal-megalin interaction because they test whether variations in Ngal reabsorption may be ascribed to variations in the megalin-Ngal interaction, providing insight into the mechanisms of clearance of serum Ngal, and allowing the optimization of mutants to excrete iron.

Structural Basis for NGAL-Megalin Interaction

Interactions with Megalin

The interaction between wild-type human Ngal (ligand-free) and chip-coupled megalin ($K_d$=~60 nM)[43] purified from human kidney cortex was previously analyzed by $\alpha_2$-macroglobulin-affinity chromatography[79]. Biacore™ T100 technology can be used to compare wild type and K6 (i.e, K3) (or other mutant) interactions with megalin. Whether ligand-binding influences Ngal-Megalin interaction can also be tested by using bacterial siderophores and catechol ligands. Data can be calculated with BIAevaluation 4.1 software (Biacore™), globally fitting data to derive kinetic and equilibrium parameters. A range of coupling and regeneration conditions can also be used, though antibody-capture often provides the cleanest data.

Megalin Mediated Endocytosis

Classical megalin-expressing cell models can be used to investigate megalin-binding and endocytosis. Such cells include HK-2[90] and Brown Norway rat yolk sac epithelia[43]. Rat yolk sac cells are important because megalin is the only receptor which mediates endocytosis of human Ngal in these cells, since uptake was completely abolished with anti-megalin antibodies[43] (the neutralizing antibodies proved more effective than megalin shRNA). Wild-type and K6 ((i.e, K3) mutant proteins (and other mutants) can be labeled with fluorescent probes (Alexa Fluor™ 488, Molecular Probes) cleaned-up by gel filtration (GE Biotech, PD10) and dialysis (Pierce 10K cassette)[35,43] in order to study their rate of uptake (50 μg/ml in serum-free DMEM for 0.5-6 hours) in the presence or absence of anti-human or anti-rat megalin antibodies (Santa Cruz; 200 μg/ml)[43] which were previously shown to block uptake of wild type human Ngal in BN cells[43]. Endocytosis of Ngal can be measured both by using a Zeiss LSM510-META inverted confocal laser scanning microscope and immunoblots of cell extracts to detect the presence of human Ngal. These experiments can determine whether the failure to capture K6 (i.e, K3) (or other mutants) can be ascribed to defective Ngal-megalin interactions and if the affinity defect or the endocytosis defect is truly partial. If so, then additional mutations can be provided to disrupt the remaining interactions with megalin. The remaining positively charged surface residues in K6 (Le, K3) (or other mutants) can be mutated using a single or combinational approach as above, and then reiteratively tested using the Biacore™ assays and the cellular uptake assays. As a result of these mutations, the role in megalin in Ngal capture and Ngal's megalin binding domain can be defined. Additionally optimized mutants can be generated.

Alternative Receptors

Our data (FIGS. 9 and 13) and a previously published report[43] suggests that megalin is an essential receptor for Ngal. However, there may be non-megalin receptor(s) in the proximal tubule. The main candidate is 24p3R (SLC22A17), which is found throughout the kidney and shown to mediate Ngal endocytosis[76], but its function is not yet confirmed. Stably transfected HEK293 cells over-expressing human 24p3R can be generated, and the uptake of Alexa Fluor™-488 labeled wild-type and K6 (i.e, K3) mutant Ngal and Ngal:Ent:$Fe^{III}$ can be determined, for example by using confocal microscopy and immunoblots. If 24p3R stimulates the uptake of wild-type Ngal, it can be a receptor for Ngal, and the K6 (i.e, K3) mutant (and other mutants) may show defective interactions with this receptor.

Distribution of Ngal Mutants In Vivo

A further test of the Ngal-megalin interaction can be performed using a megalin conditional knockout murine model[91], in which megalin is deleted in the proximal tubular epithelia using floxed-megalin mice and gGT-Cre which specifically deletes genes in 80% of cells in the S3 segment of the proximal tubule[92]. According to TE Willnow[91], these conditionally deleted mice are viable and fertile. The efficiency of the megalin deletion can be confirmed by immunohistochemical staining with anti-megalin antibodies. If the deletion is complete, $megalin^{f/f}$ mice can be bred with $megalin^{f/+}$ gGT-Cre mice to generate $megalin^{f/f}$:gGT-Cre mice (25%) and littermate controls $megalin^{f/f}$ (25%), $megalin^{f/+}$:gGT-Cre (25%) and $megalin^{f/+}$ (25%). The megalin deleted mice (n=12) can be identified by PCR-genotyping the floxed allele and the gGT-cre recombinase. Alexa Fluor™-488- or rhodamine labeled wild-type or K6 (i.e, K3) mutants (two different labels to avoid the contribution of negative (Alexa Fluor™-488) or positive (Rhodamine) charges) can be tested by i.p. injection into 4 week old mice and their trafficking analyzed by using a Zeiss LSM510-META inverted confocal laser scanning microscope and immunoblots with anti-human antibodies. Since megalin expression is limited to proximal kidney epithelia, parathyroid cells, epididymal epithelial cells, type II pneumocytes, mammary epithelial and thyroid follicular cells, the distribution of both wt and mutant Ngal in wt and knockout mice can be investigated to explore the Ngal-megalin interaction in vivo. If the capture of wt Ngal by the proximal tubule is abolished in the conditional megalin-ko kidney, and Ngal is excreted (similar to FIG. 10), megalin is likely the only Ngal receptor in the kidney and the proposed receptor 24p3R is non-essential. If this is the case, then the distribution of wt Ngal should also correlate with the distribution of megalin in different tissues. Moreover, if Ngal mutants such as K6 (i.e, K3) have poor affinity for megalin, their escape in the urine can be directly explained. On the other hand, if wt Ngal is captured in the megalin knockout proximal tubule and by cells of the body where megalin is not expressed, then alternative receptor(s) are expected. In this case, the excretion of mutant Ngal may be the result of loss-of-affinity not only for megalin, but for non-megalin receptors.

Evaluation of the Ngal:Ent:$Fe^{III}$ Interaction in Ngal Mutants

Ngal specifically binds Ent:$Fe^{III}$ and Ent with high affinities (0.4 nM and 3.57 nM, respectively)[36,75], and it fails to release bound iron even at low pH[38]. Ngal sequestered iron no longer participates in chemical reactions and the complex is stable for transport in circulation. Whether loss-of-"reabsorption" mutants still have the capacity to bind ferric siderophores at high affinity can be tested. Initial data shows that the mutants retain iron in the presence of Ent (FIG. 14) and demonstrates a distinct red coloration. The K6 (i.e, K3) Ngal:Ent interaction can be quantified and the structural effects of the introduced mutations can be determined.

Quantitative Measurement of Ent:$Fe^{III}$ Binding by Ngal

A fluorescence quenching (FQ) strategy (*Nature Chemical Biology,* 2010[38], FIG. 10) can be utilized to quantify the spectrum of Ngal and Ngal mutant:ferric siderophore interactions[93-98] to derive affinity measurements for Ent binding. Excitation $\lambda_{exc}$=281 nm and emission $\lambda_{em}$=340 nm data can be collected from 100 nM K6 (i.e, K3) Ngal mutant protein solutions (with 32 µg/mL ubiquitin and 5% DMSO), exposed to Ent:Fe. The pH sensitivity of the complex can be determined by incrementally adjusting the solution's pH until the fluorescence signal stabilizes. The data can be examined using nonlinear regression analysis using a one-site binding model (DYNAFIT)[99]. Control experiments can be performed to ensure protein stability. Alternative techniques include SPR and isothermal titration calorimetry (e. g. from the Strong group[86]).

Structural Basis for the Formation of Mutant Ngal:Ent:$Fe^{III}$

In order to confirm that mutations introduced to disable megalin binding do not interfere with ferric siderophore ligand recognition, the structure of K6 (i.e, K3)±Ent:$Fe^{III}$ can be determined by X-Ray Crystallography. Over 20 Ngal crystal structures, including human, murine and mutant forms, ±N-linked CHO, both empty and bound to a series of natural siderophores or synthetic analogs have been determined previously[36,38,93,99,100]. Since the K6 (i.e, K3) mutations affect crystal contacts in all the known Ngal crystal forms, this can be approached as a de novo structure determination. For crystallization, the protein can be highly purified by GST chromatography, followed by gel filtration and ion exchange chromatography, with purity and monodispersivity determined by reduced/non-reduced PAGE and mass-spectroscopy with concurrent static/dynamic light scattering (SLS/DLS). Monodispersed protein preparations can be screened for crystallizability using submicroliter robotics and commercially-available factorial screens. Preliminary crystals can be optimized in conventional crystallization formats using established methodologies that catalyze crystallization. Alternatively, the protein can be more stringently purified or complexed with Fabs (the structure of a murine Ngal:Fab complex [crystallized from 20% PEG 4000 and 10% isopropanol, pH=7.0; space group: $P2_12_12_1$, a=37.9 Å, b=69.4 Å, c=117.6 Å; $d_{min}$=2.15 Å, $R_{merge}$=0.04] was determined—a panel of over 16 anti-human Ngal antibody Fabs can be used for co-crystallization). Diffraction data can be collected. Data can be reduced with any of a variety of available software packages and can be phased by direct difference Fourier (for isomorphous crystals), molecular replacement (MR), MAD (generally using selenomethionine) or MIRAS (using any of a variety of derivatization strategies). These data can quantitatively characterize Ngal:Ent interactions, indicating whether K6 (i.e, K3) (or other mutants) have retained affinity for Ent:$Fe^{III}$. These studies can show that the introduced mutations impair ligand binding, and the structures can be used to engineer additional mutations.

Safe Excretion of Iron by the Delivery of Mutant NGAL: Ent:$Fe^{III}$

To test whether K6 (i.e, K3) Ngal:Ent can efficiently chelate and deliver NTBI to the urine through the kidney, the K6 (i.e, K3):Ent:$^{55}Fe^{III}$ complex (80 g) was introduced into mice (4 weeks), and collected the urine for 3 hrs in metabolic cages. As shown in FIG. 16, 23% of the injected K6 (i.e., K3)-$^{55}Fe^{III}$ complex was delivered to the urine, paralleling the percentage of K6 (i.e, K3) protein found in the urine (FIG. 13), while less than 0.1% of the wild type injectate was excreted. Only trace amounts of $^{55}Fe^{III}$ accumulated in the liver (<1%), indicating that once iron was chelated by K6 (i.e, K3):Ent, it was mainly delivered to the kidney and the urine. Based on these results, it can be tested whether K6 (i.e, K3):Ent can capture, chelate, traffic and remove endogenous NTBI.

Chelation and Excretion of NTBI by K6 (i.e, K3):Ent in Murine Models of Hemochromatosis Establishment and Evaluation of Mouse Models A mouse model of Type 1 hereditary hemochromatosis lacking the Hfe gene is available from the Jackson Labs (Stock #: 003812). These mice develop organ iron overload 12 weeks after weaning[45]. A mouse model of acquired hemochromatosis can be established as reported previously[101]. This mouse model of transfusion mediated iron overload was made by transfusing stored (14 days at 4° C.) mouse RBC (200 or 400 L at 17.0-17.5 g/dL hemoglobin) into a recipient via the retro-orbital plexus of isoflurane-anesthetized mice, which is the equivalent of transfusing a human with 1-2 units of RBC. Briefly, the RBCs are obtained from 30-50 C57BL/6 mice in CPDA-1 solution (Baxter), leukoreduced using a Neonatal High-Efficiency Leukocyte Reduction Filter (Purecell Neo) and then concentrated by centrifugation to a final hemoglobin level of 17 g/dL, as determined by Drabkin assays (Ricca)[102] and the optical density (540 nm) compared with the Count-a-Part Cyanmethemoglob-in Standards (Diagnostic Technology) [101]. Residual leukocytes are counted by cytometry (LeucoCOUNT™; BD)[101]. NTBI was previously observed in both $HFE^{-/-}$ 3.7 μM)[103] and RBC transfused (~2.5 μM) mice[101]. NTBI can be measured in these models using a standard nitrilotriacetic acid (NTA) ultrafiltration assay[101]. This can be done by incubating heparinized plasma (90 L) with NTA (800 mM, pH 7.0) and then preparing a 30K ultrafiltrate (NanoSep™, 30-kDa cutoff, polysulfone type) and measuring NTBI with ferrozine[104]. Total organ iron can be determined using a procedure which involves desiccation at 65° C., followed by acidification and detection of NTBI with a chromogen (1.6 mM bathophenanthroline)[105]. Hemoglobinemia can be detected spectrophotometrically using a PowerWave XS spectrophotometer (BioTek)[101]. Intracellular iron accumulation in the liver and spleen can be detected in paraffin sections with Perl's reagent which reveals blue granules[54] and in sections with co-immunostaining to detect macrophages with anti-mouse F4/80 antibody (eBioscience) and ABC and DAB kits (Vector Laboratories)[101].

As reported previously, a number of cytokines/chemokines, especially interleukin-6 (IL-6), monocyte chemoattractant protein-1 (MCP-1), macrophage inhibitory protein-1β (MIP-1β), and keratinocyte-derived chemokine/CXCL1 (KC/CXCL1) are increased in the plasma 2 hrs after transfusion of old stored RBC[101]. Hence, these cytokines can be measured as markers of iron overload and as a measure of treatment efficacy of Ngal. The cytokines/chemokines can be quantified using the Cytometric Bead Array Mouse Flex Kit (BD Biosciences) and plasma with a FACSCalibur cytometer (BD Biosciences) equipped with FlowJo software[101].

Treatment of Iron Overload with K6 (i.e, K3): Ent and Evaluation of Treatment Efficacy.

The K6 (i.e, K3):Ent complex can be introduced into $HFE^{-/-}$ or RBC transfused mice by intravenous infusion with a micro-osmotic pump (ALZET®). For $HFE^{-/-}$ mice, the dose of K6 (i.e, K3):Ent can be 17.9 mg K6 (i.e, K3):Ent for 12 hours, 3 times a week for 4 weeks. This dose is based on the following calculation: For $HFE^{-/-}$ mice, NTBI is ~3.7 μM and blood volume is ~1.6 ml; to maximize iron chelation and removal, equal moles of Ngal:Ent should be continually present in circulation for a 12 hour treatment with the consideration of Ngal's half life of 10 min, or approximately ~0.85 moles (~17.9 mg) of Ngal:Ent are theoretically required over 12-hours. Similarly, for the transfusion mice the dose is ~0.58 moles (~12 mg) of Ngal:Ent over 12 hours in a single treatment period. Apo-K6 (i.e, K3) is as a negative control because it does not bind iron and associated endogenous catechols would dissociate. Wt Ngal is also a useful control because it is captured by megalin, and it does not traffic iron into the urine.

The efficacy of treatment can be evaluated by the measurement of serum and urinary iron, iron concentration in the liver, spleen and kidney, intracellular iron accumulation in macrophages and hepatocytes, and cytokines/chemokines in the plasma of K6 (i.e, K3):Ent- vs K6 (i.e, K3)- or Wt-treated mice as described above. K6 (i.e, K3) Ngal can be detected in urine by immunoblot with anti-human antibodies. Preliminary data suggests that K6 (i.e, K3) will appear in the urine, and that K6 (i.e, K3):Ent will markedly diminish serum NTBI, decrease the iron content of $HFE^{-/-}$ mice and transfusion overload, and additionally normalize the levels of cytokines/chemokines in old-RBC transfusions.

Effect of K6 (i.e, K3):Ent Treatment on Iron-Mediated Cell Damage

Measurement of Redox Activity in the Kidney Peroxidized lipids are a marker of iron catalyzed oxidant stress, which are measured by malondialdehyde. The renal cortex of mice subjected to K6 (i.e, K3) treatment is separated from the medulla, homogenized[106,107] and treated with TCA and thiobarbituric acid and the supernatant read at 535 nm. Malondialdehyde, expressed in nmoles, is calculated using a molar extinction coefficient of $1.56\times10^{5}$ $M^{-1}$ $cm^{-1}$ at 535 nm. An additional measurement of kidney damage during the treatment with K6 (i.e, K3) is the detection of endogenous mouse uNgal (25 KDa) with mouse antibody (R&D system). Ngal is expressed within 3 hrs of damage by stimuli that cause AKI including radical attack, and here we will measure uNgal in the different treatment groups.

Measurement of Free Iron and Redox Activity in Mouse Urine

The data presented herein suggests that the iron will be tightly bound to K6 (i.e, K3) Ngal and redox inactive even in the acidic urine. This can be tested using the classic spectrophotometric bleomycin test of Gutteridge[57] to measure urinary "catalytic" iron in mice treated with K6 (i.e, K3), K6 (i.e, K3):Ent and wild type Ngal. Urine is collected in Chelex-treated, pyrogen-free water and an ultrafiltrate created using a Microcon™ (10K, Millipore) measured with the bleomycin assays. A standard curve is prepared with urine spiked with $FeCl_3$ and bleomycin-detectable iron recorded per mg creatinine (Abcam). A second strategy to measure redox activity can also be used—the iron mediated generation of hydroxyl radicals can be detected by the conversion of 3'-(p-hydroxyphenyl) fluorescein (HPF; Invitrogen) to fluorescein in the presence of ascorbic acid[94] (Ex 490 nm, Em 515 nm). As shown in FIGS. 17 and 18, wild type Ngal quenched the activity of catechol:$Fe^{III}$— urine from mice treated with K6 (i.e, K3), K6 (i.e, K3):Ent and Wt Ngal:Ent is tested. A positive control is Ent/catechol:$Fe^{III}$ followed by K6 (i.e, K3) which inhibits the production of superoxide radicals.

Vertebrate Animals

In Vivo Characterization of Ngal-Mediated Iron Chelation and Trafficking:

Adult female and male mice (C57BL/6) are the principal source of experimental tissues for studying the regulation of iron metabolism. We have used adult tissues from these mice for many years to discover how Ngal mediates iron trafficking (Bao et al Nat Chem Biol, 2010). Both male and female adults are used in vivo to characterize the Ngal-mediated iron transport to different tissues (e.g. liver, heart, lung, kidney, spleen, pancreas, brain) and urine (Bao et al Nat Chem Biol, in press, 2010). Animals of all ages and both sexes will be used.

Mouse is a standard model for studying the regulation of iron delivery and metabolism dating back to the 1950's, and many murine models of iron overload diseases such as $HFE^{-/-}$ mice have been established and utilized to study the pathogenesis of these diseases and potential therapeutic treatments. Further, use of mice carrying gene knockouts is a standard of the field which has yielded most of the insights to date in the functions of genes required for iron delivery and metabolism such as megalin which is required for transferrin- and Ngal-bound iron reabsorption in the kidney. There are no alternatives to the use of these mouse models because no other animal models of other species are available and studies based on cultured cell lines can not reflect the in vivo mechanism of iron delivery and metabolism. Hence, these murine models will be used to investigate the in vivo mechanism of Ngal-mediated iron delivery to various tissues and urine.

Based on data on the difference of the ability of the intraperitoneally injected wild-type and K6 (i.e, K3) mutant Ngal proteins to bypass the kidney and enter the urine, we estimated the number of mice (sample size) which are required for the experiments by using Power Analysis with parameters of $p<0.05$ and Power=0.8 and a Biomath program (www.biomath.info/power/ttest.htm), and 6 mice are suggested in each of the groups to achieve statistic significance (t-test on group means). According to the calculation, for each experimental category (control K6 (i.e, K3), K6 (i.e, K3):Ent, Wt:Ent) we will need 6 wild-type mice, 6 megalinf/f; GgT-cre+ mice, 6 $HFE^{-/-}$ mice (total=54 mice). To generate these mice, 10 mating cage, each containing 1 male and 2 females will be used (2 cages for the generation of megalinf/f, 2 cages for GgT-cre/megalinf/+, 2 cages for megalinf/f GgT-cre+, and 2 cages for homozygous HFE−/−). Similarly, for the RBC transfusions we will need 18 mice to test Ngal proteins and, in order to collect plasma from cardiac puncture, we will need 50 wild type mice to blood bank the RBC for transfusion.

No surgical procedures are planned. Genotyping: In the case of animals carrying gene knockouts (eg. Megalinf/f, GgT-cre+, HFE−/−) genotyping is necessary. The animal is genotyped at 14 days by snipping a 2-3 mm of tail dabbing the wound with lidocaine. Pressure is applied to control blood loss/

Euthanasia is performed through CO2 narcosis and cervical dislocation. Following CO2 narcosis the chest cavity is opened to assure death of the animal, and the feti are removed.

REFERENCE LIST

1. Hershko, C., and Peto, T. E. Non-transferrin plasma iron. Br. J. Haematol. 66: 149-151, 1987.
2. Breuer, W., Ronson, A., Slotki, I. N., Abramov, A., Hershko, C., and Cabantchik, Z. I. The assessment of serum nontransferrin-bound iron in chelation therapy and iron supplementation. Blood. 95: 2975-2982, 2000.
3. Andrews, N. C. Iron metabolism: Iron Deficiency and Iron Overload. Annu. Rev. Genomics Hum. Genet. 1:75-98, 2000.
4. Thakemgpol, K., Fucharoen, S., Boonyaphipat, P., Srisook, K., Sahaphong, S., Vathanophas, V., and Stitnimankam, T. Liver injury due to iron overload in thalassemia: histopathologic and ultrastructural studies. Biometals. 9: 177-183, 1996.
5. Conte, D., Piperno, A., Mandelli, C., et al. Clinical, biochemical and histological features of primary haemochromatosis: a report of 67 cases. Liver. 6: 310-315, 1986.
6. Tsukamoto, H., Home, W., Kamimura, S., Niemela, O., Parkkila, S., Yla-Herttuala, S., and Brittenham, G. M. Experimental liver cirrhosis induced by alcohol and iron. J. Clin. Invest. 96: 620-630, 1995.
7. Berdoukas, V., Bohane, T., Tobias, V., et al. Liver iron concentration and fibrosis in a cohort of transfusion-dependent patients on long-term desferrioxamine therapy. Hematol. J. 5: 572-578, 2004.
8. Liu, P., and *Olivieri*, N. Iron overload cardiomyopathies: new insights into an old disease. Cardiovasc. Drugs. Ther. 8: 101-110, 1994.
9. Buja, L. M., and Roberts, W. C. Iron in the heart. Etiology and clinical significance. Am. J. Med. 51: 209-221, 1971.
10. Schwartz, K. A., Li, Z., Schwartz, D. E., et al. Earliest cardiac toxicity induced by iron overload selectively inhibits electrical conduction. J. Appl. Physiol. 93: 746-751, 2002.
11. Oudit, G. Y., Trivieri, M. G., Khaper, N., Liu, P. P., and Backx, P. H. Role of L-type Ca2+ channels in iron transport and iron-overload cardiomyopathy. J. Mol. Med. 84: 349-364, 2006.
12. Oudit, G. Y., Sun, H., Trivieri, M. G., Koch, S. E., Dawood, F., Ackerley, C., Yazdanpanah, M., Wilson, G. J., Schwartz, A., Liu, P. P., and Backx, P. H. L-type $Ca^2$ channels provide a major pathway for iron entry into cardiomyocytes in iron-overload cardiomyopathy, Nat. Med. 9: 1187-1194, 2003.
13. Andrews, N. C. Disorders of iron metabolism. N. Engl. J. Med. 341: 1986-1995, 1999.
14. Argyropoulou, M. I., and Astrakas, L. MRI evaluation of tissue iron burden in patients with beta-thalassaemia major. Pediatr. Radiol. 37: 1191-1200, 2007.
15. Argyropoulou, M. I., Kiortsis, D. N., Astrakas, L., Metafratzi, Z., Chalissos, N., Efremidis, S. C. Liver, bone marrow, pancreas and pituitary gland iron overload in young and adult thalassemic patients: a T2 relaxometry study. Eur. Radiol. 17: 3025-3030, 2007.
16. Cunningham, M. J., Macklin, E. A., Neufeld, E. J., and Cohen, A. R. Complications of beta-thalassemia major in North America. Blood. 104: 34-39, 2004.
17. Fung, E., Harmatz, P. R., Lee, P. D., Milet, M., Bellevue, R., Jeng, M. R., Kalinyak, K. A., Hudes, M., Bhatia, S., and Vichinsky, E. P. Increased prevalence of iron-overload associated endocrinopathy in thalassaemia versus sickle-cell disease. Br. J. Haematol. 135: 574-582, 2006.
18. Kattamis, C., and Kattamis, A. C. Management of thalassemias: growth and development, hormone substitution, vitamin supplementation, and vaccination. Semin. Hematol. 32: 269-279, 1995.
19. Eschbach, J. W., and Adamson, J. W. Iron overload in renal failure patients: Changes since the introduction of erythropoietin therapy. Kidney Int. 55: S35-S43, 1999.
20. Lorenz, M., Kletzmayr, J., Huber, A., Horl, A. H., Sunder-Plassmann, G., and Fddinger, M. Iron overload in kidney transplants: Prospective analysis of biochemical and genetic markers. Kidney Int. 67, 691-697, 2005.
21. Mandalunis, P. M., and Ubios, A. M. Experimental Renal Failure and Iron Overload: A Histomorphometric Study in Rat Tibia. Toxicol. Pathol. 33; 398-403, 2005.
22. Karnon, J., Zeuner, D., Brown, J., Ades, A. E., Wonke, B., and Modell, B. Lifetime treatment costs of beta-thalassaemia major. Clin. Lab. Haematol. 21: 377-385, 1999.
23. Darbari, D. S., Kple-Faget, P., Kwagyan, J., Rana, S., Gordeuk, V. R., and Castro, O. Circumstances of death in adult sickle cell disease patients. Am. J. Hematol. 81: 858-863, 2006.
24. McCord, J. M. Oxygen-derived free radicals in postischemic tissue injury. N. Engl. J. Med. 312: 159-163, 1985.
25. Meneghini, R. Iron homeostasis, oxidative stress, and DNA damage. Free Radic. Biol. Med. 23: 783-792, 1997.
26. Kalinowski, D. S., and Richardson, D. R. The Evolution of Iron Chelators for the Treatment of Iron Overload Disease and Cancer. Pharmacol. Rev. 57: 547-583, 2005.
27. Cohen, A. R. New Advances in Iron Chelation Therapy. Hematology-American Hematology Society Hematology Education Program. 42-47, 2006.
28. Hoffbrand, A. V., Cohen, A., and Hershko, C. Role of deferiprone in chelation therapy for transfusional iron overload. Blood 102: 17-24, 2003.
29. Bosque, M. A., Domingo, J. L., and Corbella, J. Assessment of the developmental toxicity of deferoxamine in mice. Arch. Toxicol. 69: 467-471, 1995.
30. Oliveri, N. F., Buncic, J. R., Chew, E., Galant, T., Harrison R. V., Keenan, N., Logan, W., Mitchell, D., Rici, G., Skarf, B., Taylor, M., and Freedman, M. H. Visual and auditory neurotoxicity in patients receiving subcutaneous deferoxamine infusions. N. Engl. J. Med. 314: 869-873, 1986.
31. Boelaert, J. R., and de Locht, M. Side-effects of desferrioxamine in dialysis patients. Nephrol Dial Transplant. 8: S43-S46, 1993.
32. Windus D W, Stokes T J, Julian B A, Fenves A Z. Fatal *Rhizopus* infections in hemodialysis patients receiving deferoxamine. Ann. Intern. Med. 107: 678-80, 1987.
33. Kowdley, K. V., and Kapla, M. M. Iron-chelation therapy with oral deferiprone—Toxicity or Lack of Efficacy? N. Engl. J. Med. 339: 468-469, 1998.
34. Kontoghiorghes, G. J. "Deferasirox: Uncertain future following renal failure fatalities, agranulocytosis and other toxicities. Expert. Opin. Drug. Saf. 6:235-239, 2007.
35. Yang, J., Goetz, D., Li, J. Y., Wang, W., Mori, K., Setlik, D., Du, T., Erdjument-Bromage, H., Tempst, P., Strong R., and Barasch, J. An iron delivery pathway mediated by a lipocalin. Mol. cell, 10: 1045-56, 2002.
36. Goetz, D. H., Holmes, M. A., Borregaard, N., Bluhm, M. E., Raymond, K. N., and Strong, R. K. The neutrophil lipocalin NGAL is a bacteriostatic agent that interferes with siderophore-mediated iron acquisition. Mol. cell, 10: 1033-1043, 2002.
37. Flo, T. H., Smith, K. D., Sato, S., Rodriguez, D. J., Holmes, M. A., and Strong, R. K., Akira, S., and Aderem, A. Lipocalin 2 mediates an innate immune response to bacterial infection by sequestrating iron. Nature, 432: 917-921, 2004.
38. Bao, G., Clifton, M., Hoette, T. M., Mori, K., Deng, S. X., Qiu, A., Viltard, M., Williams, D., Paragas, N., Leete, T., Kulkami, R., Li, X., Lee, B., Kalandadze, A., Ratner, A. J., Pizarro, J. C., Schmidt-Ott, K., Landry, D. W., Raymond, K. N., Strong, R. K., and Barasch, J. Iron Traffics in Circulation Bound to a Siderocalin (Ngal)-Catechol Complex. Nat. Chem. Biol. in press, 2010.
39. Mishra, J., Ma, Q., Prada, A., Mitsnefes, M., Zahedi, K., Yang, J., Barasch, J., and Devarajan, P. Identification of neutrophil gelatinase-associated lipocalin as a novel early urinary biomarker for ischemic renal injury. J. Am. Soc. Nephrol. 14: 2534-43, 2003.
40. Mori, K., Lee, H. T., Rapoport, D., Drexler, I. R., Foster, K., Yang, J., Schmidt-Ott, K. M., Chen, X., Li, J. Y., Weiss, S., Mishra, J., Cheema, F. H., Markowitz, G., Suganami, T., Sawai, K., Mukoyama, M., Kunis, C., D'Agati, V., Devarajan, P., and Barasch, J. Endocytic delivery of lipocalin-siderophore-iron complex rescues the kidney from ischemia-reperfusion injury. J. Clin. Invest. 115: 610-621, 2005.
41. Mishra, J., Dent, C., Tarabishi, R., Mitsnefes, M. M., Ma, Q., Kelly, C., Ruff, S. M., Zahedi, K., Shao, M., Bean, J., Mori, K., Barasch, J., and Devarajan, P. Neutrophil gelatinase-associated lipocalin (NGAL) as a biomarker for acute renal injury after cardiac surgery. Lancet. 365: 1231-1238, 2005.
42. Nickolas, T. L., O'Rourke, M. J., Yang, J., Sise, M. E., Canetta, P. A., Barasch, N., Buchen, C., Khan, F., Mori, K., Giglio, J., Devarajan, P., and Barasch, J. Sensitivity and specificity of a single emergency department measurement of urinary neutrophil gelatinase-associated lipocalin for diagnosing acute kidney injury. Ann. Intern. Med. 148: 810-9, 2008.
43. Hvidberg, V., Jacobsen, C., Strong, R. K., Cowland, J. B., Moestrup, S. K., and Borregaar, N. The endocytic receptor megalin binds the iron transporting neutrophil-gelatinase-associated lipocalin with high affinity and mediates its cellular uptake, FEBS Letters 579: 773-777, 2005.
44. Andrews, N. C. Iron homeostasis: insights from genetics and animal models. Nat. Rev. 1: 208-217, 2000.
45. Bahram, S., Gilfillan, S., Kuhn, L. C., Moret, R., Schulze, J. B., Lebeau, A., and Schumann, K. Experimental hemochromatosis due to MHC class I HFE deficiency: immune status and iron metabolism. Proc. Natl. Acad. Sci. USA. 96: 13312-13317, 1999.
46. Borwein, S., Ghent, C. N., and Valberg, L. S. Diagnostic efficacy of screening tests for hereditary hemochromatosis. Cen. Med. Assoc. 131: 895-901, 1984.
47. Halliwell, B., and Gutteridge, J. M. Role of free radicals and catalytic metal ions in human disease: an overview. Methods Enzymol. 186: 1-85, 1990.
48. Trinder, D., Fox, C., Vautier, G., and Olynyk, J. K. Molecular pathogenesis of iron overload, Gut 51: 290-295, 2002.
49. Allen, K. J., Gurrin, L. C., Constantine, C. C., Osborne, N. J., Delatycki, M. B., Nicoll, A. J., McLaren, C. E., Bahlo, M., Nisselle, A. E., Vulpe, C. D., Anderson, G. J., Southey, M. C., Giles, G. G., English, D. R., Hopper, J. L., Olynyk, J. K., Powell, L. W., and Gertig, D. M. Iron-overload-related disease in HFE hereditary hemochromatosis. N. Engl. J. Med. 358: 221-230, 2008.
50. Landro, L. New rules may shrink ranks of blood donors. Wall Street Journal. 2007-01-10.

51. Bennett, J. M. (ed). The Myelodysplastic Syndromes: Pathobiology and Clinical Management. New York: Marcel Dekker, Inc. 2002.
52. Iron Disorders Institute, Inc. Transfusion-dependent iron overload. idInsight. Greenville, SC.
53. Schafer, A., Cheron, R. G., Dluhy, R., Cooper, B., Gleason, R. E., Soeldner, J. S., and Bunn, H. F. Clinical consequences of acquired transfusional iron overload in adults. N. Engl. J. Med. 304: 319-324, 1981.
54. Paragas, N., Nickolas, T. L., Wyatt, C., Forster, C. S., Sise, M., Morgello, S., Jagla, B., Buchen, C., Stella, P., Sanna-Cherchi, S., Carnevali, M. L., Mattei, S., Bovino, A., Argentiero, L., Magnano, A., Devarajan, P., Schmidt-Ott, K. M., Allegri, L., Klotman, P., D'Agati, V., Gharavi, A. G., and Barasch, J. Urinary NGAL marks cystic disease in HIV-associated nephropathy. J. Am. Soc. Nephrol. 20: 1687-1692, 2009.
55. Alfrey, A. Toxicity of tubule fluid iron in nephrotic syndrome. Am. J. Physiol. 263: F637-641, 1992.
56. Baliga, R., Zhang, Z., Baliga, M., and Shah, S. V. Evidence for cytochrome P-450 as a source of catalytic iron in myoglobinuric acute renal failure. Kidney Int. 49: 362-369, 1996.
57. Baliga, R., Zhang, Z., Baliga, M., Ueda, N., and Shah, S. V. In vitro and in vivo evidence suggesting a role for iron in cisplatin-induced nephrotoxicity. Kidney Int. 53: 394-401, 1998.
58. Saad, S. Y., Najjar, T. A., and Al-Rikabi, A. C. The preventive role of deferoxamine against acute doxorubicin-induced cardiac, renal and hepatic toxicity in rats. Pharmacol. Res. 43: 211-218, 2001.
59. Paller, M. S., and Jacob, H. S. Cytochrome P-450 mediates tissue-damaging hydroxyl radical formation during reoxygenation of the kidney. Proc. Natl. Acad. Sci. USA. 91: 7002-7006, 1994.
60. Baliga, R., Ueda, N., and Shah, S. V. Increase in bleomycin-detectable iron in ischaemia/reperfusion injury to rat kidneys. Biochem. J. 291: 901-905, 1993.
61. Baron, P., Gomez-Marin, O., Casas, C., Heil, J., Will, N., Condie, R., Burke, B., Najarian, J. S., and Sutherland, D. E. Renal preservation after warm ischemia using oxygen free radical scavengers to prevent reperfusion injury. J. Surg. Res. 51: 60-65. 1991.
62. Wu, Z. L., and Paller, M. S. Iron loading enhances susceptibility to renal ischemia in rats. Ren. Fail. 16: 471-480, 1994.
63. Baliga, R., Zhang, Z., Baliga, M., Ueda, N., and Shah, S. V. In vitro and in vivo evidence suggesting a role for iron in cisplatin-induced nephrotoxicity. Kidney Int. 53: 394-401, 1998.
64. Walker, P. D., and Shah, S. V. Evidence suggesting a role for hydroxyl radical in gentamicin-induced acute renal failure in rats. J. Clin. Invest. 81: 334-341, 1988.
65. Paller, M. S., and Hedlund, B. E. Role of iron in postischemic renal injury in the rat. Kidney Int. 34: 474-480, 1988.
66. Paller, M. S., and Hedlund, B. E. Extracellular iron chelators protect kidney cells from hypoxia/reoxygenation. Free Radic. Biol. Med. 17: 597-603, 1994.
67. de Vries, B., Walter, S. J., von Bonsdorff, L., Wolfs, T. G., van Heurn, L. W., Parkkinen, J., and Buurman, W. A. Reduction of circulating redox-active iron by apotransferrin protects against renal ischemia-reperfusion injury. Transplantation, 77: 669-675, 2004.
68. Zager, R. A., Burkhart, K. M., Conrad, D. S., and Gmur, D. J. Iron, heme oxygenase, and glutathione:effect on myohemoglobinuric proximal tubular injury. Kidney Int. 48: 1624-1634, 1995.
69. Paller, M. S., and Hedlund, B. E. Extracellular iron chelators protect kidney cells from hypoxia/reoxygenation. Free Radic. Biol. Med. 17: 597-603, 1994.
70. Holmes, M. A., Paulsene, W., Jide, X., Ratledge, C., and Strong, R. K. Siderocalin (Lcn 2) also binds carboxymycobactins, potentially defending against mycobacterial infections through iron sequestration. Structure 13: 29-41, 2005.
71. Loomis, L. D., and Raymond, K. N. Solution Equilibria of Enterobactin and Metal-Enterobactin Complexes. Inorg. Chem. 30: 906-911, 1991.
72. Jewett, S. L., Eggling, S., and Geller, L. Novel method to examine the formation of unstable 2:1 and 3:1 complexes of catecholamines and iron(III), J. Inorg. Biochem. 66: 165-173, 1997.
73. Keberle, H. The biochemistry of desferrioxamine and its relation to iron metabolism. Ann. N. Y. Acad. Sci. 119: 758-768, 1964.
74. Leheste, J. R. et al. Megalin knockout mice as an animal model of low molecular weight proteinuria. Am. J. Pathol. 155: 1361-1370, 1999.
75. Abergel, R. J., Wilson, M. K., Arceneaux, J. E. L, Hoette, T. M., Strong, R. K., Byers, B. R., and Raymond, K. N. Anthrax pathogen evades the mammalian immune system through stealth siderophore production. PNAS 103: 18499-18503, 2006.
76. Devireddy, L. R., Gazin, C., Zhu, X., and Green, M. R. A cell-surface receptor for lipocalin 24p3 selectively mediates apoptosis and iron uptake. Cell. 123: 1293-305, 2005.
77. Moestrup, S. K., and Verroust, P. J. Megalin- and cubilin-mediated endocytosis of protein-bound vitamins, lipids, and hormones in polarized epithelia. Annu. Rev. Nutr. 21: 407-428, 2001.
78. Liang, M. P., Banatao, DR., Klein, T. E., Brutlag, D. L., and Altman, R. B. WebFEATURE: An interactive web tool for identifying and visualizing functional sites on macromolecular structures. Nucleic Acids Res. 31: 3324-3327, 2003.
79. Moestrup, S. K. and Gliemann, J. Analysis of ligand recognition by the purified alpha 2-macroglobulin receptor (low density lipoprotein receptor-related protein). Evidence that high affinity of alpha 2-macroglobulin-proteinase complex is achieved by binding to adjacent receptors. J. Biol. Chem. 266: 14011-14017, 1991.
80. Kaiser, B. K., Barahmand-Pour, F., Paulsene, W., Medley, S., Geraghty, D. E., and Strong, R. K., Interactions between NKG2x immunoreceptors and HLA-E ligands display overlapping affinities and thermodynamics. J. Immunol. 174: 2878-2884, 2005.
81. Li, P., McDermott, G., and Strong, R. K., Crystal structures of RAE-1beta and its complex with the activating immunoreceptor NKG2D. Immunity, 16: 77-86, 2002.
82. Li, P., Morris, D. L., Willcox, B. E., Steinle, A., Spies, T., and Strong, R. K., Complex Structure of the Activating Immunoreceptor NKG2D and its MHC Class I-like Ligand MICA. Nature Immunol. 2: 443-451, 2001.
83. McBeth, C., Seamons, A., Pizarro, J. C., Fleishman, S. J., Baker, D., Kortemme, T., Goverman, J. M., and Strong, R. K., A new twist in TCR diversity revealed by a forbidden alphabeta TCR. J. Mol. Biol. 375: 1306-1319, 2008.

84. McFarland, B. J., and Strong, R. K. Thermodynamic analysis of degenerate recognition by the NKG2D immunoreceptor: not induced fit but rigid adaptation. Immunity 19: 803-812, 2003.
85. Vigdorovich, V., Strong, R. K., and Miller, A. D., Expression and characterization of a soluble, active form of the jaagsiekte sheep retrovirus receptor, Hyal2. J. Virol. 79: 79-86, 2005.
86. Xu, H., Song, L., Kim, M., Holmes, M. A., Kraft, Z., Sellhom, G., Reinherz, E. L., Stamatatos, L., and Strong, R. K. Interactions between lipids and human anti-HIV antibody 4E10 can be reduced without ablating neutralizing activity. J. Virol. 84: 1076-1088, 2010.
87. Correia, B. E., Ban, Y. E. A., Holmes, M. A., Xu, H., Ellingson, K., Kraft, Z., Carrico, C., Boni, E., Sather, N., *Zenobia*, C., Burke, K. Y., Bradley-Hewitt, T., Bruhn-Johannsen, J. F., Kalyuzhniy, O., Baker, D., Strong, R. K., Stamatatos, L., and Schief, W. R. Computational design of epitope-scaffolds allows induction of antibodies specific for a poorly immunogenic HIV vaccine epitope. Structure, in press, 2010.
88. Strong, R. K., Bratt, T., Cowland, J. B., Borregaard, N., Wiberg, F. C., and Ewald, A. J., Expression, purification, crystallization and crystallographic characterization of dimeric and monomeric human neutrophil gelatinase associated lipocalin (NGAL). Acta Cryst. D54: 93-95, 1998.
89. Bauer, S., Willie, S. T., Spies, T., and Strong, R. K. Expression, purification, crystallization and crystallographic characterization of the human MHC class I related protein MICA. Acta Cryst. D54: 451-453, 1998.
90. Ryan, M. J., et al. HK-2: an immortalized proximal tubule epithelial cell line from normal adult human kidney. Kidney Int. 45: 48-57, 1994.
91. Leheste, J. R., Melsen, F., Wellner, M., Jansen, P., Schlichting, U., Renner-Muller, I., Andreassen, T. T., Wolf, E., Bachmann, S., Nykjaer, A., and Willnow, T. E. Hypocalcemia and osteopathy in mice with kidney-specific megalin gene defect. FASEB J. 17: 247-249, 2003.
92. Dworniczak, B., Skryabin, B., Tchinda, J., Heuck, S., Seesing, F. J., Metzger, D., Chambon, P., Horst, J., Pennekamp, P. Inducible Cre/loxP Recombination in the Mouse Proximal Tubule. Nephron Experimental Nephrology, 106: el 1-e20, 2007.
93. Abergel, R. J., Clifton, M. C., Pizarro, J. C., Warner, J. A., Shuh, D. K., Strong, R. K., and Raymond, K. N., The siderocalin/enterobactin interaction: a link between mammalian immunity and bacterial iron transport. J. Am. Chem. Soc. 130: 11524-34, 2008.
94. Abergel, R. J., Moore, E. G., Strong, R. K., and Raymond, K. N., Microbial evasion of the immune system: structural modifications of enterobactin impair siderocalin recognition. J. Am. Chem. Soc. 128: 10998-9, 2006.
95. Abergel, R. J., Wilson, M. K., Arceneaux, J. E., Hoette, T. M., Strong, R. K., Byers, B. R., and Raymond, K. N. Anthrax pathogen evades the mammalian immune system through stealth siderophore production. Proc. Natl. Acad. Sci. USA 103: 18499-503, 2006.
96. Fischbach, M. A., Lin, H., Zhou, L., Yu, Y., Abergel, R. J., Liu, D. R., Raymond, K. N., Wanner, B. L., Strong, R. K., Walsh, C. T., Aderem, A., and Smith, K. D. The pathogen-associated iroA gene cluster mediates bacterial evasion of lipocalin 2. Proc. Natl. Acad. Sci. USA 103: 16502-7, 2006.
97. Hoette, T. M., Abergel, R. J., Xu, J., Strong, R. K., and Raymond, K. N. The role of electrostatics in siderophore recognition by the immunoprotein Siderocalin. J. Am. Chem. Soc. 130: 17584-92, 2008.
98. Goetz, D. H., Willie, S. T., Armen, R. S., Bratt, T., Borregaard, N., and Strong, R. K. Ligand preference inferred from the structure of neutrophil gelatinase associated lipocalin. Biochemistry, 39: 1935-41, 2000.
99. Kerjaschkit, D., Orlando, R. A., Farquhar, M. G., and Kuzmic, P. Program DYNAFIT for the analysis of enzyme kinetic data: application to HIV proteinase. Anal. Biochem. 237: 260-273, 1996.
100. Holmes, M. A., Paulsene, W., Jide, X., Ratledge, C., and Strong, R. K. Siderocalin (Lcn 2) Also Binds Carboxymycobactins, Potentially Defending against Mycobacterial Infections through Iron Sequestration. Structure, 13: 29-41, 2005.
101. Hod, E. A., Zhang, N., Sokol, S. A., Wojczyk, B. S., Francis, R. O., Ansaldi, D., Francis, K. P., Della-Latta, P., Whittier, S., Sheth, S., Hendrickson, J. E., Zimring, J. C., Brittenham, G. M., and Spitalnik, S. L. Transfusion of red blood cells after prolonged storage produces harmful effects that are mediated by iron and inflammation. Blood. 115: 4284-4292, 2010.
102. Moore, G. L., Ledford, M. E., and Merydith, A. A micromodification of the Drabkin hemoglobin assay for measuring plasma hemoglobin in the range of 5 to 2000 mg/dl. Biochem. Med. 26: 167-173, 1981.
103. Anita, C., Chua, G., Olynyk, J. K., Leedman, P. J., and Trinder, D. Nontransferrin-bound iron uptake by hepatocytes is increased in the Hfe knockout mouse model of hereditary hemochromatosis. Blood. 104: 1519-1525, 2004.
104. Evans, R. W., Rafique, R., Zarea, A., et al. Nature ofnon-transferrin-bound iron: studies on iron citrate complexes and thalassemic sera. J. Biol. Inorg. Chem. 13: 57-74, 2008.
105. Overmoyer, B. A., McLaren, C. E., and Brittenham, G. M. Uniformity of liver density and nonheme (storage) iron distribution. Arch. Pathol. Lab. Med. 111: 549-554, 1987.
106. Walker, P. D., and Shah, S. V gentamicin-induced acute renal failure in rats. J. Clin. Invest. 81: 334-341, 1988.
107. Paller, M. S., and Hedlund, B. E. Role of iron in postischemic renal injury in the rat. Kidney Int. 34: 474-480. Evidence suggesting a role for hydroxyl radical in, 1998.

Table 2 shows a listing of amino acid sequences, and the amino acid sequences of mutant NGAL proteins. Mutant NGAL proteins which were generated are shown as SEQ ID NOS: 2-10; 21-68; 247-251. Table 2 also shows putative mutant NGAL proteins having substitutions to non-positively charged amino acids at all positions on NGAL (SEQ ID NOS: 69-246, including all surface residues on NGAL, which surface residues are inclusive of positions 1-15 (SEQ ID NOS: 69-83), positions 17-26 (SEQ ID NOS: 85-94), positions 40-50 (SEQ ID NOS: 108-118), positions 57-62 (SEQ ID NOS: 125-130), positions 71-82 (SEQ ID NOS: 139-150), positions 84-89 (SEQ ID NOS: 152-157), positions 96-105 (SEQ ID NOS: 164-173), positions 114-118 (SEQ ID NOS: 182-186), positions 128-131 (SEQ ID NOS: 196-199), position 134 (SEQ ID NO: 202), positions 140-151 (SEQ ID NOS: 208-219), positions 157-165 (SEQ ID NOS: 225-233), positions 170-174 (SEQ ID NOS: 238-242). The amino acid sequence of the K3Cys protein is depicted in SEQ ID NO: 252.

| SEQ ID NO | Name | Sequence |
|---|---|---|
| SEQ ID NO: 1 | WT NGAL | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCIDG |
| SEQ ID NO: 2 | K-3 | QDSTSDLIPAPPLSSVPLQQNFQDNQFQGKWYVVGLAGNAILREDEDP QKMYATIYELKEDKSYNVTSVLERDDGCDYWIRTFVPGCQPGEFTLGN IQSYPGLTSYLVRVVSTNYNQFAMVFFKKVSQNQEYFKITLYGRTKEL TSELQENFIRFSKSLGLPENNIVEPVPIDQCIDG |
| SEQ ID NO: 3 | K-2 | QDSTSDLIPAPPLSSVPLQQNFQDNQFQGKWYVVGLAGNAILREDKDP QKMYATIYELKEDKSYNVTSVLFRDDGCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |
| SEQ ID NO: 4 | I-3 | QDSTSDLIPAPPLSKVPLQQNFQDNQFQGKWYVVGLAGNAILREDKDP QKMYATIYELKEDGSYNVTSVLERDDGCDYWIRTFVPGCQPGEFTLGN IQSYPGLTSYLVRVVSTNYNQHAMVFFKKVSQNREYFKITLYGRTKEL TSELKENFIRFSKSLGLPENHIVFPVPIDQCIDG |
| SEQ ID NO: 5 | I-1 | QDSTSDLIPAPPLSSVPLQQNFQDNQFQGKWYVVGLAGNAILREDKDP QKMYATIYELKEDKSYNVTSVLFRDDGCDYWIRTFVPGCQPGEFTLGN IKSYPGLTSYLVRVVSTNYNQHAMVFFKKVSQNQEYFKITLYGRTKEL TSELKENFIRFSKSLGLPENHIVEPVPIDQCIDG |
| SEQ ID NO: 6 | K-5 | QDSTSDLIPAPPLSSVPLQQNFQDNQFQGKWYVVGLAGNAILREDEDP QKMYATIYELKEDKSYNVTSVLFRKKKCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |
| SEQ ID NO: 7 | K-1 | QDSTSDLIPAPPLSSVPLQQNFQDNQFQGKWYVVGLAGNAILREDEDP QKMYATIYELQEDKSYNVTSVLFRKKKCDYWIRTFVPGCQPGEFTLGN IQSYPGLTSYLVRVVSTNYNQFAMVFFKKVSQNQEYFKITLYGRTKEL TSELQENFIRESKSLGLPENNIVFPVPIDQCIDG |
| SEQ ID NO: 8 | F-4 | QDSTSDLIPAPPLSSVPLQQNFQDNQFQGKWYVVGLAGNAILREDEDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELQENFIRFSKSLGLPENHIVFPVPIDQCIDG |
| SEQ ID NO: 9 | F-5 | QDSTSDLIPAPPLSSVPLQQNFQDNQFQGKWYVVGLAGNAILREDEDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELQENFIRFSKSLGLPENNIVFPVPIDQCIDG |
| SEQ ID NO: 10 | B-2 | QDSTSDLIPAPPLSSVPLQQNFQDNQFQGKWYVVGLAGNAILREDEDP QKMYATIYELKEDKSYNVTSVLFRKKKCDYWIRTFVPGCQPGEFTLGN IKSYPGLTSYLVRVVSTNYNQFAMVFFKKVSQNREYFKITLYGRTKEL TSELKENFIRFSKSLGLPENNIVFPVPIDQCIDG |
| SEQ ID NO: 11 | EcNGAL | RDPAPKLIPAPPLDRVPLQPDFKDDQFQGKWYVVGVAGNAFKKEEQGQ FTMYTTTYELKEDHSYNVTSILLRDQNCDHWIRTFIPSSQPGQFNLGD IKRYFGVQSYIVRVADTDYNQFAIVFFRKVYKNQEYFKTTLYRRTKEL TPELREKFISFAKSLGLTDDHIIFPVPIDQCIDEE |
| SEQ ID NO: 12 | CfNGAL | QDSTPSLIPAPPPLKVPLQPDFQHDQFQGKWYVIGIAGNILKKEGHGQ LKMYTTTYELKDDQSYNVTSTLLRNERCDYWNRDFVPSFQPGQFSLGD IQLYPGVQSYLVQVVATNYNQYALVYFRKVYKSQEYFKITLYGRTKEL PLELKKEFIRFAKSIGLTEDHIIFPVPIDQCIDE |
| SEQ ID NO: 13 | SsNGAL | QGTIPNWIPAPPLSKVPLQPNFQADQFQGKWYVVGLAGNAVKKEEQGR FKMYTTTYELKEDGSYNVISTLLRGQLCDNWIRTFVPSLQPGQFKLGD IKKYSGLQSYVVRVVSTNYSQFAIVFFKKVSNNQEYFKTTLYGRTKVL SPELKENFVRFAKSLGLSDDNIIFPVAIDQCIDGQ |
| SEQ ID NO: 14 | PtNGAL | QDSTSDLIPAPPLSKVPLQQNFQDNQFQGKWYVVGLAGNAILREDKDP QKMYATIYELKEDKSYNVTSVLFRKKKCDYWIRTFVPGRQPGEFTLGN IKSYPGLTSYLVRVVSTNYNQHAMVFFKKVSQNREYFKITLYGRTKEL TSELQENFIRFSKSLGLPENHIVFPVPIDQCIDG |
| SEQ ID NO: 15 | MamNGAL | QDSSSDLIPAPPLSKVPLQQNFQDNQFQGKWYVVGLSGNAVGRKDEAP LKMYATIYELKEDKSYNVTSILFRKEKCDYWIRTFVPGSQPGEFTLGN IQNHPGLTSYVVRVVSTNYKQYAMVFFKKVSQNKEYFKITLYGRTKEL TSELKENFIRFSKSLGLPENHIVESVPIDQCING |

-continued

| SEQ ID NO | Name | Sequence |
|---|---|---|
| SEQ ID NO: 16 | BtNGAL | RSSSSRLLRAPPLSRIPLQPNFQADQFQGKWYTVGVAGNAIKKEEQDP<br>LKMYSSNYELKEDGSYNVTSILLKDDLCDYWIRTFVPSSQPGQFTLGN<br>IKSYRGIRSYTVRVVNTDYNQFAIVYFKKVQRKKTYFKITLYGRTKEL<br>TPEVRENFINFAKSLGLTDDHIVFTVPIDRCIDDQ |
| SEQ ID NO: 17 | MmNGAL | QDSTQNLIPAPSLLTVPLQPDFRSDQFRGRWYVVGLAGNAVQKKTEGS<br>FTMYSTIYELQENNSYNVTSILVRDQDQGCRYWIRTFVPSSRAGQFTL<br>GNMHRYPQVQSYNVQVATTDYNQFAMVFFRKTSENKQYFKITLYGRTK<br>ELSPELKERFTRFAKSLGLKDDNIIFSVPTDQCIDN |
| SEQ ID NO: 18 | RnNGAL | QDSTQNLIPAPPLISVPLQPGFWTERFQGRWFVVGLAGNAVQKERQSR<br>FTMYSTIYELQEDNSYNVTSILVRGQGCRYWIRTFVPSSRPGQFTLGN<br>IHSYPQIQSYDVQVADTDYDQFAMVFFQKTSENKQYFKVTLYGRTKGL<br>SDELKERFVSFAKSLGLKDNNIVESVPTDQCIDN |
| SEQ ID NO: 19 | HsMegalin | MDRGPAAVACTLLLALVACLAPASGQECDSAHFRCGSGHCIPADWRCD<br>GTKDCSDDADEIGCAVVTCQQGYFKCQSEGQCIPNSWVCDQDQDCDDG<br>SDERQDCSQSTCSSHQITCSNGQCIPSEYRCDHVRDCPDGADENDCQY<br>PTCEQLTCDNGACYNTSQKCDWKVDCRDSSDEINCTEICLHNEFSCGN<br>GECIPRAYVCDHDNDCQDGSDEHACNYPTCGGYQFTCPSGRCIYQNWV<br>CDGEDDCKDNGDEDGCESGPHDVHKCSPREWSCPESGRCISIYKVCDG<br>ILDCPGREDENNTSTGKYCSMTLCSALNCQYQCHETPYGGACFCPPGY<br>IINHNDSRTCVEFDDCQIWGICDQKCESRPGRHLCHCEEGYILERGQY<br>CKANDSFGEASIIFSNGRDLLIGDIHGRSFRILVESQNRGVAVGVAFH<br>YHLQRVFWTDTVQNKVFSVDINGLNIQEVLNVSVETPENLAVDWVNNK<br>IYLVETKVNRIDMVNLDGSYRVTLITENLGHPRGIAVDPTVGYLFFSD<br>WESLSGEPKLERAFMDGSNRKDLVKTKLGWPAGVTLDMISKRVYWVDS<br>RFDYIETVTYDGIQRKTVVHGGSLIPHPFGVSLFEGQVFFTDWTKMAV<br>LKANKFTETNPQVYYQASLRPYGVTVYHSLRQPYATNPCKDNNGGCEQ<br>VCVLSHRTDNDGLGFRCKCTFGFQLDTDERHCIAVQNFLIESSQVAIR<br>GIPFTLSTQEDVMVPVSGNPSFFVGIDEDAQDSTIFFSDMSKHMIFKQ<br>KIDGTGREILAANRVENVESLAFDWISKNLYWTDSHYKSISVMRLADK<br>TRRTVVQYLNNPRSVVVHPFAGYLFFTDWFRPAKIMRAWSDGSHLLPV<br>INTTLGWPNGLAIDWAASRLYWVDAYFDKIEHSTEDGLDRRRLGHIEQ<br>MTHPFGLAIFGEHLFFTDWRLGAIIRVRKADGGEMTVIRSGIAYILHL<br>KSYDVNIQTGSNACNQPTHPNGDCSHFCFPVPNFQRVCGCPYGMRLAS<br>NHLTCEGDPTNEPPTEQCGLFSFPCKNGRCVPNYYLCDGVDDCHDNSD<br>EQLCGTLNNTCSSSAFTCGHGECIPAHWRCDKRNDCVDGSDEHNCPTH<br>APASCLDTQYTCDNHQCISKNWVCDTDNDCGDGSDEKNCNSTETCQPS<br>QFNCPNHRCIDLSFVCDGDKDCVDGSDEVGCVLNCTASQFKCASGDKC<br>IGVTNRCDGVFDCSDNSDEAGCPTRPPGMCHSDEFQCQEDGICIPNEW<br>ECDGHPDCLYGSDEHNACVPKTCPSSYFHCDNGNCIHRAWLCDRDNDC<br>GDMSDEKDCPTQPFRCPSWQWQCLGHNICVNLSVVCDGIFDCPNGTDE<br>SPLCNGNSCSDENGGCTHECVQEPFGAKCLCPLGFLLANDSKTCEDID<br>ECDILGSCSQHCYNMRGSFRCSCDTGYMLESDGRTCKVTASESLLLLV<br>ASQNKIIADSVTSQVHNIYSLVENGSYIVAVDFDSISGRIFWSDATQG<br>KTWSAFQNGTDRRVVFDSSIILTETIAIDWVGRNLYWTDYALETIEVS<br>KIDGSHRTVLISKNLTNPRGLALDPRMNEHLLFWSDWGHHPRIERASM<br>DGSMRTVIVQDKIFWPCGLTIDYPNRLLYFMDSYLDYMDFCDYNGHHR<br>RQVIASDLIIRHPYALTLFEDSVYWTDRATRRVMRANKWHGGNQSVVM<br>YNIQWPLGIVAVHPSKQPNSVNPCAFSRCSHLCLLSSQGPHFYSCVCP<br>SGWSLSPDLLNCLRDDQPFLITVRQHIIFGISLNPEVKSNDAMVPIAG<br>IQNGLDVEFDDAEQYIYWVENPGEIHRVKTDGTNRTVFASISMVGPSM<br>NLALDWISRNLYSTNPRTQSIEVLTLHGDIRYRKTLIANDGTALGVGF<br>PIGITVDPARGKLYWSDQGTDSGVPAKIASANMDGTSVKTLFTGNLEH<br>LECVTLDIEEQKLYWAVTGRGVIERGNVDGTDRMILVHQLSHPWGIAV<br>HDSFLYYTDEQYEVIERVDKATGANKIVLRDNVPNLRGLQVYHRRNAA<br>ESSNGCSNNMNACQQICLPVPGGLESCACATGEKLNPDNRSCSPYNSF<br>IVVSMLSAIRGFSLELSDHSETMVPVAGQGRNALHVDVDVSSGFIYWC<br>DFSSSVASDNAIRRIKPDGSSLMNIVTHGIGENGVRGIAVDWVAGNLY<br>FTNAFVSETLIEVLRINTTYRRVLLKVTVDMPRHIVVDPKNRYLFWAD<br>YGQRPKIERSFLDCTNRTVLVSEGIVTPRGLAVDRSDGYVYWVDDSLD<br>IIARIRINGENSEVIRYGSRYPTPYGITVFENSIIWVDRNLKKIFQAS<br>KEPENTEPPTVIRDNINWLRDVTIFDKQVQPRSPAEVNNNPCLENNGG<br>CSHLCFALPGLHTPKCDCAFGTLQSDGKNCAISTENFLIFALSNSLRS<br>LHLDPENHSPPFQTINVERTVMSLDYDSVSDRIYFTQNLASGVGQISY<br>ATLSSGIHTPTVIASGIGTADGIAFDWITRRIYYSDYLNQMINSMAED<br>GSNRTVIARVPKPRAIVLDPCQGYLYWADWDTHAKIERATLGGNFRVP<br>IVNSSLVMPSGLTLDYEEDLLYWVDASLQRIERSTLTGVDREVIVNAA<br>VHAFGLTLYGQYIYWTDLYTQRIYRANKYDGSGQIAMTTNLLSQPRGI<br>NTVVKNQKQQCNNPCEQFNGGCSHICAPGPNGAECQCPHEGNWYLANN<br>RKHCIVDNGERCGASSFTCSNGRCISEEWKCDNDNDCGDGSDEMESVC<br>ALHTCSPTAFTCANGRCVQYSYRCDYYNDCGDGSDEAGCLFRDCNATT<br>EFMCNNRRCIPREFICNGVDNCHDNNTSDEKNCPDRTCQSGYTKCHNS<br>NICIPRVYLCDGDNDCGDNSDENPTYCTTHTCSSSEFQCASGRCIPQH |

-continued

| SEQ ID NO | Name | Sequence |
|---|---|---|
| | | WYCDQETDCFDASDEPASCGHSERTCLADEFKCDGGRCIPSEWICDGD<br>NDCGDMSDEDKRHQCQNQNCSDSEFLCVNDRPPDRRCIPQSWVCDGDV<br>DCTDGYDENQNCTRRTCSENEFTCGYGLCIPKIFRCDRHNDCGDYSDE<br>RGCLYQTCQQNQFTCQNGRCISKTFVCDEDNDCGDGSDELMHLCHTPE<br>PTCPPHEFKCDNGRCIEMMKLCNHLDDCLDNSDEKGCGINECHDPSIS<br>GCDHNCTDTLTSFYCSCRPGYKLMSDKRTCVDIDECTEMPFVCSQKCE<br>NVIGSYICKCAPGYLREPDGKTCRQNSNIEPYLIFSNRYYLRNLTIDG<br>YFYSLILEGLDNVVALDFDRVEKRLYWIDTQRQVIERMELNKTNKETI<br>INHRLPAAESLAVDWVSRKLYWLDARLDGLFVSDLNGGHRRMLAQHCV<br>DANNTFCFDNPRGLALHPQYGYLYWADWGHRAYIGRVGMDGTNKSVII<br>STKLEWPNGITIDYTNDLLYWADAHLGYIEYSDLEGHHRHTVYDGALP<br>HPFAITIFEDTIYWTDWNTRTVEKGNKYDGSNRQTLVNTTHRPFDIHV<br>YHPYRQPIVSNPCGTNNGGCSHLCLIKPGGKGFTCECPDDERTLQLSG<br>STYCMPMCSSTQFLCANNEKCIPIWWKCDGQKDCSDGSDELALCPQRF<br>CRLGQFQCSDGNCTSPQTLCNAHQNCPDGSDEDRLLCENHHCDSNEWQ<br>CANKRCIPESWQCDTENDCEDNSDEDSSHCASRTCRPGQFRCANGRCI<br>PQAWKCDVDNDCGDHSDEPIEECMSSAHLCDNFTEFSCKTNYRCIPKW<br>AVCNGVDDCRDNSDEQGCEERTCHPVGDERCKNHHCIPLRWQCDGQND<br>CGDNSDEENCAPRECTESEFRCVNQQCIPSRWICDHYNDCGDNSDERD<br>CEMRTCHPEYFQCTSGHCVHSELKCDGSADCLDASDEADCPTRFPDGA<br>YCQATMFECKNHVCIPPYWKCDGDDDCGDGSDEELHLCLDVPCNSPNR<br>FRCDNNRCIYSHEVCNGVDDCGDGTDETEEHCRKPTPKPCTEYEYKCG<br>NGHCIPHDNVCDDADDCGDWSDELGCNKGKERTCAENICEQNCTQLNE<br>GGFICSCTAGFETNVFDRTSCLDINECEQFGTCPQHCRNTKGSYECVC<br>ADGETSMSDRPGKRCAAEGSSPLLLLPDNVRIRKYNLSSERFSEYLQD<br>EEYIQAVDYDWDPKDIGLSVVYYTVRGEGSRFGAIKRAYIPNFESGRN<br>NLVQEVDLKLKYVMQPDGIAVDWVGRHIYWSDVKNKRIEVAKLDGRYR<br>KWLISTDLDQPAAIAVNPKLGLMFWTDWGKEPKIESAWMNGEDRNILV<br>FEDLGWPTGLSIDYLNNDRIYWSDFKEDVIETIKYDGTDRRVIAKEAM<br>NPYSLDIFEDQLYWISKEKGEVWKQNKFGQGKKEKTLVVNPWLTQVRI<br>FHQLRYNKSVPNLCKQICSHLCLLRPGGYSCACPQGSSFIEGSTTECD<br>AAIELPINLPPPCRCMHGGNCYFDETDLPKCKCPSGYTGKYCEMAFSK<br>GISPGTTAVAVLLTILLIVVIGALAIAGFFHYRRTGSLLPALPKLPSL<br>SSLVKPSENGNGVTFRSGADLNMDIGVSGFGPETAIDRSMAMSEDFVM<br>EMGKQPIIFENPMYSARDSAVKVVQPIQVTVSENVDNKNYGSPINPSE<br>IVPETNPTSPAADGTQVTKWNLFKRKSKQTTNFENPIYAQMENEQKES<br>VAATPPPSPSLPAKPKPPSRRDPTPTYSATEDTFKDTANLVKEDSEV |
| SEQ ID NO: 20 | MmMegalin | MERGAAAAAWMLLLAIAACLAPVSGQECGSGNERCDNGYCIPASWRCD<br>GTRDCLDDTDEIGCPPRSCGSGFFLCPAEGTCIPSSWVCDQDKDCSDG<br>ADEQQNCPGTTCSSQQLTCSNGQCVPIEYRCDHVSDCPDGSDERNCYY<br>PTCDQLTCANGACYNTSQKCDHKVDCRDSSDEANCTTLCSQKEFQCGS<br>GECILRAYVCDHDNDCEDNSDEHNCNYDTCGGHQFTCSNGQCINQNWV<br>CDGDDDCQDSGDEDGCESNQRHHTCYPREWACPGSGRCISMDKVCDGV<br>PDCPEGEDENNATSGRYCGTGLCSILNCEYQCHQTPYGGECFCPPGHI<br>INSNDSRTCIDEDDCQIWGICDQKCESRQGRHQCLCEEGYILERGQHC<br>KSNDSFSAASIIFSNGRDLLVGDLHGRNFRILAESKNRGIVMGVDFHY<br>QKHRVFWTDPMQAKVESTDINGLNTQEILNVSIDAPENLAVDWINNKL<br>YLVETRVNRIDVVNLEGNQRVTLITENLGHPRGIALDPTVGYLFFSDW<br>GSLSGQPKVERAFMDGSNRKDLVTTKLGWPAGITLDLVSKRVYWVDSR<br>YDYIETVTYDGIQRKTVARGGSLVPHPFGISLFEEHVFFTDWTKMAVM<br>KANKFTDTNPQVYHQSSLTPFGVTVYHALRQPNATNPCGNNNGGCAQI<br>CVLSHRTDNGGLGYRCKCEFGFELDADEHHCVAVKNFLLESSQTAVRG<br>IPFTLSTQEDVMVPVTGSPSFFVGIDEDAQHSTIFYSDLSKNIIYQQK<br>IDGTGKEVITANRLQNVECLSFDWISRNLYWTDGGSKSVTVMKLADKS<br>RRQIISNLNNPRSIVVHPAAGYMELSDWERPAKIMRAWSDGSHLMPIV<br>NTSLGWPNGLAIDWSTSRLYWVDAFFDKIEHSNLDGLDRKRLGHVDQM<br>THPFGLTVFKDNVELTDWRLGAIIRVRKSDGGDMTVVERGISSIMHVK<br>AYDADLQTGTNYCSQTTHPNGDCSHFCFPVPNFQRVCGCPYGMKLQRD<br>QMTCEGDPAREPPTQQCGSSSFPCNNGKCVPSIFRCDGVDDCHDNSDE<br>HQCGALNNTCSSSAFTCVHGGQCIPGQWRCDKQNDCLDGSDEQNCPTR<br>SPSSTCPPTSFTCDNHMCIPKEWVCDTDNDCSDGSDEKNCQASGTCHP<br>TQFRCPDHRCISPLYVCDGDKDCVDGSDEAGCVLNCTSSQFKCADGSS<br>CINSRYRCDGVYDCKDNSDEAGCPTRPPGMCHPDEFQCQGDGTCIPNT<br>WECDGHPDCIQGSDEHNGCVPKTCSPSHFLCDNGNCIYNSWVCDGDND<br>CRDMSDEKDCPTQPFHCPSSQWQCPGYSICVNLSALCDGVEDCPNGTD<br>ESPLCNQDSCLHFNGGCTHRCIQGPFGATCVCPIGYQLANDTKTCEDV<br>NECDIPGFCSQHCVNMRGSFRCACDPEYTLESDGRTCKVTASENLLLV<br>VASRDKIIMDNITAHTHNIYSLVQDVSFVVALDFDSVTGRVFWSDLLE<br>GKTWSAFQNGTDKRVVHDSGLSLTEMIAVDWIGRNIYWTDYTLETIEV<br>SKIDGSHRTVLISKNVTKPRGLALDPRMGDNVMEWSDWGHHPRIERAS<br>MDGTMRTVIVQEKIYWPCGLSIDYPNRLIYFMDAYLDYIEFCDYDGQN<br>RRQVIASDLVLHHPHALTLFEDSVFWTDRGTHQVMQANKWHGRNQSVV<br>MYSVPQPLGIIAIHPSRQPSSPNPCASATCSHLCLLSAQEPRHYSCAC<br>PSGWNLSDDSVNCVRGDQPFLISVRENVIFGISLDPEVKSNDAMVPIS<br>GIQHGYDVEFDDSEQFIYWVENPGEIHRVKTDGSNRTAFAPLSLLGSS |

-continued

| SEQ ID NO | Name | Sequence |
|---|---|---|
| | | LGLALDWVSRNIYYTTPASRSIEVLTLRGDTRYGKTLITNDGTPLGVG<br>FPVGIAVDPARGKLYWSDHGTDSGVPAKIASANMDGTSLKILFTGNME<br>HLEVVTLDIQEQKLYWAVTSRGVIERGNVDGTERMILVHHLAHPWGLV<br>VHGSFLYYSDEQYEVIERVDKSSGSNKVVFRDNIPYLRGLRVYHHRNA<br>ADSSNGCSNNPNACQQICLPVPGGMFSCACASGFKLSPDGRSCSPYNS<br>FIVVSMLPAVRGESLELSDHSEAMVPVAGQGRNVLHADVDVANGFIYW<br>CDFSSSVRSSNGIRRIKPNGSNFTNIVTYGIGANGIRGVAVDWVAGNL<br>YFTNAFVYETLIEVIRINTTYRRVLLKVSVDMPRHIVVDPKHRYLEWA<br>DYGQKPKIERSFLDCTNRTVLVSEGIVTPRGLAVDHDTGYIYWVDDSL<br>DIIARIHRDGGESQVVRYGSRYPTPYGITVFGESIIWVDRNLRKVFQA<br>SKQPGNTDPPTVIRDSINLLRDVTIFDEHVQPLSPAELNNNPCLQSNG<br>GCSHFCFALPELPTPKCGCAFGTLEDDGKNCATSREDFLIYSLNNSLR<br>SLHFDPQDHNLPFQAISVEGMAIALDYDRRNNRIFFTQKLNPIRGQIS<br>YVNLYSGASSPTILLSNIGVTDGIAFDWINRRIYYSDESNQTINSMAE<br>DGSNRAVIARVSKPRAIVLDPCRGYMYWTDWGTNAKIERATLGGNFRV<br>PIVNTSLVWPNGLTLDLETDLLYWADASLQKIERSTLTGSNREVVIST<br>AFHSFGLTVYGQYIYWTDFYTKKIYRANKYDGSDLIAMTTRLPTQPSG<br>ISTVVKTQQQQCSNPCDQFNGGCSHICAPGPNGAECQCPHEGSWYLAN<br>DNKYCVVDTGARCNQFQFTCLNGRCISQDWKCDNDNDCGDGSDELPTV<br>CAFHTCRSTAFTCANGRCVPYHYRCDFYNDCGDNSDEAGCLFRSCNST<br>TEFTCSNGRCIPLSYVCNGINNCHDNDTSDEKNCPPITCQPDFAKCQT<br>TNICVPRAFLCDGDNDCGDGSDENPIYCASHTCRSNEFQCVSPHRCIP<br>SYWFCDGEADCVDSSDEPDTCGHSLNSCSANQFHCDNGRCISSSWVCD<br>GDNDCGDMSDEDQRHHCELQNCSSTEFTCINSRPPNRRCIPQHWVCDG<br>DADCADALDELQNCTMRACSTGEFSCANGRCIRQSFRCDRRNDCGDYS<br>DERGCSYPPCRDDQFTCQNGQCITKLYVCDEDNDCGDGSDEQEHLCHT<br>PEPTCPPHQFRCDNGHCIEMGTVCNHVDDCSDNSDEKGCGINECQDSS<br>ISHCDHNCTDTITSFYCSCLPGYKLMSDKRTCVDIDECKETPQLCSQK<br>CENVIGSYICKCAPGYIREPDGKSCRQNSNIEPYLVESNRYYIRNLTI<br>DGTSYSLILQGLGNVVALDEDRVEERLYWIDAEKQIIERMELNKTNQE<br>TIISHRLRRAESLAVDWVSRKLYWLDAILDCLFVSDLEGRQRKMLAQH<br>CVDANNTFCFENPRGIVLHPQRGYVYWADWGDHAYIARIGMDGTNKTV<br>IISTKIEWPNAITIDYTNDLLYWADAHLGYIEFSDLEGHHRHTVYDGT<br>LPHPFALTIFEDTVFWTDWNTRTVEKGNKYDGSGRVVLVNTTHKPFDI<br>HVLHPYRQPIMSNPCATNNGGCSHLCLIKAGGRGFTCECPDDFQTVQL<br>RDRTLCMPMCSSTQFLCGNNEKCIPIWWKCDGQKDCSDGSDESDLCPH<br>RFCRLGQFQCRDGNCTSPQALCNARQDCADGSDEDRVLCEHHRCEANE<br>WQCANKRCIPEYWQCDSVDDCLDNSDEDPSHCASRTCRPGQFKCNNGR<br>CIPQSWKCDVDNDCGDYSDEPIHECMTAAYNCDNHTEFSCKTNYRCIP<br>QWAVCNGFDDCRDNSDEQGCESVPCHPSGDFRCGNHHCIPLRWKCDGI<br>DDCGDNSDEESCVPRECTESEFRCADQQCIPSRWVCDQENDCGDNSDE<br>RDCEMKTCHPEHFQCTSGHCVPKALACDGRADCLDASDESACPTRFPN<br>GTYCPAAMFECKNHVCIQSFWICDGENDCVDGSDEEIHLCENVPCESP<br>QRFRCDNSRCIYGHQLCNGVDDCGDGSDEKEEHCRKPTHKPCTDTEYK<br>CSNGNCVSQHYVCDNVDDCGDLSDETGCNLGENRTCAEKICEQNCTQL<br>SNGGFICSCRPGFKPSTLDKNSCQDINECEEFGICPQSCRNSKGSYEC<br>FCVDGFKSMSTHYGERCAADGSPPLLLLPENVRIRKYNISSEKFSEYL<br>EEEEHIQAIDYDWDPEGIGLSVVYYTVLSQGSQFGAIKRAYLPDFESG<br>SNNPVREVDLGLKYLMQPDGLAVDWVGRHIYWSDAKSQRIEVATLDGR<br>YRKWLITTQLDQPAAIAVNPKLGLMFWTDQGKQPKIESAWMNGEHRSV<br>LASANLGWPNGLSIDYLNGDRIYWSDSKEDVIESIKYDGTDRRLIIND<br>AMKPFSLDIFEDQLYWVAKEKGEVWRQNKFGKGNKEKLLVVNPWLTQV<br>RIFHQLRYNQSVSNPCKQVCSHLCLLRPGGYSCACPQGSDFVTGSTVE<br>CDAASELPITMPSPCRCMHGGSCYFDENDLPKCKCSSGYSGEYCEIGL<br>SRGIPPGTTMALLLTFAMVIIVGALVLVGFFHYRKTGSLLPSLPKLPS<br>LSSLAKPSENGNGVTFRSGADVNMDIGVSPFGPETIIDRSMAMNEQFV<br>MEVGKQPVIFENPMYAAKDSTSKVGLAVQGPSVSSQVTVPENVENQNY<br>GRSIDPSEIVPEPKPASPGADETQGTKWNIFKRKPKQTTNFENPIYAE<br>MDTEQKEAVAVAPPPSPSLPAKASKRSSTPGYTATEDTEKDTANLVKE<br>DSDV |
| SEQ ID NO: 21 | A-1 | QDSTSDLIPAPPLSSVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 22 | A-2 | QDSTSDLIPAPPLSSVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSKSLGLPENHIVFPVPIDQCIDG |
| SEQ ID NO: 23 | A-3 | QDSTSDLIPAPPLSKVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |

-continued

| SEQ ID NO | Name | Sequence |
|---|---|---|
| SEQ ID NO: 24 | B-1 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IQSYPGLTSYLVRVVSTNYNQFAMVFFKKVSQNREYFKITLYGRTKEL<br>TSELKENFIRFSKSLGLPENNIVFPVPIDQCIDG |
| SEQ ID NO: 25 | B-3 | QDSTSDLIPAPPLSKVPLQQNFQDNQFQGKWYVVGLAGNAILREDEDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENNIVFPVPIDQCIDG |
| SEQ ID NO: 26 | B-4 | QDSTSDLIPAPPLSKVPLQQNFQDNQFQGKWYVVGLAGNAILREDEDP<br>QKMYATIYELKEDKSYNVTSVLFRKKKCDYWIRTFVPGCQPGEFTLGN<br>IQSYPGLTSYLVRVVSTNYNQHAMVFFKKVSQNREYFKITLYGRTKEL<br>TSELKENFIRFSKSLGLPENHIVEPVPIDQCIDG |
| SEQ ID NO: 27 | B-5 | QDSTSDLIPAPPLSKVPLQQNFQDNQFQGKWYVVGLAGNAILREDEDP<br>QKMYATIYELKEDGSYNVTSVLFRKKKCDYWIRTFVPGCQPGEFTLGN<br>IQSYPGLTSYLVRVVSTNYNQFAMVFFKKVSQNREYFKITLYGRTKEL<br>TSELQENFIRFSKSLGLPENNIVFPVPIDQCIDG |
| SEQ ID NO: 28 | C-1 | QDSTSDLIPAPPLSKVPLQQNFQDNQFQGKWYVVGLAGNAILREDKDP<br>QTMYATIYELKEDKSYNVTSVLFQKKKCDYWIRTFVPGCQPGEFTLGN<br>IKSYPGLTSYLVRVVSTNYNQHAMVFFKKVSQNQEYFKITLYGRTKEL<br>TSELQENFIRFSQSLGLPENHIVEPVPIDQCIDG |
| SEQ ID NO: 29 | C-3 | QDSTSDLIPAPPLSSVPLQQNFQDNQFQGKWYVVGLAGNAILREDKDP<br>QTMYATIYELKEDKSYNVTSVLFQKKKCDYWIRTFVPGCQPGEFTLGN<br>IKSYPGLTSYLVRVVSTNYNQHAMVFFKKVSQNREYFKITLYGRTKEL<br>TSELQENFIRFSQSLGLPENHIVFPVPIDQCIDG |
| SEQ ID NO: 30 | C-4 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNQEYFKITLYGRTKEL<br>TSELKENFIRFSQSLGLPENHIVFPVPIDQCIDG |
| SEQ ID NO: 31 | C-5 | QDSTSDLIPAPPLSKVPLQQNFQDNQFQGKWYVVGLAGNAILREDKDP<br>QKMYATIYELKEDKSYNVTSVLFQKKKCDYWIRTFVPGCQPGEFTLGN<br>IKSYPGLTSYLVRVVSTNYNQHAMVFFKKVSQNREYFKITLYGRTKEL<br>TSELKENFIRFSQSLGLPENHIVFPVPIDQCIDG |
| SEQ ID NO: 32 | D-1 | QDSTSDLIPAPPLSKVPLQQNFQDNQFQGKWYVVGLAGNAILREDKDP<br>QKMYATIYELKEDKSYNVTSVLFRDDGCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 33 | D-2 | QDSTSDLIPAPPLSKVPLQQNFQDNQFQGKWYVVGLAGNAILREDKDP<br>QKMYATIYELKEDGSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 34 | E-2 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSKSLGLPENHIVFPVPIDQCIDG |
| SEQ ID NO: 35 | F-1 | QDSTSDLIPAPPLSSVPLQQNFQDNQFQGKWYVVGLAGNAILREDEDP<br>QKMYATIYELQEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRESKSLGLPENHIVFPVPIDQCIDG |
| SEQ ID NO: 36 | F-2 | QDSTSDLIPAPPLSKVPLQQNFQDNQFQGKWYVVGLAGNAILREDEDP<br>QKMYATIYELQEDKSYNVTSVLERKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVEPVPIDQCIDG |
| SEQ ID NO: 37 | G-1 | QDSTSDLIPAPPLSSVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELQENFIRFSKSLGLPENHIVFPVPIDQCIDG |
| SEQ ID NO: 38 | G-2 | QDSTSDLIPAPPLSKVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSKSLGLPENHIVFPVPIDQCIDG |

-continued

| SEQ ID NO | Name | Sequence |
|---|---|---|
| SEQ ID NO: 39 | G-3 | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSQSLGLPENHIVEPVPIDQCIDG |
| SEQ ID NO: 40 | H-1 | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENNIVFPVPIDQCIDG |
| SEQ ID NO: 41 | H-2 | QDSTSDLIPAPPLSSVPLQQNFQDNQFQGKWYVVGLAGNAILREDKDP QKMYATIYELKEDKSYNVTSVLFRKKKCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |
| SEQ ID NO: 42 | H-3 | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQFAMVFFKKVSQNREYFKITLYGRTKEL TSELQENFIRFSKSLGLPENNIVFPVPIDQCIDG |
| SEQ ID NO: 43 | H-5 | QDSTSDLIPAPPLSSVPLQQNFQDNQFQGKWYVVGLAGNAILREDKDP QKMYATIYELKEDKSYNVTSVLFRKKKCDYWIRTFVPGCQPGEFTLGN IQSYPGLTSYLVRVVSTNYNQHAMVFFKKVSQNREYFKITLYGRTKEL TSELKENFIRFSKSLGLPENNIVFPVPIDQCIDG |
| SEQ ID NO: 44 | I-4 | QDSTSDLIPAPPLSSVPLQQNFQDNQFQGKWYVVGLAGNAILREDKDP QKMYATIYELKEDKSYNVTSVLFRDDGCDYWIRTFVPGCQPGEFTLGN IQSYPGLTSYLVRVVSTNYNQHAMVFFKKVSQNREYFKITLYGRTKEL TSELKENFIRFSKSLGLPENHIVFPVPIDQCIDG |
| SEQ ID NO: 45 | I-5 | QDSTSDLIPAPPLSSVPLQQNFQDNQFQGKWYVVGLAGNAILREDKDP QKMYATIYELKEDGSYNVTSVLFRDDGCDYWIRTFVPGCQPGEFTLGN IKSYPGLTSYLVRVVSTNYNQHAMVFFKKVSQNQEYFKITLYGRTKEL TSELKENFIRFSKSLGLPENHIVFPVPIDQCIDG |
| SEQ ID NO: 46 | L-1 | QDSTSDLIPAPPLSKVPLQQNFQDNQFQGKWYVVGLAGNAILQEDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGQTQEL TSELKENFIRESQSLGLPENHIVFPVPIDQCIDG |
| SEQ ID NO: 47 | L-2 | QDSTSDLIPAPPLSSVPLQQNFQDNQFQGKWYVVGLAGNAILQEDKDP QKMYATIYELKEDKSYNVTSVLFQKKKCDYWIRTFVPGCQPGEFTLGN IKSYPGLTSYLVRVVSTNYNQHAMVFFKKVSQNREYFKITLYGQTQEL TSELKENFIRFSQSLGLPENHIVFPVPIDQCIDG |
| SEQ ID NO: 48 | B-5-1 | QDSTSDLIPAPPLSKVPLAPDFQDNQFQGKWYVVGLAGNAILREDEDP QKMYATIYELKEDGSYNVTSVLFRKKKCDYWIRTFVPGCQPGEFTLGN IQSYPGLTSYLVRVVSTNYNQFAMVFFKKVSQNREYFKITLYGRTKEL TSELQENFIRFSKSLGLPENNIVFPVPIDQCIDG |
| SEQ ID NO: 49 | B-5-2 | QDSTSDLIPAPPLSKVPLAPDFQDNQFQGKWYVVGLAGNAILREDEDP QKMYATIYELAEDGSYNVTSVLFRKKKCDYWIRTFVPGCQPGEFTLGN IQSYPGLTSYLVRVVSTNYNQFAMVFFKKVSQNREYFKITLYGRTKEL TSELQENFIRFSKSLGLPENNIVFPVPIDQCIDG |
| SEQ ID NO: 50 | B-5-5 | QDSTSDLIPAPPLSKVPLQQNFQDNQFQGKWYVVGLAGNAILREDEDP QKMYATIYELKEDGSYNVTSVLFRKKKCDYWIRTFVPGCQPGEFTLGN IQSYPGLTSYLVRVVSTDYNQFAMVFFKKVSQNREYFKITLYGRTKEL TSELQENFIRFSKSLGLPENNIVFPVPIDQCIDG |
| SEQ ID NO: 51 | WT-1 | QDSTSDLIPAPPLSKVPLQQNFQDNQFQGKWYVVGLAGNAILREDKDP QKMYATIYELKEDKSYNVTSVLERKKKCDYWIRTFVPGCQPGEFTLGN IKSYPGLTSYLVRVVSTNYNQHAMVFFKKVSQNREYFKITLYGATAEL TSELKENFIRFSKSLGLPENHIVEPVPIDQCIDG |
| SEQ ID NO: 52 | WT-3 | QDSTSDLIPAPPLSKVPLQQNFQDNQFQGKWYVVGLAGNAILAEDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGATAEL TSELKENFIRFSASLGLPENHIVFPVPIDQCIDG |
| SEQ ID NO: 53 | WT-4 | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGATAEL TSELKENFIRFSASLGLPENHIVFPVPIDQCIDG |

-continued

| SEQ ID NO | Name | Sequence |
|---|---|---|
| SEQ ID NO: 54 | WT-4-1 | QDSTSDLIPAPPLSKVPLQQNFQDNQFQGKWYVVGLAGNAILREDKDP QKMYATIYELKEDKSYNVTSVLFAKKKCDYWIRTFVPGCQPGEFTLGN IKSYPGLTSYLVRVVSTNYNQHAMVFFKKVSQNREYFKITLYGATAEL TSELKENFIRFSASLGLPENHIVEPVPIDQCIDG |
| SEQ ID NO: 55 | WT-4-1-4 | QDSTSDLIPAPPLSKVPLQQNFQDNQFQGKWYVVGLAGNAILAEDKDP QKMYATIYELKEDKSYNVTSVLFAKKKCDYWIRTFVPGCQPGEFTLGN IKSYPGLTSYLVRVVSTNYNQHAMVFFKKVSQNREYFKITLYGATAEL TSELKENFIRFSASLGLPENHIVFPVPIDQCIDG |
| SEQ ID NO: 56 | D1-1 | QDSTSDLIPAPPLSKVPLAPDFQDNQFQGKWYVVGLAGNAILREDKDP QKMYATIYELKEDKSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCIDG |
| SEQ ID NO: 57 | D1-4 | QDSTSDLIPAPPLSKVPLQQNFQDNQFQGKWYVVGLAGNAILREDKDP QKMYATIYELKEDGSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCIDG |
| SEQ ID NO: 58 | D1-4-1 | QDSTSDLIPAPPLSKVPLQQNFQDNQFQGKWYVVGLAGNAILREDKDP QKMYATIYELAEDGSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPEDAIVFPVPIDQCIDG |
| SEQ ID NO: 59 | D1-4-2 | QDSTSDLIPAPPLSKVPLQQNFQDNQFQGKWYVVGLAGNAILREDKDP QKMYATIYELAEDGSYNVTSVLFRDDGCDYWIRTFVPGCQPGEFTLGN IASYPGLTSYLVRVVSTNYNQHAMVFFKKVSQNREYFKITLYGRTKEL TSELKENFIRESKSLGLPENHIVFPVPIDQCIDG |
| SEQ ID NO: 60 | D1-4-2-1 | QDSTSDLIPAPPLSKVPLQQNFQDNQFQGKWYVVGLAGNAILREDEDP QKMYATIYELAEDGSYNVTSVLERDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 61 | D1-4-2-1-1 | QDSTSDLIPAPPLSKVPLQQNFQDNQFQGKWYVVGLAGNAILREDEDP QTMYATIYELAEDGSYNVTSVLERDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 62 | D1-4-2-1-3 | QDSTSDLIPAPPLSKVPLQQNFQDNQFQGKWYVVGLAGNAILREDEDP QKMYATIYELAEDGSYNVTSVLFRDDGCDYWIRTFVPGCQPGEFTLGN IASYPGLTSYLVRVVSTDYNQHAMVFFKKVSESAEYFKITLYGRTKEL TSELKENFIRFSKSLGLPENHIVFPVPIDQCIDG |
| SEQ ID NO: 63 | D1-4-2-1-4 | QDSTSDLIPAPPLSKVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTDYNQHAMVFFKKVSESAEYFKITLYGRTKEL TSELKENFIRFSKSLGLPENHIVFPVPIDQCIDG |
| SEQ ID NO: 64 | D1-4-2-1-1-1 | QDSTSDLIPAPPLSSVPLQQNFQDNQFQGKWYVVGLAGNAILREDEDP QTMYATIYELAEDGSYNVTSVLERDDGCDYWIRTFVPGCQPGEFTLGN IASYPGLTSYLVRVVSTNYNQHAMVFFKKVSESAEYFKITLYGRTKEL TSELAENFIRFSKSLGLPENHIVEPVPIDQCIDG |
| SEQ ID NO: 65 | D1-4-2-1-1-2 | QDSTSDLIPAPPLSKVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELAENFIRFSKSLGLPENHIVEPVPIDQCIDG |
| SEQ ID NO: 66 | D1-4-2-1-1-4 | QDSTSDLIPAPPLSSVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 67 | K3-4 | QDSTSDLIPAPPLSSVPLQQNFQDNQFQGKWYVVGLAGNAILREDEDP QTMYATIYELKEDKSYNVTSVLFADDGCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |
| SEQ ID NO: 68 | K3-5 | QDSTSDLIPAPPLSSVPLQQNFQDNQFQGKWYVVGLAGNAILREDEDP QKMYATIYELKEDKSYNVTSVLFADDGCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |

-continued

| SEQ ID NO | Name | Sequence |
|---|---|---|
| SEQ ID NO: 69 | NGAL Mutant | $X_1$DSTSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_1$ = Q, A, N, D, C, E, G, I, L, M, F, P, S, T, W,<br>Y, V |
| SEQ ID NO: 70 | NGAL Mutant | Q$X_2$STSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_2$ = Q, A, N, D, C, E, G, I, L, M, F, P, S, T, W,<br>Y, V |
| SEQ ID NO: 71 | NGAL Mutant | QD$X_3$TSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_3$ = Q, A, N, D, C, E, G, I, L, M, F, P, S, T, W,<br>Y, V |
| SEQ ID NO: 72 | NGAL Mutant | QDS$X_4$SDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_4$ = Q, A, N, D, C, E, G, I, L, M, F, P, S, T, W,<br>Y, V |
| SEQ ID NO: 73 | NGAL Mutant | QDST$X_5$DLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_5$ = Q, A, N, D, C, E, G, I, L, M, F, P, S, T, W,<br>Y, V |
| SEQ ID NO: 74 | NGAL Mutant | QDSTS$X_6$LIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_6$ = Q, A, N, D, C, E, G, I, L, M, F, P, S, T, W,<br>Y, V |
| SEQ ID NO: 75 | NGAL Mutant | QDSTSD$X_7$IPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_7$ = Q, A, N, D, C, E, G, I, L, M, F, P, S, T, W,<br>Y, V |
| SEQ ID NO: 76 | NGAL Mutant | QDSTSDL$X_8$PAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRESKSLGLPENHIVFPVPIDQCIDG<br>$X_8$ = Q, A, N, D, C, E, G, I, L, M, F, P, S, T, W,<br>Y, V |
| SEQ ID NO: 77 | NGAL Mutant | QDSTSDLI$X_9$APPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_9$ = Q, A, N, D, C, E, G, I, L, M, F, P, S, T, W,<br>Y, V |
| SEQ ID NO: 78 | NGAL Mutant | QDSTSDLIP$X_{10}$PPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{10}$ = Q, A, N, D, C, E, G, I, L, M, F, P, S, T, W,<br>Y, V |

-continued

| SEQ ID NO | Name | Sequence |
|---|---|---|
| SEQ ID NO: 79 | NGAL Mutant | QDSTSDLIPA$X_{11}$PLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{11}$ = Q, A, N, D, C, E, G, I, L, M, F, P, S, T, W, Y, V |
| SEQ ID NO: 80 | NGAL Mutant | QDSTSDLIPAP$X_{12}$LSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{12}$ = Q, A, N, D, C, E, G, I, L, M, F, P, S, T, W, Y, V |
| SEQ ID NO: 81 | NGAL Mutant | QDSTSDLIPAPP$X_{13}$SKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{13}$ = Q, A, N, D, C, E, G, I, L, M, F, P, S, T, W, Y, V |
| SEQ ID NO: 82 | NGAL Mutant | QDSTSDLIPAPPL$X_{14}$KVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{14}$ = Q, A, N, D, C, E, G, I, L, M, F, P, S, T, W, Y, V |
| SEQ ID NO: 83 | NGAL Mutant | QDSTSDLIPAPPLS$X_{15}$VPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{15}$ = Q, A, N, D, C, E, G, I, L, M, F, P, S, T, W, Y, V, K |
| SEQ ID NO: 84 | NGAL Mutant | QDSTSDLIPAPPLSK$X_{16}$PLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{16}$ = Q, A, N, D, C, E, G, I, L, M, F, P, S, T, W, Y, V |
| SEQ ID NO: 85 | NGAL Mutant | QDSTSDLIPAPPLSKV$X_{17}$LQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{17}$ = Q, A, N, D, C, E, G, I, L, M, F, P, S, T, W, Y, V |
| SEQ ID NO: 86 | NGAL Mutant | QDSTSDLIPAPPLSKVP$X_{18}$QQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{18}$ = Q, A, N, D, C, E, G, I, L, M, F, P, S, T, W, Y, V |
| SEQ ID NO: 87 | NGAL Mutant | QDSTSDLIPAPPLSKVPL$X_{19}$QNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{19}$ = Q, A, N, D, C, E, G, I, L, M, F, P, S, T, W, Y, V |
| SEQ ID NO: 88 | NGAL Mutant | QDSTSDLIPAPPLSKVPLQ$X_{20}$NFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{20}$ = Q, A, N, D, C, E, G, I, L, M, F, P, S, T, W, Y, V |

-continued

| SEQ ID NO | Name | Sequence |
|---|---|---|
| SEQ ID NO: 89 | NGAL Mutant | QDSTSDLIPAPPLSKVPLQQ$X_{21}$FQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{21}$ = Q, A, N, D, C, E, G, I, L, M, F, P, S, T, W,<br>Y, V |
| SEQ ID NO: 90 | NGAL Mutant | QDSTSDLIPAPPLSKVPLQQN$X_{22}$QDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{22}$ = Q, A, N, D, C, E, G, I, L, M, F, P, S, T, W,<br>Y, V |
| SEQ ID NO: 91 | NGAL Mutant | QDSTSDLIPAPPLSKVPLQQNF$X_{23}$DNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{23}$ = Q, A, N, D, C, E, G, I, L, M, F, P, S, T, W,<br>Y, V |
| SEQ ID NO: 92 | NGAL Mutant | QDSTSDLIPAPPLSKVPLQQNFQ$X_{24}$NQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{24}$ = Q, A, N, D, C, E, G, I, L, M, F, P, S, T, W,<br>Y, V |
| SEQ ID NO: 93 | NGAL Mutant | QDSTSDLIPAPPLSKVPLQQNFQD$X_{25}$QFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{25}$ = Q, A, N, D, C, E, G, I, L, M, F, P, S, T, W,<br>Y, V |
| SEQ ID NO: 94 | NGAL Mutant | QDSTSDLIPAPPLSKVPLQQNFQDN$X_{26}$FQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{26}$ = Q, A, N, D, C, E, G, I, L, M, F, P, S, T, W,<br>Y, V |
| SEQ ID NO: 95 | NGAL Mutant | QDSTSDLIPAPPLSKVPLQQNFQDNQ$X_{27}$QGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{27}$ = Q, A, N, D, C, E, G, I, L, M, F, P, S, T, W,<br>Y, V |
| SEQ ID NO: 96 | NGAL Mutant | QDSTSDLIPAPPLSKVPLQQNFQDNQF$X_{28}$GKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{28}$ = Q, A, N, D, C, E, G, I, L, M, F, P, S, T, W,<br>Y, V |
| SEQ ID NO: 97 | NGAL Mutant | QDSTSDLIPAPPLSKVPLQQNFQDNQFQ$X_{29}$KWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{29}$ = Q, A, N, D, C, E, G, I, L, M, F, P, S, T, W,<br>Y, V |
| SEQ ID NO: 98 | NGAL Mutant | QDSTSDLIPAPPLSKVPLQQNFQDNQFQG$X_{30}$WYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{30}$ = Q, A, N, D, C, E, G, I, L, M, F, P, S, T, W,<br>Y, V, K |

-continued

| SEQ ID NO | Name | Sequence |
|---|---|---|
| SEQ ID NO: 99 | NGAL Mutant | QDSTSDLIPAPPLSKVPLQQNFQDNQFQGK$X_{31}$YVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{31}$ = Q, A, N, D, C, E, G, I, L, M, F, P, S, T, W,<br>Y, V |
| SEQ ID NO: 100 | NGAL Mutant | QDSTSDLIPAPPLSKVPLQQNFQDNQFQGKW$X_{32}$VVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{32}$ = Q, A, N, D, C, E, G, I, L, M, F, P, S, T, W,<br>Y, V |
| SEQ ID NO: 101 | NGAL Mutant | QDSTSDLIPAPPLSKVPLQQNFQDNQFQGKWY$X_{33}$VGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{33}$ = Q, A, N, D, C, E, G, I, L, M, F, P, S, T, W,<br>Y, V |
| SEQ ID NO: 102 | NGAL Mutant | QDSTSDLIPAPPLSKVPLQQNFQDNQFQGKWYV$X_{34}$GLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{34}$ = Q, A, N, D, C, E, G, I, L, M, F, P, S, T, W,<br>Y, V |
| SEQ ID NO: 103 | NGAL Mutant | QDSTSDLIPAPPLSKVPLQQNFQDNQFQGKWYVV$X_{35}$LAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{35}$ = Q, A, N, D, C, E, G, I, L, M, F, P, S, T, W,<br>Y, V |
| SEQ ID NO: 104 | NGAL Mutant | QDSTSDLIPAPPLSKVPLQQNFQDNQFQGKWYVVG$X_{36}$AGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{36}$ = Q, A, N, D, C, E, G, I, L, M, F, P, S, T, W,<br>Y, V |
| SEQ ID NO: 105 | NGAL Mutant | QDSTSDLIPAPPLSKVPLQQNFQDNQFQGKWYVVGL$X_{37}$GNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{37}$ = Q, A, N, D, C, E, G, I, L, M, F, P, S, T, W,<br>Y, V |
| SEQ ID NO: 106 | NGAL Mutant | QDSTSDLIPAPPLSKVPLQQNFQDNQFQGKWYVVGLA$X_{38}$NAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{38}$ = Q, A, N, D, C, E, G, I, L, M, F, P, S, T, W,<br>Y, V |
| SEQ ID NO: 107 | NGAL Mutant | QDSTSDLIPAPPLSKVPLQQNFQDNQFQGKWYVVGLAG$X_{39}$AILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{39}$ = Q, A, N, D, C, E, G, I, L, M, F, P, S, T, W,<br>Y, V |
| SEQ ID NO: 108 | NGAL Mutant | QDSTSDLIPAPPLSKVPLQQNFQDNQFQGKWYVVGLAGN$X_{40}$ILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{40}$ = Q, A, N, D, C, E, G, I, L, M, F, P, S, T, W,<br>Y, V |

-continued

| SEQ ID NO | Name | Sequence |
|---|---|---|
| SEQ ID NO: 109 | NGAL Mutant | QDSTSDLIPAPPLSKVPLQQNFQDNQFQGKWYVVGLAGNA$X_{41}$LREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{41}$ = Q, A, N, D, C, E, G, I, L, M, F, P, S, T, W, Y, V |
| SEQ ID NO: 110 | NGAL Mutant | QDSTSDLIPAPPLSKVPLQQNFQDNQFQGKWYVVGLAGNAI$X_{42}$REDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{42}$ = Q, A, N, D, C, E, G, I, L, M, F, P, S, T, W, Y, V |
| SEQ ID NO: 111 | NGAL Mutant | QDSTSDLIPAPPLSKVPLQQNFQDNQFQGKWYVVGLAGNAIL$X_{43}$EDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{43}$ = Q, A, N, D, C, E, G, I, L, M, F, P, S, T, W, Y, V, R |
| SEQ ID NO: 112 | NGAL Mutant | QDSTSDLIPAPPLSKVPLQQNFQDNQFQGKWYVVGLAGNAILR$X_{44}$DKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{44}$ = Q, A, N, D, C, E, G, I, L, M, F, P, S, T, W, Y, V |
| SEQ ID NO: 113 | NGAL Mutant | QDSTSDLIPAPPLSKVPLQQNFQDNQFQGKWYVVGLAGNAILRE$X_{45}$KD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{45}$ = Q, A, N, D, C, E, G, I, L, M, F, P, S, T, W, Y, V |
| SEQ ID NO: 114 | NGAL Mutant | QDSTSDLIPAPPLSKVPLQQNFQDNQFQGKWYVVGLAGNAILRED$X_{46}$D PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{46}$ = Q, A, N, D, C, E, G, I, L, M, F, P, S, T, W, Y, V, K |
| SEQ ID NO: 115 | NGAL Mutant | QDSTSDLIPAPPLSKVPLQQNFQDNQFQGKWYVVGLAGNAILREDK$X_{47}$ PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{47}$ = Q, A, N, D, C, E, G, I, L, M, F, P, S, T, W, Y, V |
| SEQ ID NO: 116 | NGAL Mutant | QDSTSDLIPAPPLSKVPLQQNFQDNQFQGKWYVVGLAGNAILREDKD$X_{48}$ QKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{48}$ = Q, A, N, D, C, E, G, I, L, M, F, P, S, T, W, Y, V |
| SEQ ID NO: 117 | NGAL Mutant | QDSTSDLIPAPPLSKVPLQQNFQDNQFQGKWYVVGLAGNAILREDKDP $X_{49}$KMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{49}$ = Q, A, N, D, C, E, G, I, L, M, F, P, S, T, W, Y, V |
| SEQ ID NO: 118 | NGAL Mutant | QDSTSDLIPAPPLSKVPLQQNFQDNQFQGKWYVVGLAGNAILREDKDP Q$X_{50}$MYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG $X_{50}$ = Q, A, N, D, C, E, G, I, L, M, F, P, S, T, W, Y, V, K |

-continued

| SEQ ID NO | Name | Sequence |
|---|---|---|
| SEQ ID NO: 119 | NGAL Mutant | QDSTSDLIPAPPLSKVPLQQNFQDNQFQGKWYVVGLAGNAILREDKDP QKX$_{51}$YATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{51}$ = Q, A, N, D, C, E, G, I, L, M, F, P, S, T, W, Y, V |
| SEQ ID NO: 120 | NGAL Mutant | QDSTSDLIPAPPLSKVPLQQNFQDNQFQGKWYVVGLAGNAILREDKDP QKMX$_{52}$ATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{52}$ = Q, A, N, D, C, E, G, I, L, M, F, P, S, T, W, Y, V |
| SEQ ID NO: 121 | NGAL Mutant | QDSTSDLIPAPPLSKVPLQQNFQDNQFQGKWYVVGLAGNAILREDKDP QKMYX$_{53}$TIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{53}$ = Q, A, N, D, C, E, G, I, L, M, F, P, S, T, W, Y, V |
| SEQ ID NO: 122 | NGAL Mutant | QDSTSDLIPAPPLSKVPLQQNFQDNQFQGKWYVVGLAGNAILREDKDP QKMYAX$_{54}$IYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{54}$ = Q, A, N, D, C, E, G, I, L, M, F, P, S, T, W, Y, V |
| SEQ ID NO: 123 | NGAL Mutant | QDSTSDLIPAPPLSKVPLQQNFQDNQFQGKWYVVGLAGNAILREDKDP QKMYATX$_{55}$YELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{55}$ = Q, A, N, D, C, E, G, I, L, M, F, P, S, T, W, Y, V |
| SEQ ID NO: 124 | NGAL Mutant | QDSTSDLIPAPPLSKVPLQQNFQDNQFQGKWYVVGLAGNAILREDKDP QKMYATIX$_{56}$ELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{56}$ = Q, A, N, D, C, E, G, I, L, M, F, P, S, T, W, Y, V |
| SEQ ID NO: 125 | NGAL Mutant | QDSTSDLIPAPPLSKVPLQQNFQDNQFQGKWYVVGLAGNAILREDKDP QKMYATIYX$_{57}$LKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{57}$ = Q, A, N, D, C, E, G, I, L, M, F, P, S, T, W, Y, V |
| SEQ ID NO: 126 | NGAL Mutant | QDSTSDLIPAPPLSKVPLQQNFQDNQFQGKWYVVGLAGNAILREDKDP QKMYATIYEX$_{58}$KEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{58}$ = Q, A, N, D, C, E, G, I, L, M, F, P, S, T, W, Y, V |
| SEQ ID NO: 127 | NGAL Mutant | QDSTSDLIPAPPLSKVPLQQNFQDNQFQGKWYVVGLAGNAILREDKDP QKMYATIYELX$_{59}$EDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{59}$ = Q, A, N, D, C, E, G, I, L, M, F, P, S, T, W, Y, V, K |
| SEQ ID NO: 128 | NGAL Mutant | QDSTSDLIPAPPLSKVPLQQNFQDNQFQGKWYVVGLAGNAILREDKDP QKMYATIYELKX$_{60}$DKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG X$_{60}$ = Q, A, N, D, C, E, G, I, L, M, F, P, S, T, W, Y, V |

-continued

| SEQ ID NO | Name | Sequence |
|---|---|---|
| SEQ ID NO: 129 | NGAL Mutant | QDSTSDLIPAPPLSKVPLQQNFQDNQFQGKWYVVGLAGNAILREDKDP<br>QKMYATIYELKE$X_{61}$KSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{61}$ = Q, A, N, D, C, E, G, I, L, M, F, P, S, T, W, Y, V |
| SEQ ID NO: 130 | NGAL Mutant | QDSTSDLIPAPPLSKVPLQQNFQDNQFQGKWYVVGLAGNAILREDKDP<br>QKMYATIYELKED$X_{62}$SYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{62}$ = Q, A, N, D, C, E, G, I, L, M, F, P, S, T, W, Y, V, K |
| SEQ ID NO: 131 | NGAL Mutant | QDSTSDLIPAPPLSKVPLQQNFQDNQFQGKWYVVGLAGNAILREDKDP<br>QKMYATIYELKEDK$X_{63}$YNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{63}$ = Q, A, N, D, C, E, G, I, L, M, F, P, S, T, W, Y, V |
| SEQ ID NO: 132 | NGAL Mutant | QDSTSDLIPAPPLSKVPLQQNFQDNQFQGKWYVVGLAGNAILREDKDP<br>QKMYATIYELKEDKS$X_{64}$NVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{64}$ = Q, A, N, D, C, E, G, I, L, M, F, P, S, T, W, Y, V |
| SEQ ID NO: 133 | NGAL Mutant | QDSTSDLIPAPPLSKVPLQQNFQDNQFQGKWYVVGLAGNAILREDKDP<br>QKMYATIYELKEDKSY$X_{65}$VTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{65}$ = Q, A, N, D, C, E, G, I, L, M, F, P, S, T, W, Y, V |
| SEQ ID NO: 134 | NGAL Mutant | QDSTSDLIPAPPLSKVPLQQNFQDNQFQGKWYVVGLAGNAILREDKDP<br>QKMYATIYELKEDKSYN$X_{66}$TSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{66}$ = Q, A, N, D, C, E, G, I, L, M, F, P, S, T, W, Y, V |
| SEQ ID NO: 135 | NGAL Mutant | QDSTSDLIPAPPLSKVPLQQNFQDNQFQGKWYVVGLAGNAILREDKDP<br>QKMYATIYELKEDKSYNV$X_{67}$SVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{67}$ = Q, A, N, D, C, E, G, I, L, M, F, P, S, T, W, Y, V |
| SEQ ID NO: 136 | NGAL Mutant | QDSTSDLIPAPPLSKVPLQQNFQDNQFQGKWYVVGLAGNAILREDKDP<br>QKMYATIYELKEDKSYNVT$X_{68}$VLFRKKKCDYWIRTFVPGCQPGEFTLG<br>NIKSYPGLTSYLVRVVSTNYNQHAMVFFKKVSQNREYFKITLYGRTKE<br>LTSELKENFIRESKSLGLPENHIVFPVPIDQCIDG<br>$X_{68}$ = Q, A, N, D, C, E, G, I, L, M, F, P, S, T, W, Y, V |
| SEQ ID NO: 137 | NGAL Mutant | QDSTSDLIPAPPLSKVPLQQNFQDNQFQGKWYVVGLAGNAILREDKDP<br>QKMYATIYELKEDKSYNVTS$X_{69}$LFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{69}$ = Q, A, N, D, C, E, G, I, L, M, F, P, S, T, W, Y, V |
| SEQ ID NO: 138 | NGAL Mutant | QDSTSDLIPAPPLSKVPLQQNFQDNQFQGKWYVVGLAGNAILREDKDP<br>QKMYATIYELKEDKSYNVTSV$X_{70}$FRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{70}$ = Q, A, N, D, C, E, G, I, L, M, F, P, S, T, W, Y, V |

-continued

| SEQ ID NO | Name | Sequence |
|---|---|---|
| SEQ ID NO: 139 | NGAL Mutant | QDSTSDLIPAPPLSKVPLQQNFQDNQFQGKWYVVGLAGNAILREDKDP<br>QKMYATIYELKEDKSYNVTSVL$X_{71}$RKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{71}$ = Q, A, N, D, C, E, G, I, L, M, F, P, S, T, W,<br>Y, V |
| SEQ ID NO: 140 | NGAL Mutant | QDSTSDLIPAPPLSKVPLQQNFQDNQFQGKWYVVGLAGNAILREDKDP<br>QKMYATIYELKEDKSYNVTSVLF$X_{72}$KKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{72}$ = Q, A, N, D, C, E, G, I, L, M, F, P, S, T, W,<br>Y, V, R |
| SEQ ID NO: 141 | NGAL Mutant | QDSTSDLIPAPPLSKVPLQQNFQDNQFQGKWYVVGLAGNAILREDKDP<br>QKMYATIYELKEDKSYNVTSVLFR$X_{73}$KKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{73}$ = Q, A, N, D, C, E, G, I, L, M, F, P, S, T, W,<br>Y, V, K |
| SEQ ID NO: 142 | NGAL Mutant | QDSTSDLIPAPPLSKVPLQQNFQDNQFQGKWYVVGLAGNAILREDKDP<br>QKMYATIYELKEDKSYNVTSVLFRK$X_{74}$KCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{74}$ = Q, A, N, D, C, E, G, I, L, M, F, P, S, T, W,<br>Y, V, K |
| SEQ ID NO: 143 | NGAL Mutant | QDSTSDLIPAPPLSKVPLQQNFQDNQFQGKWYVVGLAGNAILREDKDP<br>QKMYATIYELKEDKSYNVTSVLFRKK$X_{75}$CDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{75}$ = Q, A, N, D, C, E, G, I, L, M, F, P, S, T, W,<br>Y, V, K |
| SEQ ID NO: 144 | NGAL Mutant | QDSTSDLIPAPPLSKVPLQQNFQDNQFQGKWYVVGLAGNAILREDKDP<br>QKMYATIYELKEDKSYNVTSVLFRKKK$X_{76}$DYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{76}$ = Q, A, N, D, C, E, G, I, L, M, F, P, S, T, W,<br>Y, V |
| SEQ ID NO: 145 | NGAL Mutant | QDSTSDLIPAPPLSKVPLQQNFQDNQFQGKWYVVGLAGNAILREDKDP<br>QKMYATIYELKEDKSYNVTSVLFRKKKC$X_{77}$YWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{77}$ = Q, A, N, D, C, E, G, I, L, M, F, P, S, T, W,<br>Y, V |
| SEQ ID NO: 146 | NGAL Mutant | QDSTSDLIPAPPLSKVPLQQNFQDNQFQGKWYVVGLAGNAILREDKDP<br>QKMYATIYELKEDKSYNVTSVLFRKKKCD$X_{78}$WIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{78}$ = Q, A, N, D, C, E, G, I, L, M, F, P, S, T, W,<br>Y, V |
| SEQ ID NO: 147 | NGAL Mutant | QDSTSDLIPAPPLSKVPLQQNFQDNQFQGKWYVVGLAGNAILREDKDP<br>QKMYATIYELKEDKSYNVTSVLFRKKKCDY$X_{79}$IRTFVPGCQPGEFTLG<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{79}$ = Q, A, N, D, C, E, G, I, L, M, F, P, S, T, W,<br>Y, V |
| SEQ ID NO: 148 | NGAL Mutant | QDSTSDLIPAPPLSKVPLQQNFQDNQFQGKWYVVGLAGNAILREDKDP<br>QKMYATIYELKEDKSYNVTSVLFRKKKCDYW$X_{80}$RTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{80}$ = Q, A, N, D, C, E, G, I, L, M, F, P, S, T, W,<br>Y, V |
| SEQ ID NO: 149 | NGAL Mutant | QDSTSDLIPAPPLSKVPLQQNFQDNQFQGKWYVVGLAGNAILREDKDP<br>QKMYATIYELKEDKSYNVTSVLFRKKKCDYWI$X_{81}$TFVPGCQPGEFTLG<br>NIKSYPGLTSYLVRVVSTNYNQHAMVFFKKVSQNREYFKITLYGRTKE |

-continued

| SEQ ID NO | Name | Sequence |
|---|---|---|
| | | LTSELKENFIRFSKSLGLPENHIVFPVPIDQCIDG<br>$X_{81}$ = Q, A, N, D, C, E, G, I, L, M, F, P, S, T, W, Y, V, R |
| SEQ ID NO: 150 | NGAL Mutant | QDSTSDLIPAPPLSKVPLQQNFQDNQFQGKWYVVGLAGNAILREDKDP<br>QKMYATIYELKEDKSYNVTSVLERKKKCDYWIRX$_{82}$FVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{82}$ = Q, A, N, D, C, E, G, I, L, M, F, P, S, T, W, Y, V |
| SEQ ID NO: 151 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTX$_{83}$VPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{83}$ = Q, A, N, D, C, E, G, I, L, M, F, P, S, T, W, Y, V |
| SEQ ID NO: 152 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFX$_{84}$PGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{84}$ = Q, A, N, D, C, E, G, I, L, M, F, P, S, T, W, Y, V |
| SEQ ID NO: 153 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVX$_{85}$GCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{85}$ = Q, A, N, D, C, E, G, I, L, M, F, P, S, T, W, Y, V |
| SEQ ID NO: 154 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPX;&CQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{86}$ = Q, A, N, D, C, E, G, I, L, M, F, P, S, T, W, Y, V |
| SEQ ID NO: 155 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGX$_{87}$QPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{87}$ = Q, A, N, D, C, E, G, I, L, M, F, P, S, T, W, Y, V |
| SEQ ID NO: 156 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCX$_{8}$:PGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{88}$ = Q, A, N, D, C, E, G, I, L, M, F, P, S, T, W, Y, V |
| SEQ ID NO: 157 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQX$_{89}$GEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{89}$ = Q, A, N, D, C, E, G, I, L, M, F, P, S, T, W, Y, V |
| SEQ ID NO: 158 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPX$_{90}$EFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{90}$ = Q, A, N, D, C, E, G, I, L, M, F, P, S, T, W, Y, V |
| SEQ ID NO: 159 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGX$_{91}$FTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{91}$ = Q, A, N, D, C, E, G, I, L, M, F, P, S, T, W, Y, V |

-continued

| SEQ ID NO | Name | Sequence |
|---|---|---|
| SEQ ID NO: 160 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGE$X_{92}$TLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{92}$ = Q, A, N, D, C, E, G, I, L, M, F, P, S, T, W,<br>Y, V |
| SEQ ID NO: 161 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEF$X_{93}$LG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{93}$ = Q, A, N, D, C, E, G, I, L, M, F, P, S, T, W,<br>Y, V |
| SEQ ID NO: 162 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFT$X_{94}$G<br>NIKSYPGLTSYLVRVVSTNYNQHAMVFFKKVSQNREYFKITLYGRTKE<br>LTSELKENFIRFSKSLGLPENHIVEPVPIDQCIDG<br>$X_{94}$ = Q, A, N, D, C, E, G, I, L, M, F, P, S, T, W,<br>Y, V |
| SEQ ID NO: 163 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTL$X_{95}$<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{95}$ = Q, A, N, D, C, E, G, I, L, M, F, P, S, T, W,<br>Y, V |
| SEQ ID NO: 164 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGX<br>$_{96}$IKSYPGLTSYLVRVVSTNYNQHAMVFFKKVSQNREYFKITLYGRTKE<br>LTSELKENFIRFSKSLGLPENHIVEPVPIDQCIDG<br>$X_{96}$ = Q, A, N, D, C, E, G, I, L, M, F, P, S, T, W,<br>Y, V |
| SEQ ID NO: 165 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>$X_{97}$KSYPGLTSYLVRVVSTNYNQHAMVFFKKVSQNREYFKITLYGRTKE<br>LTSELKENFIRFSKSLGLPENHIVFPVPIDQCIDG<br>$X_{97}$ = Q, A, N, D, C, E, G, I, L, M, F, P, S, T, W,<br>Y, V |
| SEQ ID NO: 166 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>I$X_{98}$SYPGLTSYLVRVVSTNYNQHAMVFFKKVSQNREYFKITLYGRTKE<br>LTSELKENFIRFSKSLGLPENHIVFPVPIDQCIDG<br>$X_{98}$ = Q, A, N, D, C, E, G, I, L, M, F, P, S, T, W,<br>Y, V, K |
| SEQ ID NO: 167 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IK$X_{99}$YPGLTSYLVRVVSTNYNQHAMVFFKKVSQNREYFKITLYGRTKE<br>LTSELKENFIRFSKSLGLPENHIVEPVPIDQCIDG<br>$X_{99}$ = Q, A, N, D, C, E, G, I, L, M, F, P, S, T, W,<br>Y, V |
| SEQ ID NO: 168 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKS$X_{100}$PGLTSYLVRVVSTNYNQHAMVFFKKVSQNREYFKITLYGRTK<br>ELTSELKENFIRFSKSLGLPENHIVFPVPIDQCIDG<br>$X_{100}$ = Q, A, N, D, C, E, G, I, L, M, F, P, S, T,<br>W, Y, V |
| SEQ ID NO: 169 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSY$X_{101}$GLTSYLVRVVSTNYNQHAMVFFKKVSQNREYFKITLYGRTK<br>ELTSELKENFIRFSKSLGLPENHIVFPVPIDQCIDG<br>$X_{101}$ = Q, A, N, D, C, E, G, I, L, M, F, P, S, T,<br>W, Y, V |
| SEQ ID NO: 170 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYP$X_{102}$LTSYLVRVVSTNYNQHAMVFFKKVSQNREYFKITLYGRTK |

-continued

| SEQ ID NO | Name | Sequence |
|---|---|---|
| | | ELTSELKENFIRFSKSLGLPENHIVFPVPIDQCIDG<br>$X_{102}$ = Q, A, N, D, C, E, G, I, L, M, F, P, S, T, W, Y, V |
| SEQ ID NO: 171 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGX$_{103}$TSYLVRVVSTNYNQHAMVFFKKVSQNREYFKITLYGRTK<br>ELTSELKENFIRFSKSLGLPENHIVFPVPIDQCIDG<br>$X_{103}$ = Q, A, N, D, C, E, G, I, L, M, F, P, S, T, W, Y, V |
| SEQ ID NO: 172 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLX$_{104}$SYLVRVVSTNYNQHAMVFFKKVSQNREYFKITLYGRTK<br>ELTSELKENFIRFSKSLGLPENHIVEPVPIDQCIDG<br>$X_{104}$ = Q, A, N, D, C, E, G, I, L, M, F, P, S, T, W, Y, V |
| SEQ ID NO: 173 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTX$_{1\ 5}$YLVRVVSTNYNQHAMVFFKKVSQNREYFKITLYGRTK<br>ELTSELKENFIRFSKSLGLPENHIVFPVPIDQCIDG<br>$X_{1\ 5}$ = Q, A, N, D, C, E, G, I, L, M, F, P, S, T, W, Y, V |
| SEQ ID NO: 174 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSX$_{106}$LVRVVSTNYNQHAMVFFKKVSQNREYFKITLYGRTK<br>ELTSELKENFIRFSKSLGLPENHIVFPVPIDQCIDG<br>$X_{106}$ = Q, A, N, D, C, E, G, I, L, M, F, P, S, T, W, Y, V |
| SEQ ID NO: 175 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYX$_{107}$VRVVSTNYNQHAMVFFKKVSQNREYFKITLYGRTK<br>ELTSELKENFIRFSKSLGLPENHIVFPVPIDQCIDG<br>$X_{107}$ = Q, A, N, D, C, E, G, I, L, M, F, P, S, T, W, Y, V |
| SEQ ID NO: 176 | NGAL Mutant | QDSTSDLIPAPPLSKVPLQQNFQDNQFQGKWYVVGLAGNAILREDKDP<br>QKMYATIYELKEDKSYNVTSVLERKKKCDYWIRTFVPGCQPGEFTLGN<br>IKSYPGLTSYLX$_{108}$RVVSTNYNQHAMVFFKKVSQNREYFKITLYGRTK<br>ELTSELKENFIRFSKSLGLPENHIVFPVPIDQCIDG<br>$X_{108}$ = Q, A, N, D, C, E, G, I, L, M, F, P, S, T, W, Y, V |
| SEQ ID NO: 177 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVX$_{109}$VVSTNYNQHAMVFFKKVSQNREYFKITLYGRTK<br>ELTSELKENFIRFSKSLGLPENHIVFPVPIDQCIDG<br>$X_{109}$ = Q, A, N, D, C, E, G, I, L, M, F, P, S, T, W, Y, V, R |
| SEQ ID NO: 178 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRX$_{110}$VSTNYNQHAMVFFKKVSQNREYFKITLYGRTK<br>ELTSELKENFIRFSKSLGLPENHIVFPVPIDQCIDG<br>$X_{110}$ = Q, A, N, D, C, E, G, I, L, M, F, P, S, T, W, Y, V |
| SEQ ID NO: 179 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVX$_{111}$STNYNQHAMVFFKKVSQNREYFKITLYGRTK<br>ELTSELKENFIRESKSLGLPENHIVFPVPIDQCIDG<br>$X_{111}$ = Q, A, N, D, C, E, G, I, L, M, F, P, S, T, W, Y, V |
| SEQ ID NO: 180 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVX$_{112}$TNYNQHAMVFFKKVSQNREYFKITLYGRTK<br>ELTSELKENFIRFSKSLGLPENHIVFPVPIDQCIDG<br>$X_{112}$ = Q, A, N, D, C, E, G, I, L, M, F, P, S, T, W, Y, V |

-continued

| SEQ ID NO | Name | Sequence |
|---|---|---|
| SEQ ID NO: 181 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVS$X_{113}$NYNQHAMVFFKKVSQNREYFKITLYGRTK ELTSELKENFIRFSKSLGLPENHIVFPVPIDQCIDG $X_{113}$ = Q, A, N, D, C, E, G, I, L, M, F, P, S, T, W, Y, V |
| SEQ ID NO: 182 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVST$X_{114}$YNQHAMVFFKKVSQNREYFKITLYGRTK ELTSELKENFIRFSKSLGLPENHIVFPVPIDQCIDG $X_{114}$ = Q, A, N, D, C, E, G, I, L, M, F, P, S, T, W, Y, V |
| SEQ ID NO: 183 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTN$X_{115}$NQHAMVFFKKVSQNREYFKITLYGRTK ELTSELKENFIRFSKSLGLPENHIVFPVPIDQCIDG $X_{115}$ = Q, A, N, D, C, E, G, I, L, M, F, P, S, T, W, Y, V |
| SEQ ID NO: 184 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNY$X_{116}$QHAMVFFKKVSQNREYFKITLYGRTK ELTSELKENFIRFSKSLGLPENHIVFPVPIDQCIDG $X_{116}$ = Q, A, N, D, C, E, G, I, L, M, F, P, S, T, W, Y, V |
| SEQ ID NO: 185 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYN$X_{117}$HAMVFFKKVSQNREYFKITLYGRTK ELTSELKENFIRFSKSLGLPENHIVFPVPIDQCIDG $X_{117}$ = Q, A, N, D, C, E, G, I, L, M, F, P, S, T, W, Y, V |
| SEQ ID NO: 186 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQ$X_{118}$AMVFFKKVSQNREYFKITLYGRTK ELTSELKENFIRFSKSLGLPENHIVFPVPIDQCIDG $X_{118}$ = Q, A, N, D, C, E, G, I, L, M, F, P, S, T, W, Y, V, H |
| SEQ ID NO: 187 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQH$X_{119}$MVFFKKVSQNREYFKITLYGRTK ELTSELKENFIRFSKSLGLPENHIVFPVPIDQCIDG $X_{119}$ = Q, A, N, D, C, E, G, I, L, M, F, P, S, T, W, Y, V |
| SEQ ID NO: 188 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHA$X_{120}$VFFKKVSQNREYFKITLYGRTK ELTSELKENFIRFSKSLGLPENHIVFPVPIDQCIDG $X_{120}$ = Q, A, N, D, C, E, G, I, L, M, F, P, S, T, W, Y, V |
| SEQ ID NO: 189 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAM$X_{121}$FFKKVSQNREYFKITLYGRTK ELTSELKENFIRFSKSLGLPENHIVFPVPIDQCIDG $X_{121}$ = Q, A, N, D, C, E, G, I, L, M, F, P, S, T, W, Y, V |
| SEQ ID NO: 190 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMV$X_{122}$FKKVSQNREYFKITLYGRTK ELTSELKENFIRFSKSLGLPENHIVFPVPIDQCIDG $X_{122}$ = Q, A, N, D, C, E, G, I, L, M, F, P, S, T, W, Y, V |
| SEQ ID NO: 191 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVF$X_{123}$KKVSQNREYFKITLYGRTK |

-continued

| SEQ ID NO | Name | Sequence |
|---|---|---|
| | | ELTSELKENFIRFSKSLGLPENHIVFPVPIDQCIDG<br>$X_{123}$ = Q, A, N, D, C, E, G, I, L, M, F, P, S, T, W, Y, V |
| SEQ ID NO: 192 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFF$X_{124}$KVSQNREYFKITLYGRTK<br>ELTSELKENFIRFSKSLGLPENHIVFPVPIDQCIDG<br>$X_{124}$ = Q, A, N, D, C, E, G, I, L, M, F, P, S, T, W, Y, V, K |
| SEQ ID NO: 193 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFK$X_{125}$VSQNREYFKITLYGRTK<br>ELTSELKENFIRESKSLGLPENHIVEPVPIDQCIDG<br>$X_{125}$ = Q, A, N, D, C, E, G, I, L, M, F, P, S, T, W, Y, V, K |
| SEQ ID NO: 194 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKK$X_{126}$SQNREYFKITLYGRTK<br>ELTSELKENFIRESKSLGLPENHIVFPVPIDQCIDG<br>$X_{126}$ = Q, A, N, D, C, E, G, I, L, M, F, P, S, T, W, Y, V |
| SEQ ID NO: 195 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKV$X_{127}$QNREYFKITLYGRTK<br>ELTSELKENFIRFSKSLGLPENHIVFPVPIDQCIDG<br>$X_{127}$ = Q, A, N, D, C, E, G, I, L, M, F, P, S, T, W, Y, V |
| SEQ ID NO: 196 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVS$X_{128}$NREYFKITLYGRTK<br>ELTSELKENFIRFSKSLGLPENHIVFPVPIDQCIDG<br>$X_{128}$ = Q, A, N, D, C, E, G, I, L, M, F, P, S, T, W, Y, V |
| SEQ ID NO: 197 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQ$X_{129}$REYFKITLYGRTK<br>ELTSELKENFIRFSKSLGLPENHIVFPVPIDQCIDG<br>$X_{129}$ = Q, A, N, D, C, E, G, I, L, M, F, P, S, T, W, Y, V |
| SEQ ID NO: 198 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQN$X_{130}$EYFKITLYGRTK<br>ELTSELKENFIRFSKSLGLPENHIVFPVPIDQCIDG<br>$X_{130}$ = Q, A, N, D, C, E, G, I, L, M, F, P, S, T, W, Y, V, R |
| SEQ ID NO: 199 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNR$X_{131}$YFKITLYGRTK<br>ELTSELKENFIRFSKSLGLPENHIVFPVPIDQCIDG<br>$X_{131}$ = Q, A, N, D, C, E, G, I, L, M, F, P, S, T, W, Y, V |
| SEQ ID NO: 200 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNRE$X_{132}$FKITLYGRTK<br>ELTSELKENFIRFSKSLGLPENHIVFPVPIDQCIDG<br>$X_{132}$ = Q, A, N, D, C, E, G, I, L, M, F, P, S, T, W, Y, V |
| SEQ ID NO: 201 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREY$X_{133}$KITLYGRTK<br>ELTSELKENFIRFSKSLGLPENHIVFPVPIDQCIDG<br>$X_{133}$ = Q, A, N, D, C, E, G, I, L, M, F, P, S, T, W, Y, V |

-continued

| SEQ ID NO | Name | Sequence |
|---|---|---|
| SEQ ID NO: 202 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYF$X_{134}$ITLYGRTK<br>ELTSELKENFIRFSKSLGLPENHIVFPVPIDQCIDG<br>$X_{134}$ = Q, A, N, D, C, E, G, I, L, M, F, P, S, T,<br>W, Y, V, K |
| SEQ ID NO: 203 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFK$X_{135}$TLYGRTK<br>ELTSELKENFIRFSKSLGLPENHIVFPVPIDQCIDG<br>$X_{135}$ = Q, A, N, D, C, E, G, I, L, M, F, P, S, T,<br>W, Y, V |
| SEQ ID NO: 204 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKI$X_{136}$LYGRTK<br>ELTSELKENFIRFSKSLGLPENHIVFPVPIDQCIDG<br>$X_{136}$ = Q, A, N, D, C, E, G, I, L, M, F, P, S, T,<br>W, Y, V |
| SEQ ID NO: 205 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKIT$X_{137}$YGRTK<br>ELTSELKENFIRFSKSLGLPENHIVFPVPIDQCIDG<br>$X_{137}$ = Q, A, N, D, C, E, G, I, L, M, F, P, S, T,<br>W, Y, V |
| SEQ ID NO: 206 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITL$X_{138}$GRTK<br>ELTSELKENFIRFSKSLGLPENHIVEPVPIDQCIDG<br>$X_{138}$ = Q, A, N, D, C, E, G, I, L, M, F, P, S, T,<br>W, Y, V |
| SEQ ID NO: 207 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLY$X_{139}$RTK<br>ELTSELKENFIRFSKSLGLPENHIVFPVPIDQCIDG<br>$X_{139}$ = Q, A, N, D, C, E, G, I, L, M, F, P, S, T,<br>W, Y, V |
| SEQ ID NO: 208 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYG$X_{140}$TK<br>ELTSELKENFIRFSKSLGLPENHIVFPVPIDQCIDG<br>$X_{140}$ = Q, A, N, D, C, E, G, I, L, M, F, P, S, T,<br>W, Y, V, R |
| SEQ ID NO: 209 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGR$X_{141}$K<br>ELTSELKENFIRFSKSLGLPENHIVFPVPIDQCIDG<br>$X_{141}$ = Q, A, N, D, C, E, G, I, L, M, F, P, S, T,<br>W, Y, V |
| SEQ ID NO: 210 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRT$X_{142}$<br>ELTSELKENFIRFSKSLGLPENHIVFPVPIDQCIDG<br>$X_{142}$ = Q, A, N, D, C, E, G, I, L, M, F, P, S, T,<br>W, Y, V, K |
| SEQ ID NO: 211 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTK$X_{14}$<br>$_{3}$LTSELKENFIRESKSLGLPENHIVFPVPIDQCIDG<br>$X_{143}$ = Q, A, N, D, C, E, G, I, L, M, F, P, S, T,<br>W, Y, V |
| SEQ ID NO: 212 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEX |

-continued

| SEQ ID NO | Name | Sequence |
|---|---|---|
| | | $_{144}$TSELKENFIRFSKSLGLPENHIVFPVPIDQCIDG<br>$X_{144}$ = Q, A, N, D, C, E, G, I, L, M, F, P, S, T,<br>W, Y, V |
| SEQ ID NO: 213 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>$X_{145}$SELKENFIRESKSLGLPENHIVFPVPIDQCIDG<br>$X_{145}$ = Q, A, N, D, C, E, G, I, L, M, F, P, S, T,<br>W, Y, V |
| SEQ ID NO: 214 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>T$X_{146}$ELKENFIRFSKSLGLPENHIVEPVPIDQCIDG<br>$X_{146}$ = Q, A, N, D, C, E, G, I, L, M, F, P, S, T,<br>W, Y, V |
| SEQ ID NO: 215 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TS$X_{147}$LKENFIRFSKSLGLPENHIVEPVPIDQCIDG<br>$X_{147}$ = Q, A, N, D, C, E, G, I, L, M, F, P, S, T,<br>W, Y, V |
| SEQ ID NO: 216 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSE$X_{148}$KENFIRFSKSLGLPENHIVFPVPIDQCIDG<br>$X_{148}$ = Q, A, N, D, C, E, G, I, L, M, F, P, S, T,<br>W, Y, V |
| SEQ ID NO: 217 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSEL$X_{149}$ENFIRFSKSLGLPENHIVFPVPIDQCIDG<br>$X_{149}$ = Q, A, N, D, C, E, G, I, L, M, F, P, S, T,<br>W, Y, V, K |
| SEQ ID NO: 218 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELK$X_{150}$NFIRFSKSLGLPENHIVFPVPIDQCIDG<br>$X_{150}$ = Q, A, N, D, C, E, G, I, L, M, F, P, S, T,<br>W, Y, V |
| SEQ ID NO: 219 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKE$X_{151}$FIRFSKSLGLPENHIVFPVPIDQCIDG<br>$X_{151}$ = Q, A, N, D, C, E, G, I, L, M, F, P, S, T,<br>W, Y, V |
| SEQ ID NO: 220 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKEN$X_{152}$IRFSKSLGLPENHIVFPVPIDQCIDG<br>$X_{152}$ = Q, A, N, D, C, E, G, I, L, M, F, P, S, T,<br>W, Y, V |
| SEQ ID NO: 221 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENF$X_{153}$RFSKSLGLPENHIVFPVPIDQCIDG<br>$X_{153}$ = Q, A, N, D, C, E, G, I, L, M, F, P, S, T,<br>W, Y, V |
| SEQ ID NO: 222 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFI$X_{154}$FSKSLGLPENHIVFPVPIDQCIDG<br>$X_{154}$ = Q, A, N, D, C, E, G, I, L, M, F, P, S, T,<br>W, Y, V, R |

-continued

| SEQ ID NO | Name | Sequence |
|---|---|---|
| SEQ ID NO: 223 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIR$X_{155}$SKSLGLPENHIVFPVPIDQCIDG<br>$X_{155}$ = Q, A, N, D, C, E, G, I, L, M, F, P, S, T,<br>W, Y, V |
| SEQ ID NO: 224 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRF$X_{156}$KSLGLPENHIVFPVPIDQCIDG<br>$X_{156}$ = Q, A, N, D, C, E, G, I, L, M, F, P, S, T,<br>W, Y, V |
| SEQ ID NO: 225 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRES$X_{157}$SLGLPENHIVEPVPIDQCIDG<br>$X_{157}$ = Q, A, N, D, C, E, G, I, L, M, F, P, S, T,<br>W, Y, V, K |
| SEQ ID NO: 226 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSK$X_{15}$:LGLPENHIVFPVPIDQCIDG<br>$X_{158}$ = Q, A, N, D, C, E, G, I, L, M, F, P, S, T,<br>W, Y, V |
| SEQ ID NO: 227 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKS$X_{159}$GLPENHIVFPVPIDQCIDG<br>$X_{159}$ = Q, A, N, D, C, E, G, I, L, M, F, P, S, T,<br>W, Y, V |
| SEQ ID NO: 228 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSL$X_{160}$LPENHIVFPVPIDQCIDG<br>$X_{160}$ = Q, A, N, D, C, E, G, I, L, M, F, P, S, T,<br>W, Y, V |
| SEQ ID NO: 229 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLG$X_{161}$PENHIVFPVPIDQCIDG<br>$X_{161}$ = Q, A, N, D, C, E, G, I, L, M, F, P, S, T,<br>W, Y, V |
| SEQ ID NO: 230 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGL$X_{162}$ENHIVFPVPIDQCIDG<br>$X_{162}$ = Q, A, N, D, C, E, G, I, L, M, F, P, S, T,<br>W, Y, V |
| SEQ ID NO: 231 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLP$X_{163}$NHIVFPVPIDQCIDG<br>$X_{163}$ = Q, A, N, D, C, E, G, I, L, M, F, P, S, T,<br>W, Y, V |
| SEQ ID NO: 232 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRESKSLGLPE$X_{164}$HIVFPVPIDQCIDG<br>$X_{164}$ = Q, A, N, D, C, E, G, I, L, M, F, P, S, T,<br>W, Y, V |
| SEQ ID NO: 233 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL |

-continued

| SEQ ID NO | Name | Sequence |
|---|---|---|
| | | TSELKENFIRESKSLGLPENX$_{165}$IVFPVPIDQCIDG<br>X$_{165}$ = Q, A, N, D, C, E, G, I, L, M, F, P, S, T,<br>W, Y, V, H |
| SEQ ID NO: 234 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRESKSLGLPENHX$_{166}$VFPVPIDQCIDG<br>X$_{166}$ = Q, A, N, D, C, E, G, I, L, M, F, P, S, T,<br>W, Y, V |
| SEQ ID NO: 235 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIX$_{167}$FPVPIDQCIDG<br>X$_{167}$ = Q, A, N, D, C, E, G, I, L, M, F, P, S, T,<br>W, Y, V |
| SEQ ID NO: 236 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVX$_{16}$:PVPIDQCIDG<br>X$_{168}$ = Q, A, N, D, C, E, G, I, L, M, F, P, S, T,<br>W, Y, V |
| SEQ ID NO: 237 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFX$_{169}$VPIDQCIDG<br>X$_{169}$ = Q, A, N, D, C, E, G, I, L, M, F, P, S, T,<br>W, Y, V |
| SEQ ID NO: 238 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPX$_{170}$PIDQCIDG<br>X$_{170}$ = Q, A, N, D, C, E, G, I, L, M, F, P, S, T,<br>W, Y, V |
| SEQ ID NO: 239 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVX$_{171}$IDQCIDG<br>X$_{171}$ = Q, A, N, D, C, E, G, I, L, M, F, P, S, T,<br>W, Y, V |
| SEQ ID NO: 240 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPX$_{172}$DQCIDG<br>X$_{172}$ = Q, A, N, D, C, E, G, I, L, M, F, P, S, T,<br>W, Y, V |
| SEQ ID NO: 241 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIX$_{173}$QCIDG<br>X$_{173}$ = Q, A, N, D, C, E, G, I, L, M, F, P, S, T,<br>W, Y, V |
| SEQ ID NO: 242 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDX$_{174}$CIDG<br>X$_{174}$ = Q, A, N, D, C, E, G, I, L, M, F, P, S, T,<br>W, Y, V |
| SEQ ID NO: 243 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQX$_{175}$IDG<br>X$_{175}$ = Q, A, N, D, C, E, G, I, L, M, F, P, S, T,<br>W, Y, V |

-continued

| SEQ ID NO | Name | Sequence |
|---|---|---|
| SEQ ID NO: 244 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQC$X_{176}$DG<br>$X_{176}$ = Q, A, N, D, C, E, G, I, L, M, F, P, S, T,<br>W, Y, V |
| SEQ ID NO: 245 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVEPVPIDQCI$X_{177}$G<br>$X_{177}$ = Q, A, N, D, C, E, G, I, L, M, F, P, S, T,<br>W, Y, V |
| SEQ ID NO: 246 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCID$X_{178}$<br>$X_{178}$ = Q, A, N, D, C, E, G, I, L, M, F, P, S, T,<br>W, Y, V |
| SEQ ID NO: 247 | D1-4-2-1-4-2 | QDSTSDLIPAPPLSKVPLQQNFQDNQFQGKWYVVGLAGNAILREDEDP<br>QTMYATIYELAEDGSYNVTSVLFADDGCDYWIRTFVPGCQPGEFTLGN<br>IASYPGLTSYLVRVVSTDYNQHAMVFFKKVSESAEYFKITLYGRTKEL<br>TSELKENFIRFSKSLGLPENHIVFPVPIDQCIDG |
| SEQ ID NO: 248 | D1-4-2-1-4-3 | QDSTSDLIPAPPLSSVPLQQNFQDNQFQGKWYVVGLAGNAILREDEDP<br>QTMYATIYELAEDGSYNVTSVLFRDDGCDYWIRTFVPGCQPGEFTLGN<br>IASYPGLTSYLVRVVSTDYDEFAMVFFKKVSESAEYFKITLYGRTKEL<br>TSELKENFIRFSKSLGLPENHIVFPVPIDQCIDG |
| SEQ ID NO: 249 | K3-4-2 | QDSTSDLIPAPPLSSVPLQQNFQDNQFQGKWYVVGLAGNAILREDEDP<br>QTMYATIYELKEDGSYNVTSVLFADDGCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 250 | K3-3Con | QDSTSDLIPAPPLSSVPLQQNFQDNQFQGKWYVVGLAGNAILAEDEDP<br>QKMYATIYELKEDKSYNVTSVLFRDDGCDYWIRTFVPGCQPGEFTLGN<br>IQSYPGLTSYLVRVVSTNYNQFAMVFFKKVSQNQEYFKITLYGATAEL<br>TSELQENFIRFSASLGLPENNIVFPVPIDQCIDG |
| SEQ ID NO: 251 | K3-4Con | QDSTSDLIPAPPLSSVPLQQNFQDNQFQGKWYVVGLAGNAILAEDEDP<br>QKMYATIYELKEDKSYNVTSVLFRDDGCDYWIRTFVPGCQPGEFTLGN<br>IQSYPGLTSYLVRVVSTNYNQFAMVFFKKVSQNQEYFKITLYGRTKEL<br>TSELQENFIRFSASLGLPENNIVFPVPIDQCIDG |
| SEQ ID NO: 252 | K3Cys | QDSTSDLIPAPPLSSVPLQQNFQDNQFQGKWYVVGLAGNAILREDEDP<br>QKMYATIYELKEDKSYNVTSVLERDDGCDYWIRTFVPGSQPGEFTLGN<br>IQSYPGLTSYLVRVVSTNYNQFAMVFFKKVSQNQEYFKITLYGRTKEL<br>TSELQENFIRESKSLGLPENNIVFPVPIDQCIDG |

Example 3

The superscripted numbers in this Example refer to the numbered references in the list of references that follows this Example. Ngal mutant Mut1 or mutant 1 refers to the K3 NGAL protein of SEQ ID NO: 2. Ngal mutant Mut2 or mutant 2 refers to the K3Cys protein protein of SEQ ID NO: 252.

Iron is specifically bound by transferrin in circulation, which preserves its bioavailability and prevents its redox toxicity. However, non-transferrin-bound iron (NTBI) appears in patients with a variety of diseases[1-3]. NTBI damages liver[4-7], heart[8-12], endocrine glands[13-18] and kidney[19-21] and severe overload can be fatal[22,23]. To date, two small molecules, deferoxamine (DFO) and deferiprone are available for the chelation of NTBI and the treatment of iron overload. However, these molecules demonstrate significant toxicity. We have discovered an endogenous mechanism of iron transport (Barasch: Molecular Cell, 2002; Nature N&V, 2005; Nature Chemical Biology, 2010), which we realized could be manipulated to safely export iron from the body.

Figures 6A, 6B:
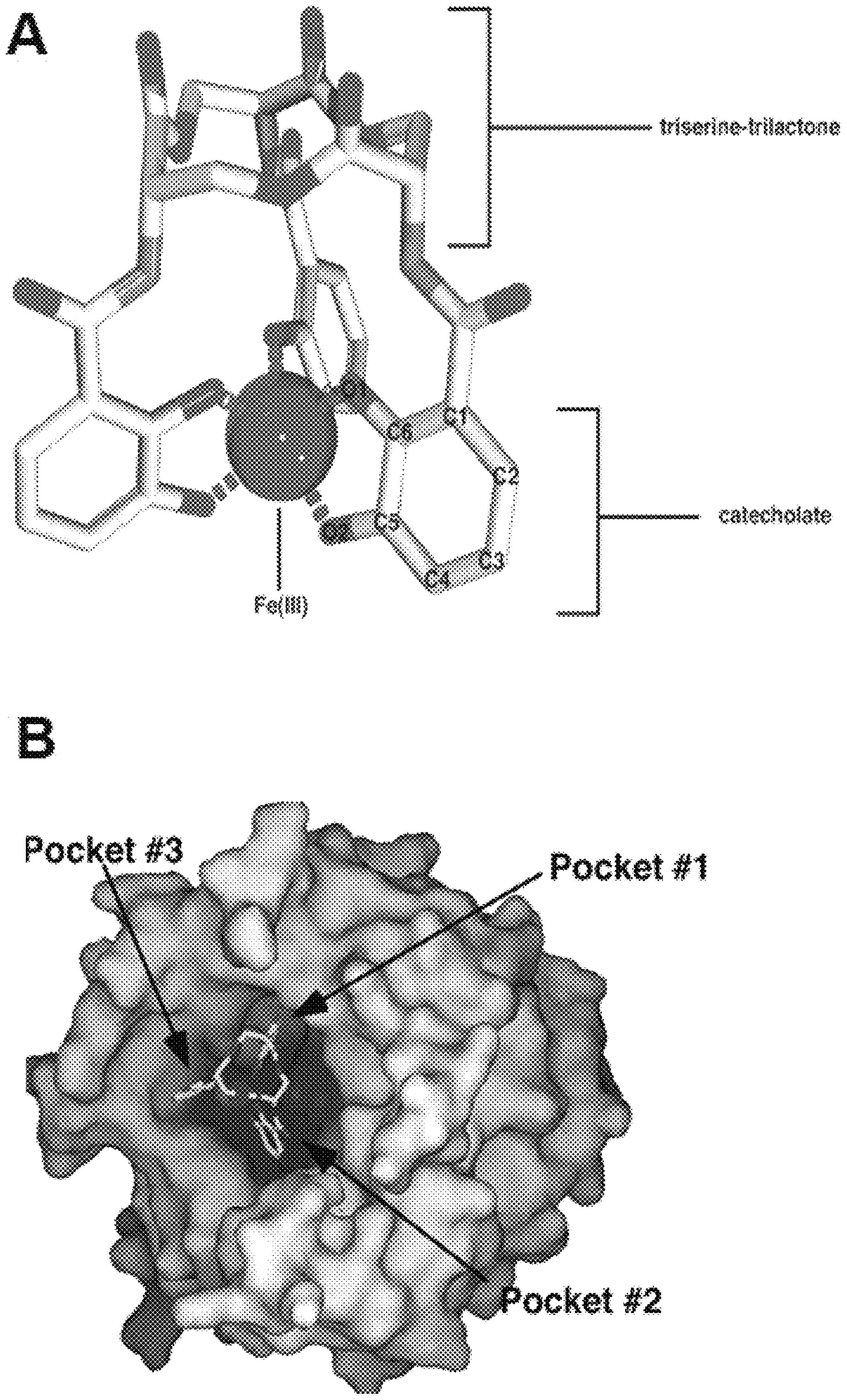
FIGS. 6A-6B.

The Ngal protein is expressed by damaged epithelia (AKI: *JASN,* 2003*; JCI,* 2005*; Lancet,* 2005*; Ann Int Med,* 2008) and then it is rapidly secreted. Ngal captures catecholate-type bacterial siderophores (Enterochelin, Ent)[3] and endogenous catechols[6] (FIGS. 6A-6B). Ngal:catechol:Fe complexes are stable for transport. They are filtered from the blood by the glomerulus and captured by proximal tubule megalin where Ngal is degraded and its iron recycled[38]. Here we evaluated Ngal mutants that we believe bypass megalin, yet still bind Ent:iron, hence providing an unexpected, novel, therapeutic that can safely excrete NTBI in the urine.

Evaluation of the Ngal-Megalin Interaction by the Generation of Ngal Mutants: We produced a series of defined mutations in the positive surface residues of Ngal and identified clones that traffic into the urine (i.e. bypassing megalin). The appearance in the urine was detected by immunoblot. In order to increase the export of the mutant Ngal, we introduced a new mutation in the so called unpaired cysteine to block the homodimerization of Ngal. This resulted in nearly complete loss of Ngal from the mouse by filtration and urinary excretion—most likely a result of the lower molecular weight of the monomeric-non dimerizable species. This new species of Ngal (called mut2) appeared earlier in the urine than mutants (e.g. mut1) that were still capable of dimerization (FIGS. 22A-22B). We next examined a wide range of organs and found that while wt Ngal was most prominently captured by proximal tubule (and also in Kupfer cells), our mutants were not recognized by the proximal tubule and in fact mutant 2 was depleted from all sites of cellular capture (because it was rapidly excreted, FIG. 25). Further examination revealed that the mutants did in fact have one site of capture in the kidney and that was in cells of the collecting duct. This could be seen when the microscopic image was amplified by increasing exposure time. By staining with antibodies for the two cell types found in the collecting ducts (FIG. 26), both principal and intercalated cells take up the mutant Ngal (in marked contrast to proximal tubules). Numerical counts of the cells that captured Ngal showed that 64.7% were AQ2+ principal cells (n=769/1188) and 27.3% were ATPase+(n=158/579) and 23.5% (n=190/807) were AE1+ indicating that approximately ⅓ of the cells that captured NGAL expressed marker genes typical of alpha intercalated cells. In order to model these findings and to determine whether the uptake represented a cell autonomous process, we utilized a variety of cell lines. While all cell lines took up fluorescent dextran, LLCPK took up wild type Ngal, not the mutant species, intercalated cells took up both wild type and mutant Ngal and UB cells took up neither wild type nor mutant Ngal (FIG. 27). Taken together, the data indicate that megalin (expressed in the proximal tubule and in the LLCPK cell line) captures Ngal, but the mutant form of Ngal can bypass these cells. Additionally, collecting duct cells may express non-megalin Ngal receptors. This extensive characterization indicated that by manipulating the surface residues and the dimerization site for Ngal, we have created a protein which can traffic from the periphery into the urine.

Ngal:Ent:$Fe^{III}$ Interaction in Ngal Mutants In order to utilize Ngal as a therapeutic agent to remove iron from overloaded mice, we examined the Ngal:iron complex. We decided to use the siderophore Ent as the iron binding co-factor, not only because it has a high affinity for the Ngal calyx (0.4 nM and 3.57 nM, respectively) but also because it fails to release bound iron even at low pH. First, x-ray crystallographic studies of mutant1 were performed. Since our mutants affect crystal contacts in all the known Ngal crystal forms, he approached this as a de novo structural determination. He found that the mutant could be superimposed on wild type Ngal, implying that our extensive mutagenesis did not dramatically alter the overall structure of the protein (FIG. 28). Second, we examined whether ligation by iron siderophores created a stabilized structure that quenched the endogenous chemical reactivity of iron. Using both fluorescein activation assays and ferric reduction assays, we found that the mutants of NGAL bound siderophores and iron without triggering redox activity (FIGS. 29A-29C).

Safe Excretion of Iron by the Delivery of Mutant NGAL: Ent:$Fe^{III}$

To test whether mutant Ngal can efficiently chelate and deliver NTBI to the urine through the kidney, we introduced the bacterially expressed Ngal ligated to Ent:$^{59}Fe^{III}$ into mice, and collected the urine for 3 hrs. We found that mutant 1 delivered 23% of the injected mutant 1 Ngal-$^{59}Fe^{III}$ complex to the urine, paralleling the percentage of the protein found in the urine, while less than 0.1% of the wild type injectate was excreted. When we injected mutant2 (cysteine mutation), nearly 100% of the iron was found in the urine. In FIG. 23, we can see that only trace amounts of wild type $^{59}Fe^{III}$ (in the Ngal:Ent complex) was found in the urine—almost all of it accumulated in the kidney, but mutant 2 was not retained in the kidney, but rather it was all found in the urine.

Based on these results, we are planning to test whether mutant 2 can capture, chelate, traffic and remove endogenous NTBI. To do this however requires mammalian expressed Ngal rather than the bacterial species to avoid the effects on iron metabolism of endotoxins. We are now quite advanced in purification of Ngal from 293 cells grown in spinner suspension. The purification utilizes Blue and Heparin Sepharose™, gel filtration and anion exchange. The last step of the process is seen in FIG. 30. Note that the small peak contains the majority of Ngal protein. We think this protocol will produce enough Ngal for depletion experiments.

REFERENCES

1. Hershko, C., and Peto, T. E. Non-transferrin plasma iron. Br. J. Haematol. 66: 149-151, 1987.
2. Breuer, W., Ronson, A., Slotki, I. N., Abramov, A., Hershko, C., and Cabantchik, Z. I. The assessment of serum nontransferrin-bound iron in chelation therapy and iron supplementation. Blood. 95: 2975-2982, 2000.
3. Andrews, N. C. Iron metabolism: Iron Deficiency and Iron Overload. Annu. Rev. Genomics Hum. Genet. 1:75-98, 2000.
4. Thakemgpol, K., Fucharoen, S., Boonyaphipat, P., Srisook, K., Sahaphong, S., Vathanophas, V., and Stitnimankam, T. Liver injury due to iron overload in thalassemia: histopathologic and ultrastructural studies. Biometals. 9: 177-183, 1996.
5. Conte, D., Piperno, A., Mandelli, C., et al. Clinical, biochemical and histological features of primary haemochromatosis: a report of 67 cases. Liver. 6: 310-315, 1986.
6. Tsukamoto, H., Home, W., Kamimura, S., Niemela, O., Parkkila, S., Yla-Herttuala, S., and Brittenham, G. M. Experimental liver cirrhosis induced by alcohol and iron. J. Clin. Invest. 96: 620-630, 1995.
7. Berdoukas, V., Bohane, T., Tobias, V., et al. Liver iron concentration and fibrosis in a cohort of transfusion-dependent patients on long-term desferrioxamine therapy. Hematol. J. 5: 572-578, 2004.
8. Liu, P., and Olivieri, N. Iron overload cardiomyopathies: new insights into an old disease. Cardiovasc. Drugs. Ther. 8:101-110, 1994.
9. Buja, L. M., and Roberts, W. C. Iron in the heart. Etiology and clinical significance. Am. J. Med. 51: 209-221, 1971.
10. Schwartz, K. A., Li, Z., Schwartz, D. E., et al. Earliest cardiac toxicity induced by iron overload selectively inhibits electrical conduction. J. Appl. Physiol. 93: 746-751, 2002.
11. Oudit, G. Y., Trivieri, M. G., Khaper, N., Liu, P. P., and Backx, P. H. Role of L-type Ca2+ channels in iron transport and iron-overload cardiomyopathy. J. Mol. Med. 84: 349-364, 2006.
12. Oudit, G. Y., Sun, H., Trivieri, M. G., Koch, S. E., Dawood, F., Ackerley, C., Yazdanpanah, M., Wilson, G. J., Schwartz, A., Liu, P. P., and Backx, P. H. L-type $Ca^{2+}$ channels provide a major pathway for iron entry into cardiomyocytes in iron-overload cardiomyopathy, Nat. Med. 9: 1187-1194, 2003.
13. Andrews, N. C. Disorders of iron metabolism. N. Engl. J. Med. 341: 1986-1995, 1999.
14. Argyropoulou, M. I., and Astrakas, L. MRI evaluation of tissue iron burden in patients with beta-thalassaemia major. Pediatr. Radiol. 37: 1191-1200, 2007.
15. Argyropoulou, M. I., Kiortsis, D. N., Astrakas, L., Metafratzi, Z., Chalissos, N., Efremidis, S. C. Liver, bone marrow, pancreas and pituitary gland iron overload in young and adult thalassemic patients: a T2 relaxometry study. Eur. Radiol. 17: 3025-3030, 2007.
16. Cunningham, M. J., Macklin, E. A., Neufeld, E. J., and Cohen, A. R. Complications of beta-thalassemia major in North America. Blood. 104: 34-39, 2004.
17. Fung, E., Harmatz, P. R., Lee, P. D., Milet, M., Bellevue, R., Jeng, M. R., Kalinyak, K. A., Hudes, M., Bhatia, S., and Vichinsky, E. P. Increased prevalence of iron-overload associated endocrinopathy in thalassaemia versus sickle-cell disease. Br. J. Haematol. 135: 574-582, 2006.
18. Kattamis, C., and Kattamis, A. C. Management of thalassemias: growth and development, hormone substitution, vitamin supplementation, and vaccination. Semin. Hematol. 32: 269-279, 1995.
19. Eschbach, J. W., and Adamson, J. W. Iron overload in renal failure patients: Changes since the introduction of erythropoietin therapy. Kidney Int. 55: S35-S43, 1999.
20. Lorenz, M., Kletzmayr, J., Huber, A., Hörl, A. H., Sunder-Plassmann, G., and Fddinger, M. Iron overload in kidney transplants: Prospective analysis of biochemical and genetic markers. Kidney Int. 67, 691-697, 2005.
21. Mandalunis, P. M., and Ubios, A. M. Experimental Renal Failure and Iron Overload: A Histomorphometric Study in Rat Tibia. Toxicol. Pathol. 33; 398-403, 2005.
22. Karnon, J., Zeuner, D., Brown, J., Ades, A. E., Wonke, B., and Modell, B. Lifetime treatment costs of beta-thalassaemia major. Clin. Lab. Haematol. 21: 377-385, 1999.
23. Darbari, D. S., Kple-Faget, P., Kwagyan, J., Rana, S., Gordeuk, V. R., and Castro, O. Circumstances of death in adult sickle cell disease patients. Am. J. Hematol. 81: 858-863, 2006.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A method of treating a urinary tract infection in a subject in need thereof, the method comprising administering to the subject an effective amount of a pharmaceutical composition comprising:

(i) a polypeptide that comprises an amino acid sequence that is at least 99% identical to SEQ ID NO: 2;

(ii) a polypeptide that comprises SEQ ID NO: 2;

(iii) a polypeptide that comprises an amino acid sequence that is at least 99% identical to SEQ ID NO: 252, wherein the polypeptide does not comprise a cysteine at amino acid 87 of SEQ ID NO: 252; or (iv) a polypeptide that comprises SEQ ID NO: 252.

2. The method of claim 1, wherein the method comprises administering to the subject an effective amount of a pharmaceutical composition comprising a polypeptide that comprises an amino acid sequence that is at least 99% identical to SEQ ID NO: 2.

3. The method of claim 1, wherein the method comprises administering to the subject an effective amount of a pharmaceutical composition comprising a polypeptide that comprises SEQ ID NO: 2.

4. The method of claim 1, wherein the method comprises administering to the subject an effective amount of a pharmaceutical composition comprising a polypeptide that comprises an amino acid sequence that is at least 99% identical to SEQ ID NO: 252, wherein the polypeptide does not comprise a cysteine at amino acid 87 of SEQ ID NO: 252.

5. The method of claim 1, wherein the method comprises administering to the subject an effective amount of a pharmaceutical composition comprising a polypeptide that comprises SEQ ID NO: 252.

6. The method of claim 4, wherein the polypeptide comprises a serine at amino acid 87 of SEQ ID NO: 252.

7. The method of claim 1, wherein the pharmaceutical composition further comprises a siderophore.

8. The method of claim 2, wherein the pharmaceutical composition further comprises a siderophore.

9. The method of claim 3, wherein the pharmaceutical composition further comprises a siderophore.

10. The method of claim 4, wherein the pharmaceutical composition further comprises a siderophore.

11. The method of claim 5, wherein the pharmaceutical composition further comprises a siderophore.

12. The method of claim 7, wherein the siderophore is selected from enterochelin, pyrogallol, carboxymycobactin, bacillibactin, or catechol.

13. The method of claim 7, wherein the siderophore is pH insensitive.

14. The method of claim 7, wherein the siderophore binds to the polypeptide and iron in the urine.

15. The method of claim 7, wherein the siderophore binds to the polypeptide and iron at blood pH.

16. The method of claim 7, wherein the siderophore binds to the polypeptide and iron in the blood.

17. The method of claim 7, wherein the polypeptide and the siderophore are present in a 1:1 molar ratio.

18. The method of claim 7, wherein the siderophore binds to the polypeptide and iron at pH 4.0 to 7.5.

19. The method of claim 5, wherein the subject is a human.

20. The method of claim 7, wherein the subject is a human.

* * * * *